US009012599B2

(12) United States Patent
Stoessel et al.

(10) Patent No.: US 9,012,599 B2
(45) Date of Patent: Apr. 21, 2015

(54) NITROGEN-CONTAINING CONDENSED HETEROCYCLIC COMPOUNDS FOR OLEDS

(75) Inventors: Philipp Stoessel, Frankfurt am Main (DE); Esther Breuning, Ober-Ramstadt (DE); Dominik Joosten, Frankfurt am Main (DE); Christof Pflumm, Frankfurt am Main (DE); Amir Hossain Parham, Frankfurt am Main (DE)

(73) Assignee: Merck Patent GmbH (DE)

( * ) Notice: Subject to any disclaimer, the term of this patent is extended or adjusted under 35 U.S.C. 154(b) by 291 days.

(21) Appl. No.: 13/510,425

(22) PCT Filed: Oct. 20, 2010

(86) PCT No.: PCT/EP2010/006414
§ 371 (c)(1),
(2), (4) Date: May 17, 2012

(87) PCT Pub. No.: WO2011/060867
PCT Pub. Date: May 26, 2011

(65) Prior Publication Data
US 2012/0232241 A1    Sep. 13, 2012

(30) Foreign Application Priority Data

Nov. 18, 2009   (DE) .......................... 10 2009 053 836

(51) Int. Cl.
| | | |
|---|---|---|
| C08G 73/06 | (2006.01) |
| C07D 471/04 | (2006.01) |
| C07D 455/03 | (2006.01) |
| C07D 471/14 | (2006.01) |
| C07D 471/22 | (2006.01) |
| C07D 498/14 | (2006.01) |
| C07D 498/22 | (2006.01) |
| C07D 513/04 | (2006.01) |
| C07D 513/14 | (2006.01) |
| C07D 513/22 | (2006.01) |
| C07D 519/00 | (2006.01) |
| C07F 7/08 | (2006.01) |
| C07F 9/6568 | (2006.01) |
| C07F 15/00 | (2006.01) |
| C09K 11/06 | (2006.01) |
| H05B 33/14 | (2006.01) |
| C09B 57/00 | (2006.01) |
| C08G 61/00 | (2006.01) |

(52) U.S. Cl.
CPC ............ *C07D 471/04* (2013.01); *C07D 455/03* (2013.01); *C07D 471/14* (2013.01); *C07D 471/22* (2013.01); *C07D 498/14* (2013.01); *C07D 498/22* (2013.01); *C07D 513/04* (2013.01); *C07D 513/14* (2013.01); *C07D 513/22* (2013.01); *C07D 519/00* (2013.01); *C07F 7/0816* (2013.01); *C07F 9/65683* (2013.01); *C07F 9/65685* (2013.01); *C07F 15/0026* (2013.01); *C07F 15/0033* (2013.01); *C07F 15/0086* (2013.01); *C09K 11/06* (2013.01); *C09K 2211/1011* (2013.01); *C09K 2211/1029* (2013.01); *C09K 2211/1033* (2013.01); *C09K 2211/1037* (2013.01); *C09K 2211/104* (2013.01); *C09K 2211/1044* (2013.01); *C09K 2211/1048* (2013.01); *C09K 2211/1059* (2013.01); *C09K 2211/1088* (2013.01); *C09K 2211/1092* (2013.01); *C09K 2211/1096* (2013.01); *H05B 33/14* (2013.01); *C09B 57/00* (2013.01)

(58) Field of Classification Search
CPC ..................................................... C07D 471/04
USPC ......................................... 528/423, 424, 397
See application file for complete search history.

(56) References Cited

U.S. PATENT DOCUMENTS

| | | |
|---|---|---|
| 2009/0230857 A1 | 9/2009 | Choi et al. |
| 2009/0295275 A1 | 12/2009 | Parham et al. |
| 2010/0051928 A1 | 3/2010 | Fukuzaki |

FOREIGN PATENT DOCUMENTS

WO    WO-2007031165 A2    3/2007

OTHER PUBLICATIONS

Henry, John B., et al., "Calculation of hte Redox Properties of Aromatics and Prediction of Their Coupling Mechanism and Oligomer Redox Properties", J. Phys. Chem. A., vol. 113, (2009), pp. 13023-13028.
Crawford, Lynne A., et al., "Synthesis of Azapyrrolo[3,2,1-*jk*]Carbazoles, Azaindolo[3,2,1-*jk*]Carbazoles, and Carbazole-1-Carbonitriles by Gas-Phase Cyclization of Aryl Radicals", Synthesis 2010, No. 6, pp. 923-928, XP002623203.
Eshimbetov, A.G., et al., "Theoretical and UV Spectral Study of Isomeric 1-(Quinolinyl)-β-Carbolines Conformations", Spectrochimica Acta Part A 67, (2007), pp. 1139-1143.
Abramov, et. al., "Synthesis of six-membered O-, N-, and S- containing heterocyclic compounds condensed with phthalonitrile fragment" Chemical Abstracts, XP002623205 2005.
Held, I., et al., "The Stability of Acylpyridinium Cations and Their Relation to the Catalytic Activity of Pyridine Bases", Synthesis 2005, No. 9, pp. 1425-1430, XP00262206.
Molina, Pedro, et al., "Iminophosphorane-Mediated Synthesis of the Fascaplysin Alkaloid of Marine Origin and Nitramarine", Tetrahedron Letters, vol. 35, No. 47, (1994), pp. 8851-8854.

(Continued)

*Primary Examiner* — Duc Truong
(74) *Attorney, Agent, or Firm* — Drinker Biddle & Reath LLP

(57) ABSTRACT

The present invention relates to compounds of the formula (1), formula (2), formula (3) and formula (4) which are suitable for use in electronic devices, in particular organic electroluminescent devices.

14 Claims, No Drawings

(56) References Cited

OTHER PUBLICATIONS

International Search Report for PCT/EP2010/006414 mailed Mar. 1, 2011.

Stuckwisch et al., "Synthesis of 5,9-Dithia-6,813b-triazanapth[3,2,1-de] anthracene (1)", Journal of Heterocyclic Chemistry, vol. 2, No. 2, p. 211 (1965).
Khimiya Prirodnykh Soedineni J., No. 5, pp. 635-638 (1982).
Abramov et al., "Synthesis of substituted azines with the participation of 4-bromo-5-nitrophthalonitrile", Mendeleev Commun., vol. 12, No. 3, pp. 120-121 (2002).

NITROGEN-CONTAINING CONDENSED HETEROCYCLIC COMPOUNDS FOR OLEDS

CROSS-REFERENCE TO RELATED APPLICATIONS

This application is a national stage application (under 35 U.S.C. §371) of PCT/EP2010/006414, filed Oct. 20, 2010, which claims benefit of German Application 10 2009 053 836.4, filed Nov. 18, 2009.

The present invention relates to materials for use in electronic devices, in particular in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement, for example with respect to efficiency, operating voltage and lifetime, in OLEDs, in particular also in OLEDs which exhibit triplet emission (phosphorescence). This applies, in particular, to OLEDs which emit in the relatively short-wavelength range, for example green or blue.

The properties of phosphorescent OLEDs are not determined only by the triplet emitters employed. In particular, the other materials used, such as matrix materials, hole-blocking materials, electron-transport materials, hole-transport materials and electron- or exciton-blocking materials, are also of particular importance here. Improvements in these materials may thus also result in significant improvements in the OLED properties. There is also a need for improvement in these materials for fluorescent OLEDs.

In accordance with the prior art, use is made of, inter alia, ketones (for example in accordance with WO 04/093207 or WO 10/006,680) or phosphine oxides (for example in accordance with WO 05/003253), as matrix materials for phosphorescent emitters. However, there is still a need for improvement on use of these matrix materials as in the case of other matrix materials, in particular with respect to the efficiency and lifetime of the device.

The object of the present invention is the provision of compounds which are suitable for use in a fluorescent or fluorescent OLED, in particular a phosphorescent OLED, for example as matrix material or as hole-transport/electron-blocking material or exciton-blocking material or as electron-transport or hole-blocking material. In particular, the object of the present invention is to provide matrix materials which are also suitable for use in green- and blue-phosphorescent OLEDs.

Surprisingly, it has been found that certain compounds described in greater detail below achieve this object and result in significant improvements in the organic electroluminescent device, in particular with respect to the lifetime, efficiency and operating voltage. This also applies, in particular, to green- and blue-phosphorescent electroluminescent devices, especially on use of the compounds according to the invention as matrix material. The present invention therefore relates to these materials and to organic electroluminescent devices which comprise compounds of this type.

WO 07/031,165 discloses bridged triarylamine structures having a similar basic structure to the compounds according to the invention. However, compounds in which one or more carbon atoms of the skeleton have been replaced by nitrogen are not disclosed therein. Furthermore, these compounds are only described as emitter or as hole-transport material, but not as matrix material for phosphorescent emitters or as electron-transport material.

US 2009/0136779 discloses compounds having a similar basic structure as matrix for phosphorescent emitters. However, compounds in which one or more carbon atoms of the skeleton have been replaced by nitrogen are not disclosed therein.

However, it has been found, surprisingly, that it is precisely the replacement of one or more carbon atoms of the skeleton by nitrogen results in an improvement in the electronic properties.

The present invention therefore relates to a compound of the following formula (1), formula (2), formula (3) or formula (4):

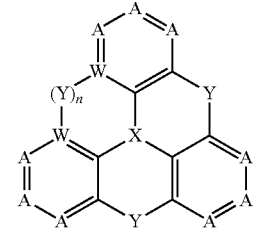

formula (1)

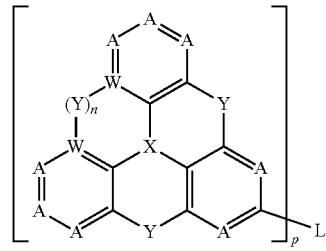

formula (2)

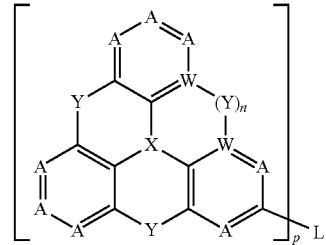

formula (3)

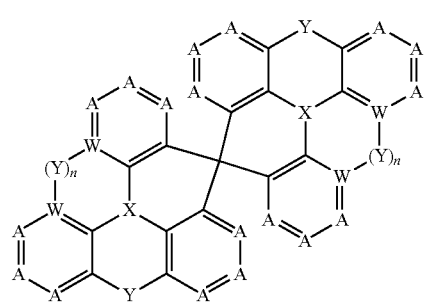

formula (4)

where the following applies to the symbols and indices used:

A is on each occurrence, identically or differently, CR or N;

W is C if a group Y is bonded to this group W, i.e. n is equal to 1, and is CR or N if no group Y is bonded to this group W, i.e. n is equal to 0;

with the proviso that at least one symbol A and/or at least one symbol W stands for N;

X is on each occurrence, identically or differently, N, P or P=O;

Y is, identically or differently on each occurrence, $C(R^1)_2$, $NR^1$, O, S, C=O, C=S, $C=NR^1$, $C=C(R^1)_2$, $Si(R^1)_2$, $BR^1$, $PR^1$, $AsR^1$, $SbR^1$, $BiR^1$, $P(=O)R^1$, $As(=O)R^1$, $Bi(=O)R^1$, SO, SeO, TeO, $SO_2$, $SeO_2$, $TeO_2$ or a combination of two of these groups, which may be identical or different, or a chemical bond, with the proviso that all three groups Y in a unit do not all simultaneously stand for a single bond;

R, $R^1$ are selected on each occurrence, identically or differently, from the group consisting of H, D, F, Cl, Br, I, CN, $NO_2$, $N(Ar)_2$, $N(R^2)_2$, C(=O)Ar, $C(=O)R^1$, $P(=O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, an aromatic or heteroaromatic ring system having 5 to 80, preferably 5 to 60, aromatic ring atoms, which may in each case be substituted by one or more radicals $R^2$, an aryloxy or heteroaryloxy group having 5 to 60 aromatic ring atoms, which may be substituted by one or more radicals $R^2$, or an aralkyl or heteroaralkyl group having 5 to 60 aromatic ring atoms, which may be substituted by one or more radicals $R^2$, where two or more adjacent substituents R or two substituents $R^1$ which are bonded in the same group Y may optionally form a mono- or polycyclic, aliphatic, aromatic or heteroaromatic ring system, which may be substituted by one or more radicals $R^2$, with one another;

$R^2$ is selected on each occurrence, identically or differently, from the group consisting of H, D, F, Cl, Br, I, CN, $NO_2$, $N(Ar)_2$, $N(R^3)_2$, C(=O)Ar, $C(=O)R^3$, $P(=O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^3$, an aryloxy or heteroaryloxy group having 5 to 60 aromatic ring atoms, which may be substituted by one or more radicals $R^3$, or an aralkyl or heteroaralkyl group having 5 to 60 aromatic ring atoms, where two or more adjacent substituents $R^2$ may optionally form a monocyclic or polycyclic, aliphatic, aromatic or heteroaromatic ring system, which may be substituted by one or more radicals $R^3$;

$R^3$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^3$ may form a mono- or polycyclic, aliphatic, aromatic or heteroaromatic ring system with one another;

Ar is on each occurrence, identically or differently, an aromatic or heteroaromatic ring system having 5-30 aromatic ring atoms, which may be substituted by one or more non-aromatic radicals $R^3$; two radicals Ar here which are bonded to the same N atom or P atom may also be bridged to one another by a single bond or a bridge selected from $N(R^3)$, $C(R^3)_2$, O or S;

L is a di-, tri-, tetra-, penta- or hexavalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms or an alkenylene or alkynylene group having 2 to 40 C atoms, each of which may be substituted by one or more radicals $R^2$, where one or more non-adjacent $CH_2$ groups may be replaced by $-R^2C=CR^2-$, $-C≡C-$, $Si(R^2)_2$, $Ge(R^2)_2$, $Sn(R^2)_2$, C=O, C=S, C=Se, $C=NR^2$, $P(=O)R^2$, $3=0$, $SO_2$, $-O-$, $-S-$ or $-CONR^2-$ and where one or more H atoms may be replaced by D, F, Cl, Br, I, CN or $NO_2$, or a di-, tri-, tetra-, penta- or hexavalent aromatic or heteroaromatic ring system having 5 to 80, preferably 5 to 40, aromatic ring atoms, which may be substituted by one or more radicals $R^2$, or $P(R^2)_{3-p}$, $P(=O)(R^2)_{3-p}$, $C(R^2)_{4-p}$, $Si(R^2)_{4-p}$, $N(Ar)_{3-p}$, or a combination of two, three, four or five of these systems; or L is a chemical bond;

n is on each occurrence, identically or differently, 0 or 1;

p is 2, 3, 4, 5 or 6, with the proviso that p is not greater than the maximum valence of L;

the following compounds are excluded from the invention:

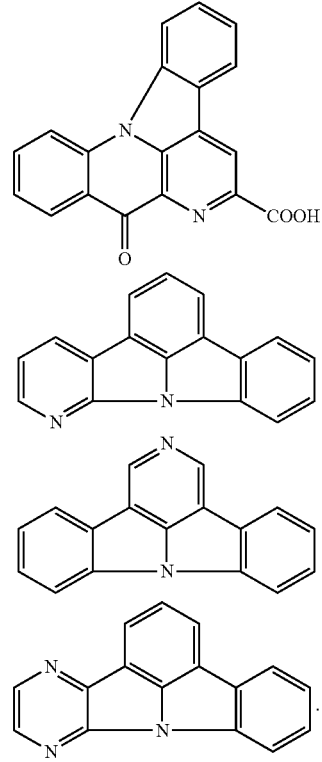

In a preferred embodiment of the invention, the compounds of the formulae (1) to (3) contain in each unit as group Y a single bond and one or two bridges Y, each having one bridging atom, or one or two bridges Y, each having two bridging atoms. The compounds of the formulae (1) to (3) particularly preferably comprise in each unit as group Y a single bond and one or two bridges Y, each having one bridging atom. In a further preferred embodiment of the invention, the compounds of the formula (4) contain in each unit as group Y a single bond.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic rings linked to one another by a single bond, such as, for example, biphenyl, are, by contrast, not referred to as an aryl or heteroaryl group, but instead as an aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hydridised C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are connected, for example, by a short alkyl group. Furthermore, aromatic rings linked to one another by a single bond, such as, for example, biphenyl, are referred to as an aromatic ring system in the sense of this invention.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclo-pentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl and octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclo-pentenylthio, hexenylthio, cyclohexenylthio, heptenylthio, cycloheptenyl-thio, octenylthio, cyclooctenylthio, ethynylthio, propynylthio, butynylthio, pentynylthio, hexynylthio, heptynylthio or octynylthio. In general, alkyl, alkenyl, alkynyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, furthermore preferably F or CN, particularly preferably CN.

An aromatic or heteroaromatic ring system having 5-80 aromatic ring atoms, which may also in each case be substituted by the above-mentioned radicals $R^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or transindenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

In a preferred embodiment of the invention, at least one group Y in each unit stands for a single bond. Preferred compounds are therefore the compounds of the formulae (5) to (10):

formula (5)

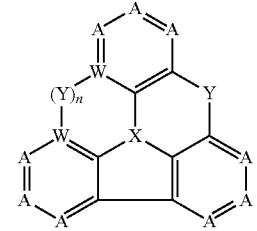

-continued

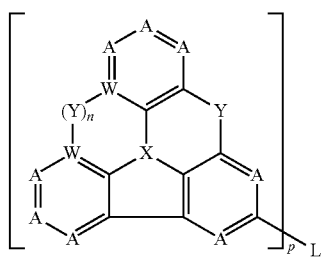
formula (6)

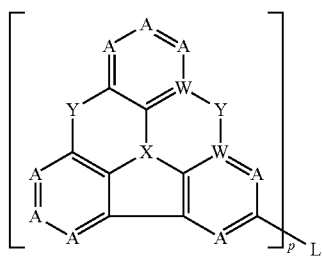
formula (7)

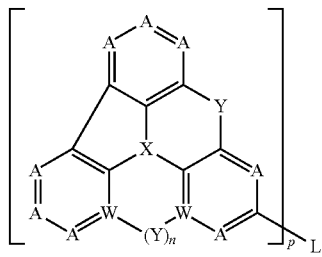
formula (8)

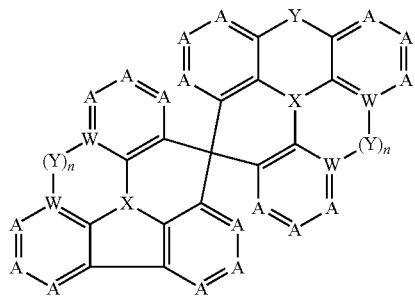
formula (9)

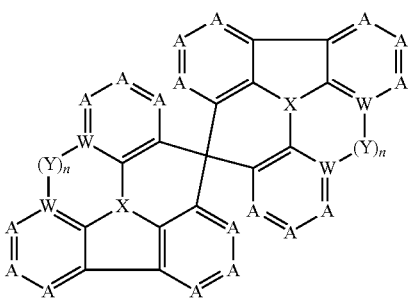
formula (10)

where the symbols and indices used have the meanings given above.

In a preferred embodiment of the invention, a total of one, two or three symbols A or W per unit stand for N and the other symbols A and W stand for CR or C. Particularly preferably, one or two symbols A or W per unit stand for N, very particularly preferably precisely one symbol A or W stands for N, and the other symbols A and W stand for CR or C.

"Unit" here is taken to mean the structure of the formula (1) or, in the formulae (2) and (3), in each case each of the groups which is bonded to L, or, in the formula (4), in each case each of the groups which is bonded to the spiro carbon atom. The corresponding meanings apply to the formulae (5) to (10).

In a further preferred embodiment of the invention, at least one symbol A stands for N and the symbols W stand for CR or C, irrespective of whether a group Y is bonded to W or not, i.e. whether the index N is equal to 0 or 1.

The symbols W particularly preferably stand for CH or C, irrespective of whether a group Y is bonded to W or not.

Preferred embodiments of the formula (1) are therefore the compounds of the following formulae (11) to (31):

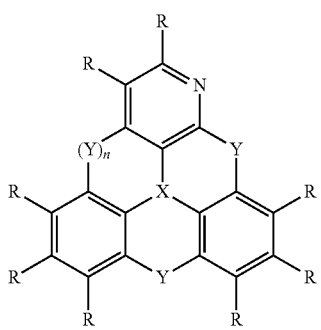
Formel (11)

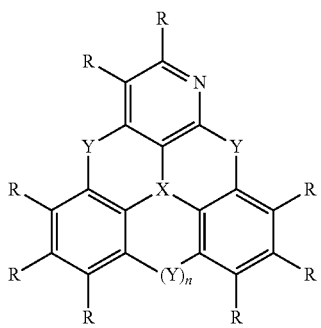
Formel (12)

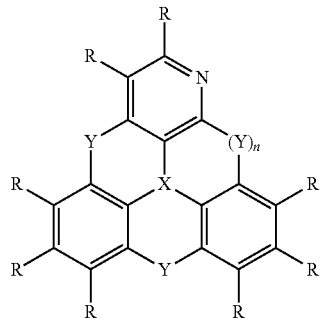
Formel(13)

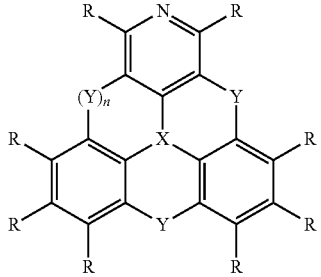
Formel (14)

Formel (15)
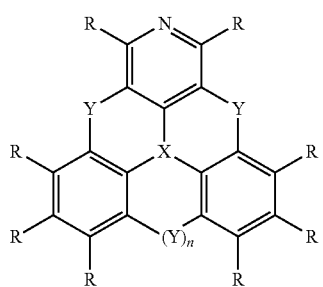
Formel (16)
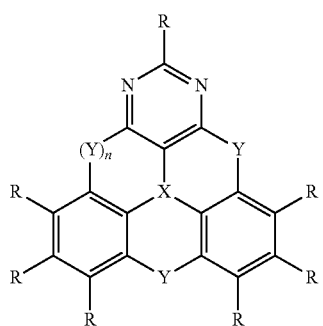
Formel (17)
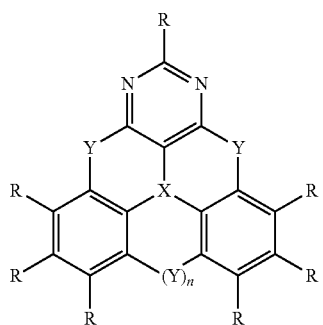
Formel (18)
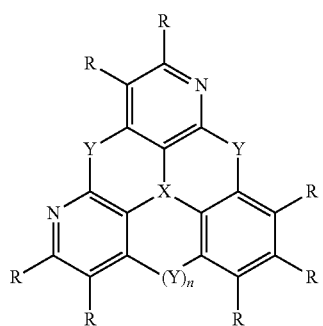
Formel (19)
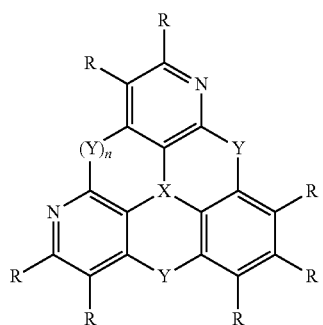
formula (20)
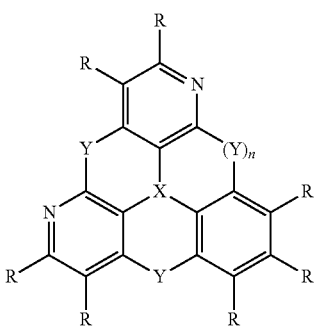
formula (21)
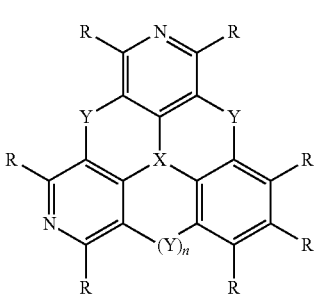
formula (22)
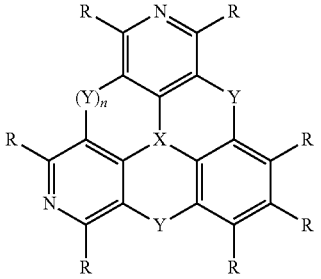
formula (23)
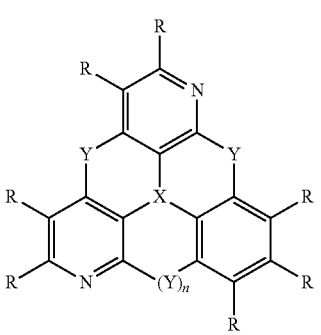
formula (24)
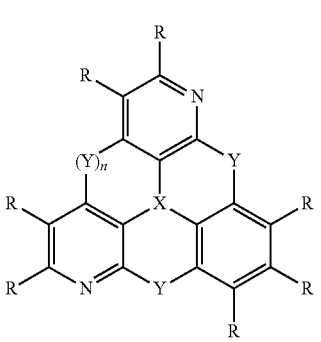

-continued formula (25)
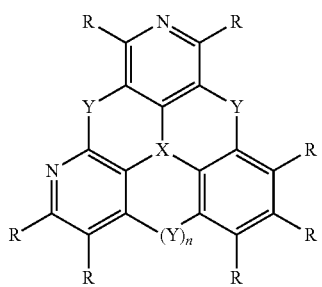

formula (26)
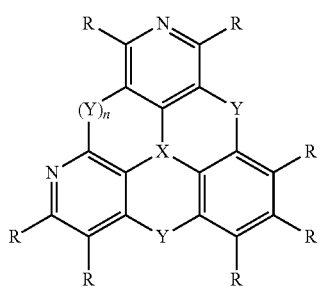

formula (27)
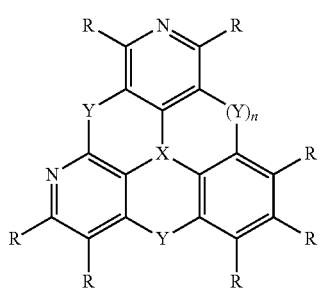

formula (28)
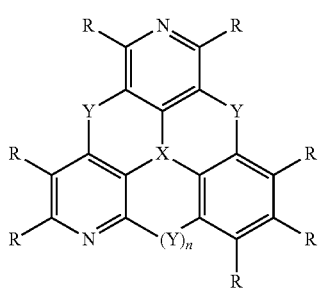

formula (29)
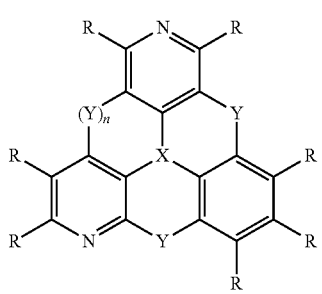

-continued formula (30)
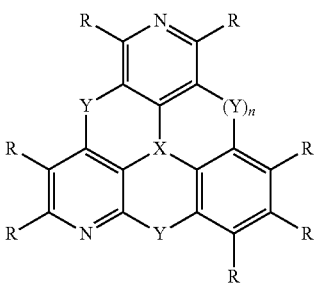

formula (31)
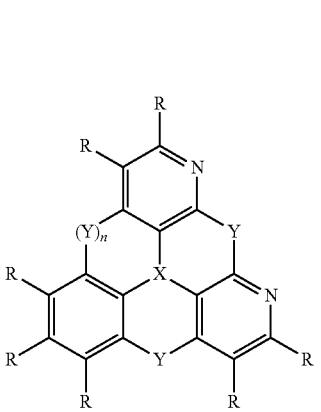

where the symbols and indices used have the meanings given above.

Preferred embodiments of the formulae (2) and (3) are correspondingly compounds of the above-mentioned formulae (11) to (31) in which in each case two or more of these units, which may be identical or different, but are preferably identical, are bridged to one another by a divalent or polyvalent group L, which is in each case bonded instead of a substituent R in the para-position to X.

Preferred embodiments of the formula (4) are correspondingly compounds of the above-mentioned formulae (11) to (31) in which in each case two of these units, which may be identical or different, but are preferably identical, are bridged to one another by a spiro carbon atom, which is present instead of a group Y.

In the compounds of the formulae (11) to (31), at least one group Y particularly preferably stands for a single bond. Particular preference is therefore given to the compounds of the following formulae (11a) to (31b):

formula (11a)
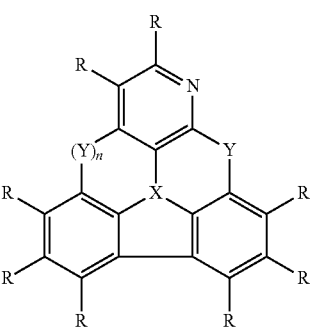

formula (11b)
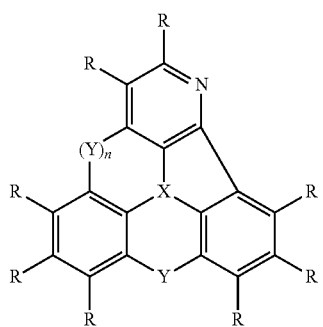
formula (12a)
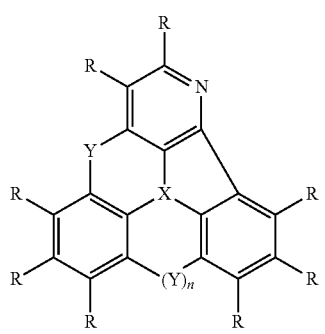
formula (12b)
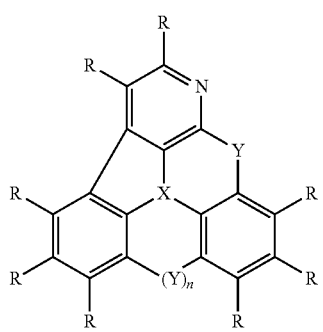
formula (13a)
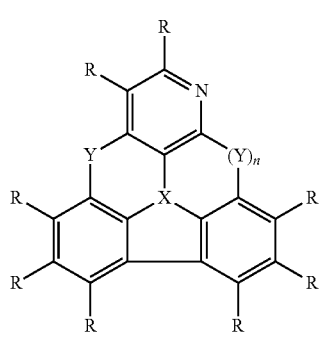
formula (13b)
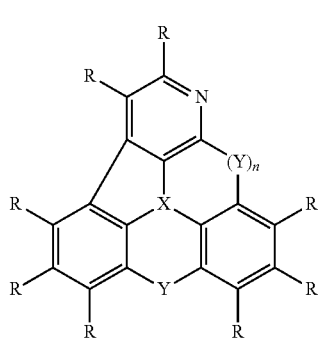
formula (14a)
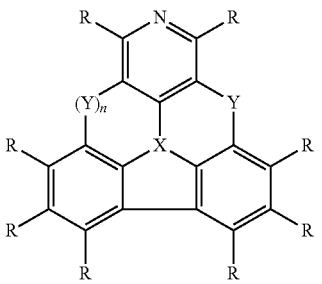
formula (14b)
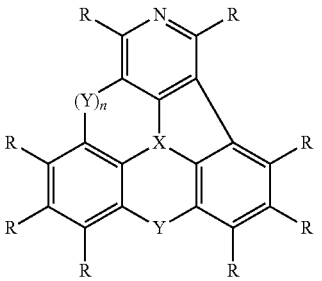
formula (15a)
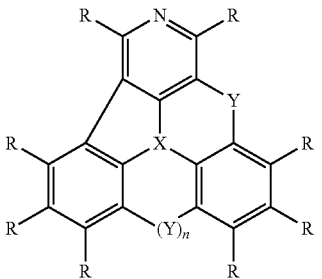
formula (16a)
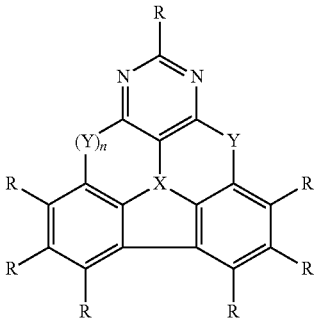
formula (16b)
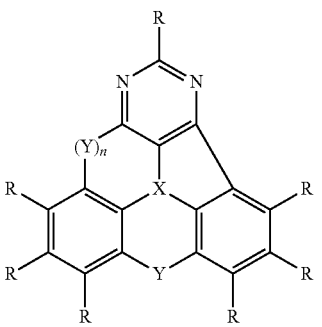

formula (17a)
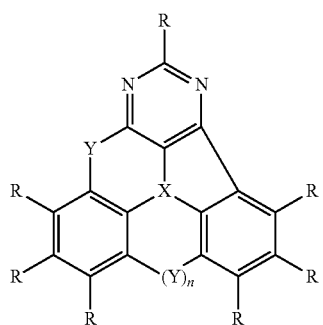
formula (18a)
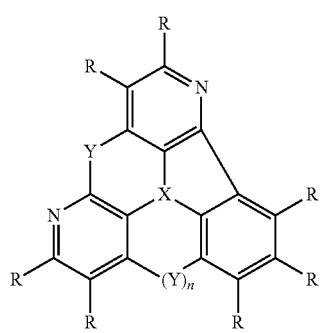
formula (18b)
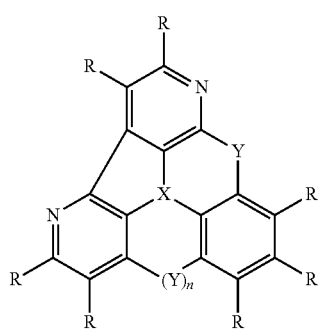
formula (19a)
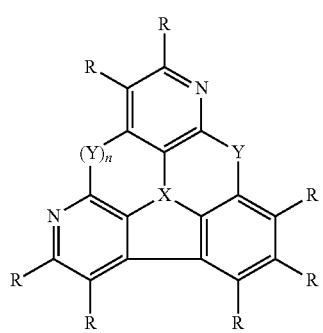
formula (19b)
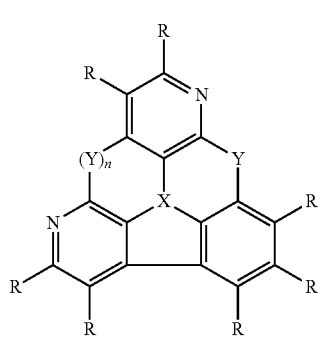
formula (20a)
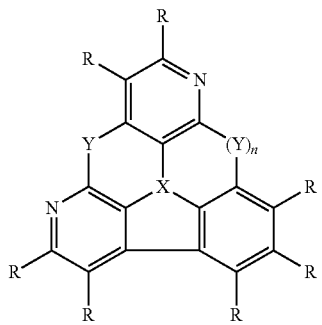
formula (20b)
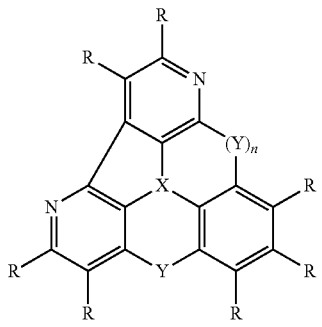
formula (21a)
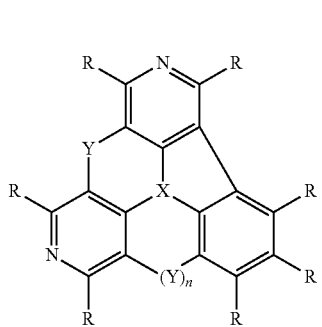
formula (21b)
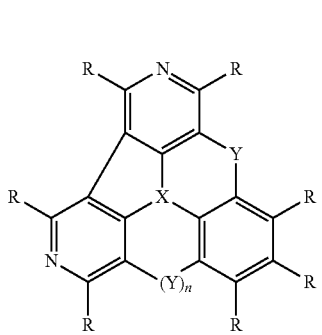
formula (22a)
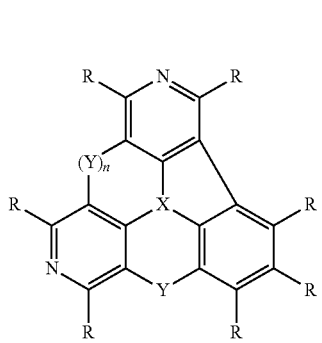

formula (23a)
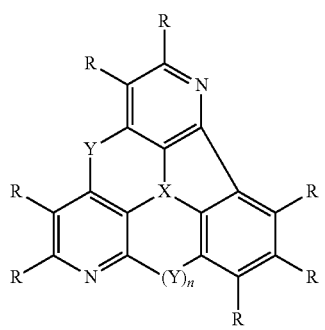
formula (23b)
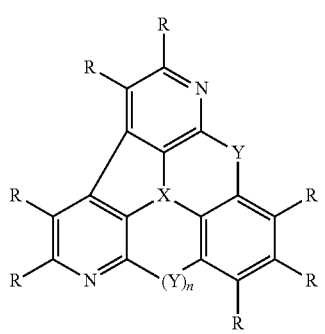
formula (24a)
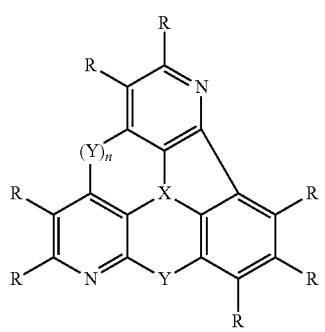
formula (25a)
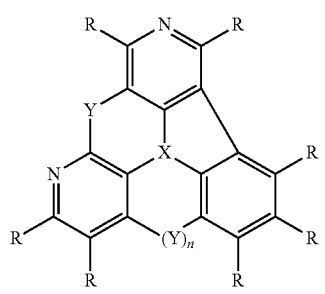
formula (25b)
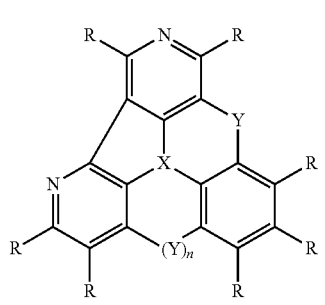
formula (26a)
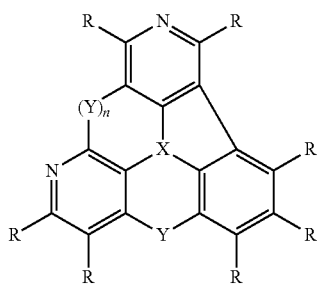
formula (26b)
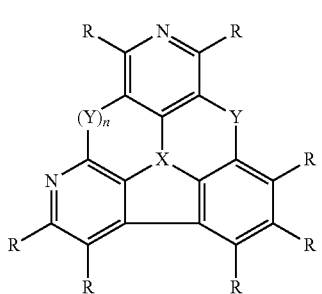
formula (27a)
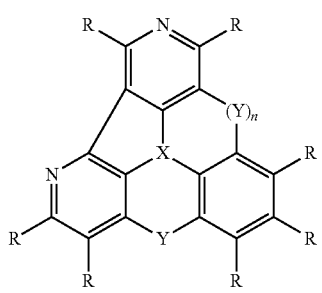
formula (27a)
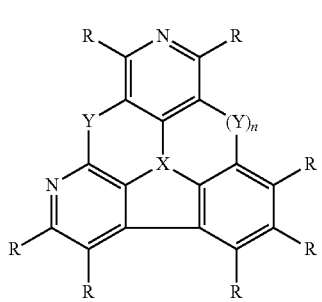
formula (28a)
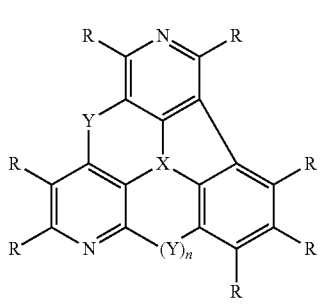

formula (28b)
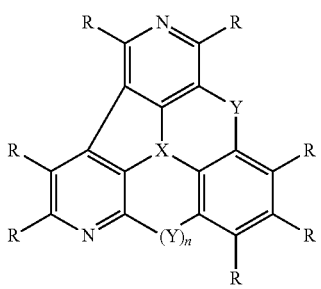

formula (29a)
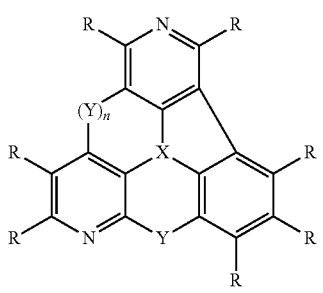

formula (29b)
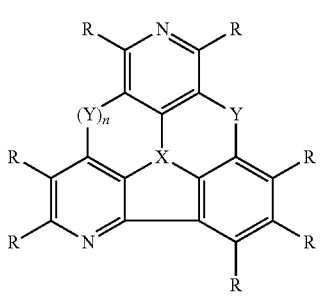

formula (30a)
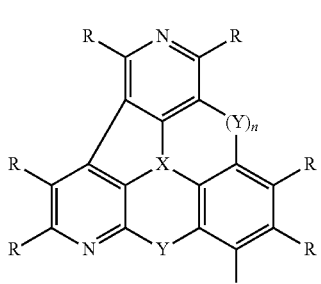

formula (30b)
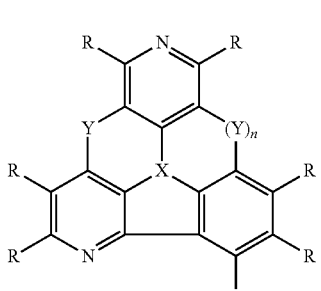

formula (31a)
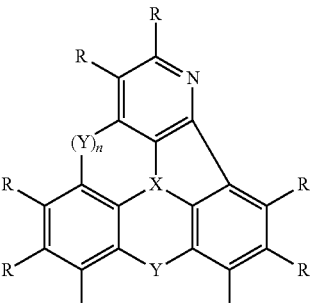

formula (31b)
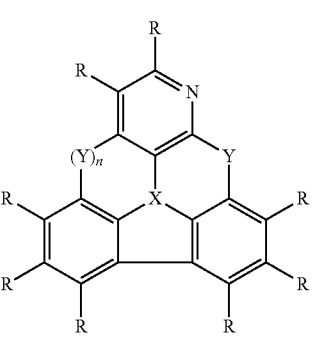

where the symbols and indices used have the same meanings as indicated above.

Particularly preferred embodiments of the formulae (2) and (3) are correspondingly compounds of the above-mentioned formulae (11a) to (31b) in which in each case two or more of these units, which may be identical or different, but are preferably identical, are bridged to one another by a divalent or polyvalent group L, which is in each case bonded instead of a substituent R in the para-position to X.

Particularly preferred embodiments of the formula (4) are correspondingly compounds of the above-mentioned formulae (11a) to (31b) in which in each case two or these units, which may be identical or different, but are preferably identical, are bridged to one another by a spiro carbon atom, which is present instead of a group Y.

In a preferred embodiment of the compounds of the formulae (1) to (31) and (11a) to (31b), X stands on each occurrence, identically or differently, for N or P. X particularly preferably stands for N.

In a further preferred embodiment of the compounds of the formulae (1) to (31) and (11a) to (31b), Y stands on each occurrence, identically or differently, for $C(R^1)_2$, $NR^1$, O, S, C=O or a chemical bond. In compounds of the formulae (1), (2), (3) and (4), one group Y preferably stands for a chemical bond and the other groups Y preferably stand on each occurrence, identically or differently, for $C(R^1)_2$, $NR^1$, O, S, C=O or a chemical bond. In compounds of the formulae (5) to (10), the groups Y preferably stand on each occurrence, identically or differently, for $C(R^1)_2$, $NR^1$, O, S, C=O or a chemical bond. In compounds of the formulae (1), (2) and (3), all three groups Y in a unit do not simultaneously stand for a chemical bond, and in compounds of the formulae (5) to (8), both groups Y do not simultaneously stand for a chemical bond. The groups Y which are not equal to a chemical bond particularly preferably stand, identically or differently on each occurrence, for $C(R^1)_2$, $NR^1$, O or S, very particularly preferably for $C(R^1)_2$ or $NR^1$, in particular for $C(R^1)_2$.

If the compounds of the formulae (11) to (31) are substituted by radicals R other than hydrogen or deuterium, these radicals R are then preferably in each case bonded in the para-position to the group X. Preference is therefore given to the compounds of the following formulae (11c) to (31c):
formula (11c)
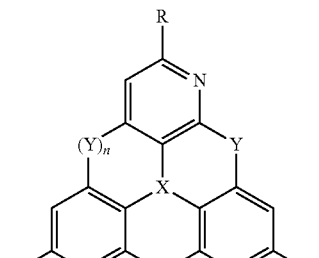
formula (12c)
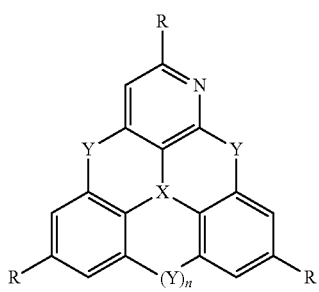
formula (13c)
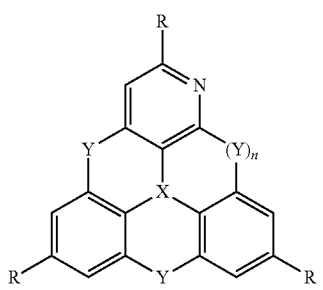
formula (14c)
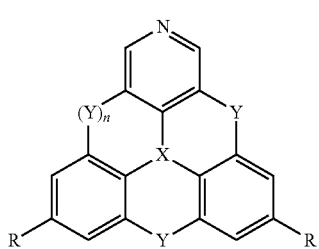
formula (15c)
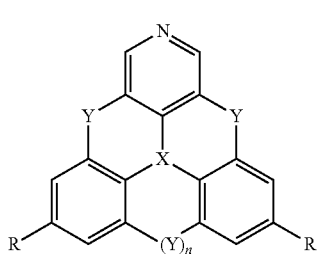
-continued
formula (16c)
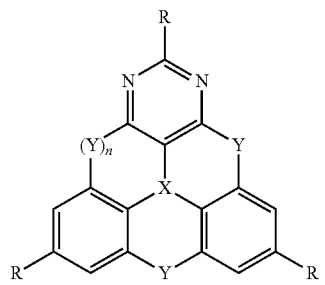
formula (17c)
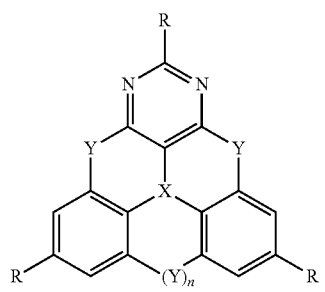
formula (18c)
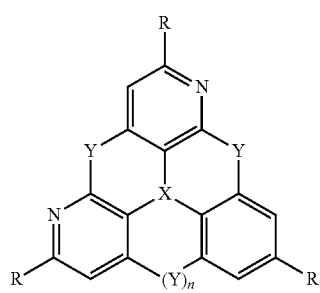
formula (19c)
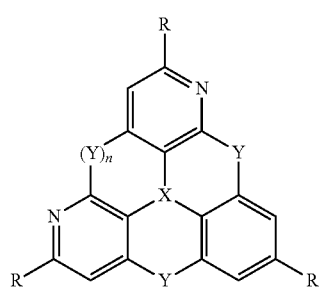
formula (20c)
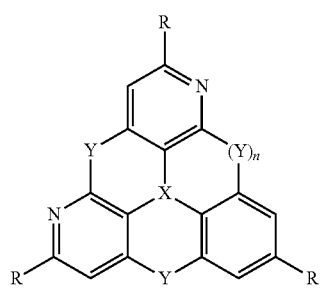

formula (21c)
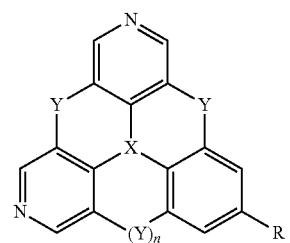

formula (22c)
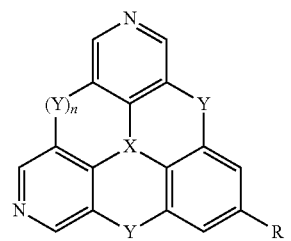

formula (23c)
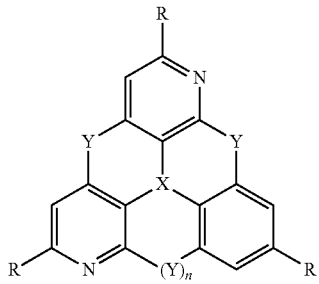

formula (24c)
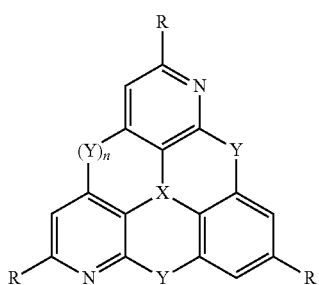

formula (25c)
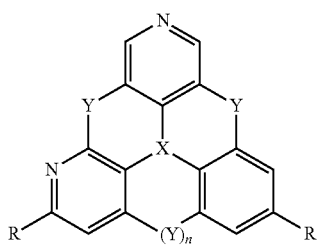

formula (26c)
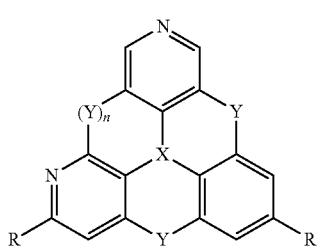

formula (27c)
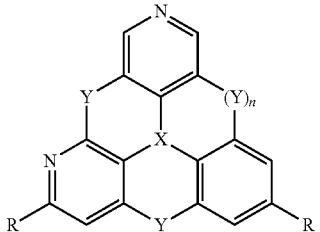

formula (28c)
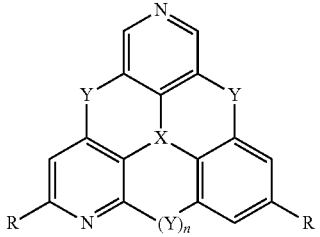

formula (29c)
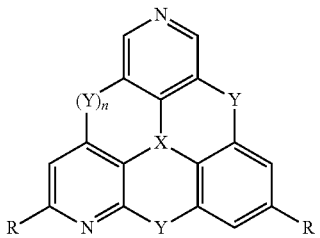

formula (30c)
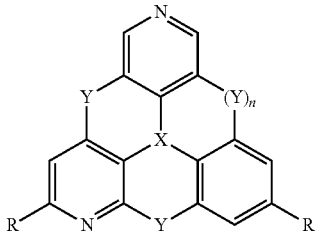

formula (31c)
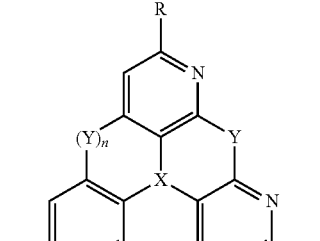

where the symbols and indices used have the meanings given above.

If the compounds of the formulae (11a) to (31b) are substituted by radicals R other than hydrogen or deuterium, these radicals R are then preferably each bonded in the para-position to the group X. Particular preference is therefore given to the compounds of the following formulae (11d) to (31e):

formula (11d)
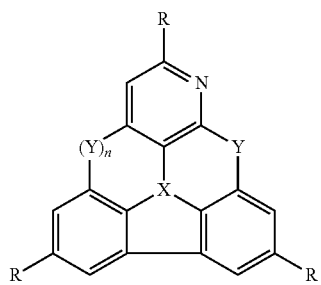
formula (11e)
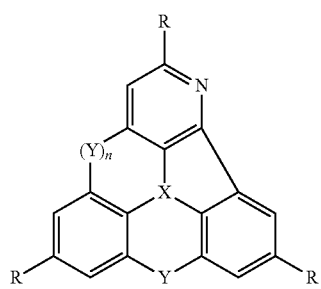
formula (12d)
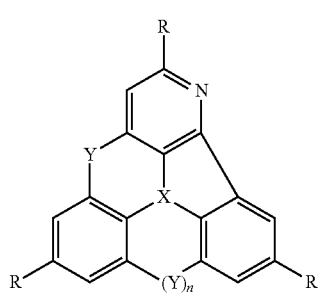
formula (12e)
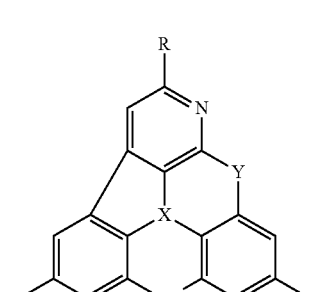
formula (13d)
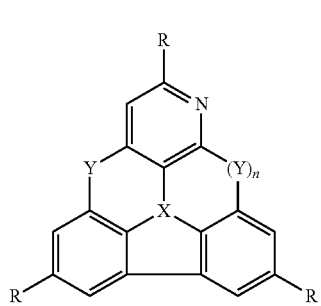
formula (13e)
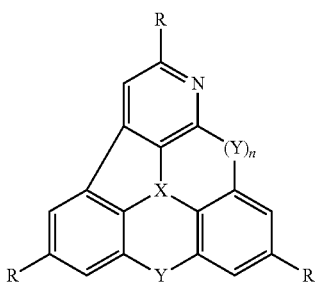
formula (14d)
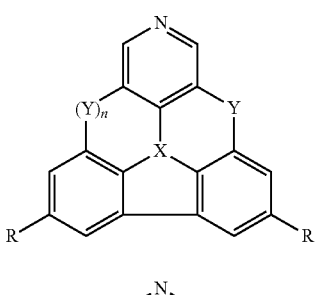
formula (14e)
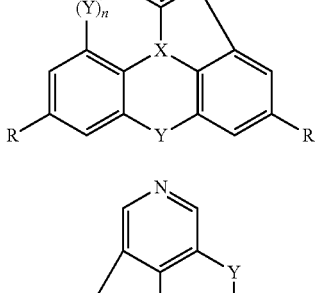
formula (15d)
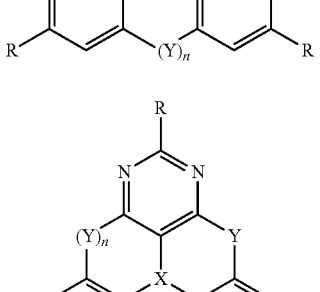
formula (16e)
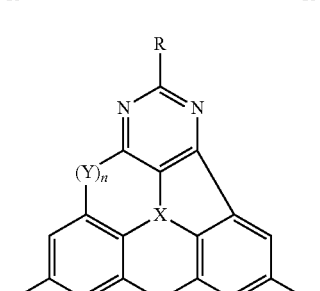
formula (16d)

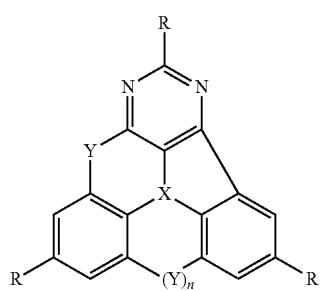
formula (17e)
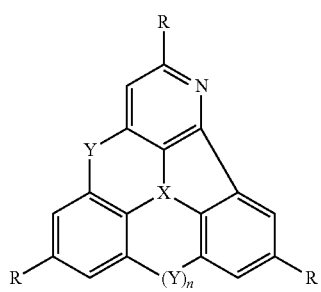
formula (18d)
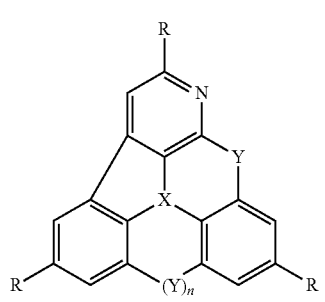
formula (18e)
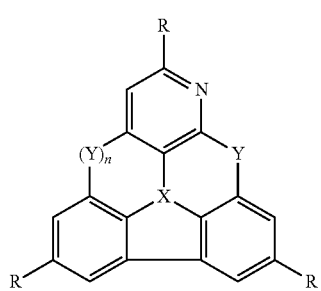
formula (19d)
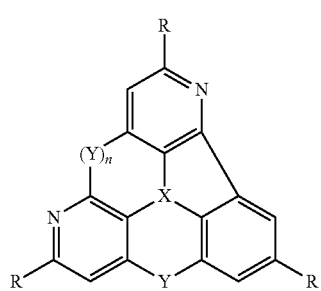
formula (19e)
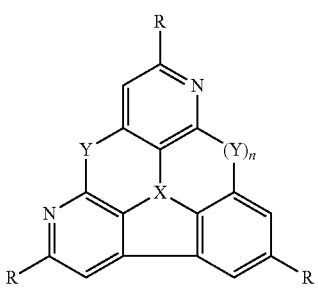
formula (20d)
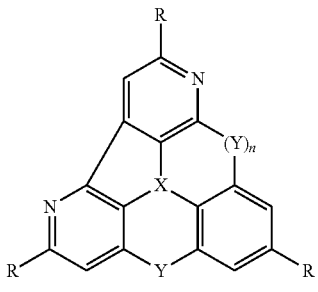
formula (20e)
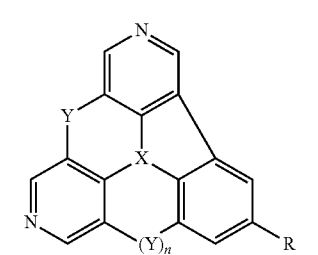
formula (21d)
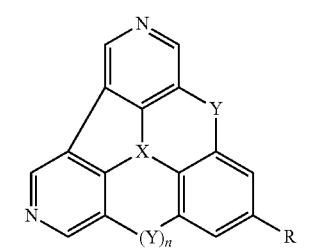
formula (21e)
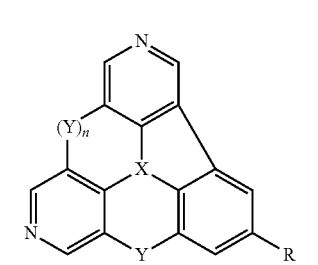
formula (22d)
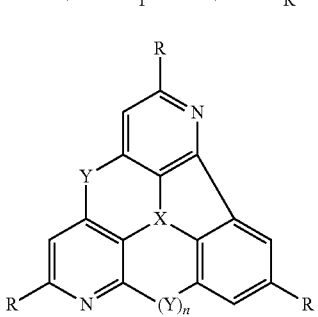
formula (23d)

formula (23e)
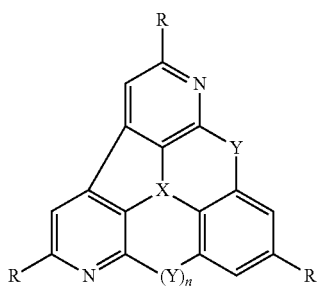
formula (24d)
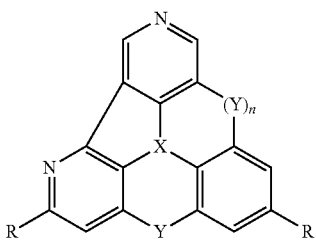
formula (27d)
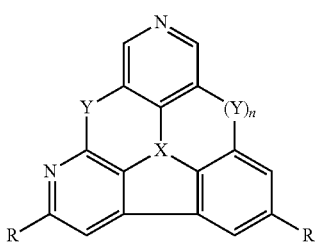
formula (27e)
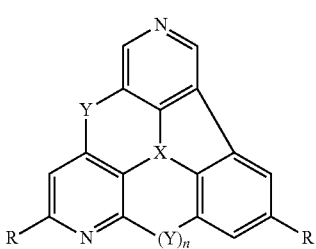
formula (28d)
formula (25d)
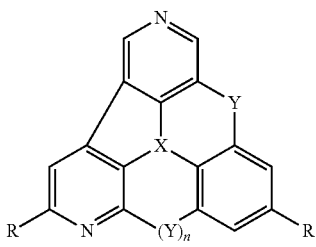
formula (25e)
formula (28e)
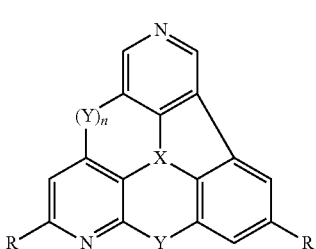
formula (26d)
formula (29d)
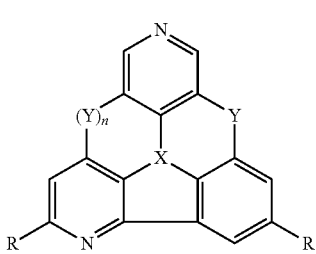
formula (26e)
formula (29e)

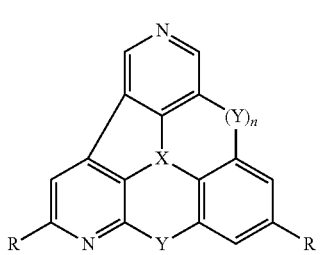

formula (30d)

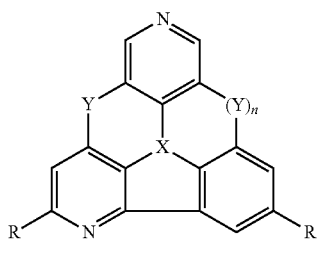

formula (30e)

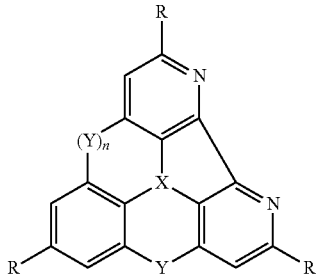

formula (31d)

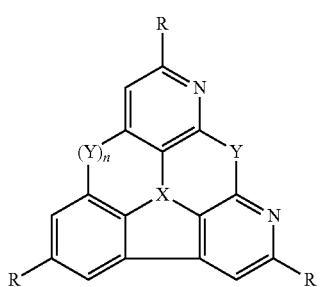

formula (31e)

where the symbols and indices used have the meanings given above.

In the structures of the formulae (11c) to (31c) and (11d) to (31e), the positions drawn as unsubstituted may each carry a deuterium instead of the hydrogen.

Particularly preferred embodiments of the formulae (2) and (3) are correspondingly compounds of the above-mentioned formulae (11c) to (31c) and (11d) to (31e) in which in each case two or more of these units are bridged to one another by a divalent or polyvalent group L, which is in each case bonded instead of a substituent R.

Particularly preferred embodiments of the formula (4) are correspondingly compounds of the above-mentioned formulae (11c) to (31c) and (11d) to (31e) in which in each case two of these units, which may be identical or different, but are preferably identical, are bridged to one another by a spiro carbon atom, which is present instead of the group Y.

Possible substituents R in the compounds according to the invention are various groups, depending on the use of the compounds. In a preferred embodiment of the compounds of the formulae (1) to (31) and (11a) to (31e), R is selected on each occurrence, identically or differently, from the group consisting of H, D, F, CN, $N(Ar)_2$, C(=O)Ar, $P(=O)(Ar)_2$, a straight-chain alkyl group having 1 to 10 C atoms or a branched or cyclic alkyl group having 3 to 10 C atoms or an alkenyl group having 2 to 10 C atoms, each of which may be substituted by one or more radicals $R^2$, where one or more non-adjacent $CH_2$ groups may be replaced by O or S and where one or more H atoms may be replaced by D or F, an aromatic or heteroaromatic ring system having 6 to 30 aromatic ring atoms, which may in each case be substituted by one or more radicals $R^2$, where two or more adjacent substituents R may optionally form a monocyclic or polycyclic, aliphatic, aromatic or heteroaromatic ring system, which may be substituted by one or more radicals $R^2$. In a particularly preferred embodiment of the compounds of the formulae (1) to (31) and (11a) to (31e), R is selected on each occurrence, identically or differently, from the group consisting of H, D, $N(Ar)_2$, a straight-chain alkyl group having 1 to 4 C atoms or a branched alkyl group having 3 or 4 C atoms, each of which may be substituted by one or more radicals $R^1$, where one or more H atoms may be replaced by D, or an aromatic or heteroaromatic ring system having 6 to 18 aromatic ring atoms, which may in each case be substituted by one or more radicals $R^2$.

Substituents $R^1$ which are bonded in Y are preferably selected from the group consisting of alkyl groups having 1 to 10 C atoms or aromatic or heteroaromatic ring systems having 5 to 20 aromatic ring atoms, which may in each case be substituted by one or more radicals $R^2$. Two radicals $R^1$ here which are bonded in the same group Y may also form a ring system with one another and thus form a spiro system.

For compounds which are processed by vacuum evaporation, the alkyl groups in the radicals R or $R^1$ preferably have not more than four C atoms, particularly preferably not more than one C atom. For compounds which are processed from solution, particularly suitable compounds are also those which are substituted by alkyl groups having up to 10 C atoms or which are substituted by oligoarylene groups, for example ortho-, meta-, para- or branched terphenyl or quaterphenyl groups or ortho-, meta- or para-biphenyl groups.

In a preferred embodiment of the compounds of the formulae (1) to (31) and (11a) to (31e), the substituents $R^2$ are selected on each occurrence, identically or differently, from the group consisting of H, D, F, CN, $N(Ar)_2$, C(=O)Ar, $P(=O)(Ar)_2$, a straight-chain alkyl group having 1 to 10 C atoms or a branched or cyclic alkyl group having 3 to 10 C atoms or an alkenyl group having 2 to 10 C atoms, where one or more H atoms may be replaced by D or F, an aromatic or heteroaromatic ring system having 6 to 30 aromatic ring atoms, which may in each case be substituted by one or more radicals $R^3$. In a particularly preferred embodiment of the compounds of the formulae (1) to (31) and (11a) to (31e), $R^2$ is selected on each occurrence, identically or differently, from the group consisting of H, D, a straight-chain alkyl group having 1 to 4 C atoms or a branched alkyl group having 3 or 4 C atoms or an aromatic or heteroaromatic ring system having 6 to 18 aromatic ring atoms.

In a further preferred embodiment of the invention, L is a divalent or polyvalent straight-chain alkylene or alkylidene group having 1 to 10 C atoms or a branched or cyclic alkylene or alkylidene group having 3 to 10 C atoms, which may be substituted by in each case one or more radicals $R^2$, where one or more H atoms may be replaced by D or F, or an at least divalent aromatic or heteroaromatic ring system having 5 to 24 aromatic ring atoms, which may be substituted by one or more radicals $R^2$, or L is a chemical bond.

If the compound according to the invention is employed as matrix material for a phosphorescent emitter, as electron-transport material or as hole-blocking material, at least one substituent R, $R^1$ and/or $R^2$, preferably R, is preferably an electron-deficient group, in particular selected from structures of the following formulae (32) to (35):

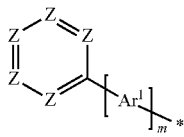

formula (32)

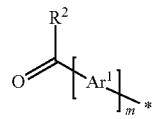

formula (33)

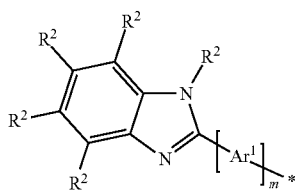

formula (34)

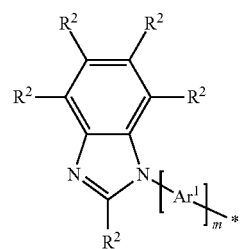

formula (35)

and/or at least one group L preferably stands for a group of the following formulae (36) to (38):

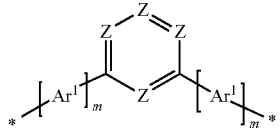

formula (36)

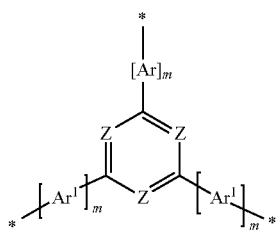

formula (37)

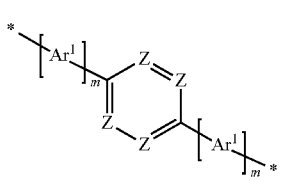

formula (38)

where $R^2$ has the meaning given above, * indicates the position of the bonding of the group of the formulae (32) to (38), and furthermore:

Z is on each occurrence, identically or differently, $CR^2$ or N, with the proviso that one group Z, two groups Z or three groups Z stand for N;

$Ar^1$ is, identically or differently on each occurrence, a divalent aryl or heteroaryl group having 5 to 16 C atoms, which may be substituted by one or more radicals $R^2$;

m is on each occurrence, identically or differently, 0, 1, 2 or 3.

In a particularly preferred embodiment of the invention, at least one substituent R stands for a group of the above-mentioned formula (32) and/or at least the group L stands for a group of the above-mentioned formulae (36) to (38), where in each case two or three symbols Z stand for N and the other symbols Z stand for $CR^2$. Particularly preferred groups R are therefore the groups of the following formulae (39) to (45), and particularly preferred groups L are the groups of the following formulae (46) to (53):

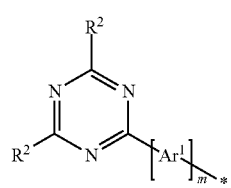

formula (39)

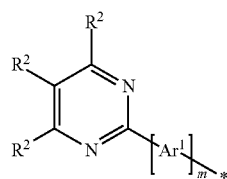

formula (40)

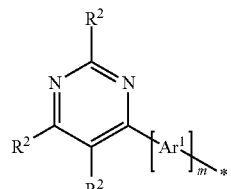

formula (41)

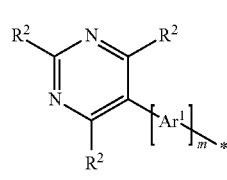

formula (42)

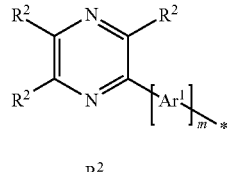

formula (43)

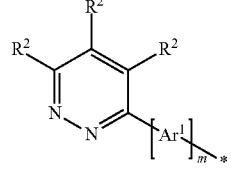

formula (44)

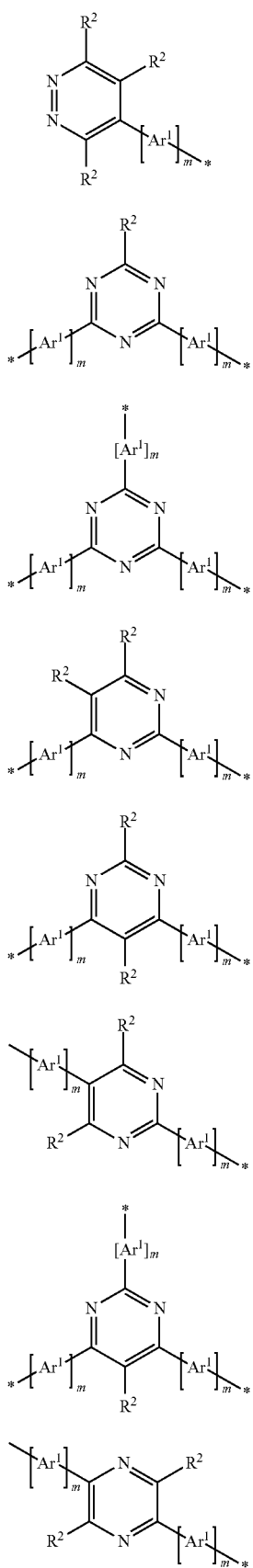

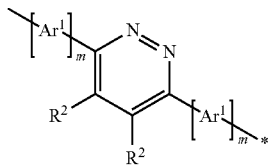

where the symbols and indices used have the meanings given above.

If R stands for a group of the formula (39), $R^2$ in this group then preferably stands for an aromatic or heteroaromatic ring system having 5 to 24 aromatic ring atoms, which may be substituted by one or more radicals $R^3$, in particular for phenyl, ortho-, meta- or para-biphenyl, ortho-, meta-, para- or branched terphenyl or ortho-, meta-, para- or branched quaterphenyl.

If R stands for a group of the formulae (40) to (53), $R^2$ in these groups then preferably stands, identically or differently on each occurrence, for H, D or an aromatic or heteroaromatic ring system having 5 to 24 aromatic ring atoms, which may be substituted by one or more radicals $R^3$, in particular for phenyl, ortho-, meta- or para-biphenyl, ortho-, meta-, para- or branched terphenyl or ortho-, meta-, para- or branched quaterphenyl.

If the compound according to the invention is employed as matrix material for a phosphorescent emitter, as hole-transport material or as electron- or exciton-blocking material, at least one substituent R or $R^1$, preferably R, is preferably selected from the group consisting of —$NAr_2$, carbazole derivatives, indenocarbazole derivatives, indolocarbazole derivatives, azacarbazole derivatives, indole derivatives, furan derivatives, benzofuran derivatives, dibenzofuran derivatives, thiophene derivatives, benzothiophene derivatives or dibenzothiophene derivatives, each of which may be substituted by one or more radicals $R^2$. These groups are preferably selected from the groups of the following formulae (54) to (67):

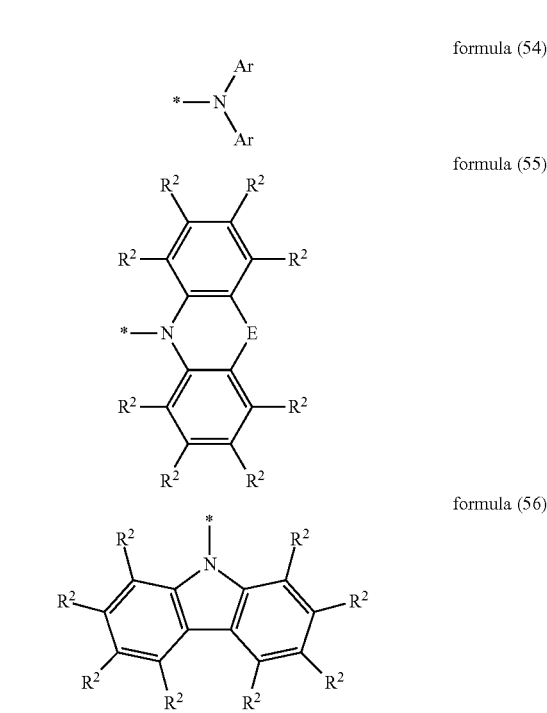

formula (57)
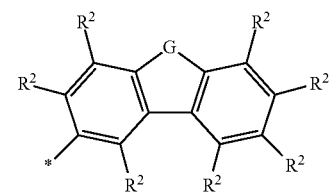

formula (58)
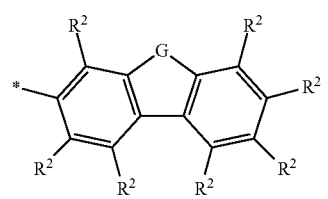

formula (59)
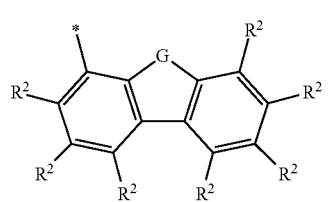

formula (60)
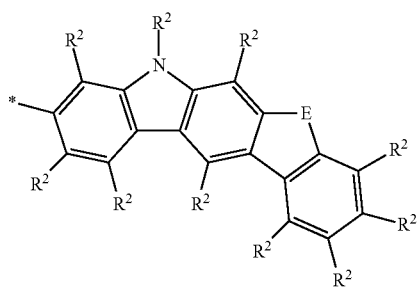

formula (61)
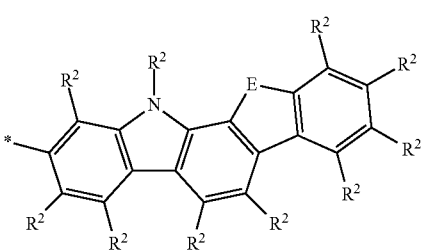

formula (62)
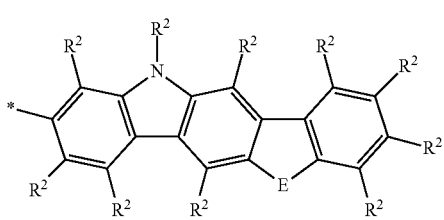

formula (63)
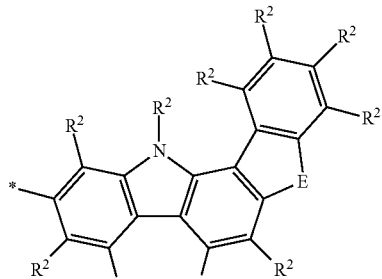

formula (64)
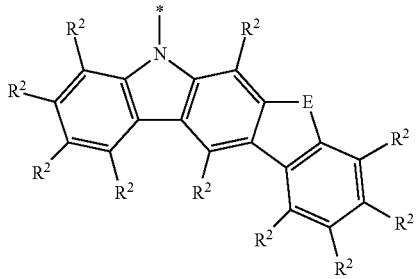

formula (65)
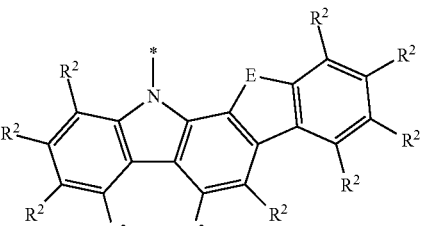

formula (66)
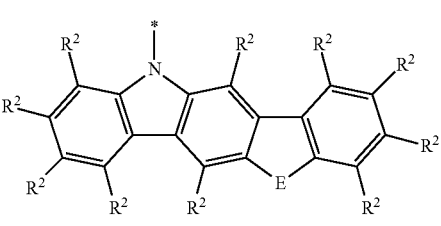

formula (67)
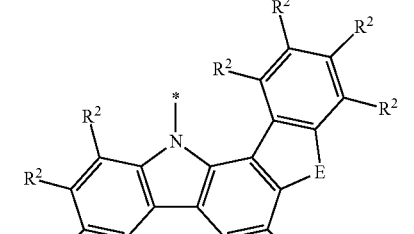

where the symbols used have the meanings given above, and furthermore:

E is selected from the group consisting of $C(R^2)_2$, $NR^2$, O or S;

G is selected from the group consisting of $NR^2$, O or S.

In a further preferred embodiment of the invention, the symbols R in the compounds according to the invention which do not stand for a group of the above-mentioned formulae (32) to (67) stand for H or D.

Preference is furthermore also given to compounds which simultaneously have both electron-transporting substituents R or $R^1$ which are selected from the above-mentioned formulae (32) to (53) and also hole-transporting substituents R or $R^1$ which are selected from the above-mentioned formulae (54) to (67).

In a further preferred embodiment, the index n is equal to 0 and W is, identically or differently on each occurrence, CR, in particular CH.

In a further preferred embodiment of the invention, the index p=2 or 3, particularly preferably 2.

In a further preferred embodiment, one or two groups R or $R^1$, preferably R, stand for a group of the above-mentioned formulae (32) to (67), particularly preferably precisely one group R, and the other groups R stand for H or D.

In a particularly preferred embodiment of the invention, the preferences indicated above arise simultaneously. Particularly preferred embodiments are thus compounds of the above-mentioned formulae (1) to (31) and (11a) to (31e) in which the preferences indicated above apply simultaneously, i.e. in which:

X is on each occurrence, identically or differently, N or P;
Y is on each occurrence, identically or differently, $C(R^1)_2$, $NR^1$, O, S, C=O or a chemical bond; in compounds of the formulae (1), (2), (3) and (4), one group Y preferably stands for a chemical bond and the other groups Y preferably stand on each occurrence, identically or differently, for $C(R^1)_2$, $NR^1$, O, S, C=O or a chemical bond, and in compounds of the formulae (5) to (10), the groups Y preferably stand on each occurrence, identically or differently, for $C(R^1)_2$, $NR^1$, O, S, C=O or a chemical bond; the groups Y which are not equal to a chemical bond particularly preferably stand, identically or differently on each occurrence, for $C(R^1)_2$, $NR^1$, O or S;
R is selected on each occurrence, identically or differently, from the group consisting of H, D, F, CN, $N(Ar)_2$, C(=O)Ar, $P(=O)(Ar)_2$, a straight-chain alkyl group having 1 to 10 C atoms or a branched or cyclic alkyl group having 3 to 10 C atoms or an alkenyl group having 2 to 10 C atoms, each of which may be substituted by one or more radicals $R^2$, where one or more non-adjacent $CH_2$ groups may be replaced by O or S and where one or more H atoms may be replaced by D or F, an aromatic or heteroaromatic ring system having 6 to 30 aromatic ring atoms, which may in each case be substituted by one or more radicals $R^2$, where two or more adjacent substituents R may optionally form a monocyclic or polycyclic, aliphatic, aromatic or heteroaromatic ring system, which may be substituted by one or more radicals $R^2$;
$R^1$ is selected from the group consisting of alkyl groups having 1 to 10 C atoms or aromatic or heteroaromatic ring systems having 5 to 20 aromatic ring atoms, each of which may be substituted by one or more radicals $R^2$, where, in addition, two radicals $R^1$ which are bonded in the same group Y may form a ring system with one another and may thus form a spiro system;
L is a divalent or polyvalent straight-chain alkylene or alkylidene group having 1 to 10 C atoms or a branched or cyclic alkylene or alkylidene group having 3 to 10 C atoms, which may be substituted by in each case one or more radicals $R^2$, where one or more H atoms may be replaced by D or F, or an at least divalent aromatic or heteroaromatic ring system having 5 to 24 aromatic ring atoms, which may be substituted by one or more radicals $R^2$; or L is a chemical bond; or L is a group of one of the above-mentioned formulae (36) to (38) or (46) to (53);
n is on each occurrence, identically or differently, 0 or 1;
p is 2 or 3.

The other symbols and indices used have the meanings given above.

In a very particularly preferred embodiment of the invention, the following applies to the compounds of the above-mentioned formulae (1) to (31) and (11a) to (31e):

X is on each occurrence N;
Y is on each occurrence, identically or differently, $C(R^1)_2$, $NR^1$ or a chemical bond; in compounds of the formulae (1), (2), (3) and (4), one group Y preferably stands for a chemical bond and the other groups Y preferably stand on each occurrence, identically or differently, for $C(R^1)_2$, $NR^1$ or a chemical bond, and in compounds of the formulae (5) to (10), the groups Y preferably stand on each occurrence, identically or differently, for $C(R^1)_2$, $NR^1$ or a chemical bond;
R is selected on each occurrence, identically or differently, from the group consisting of H, D, $N(Ar)_2$, a straight-chain alkyl group having 1 to 4 C atoms or a branched alkyl group having 3 or 4 C atoms, each of which may be substituted by one or more radicals $R^2$, where one or more H atoms may be replaced by D, an aromatic or heteroaromatic ring system having 6 to 30 aromatic ring atoms, which may in each case be substituted by one or more radicals $R^2$; at least one group R is particularly preferably selected from the groups of the formulae (32) to (67);
$R^1$ is selected from the group consisting of alkyl groups having 1 to 5 C atoms or aromatic or heteroaromatic ring systems having 5 to 18 aromatic ring atoms, each of which may be substituted by one or more radicals $R^2$, where, in addition, two radicals $R^1$ which are bonded in the same group Y may form a ring system with one anther and may thus form a spiro system;
L is a divalent or polyvalent straight-chain alkylene or alkylidene group having 1 to 4 C atoms or a branched or cyclic alkylene or alkylidene group having 3 or 4 C atoms, which may be substituted by in each case one or more radicals $R^2$, where one or more H atoms may be replaced by D or F, or an at least divalent aromatic or heteroaromatic ring system having 5 to 18 aromatic ring atoms, which may be substituted by one or more radicals $R^2$; or L is a chemical bond; or L is a group of one of the above-mentioned formulae (36) to (38) or (46) to (53);
n is 0;
p is 2.

The other symbols and indices used have the meanings given above.

Very particularly preferred embodiments of the formulae (2) and (3) are correspondingly compounds of the above-mentioned formulae (11a) to (31e) in which in each case two or more of these units are bridged to one another by a divalent group L, which is in each case bonded instead of the substituent R in the para-position to X, where furthermore the above-mentioned preferences for X, Y, R, $R^1$, L, n and p apply.

Very particularly preferred embodiments of the formula (4) are correspondingly compounds of the above-mentioned formulae (11a) to (31e) in which in each case two of these units are bridged to one another by a spiro carbon atom, which is present instead of a group Y, where furthermore the above-mentioned preferences for X, Y, R, $R^1$ and n apply.

Preference is furthermore given to the compounds of the formulae (1) to (31) and (11a) to (31e) in which two groups Y stand for single bonds.

Examples of preferred compounds in accordance with the embodiments indicated above or compounds as can be preferably be employed in organic electronic devices are the compounds of the following structures.

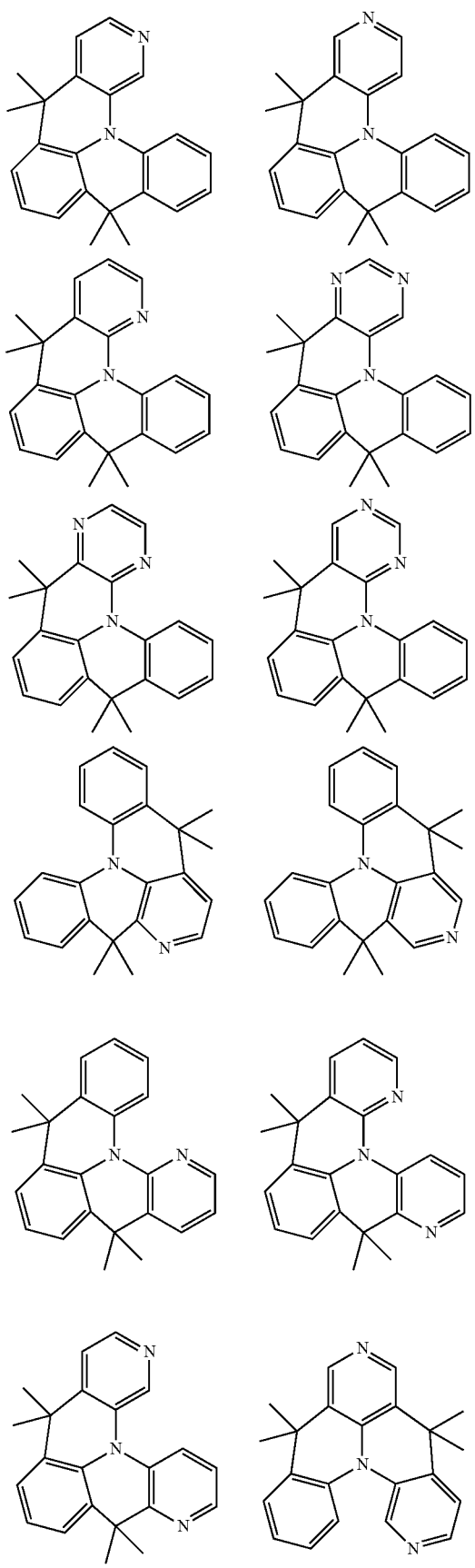
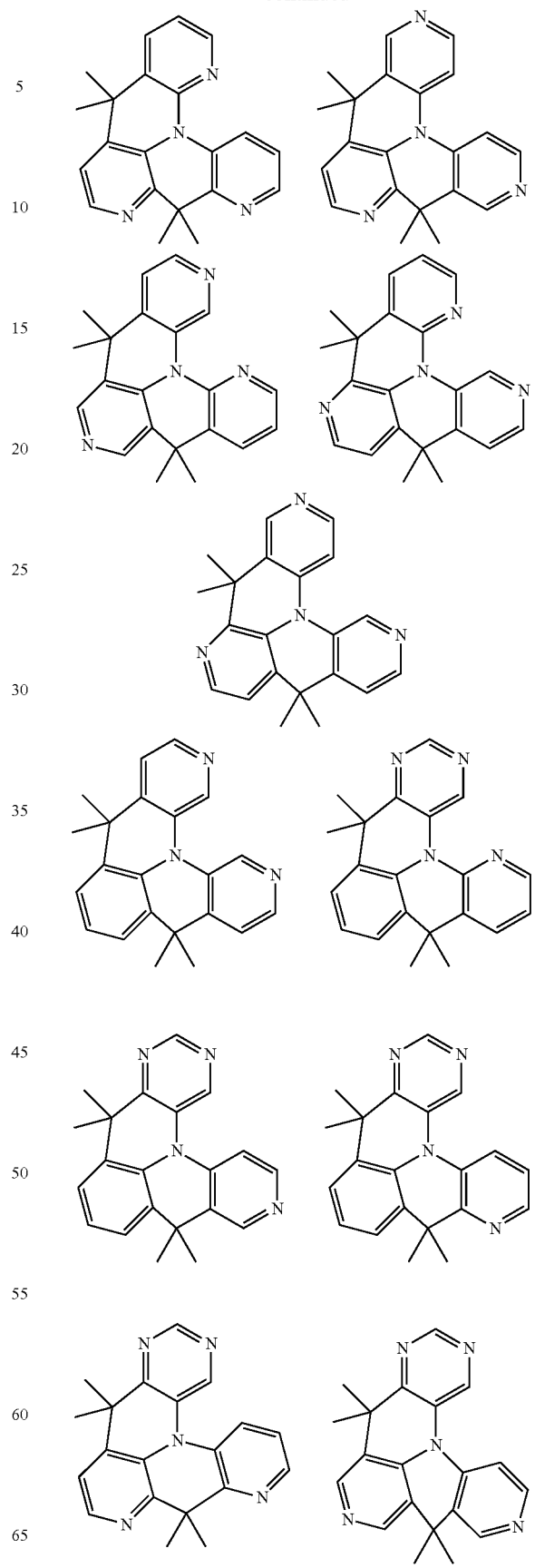

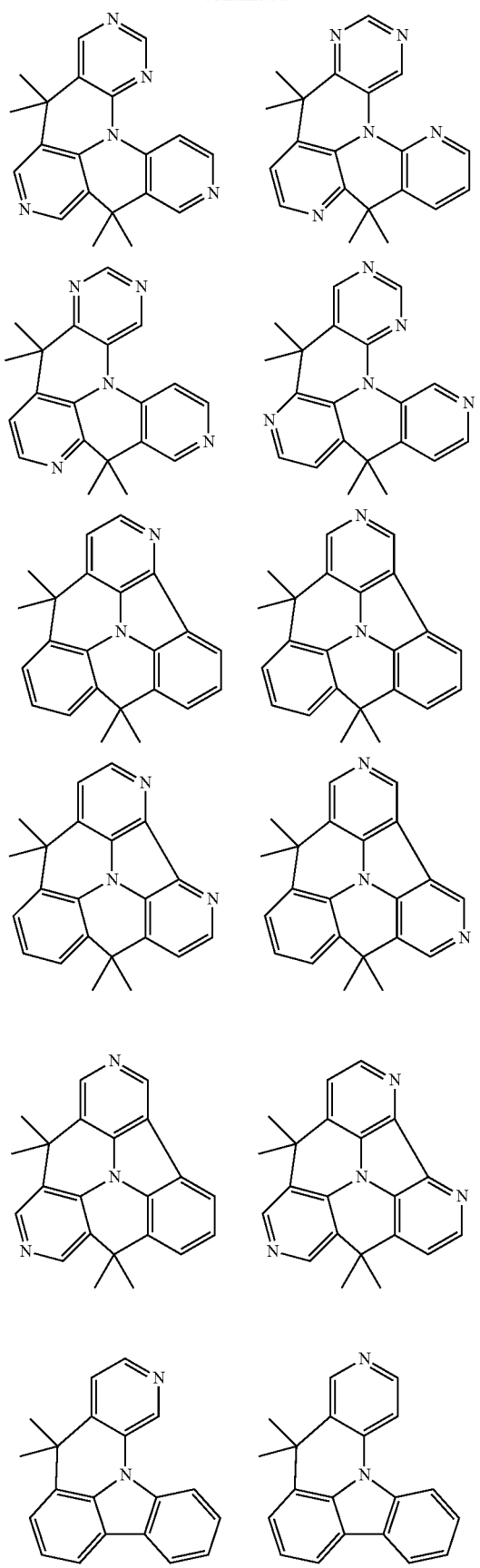
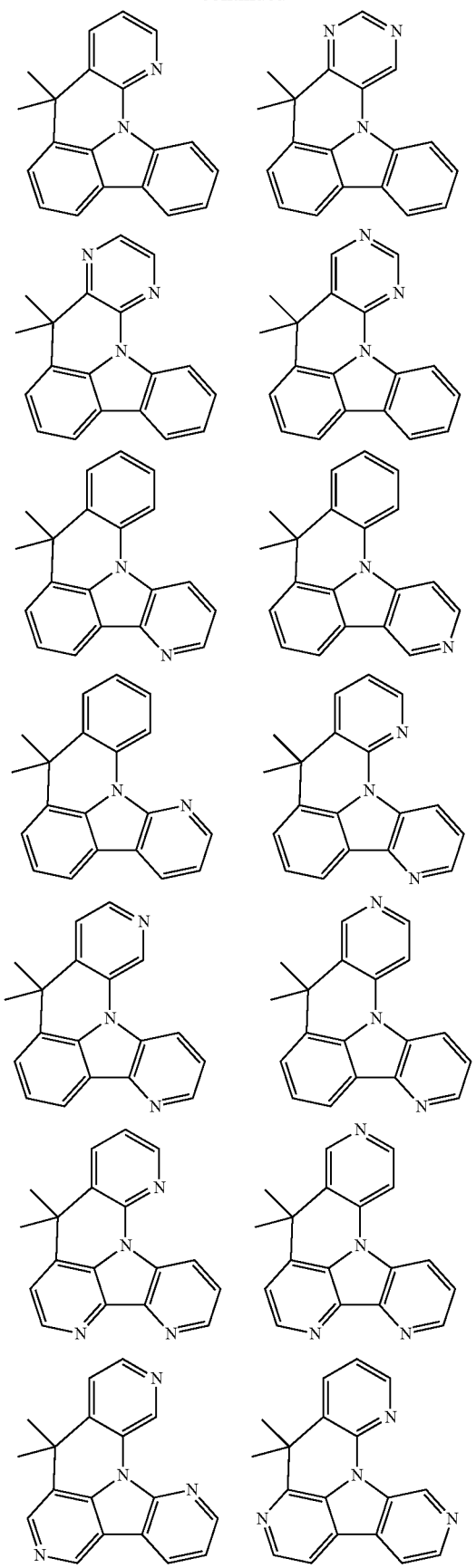

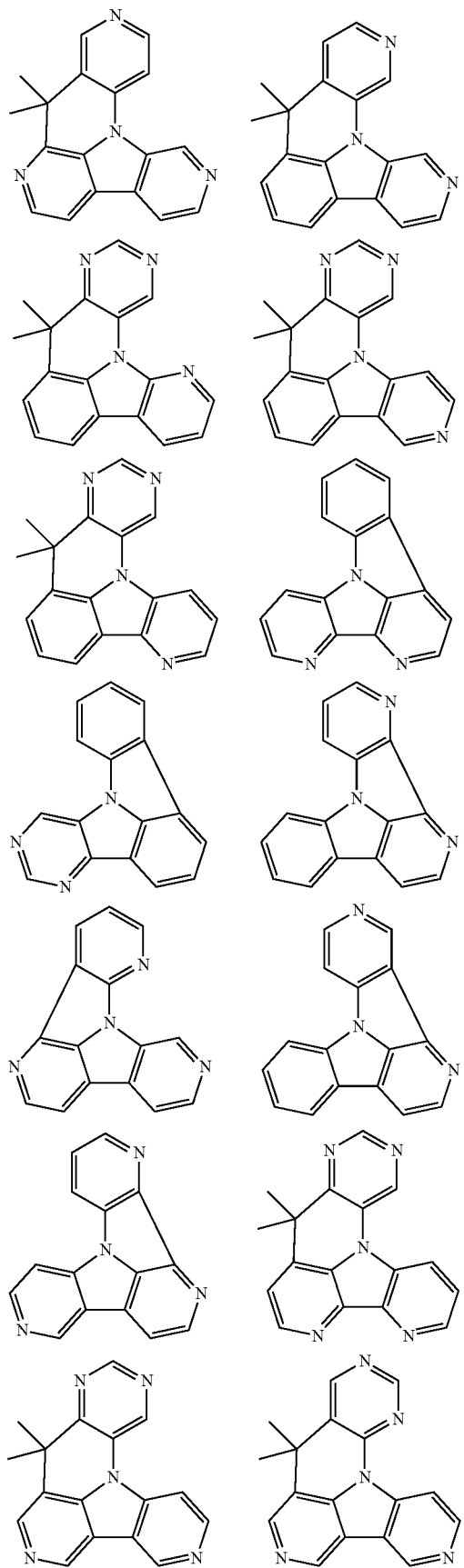
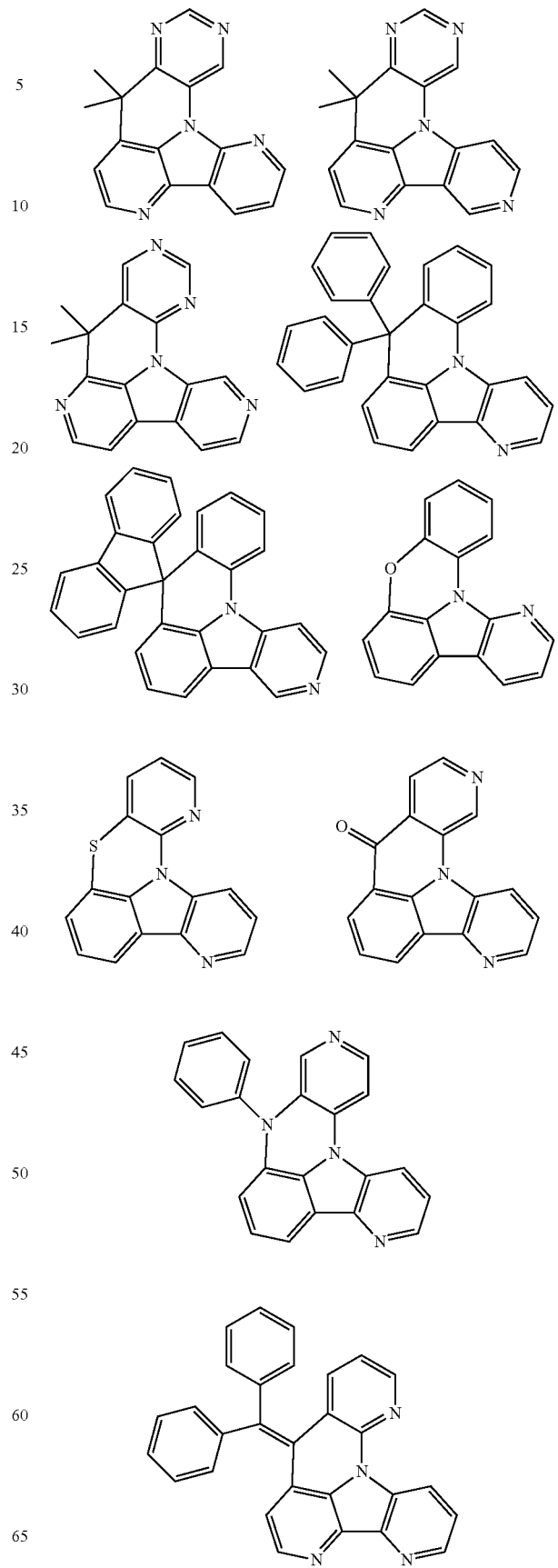

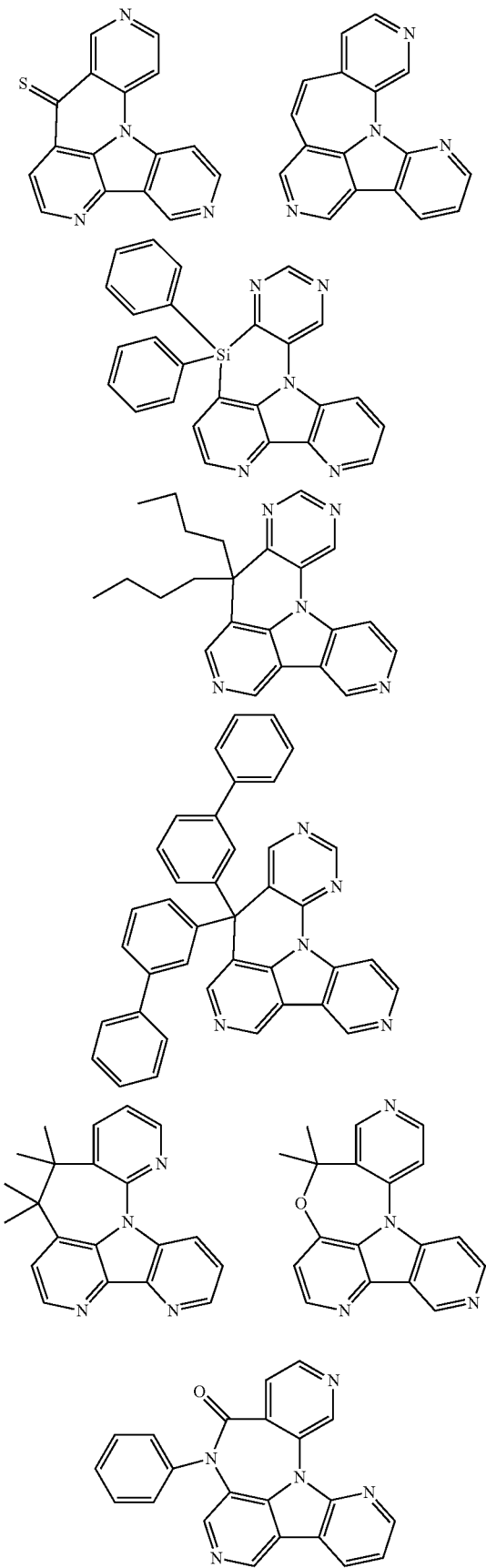
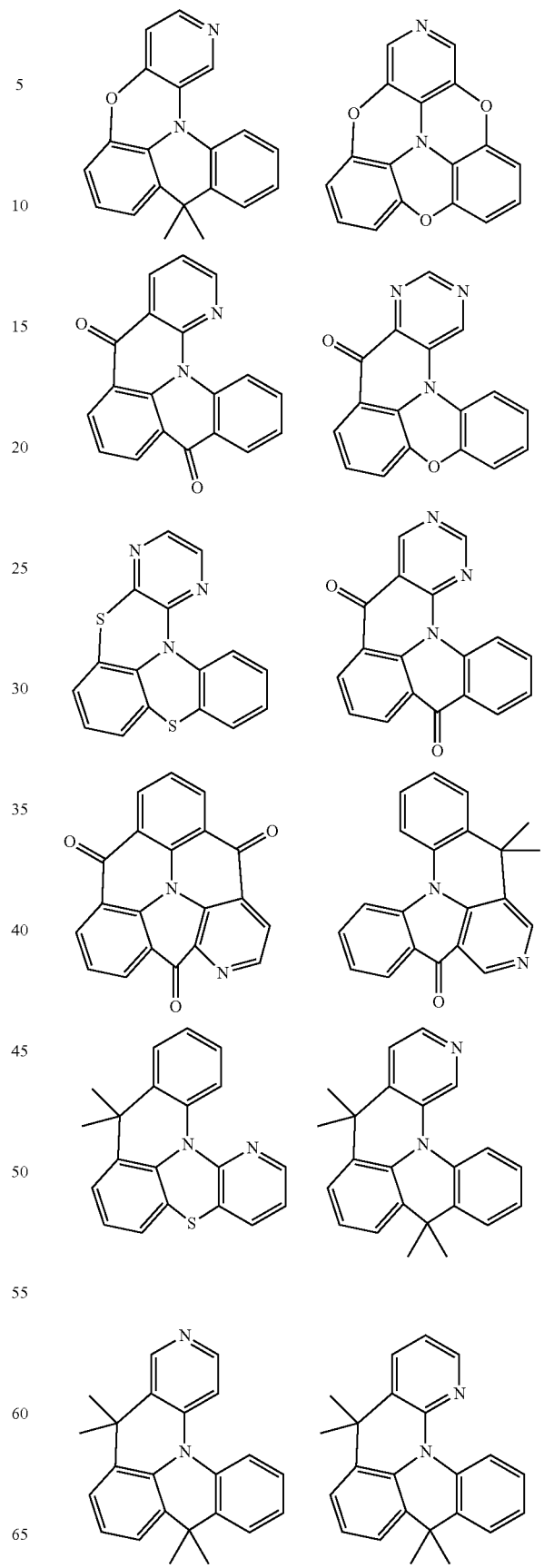

49
-continued
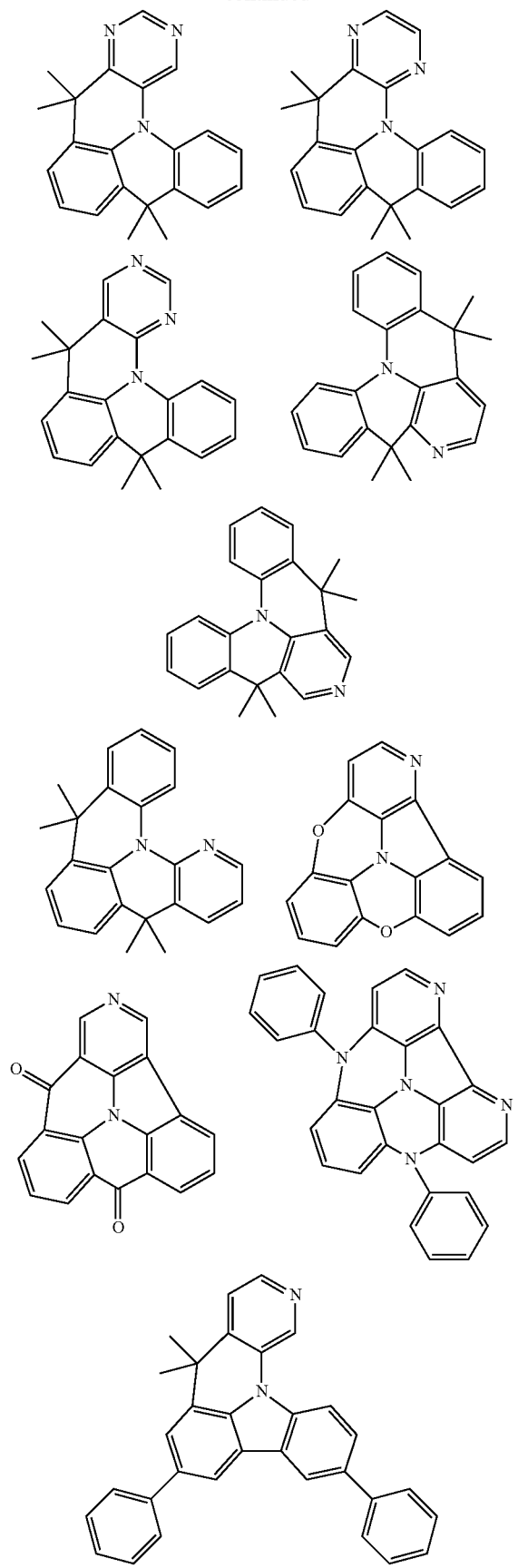
50
-continued
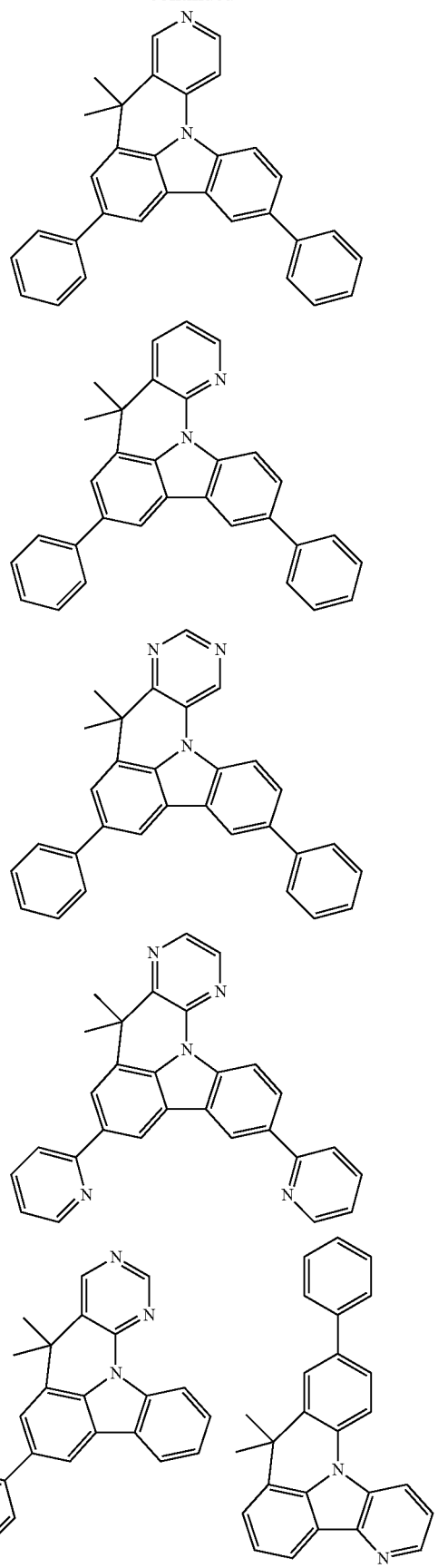

51
-continued
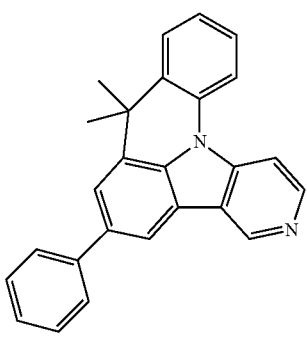
52
-continued
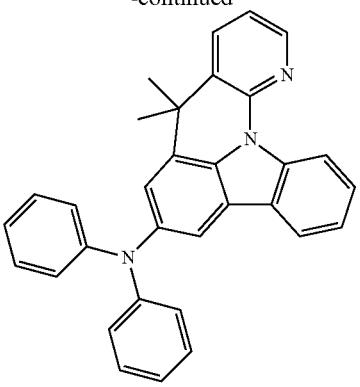
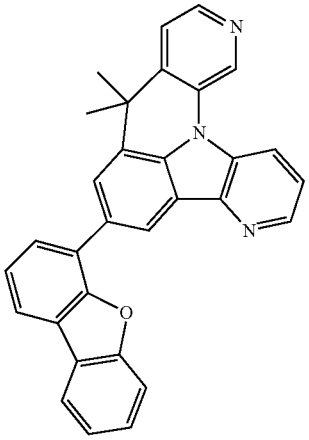
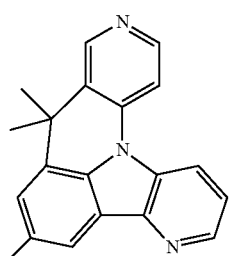
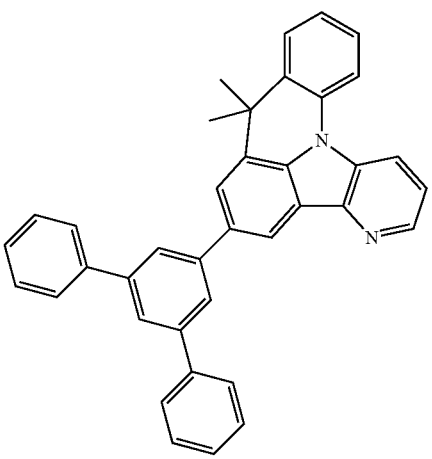

53
-continued
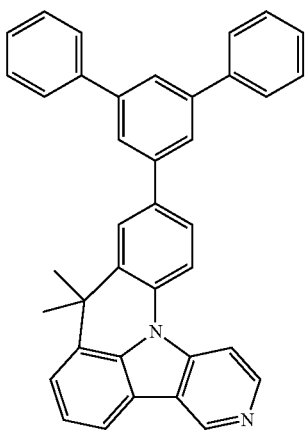
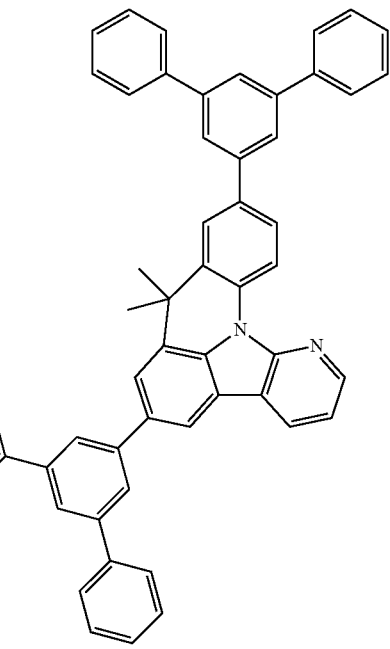
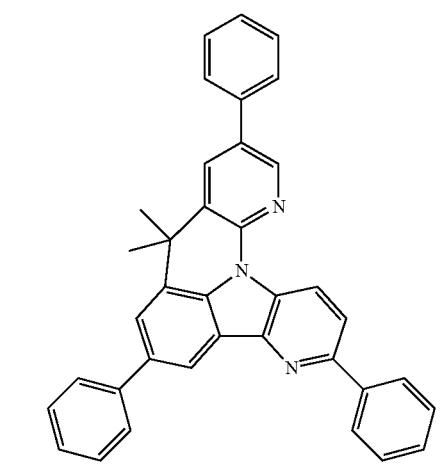
54
-continued
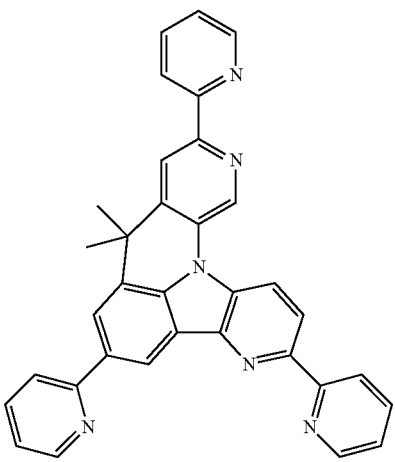
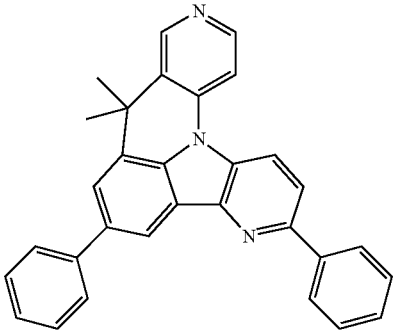
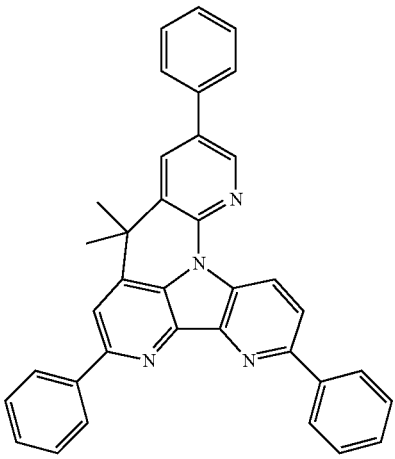
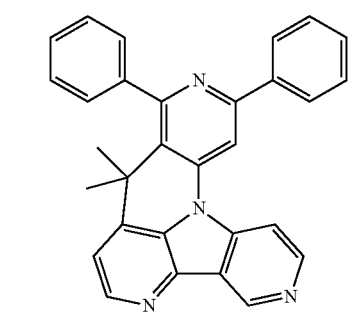

55

56

57
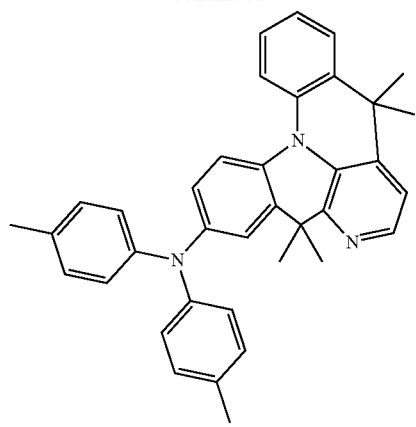
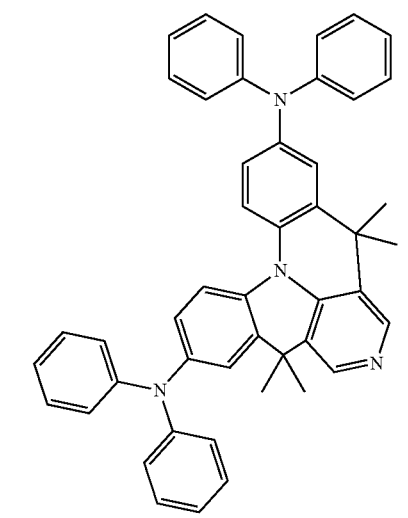
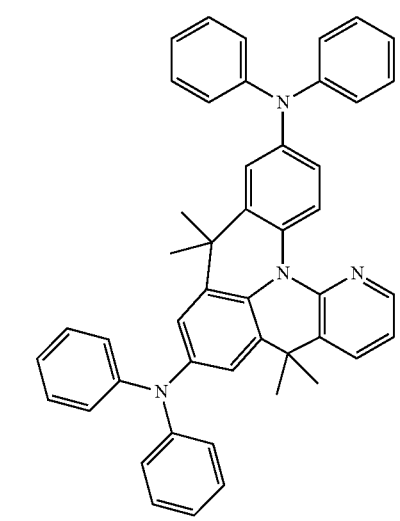
58
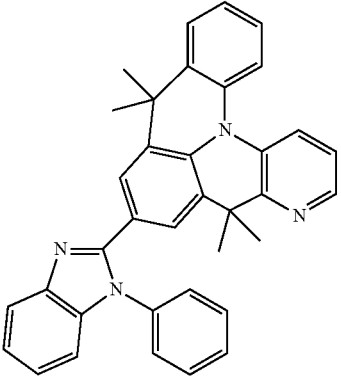
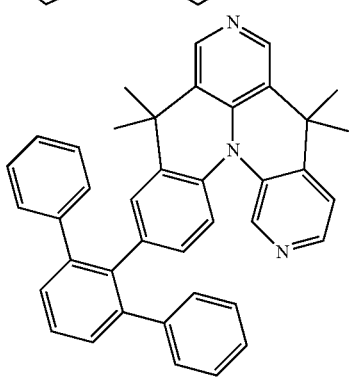
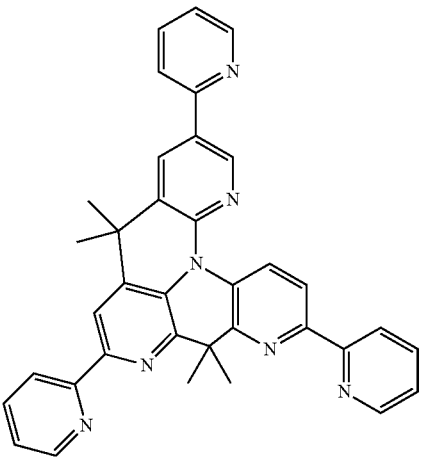

59
-continued
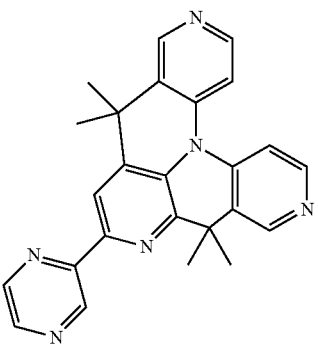
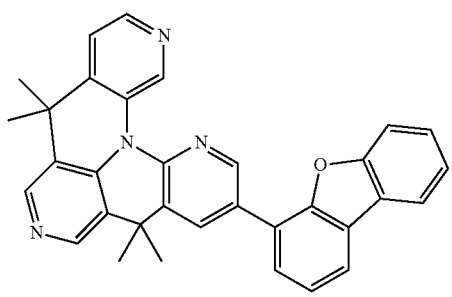
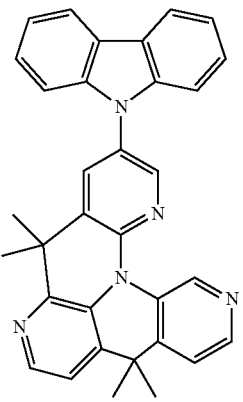
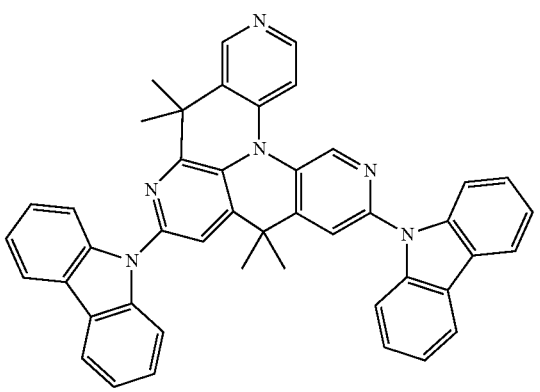
60
-continued
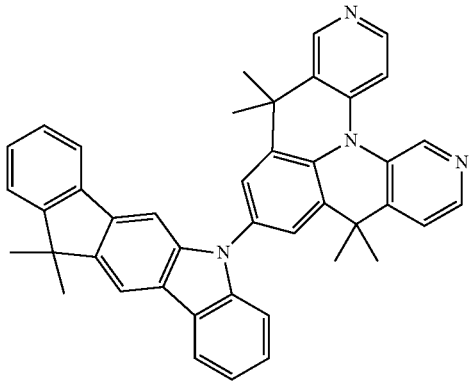
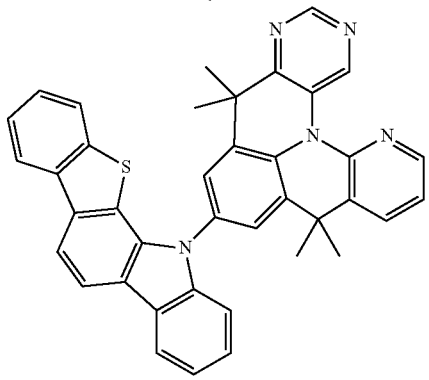
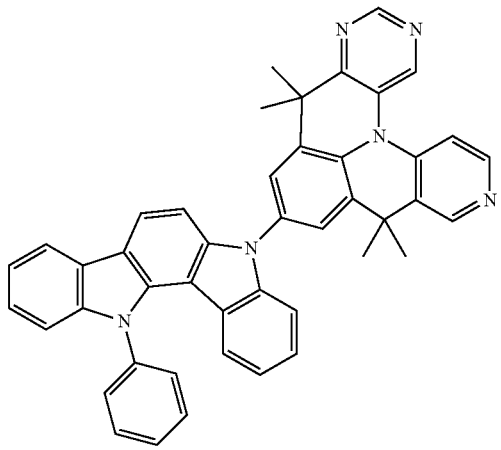
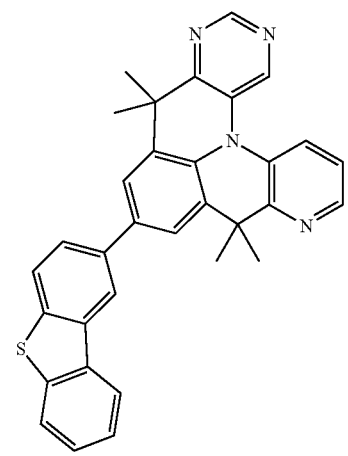

61
-continued
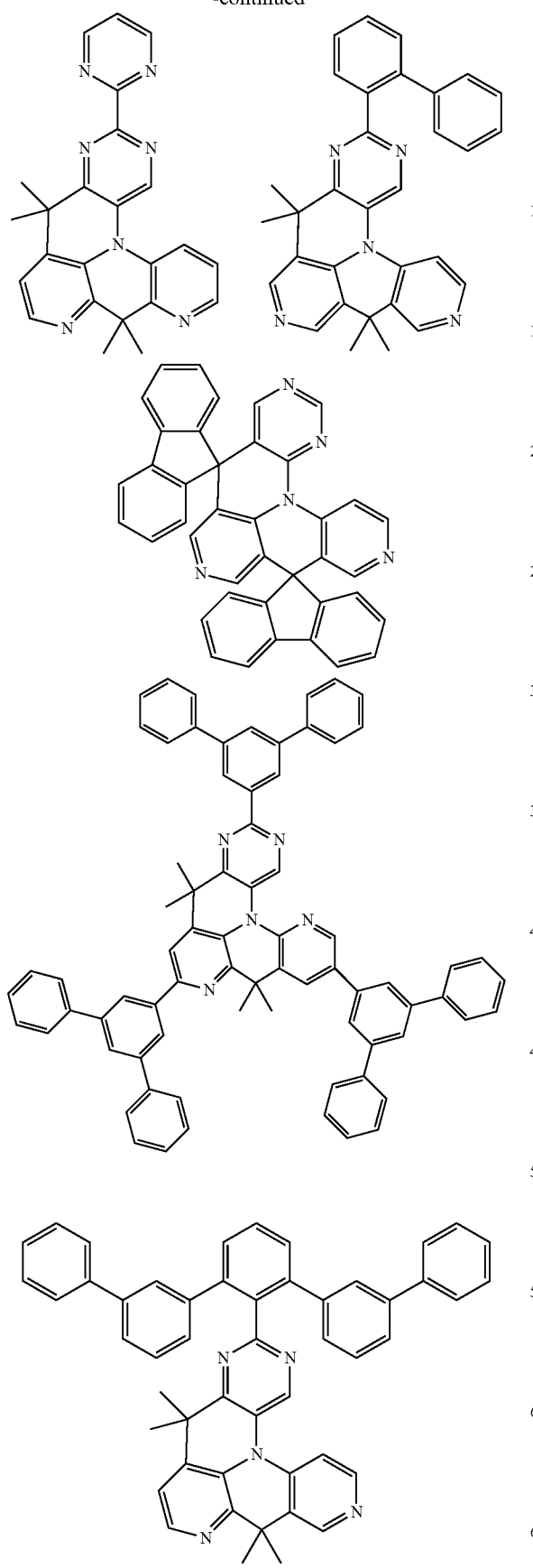
62
-continued
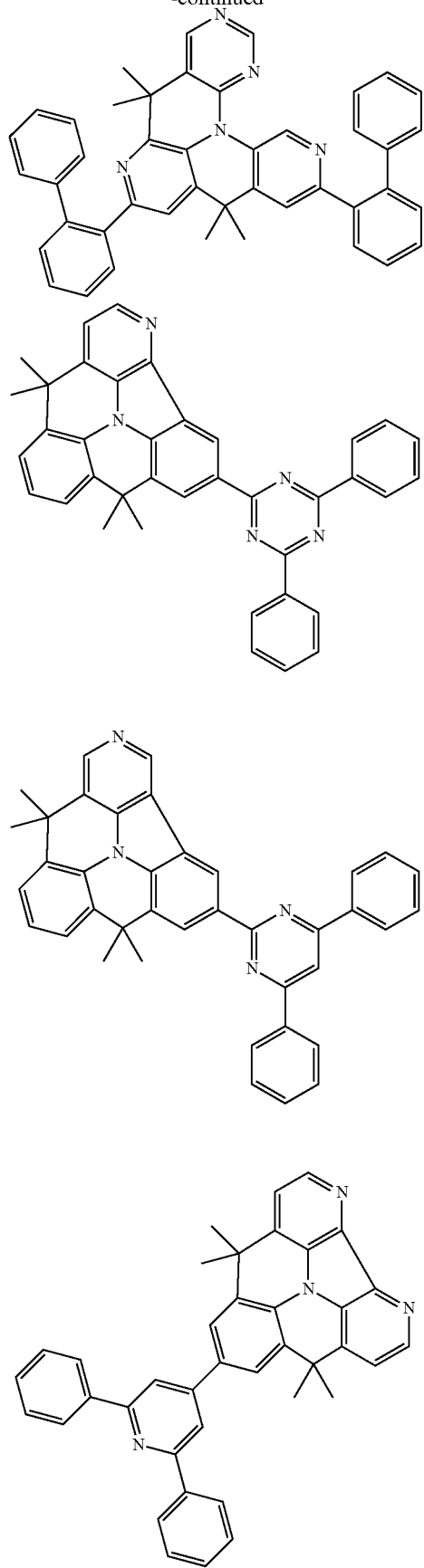

63
-continued
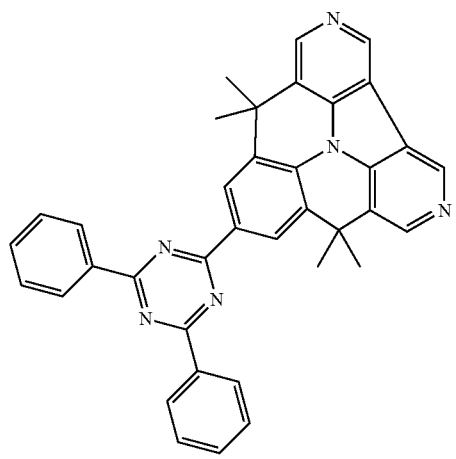
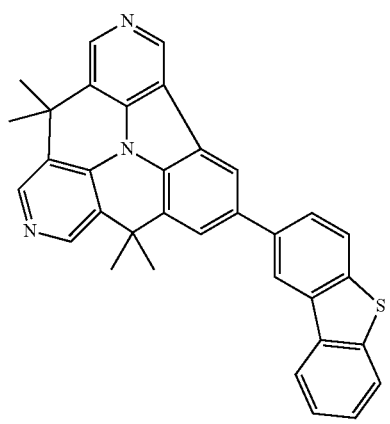
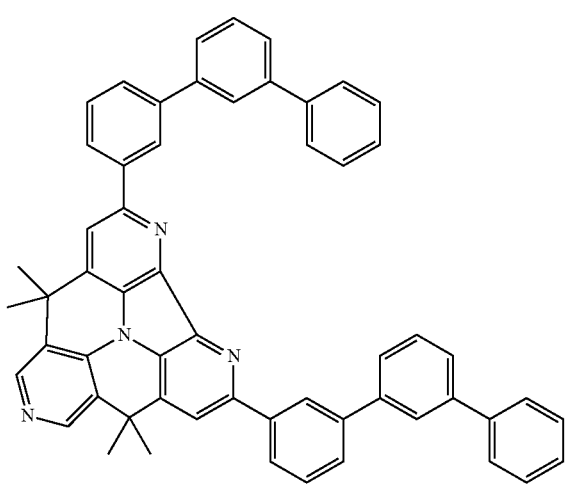
64
-continued
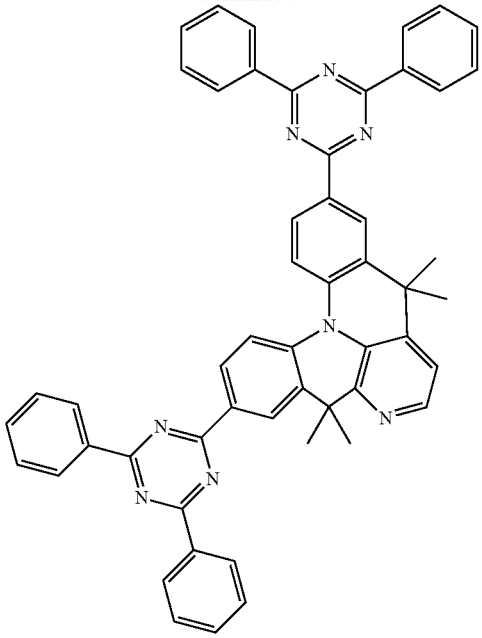
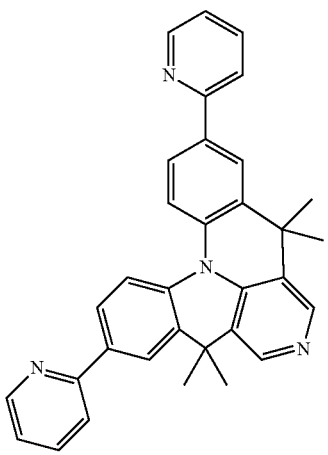
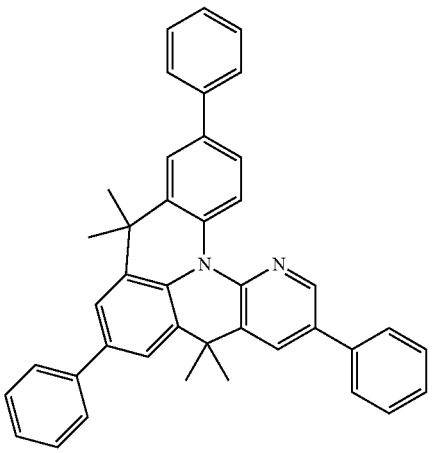

65
-continued
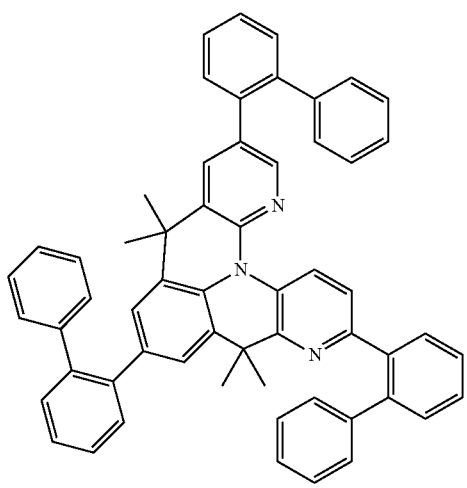
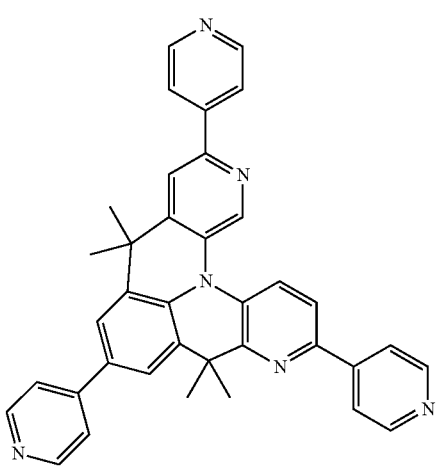
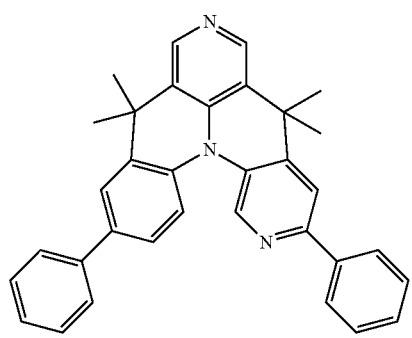
66
-continued
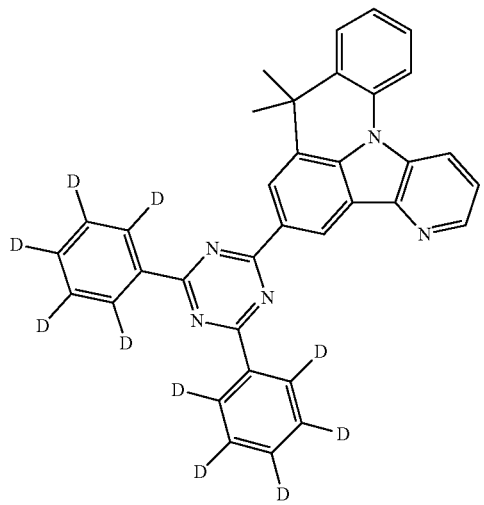
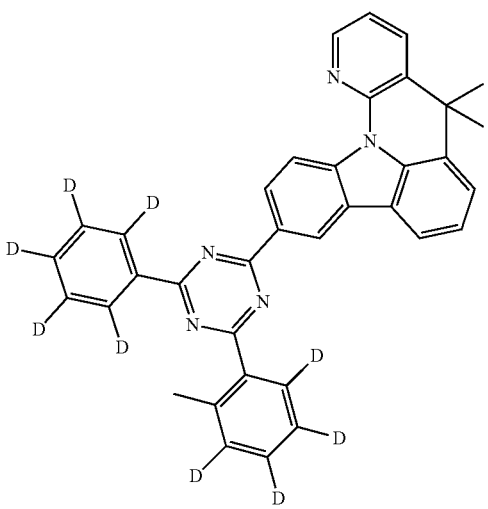
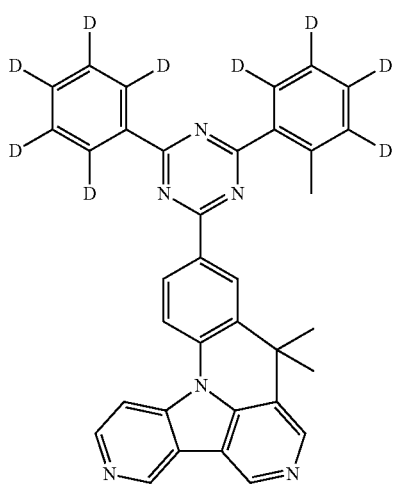

67
-continued
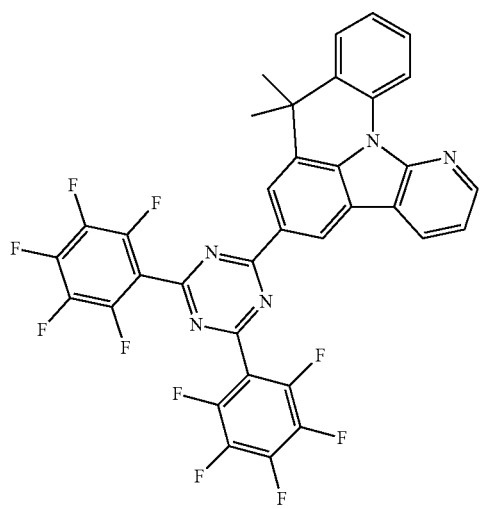
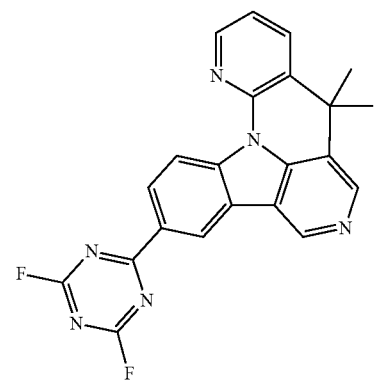
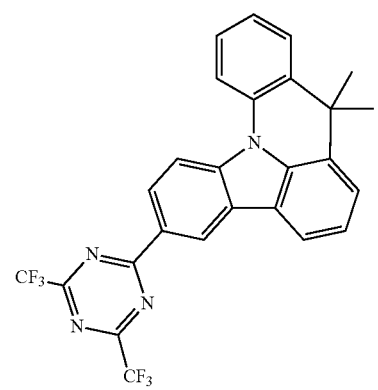
68
-continued
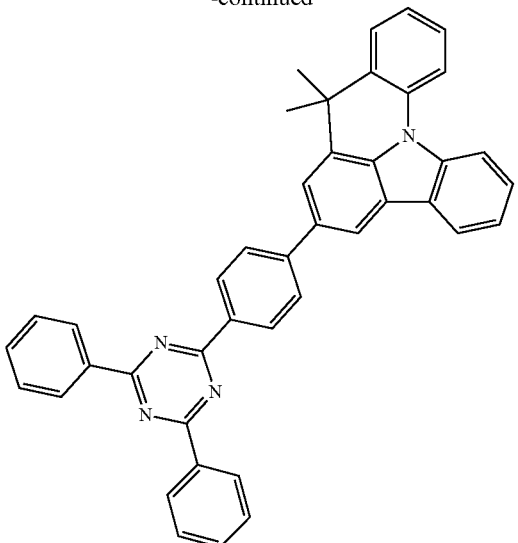
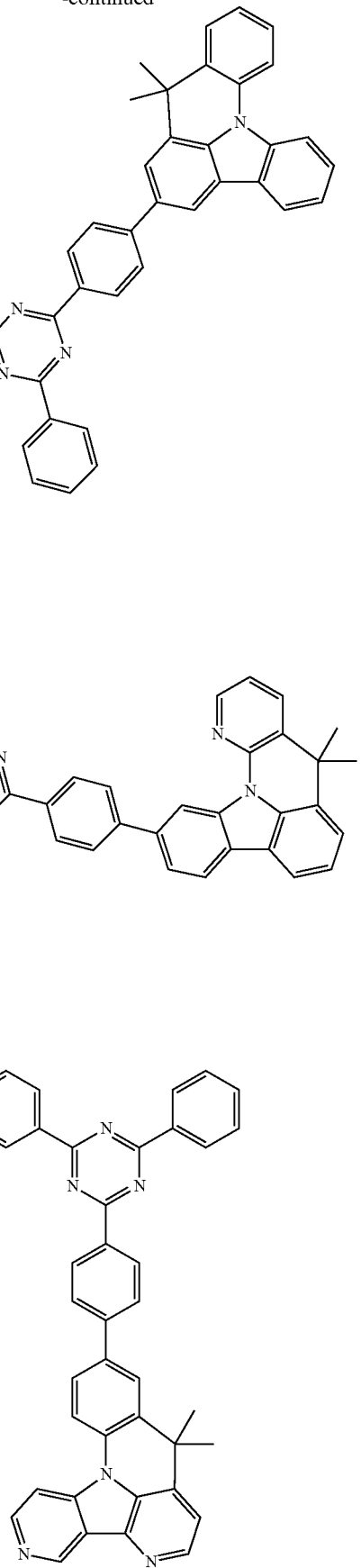

69
-continued
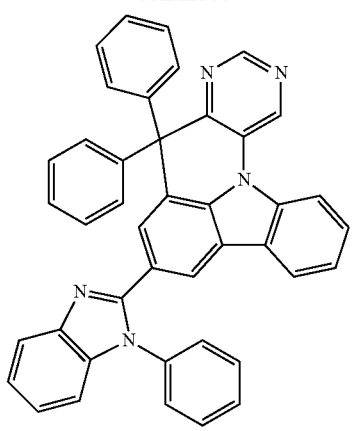
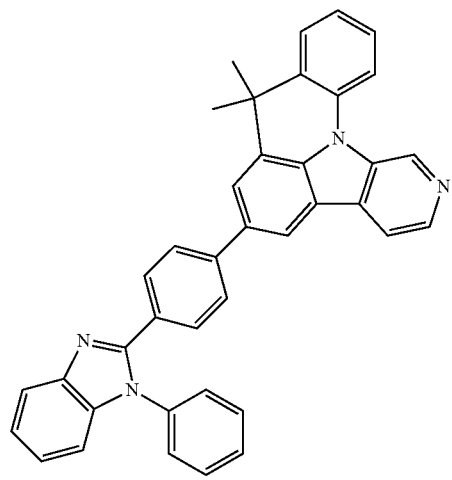
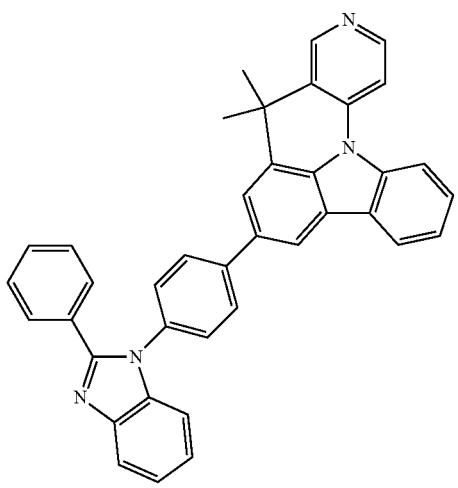
70
-continued
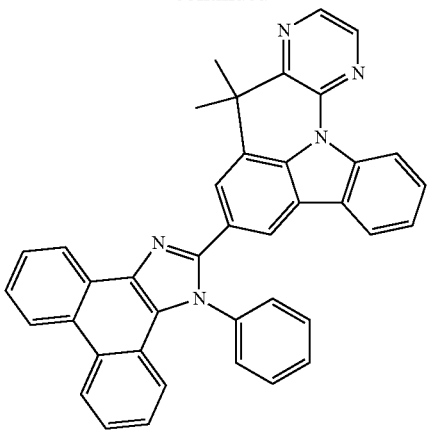
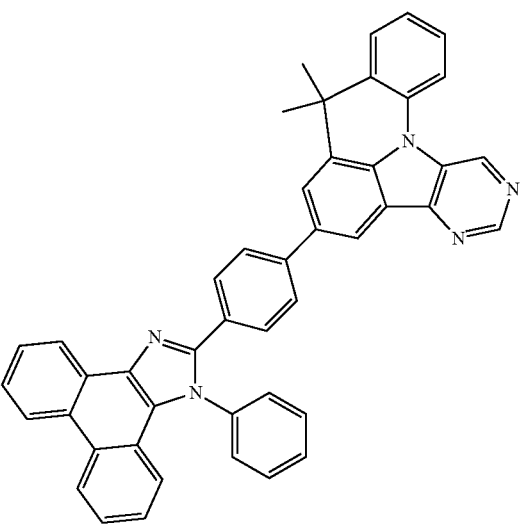
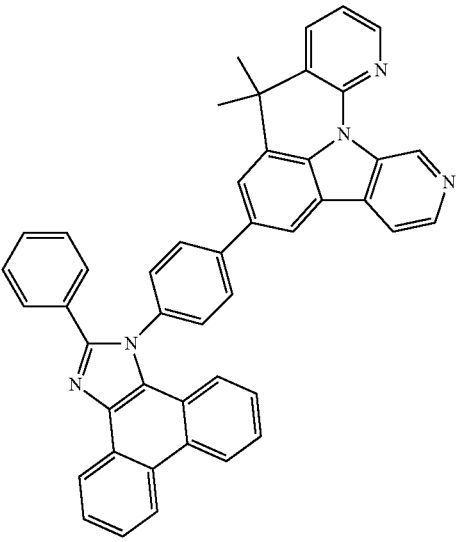

71
-continued
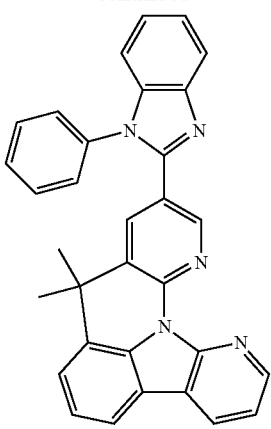
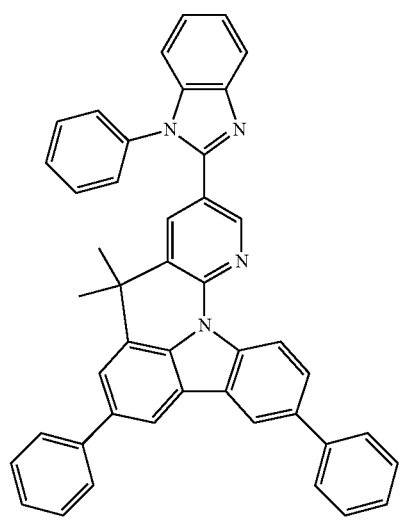
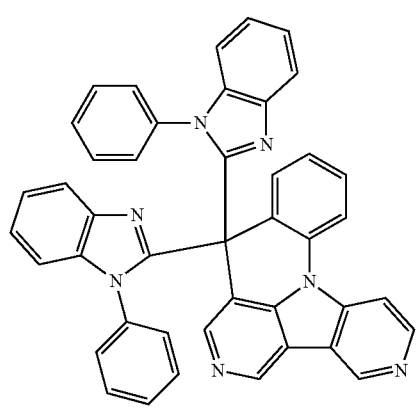
72
-continued
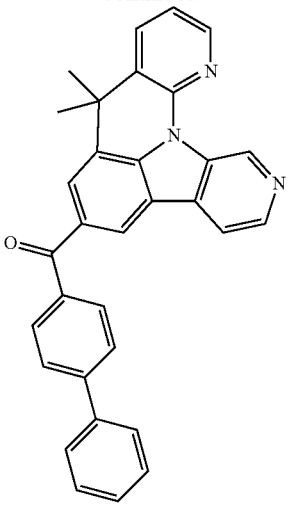
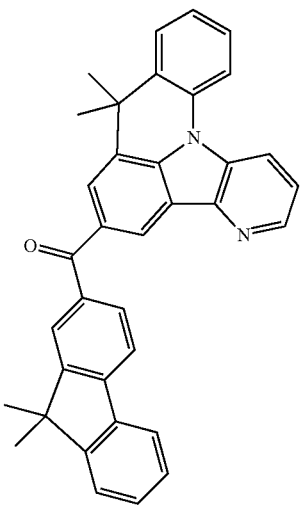
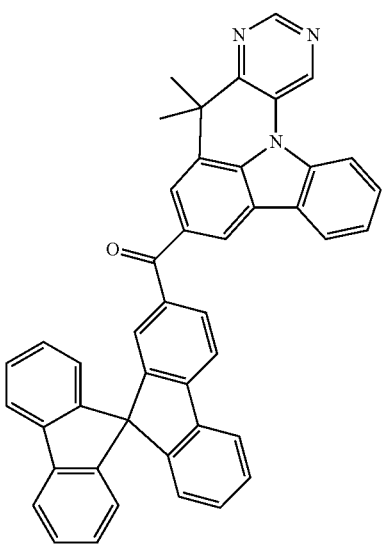

73
-continued
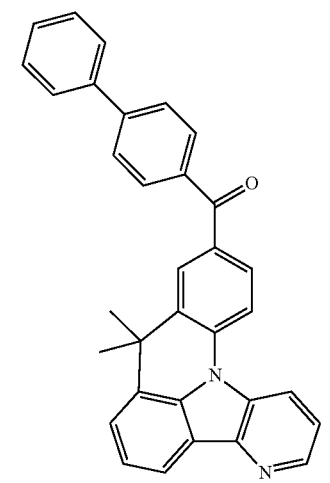
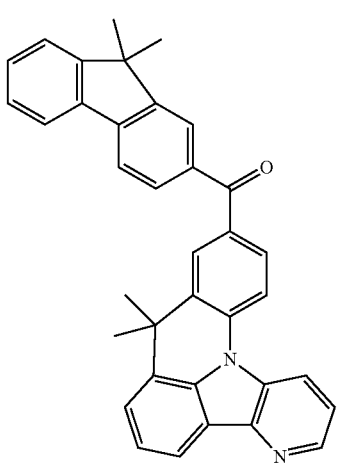
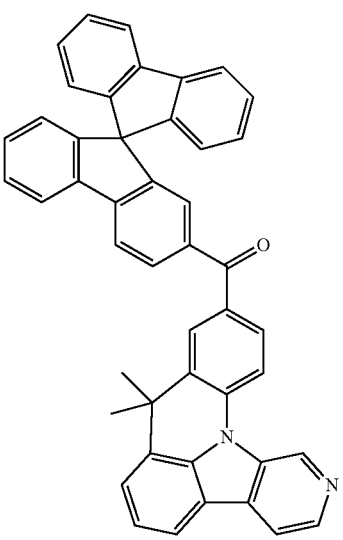
74
-continued
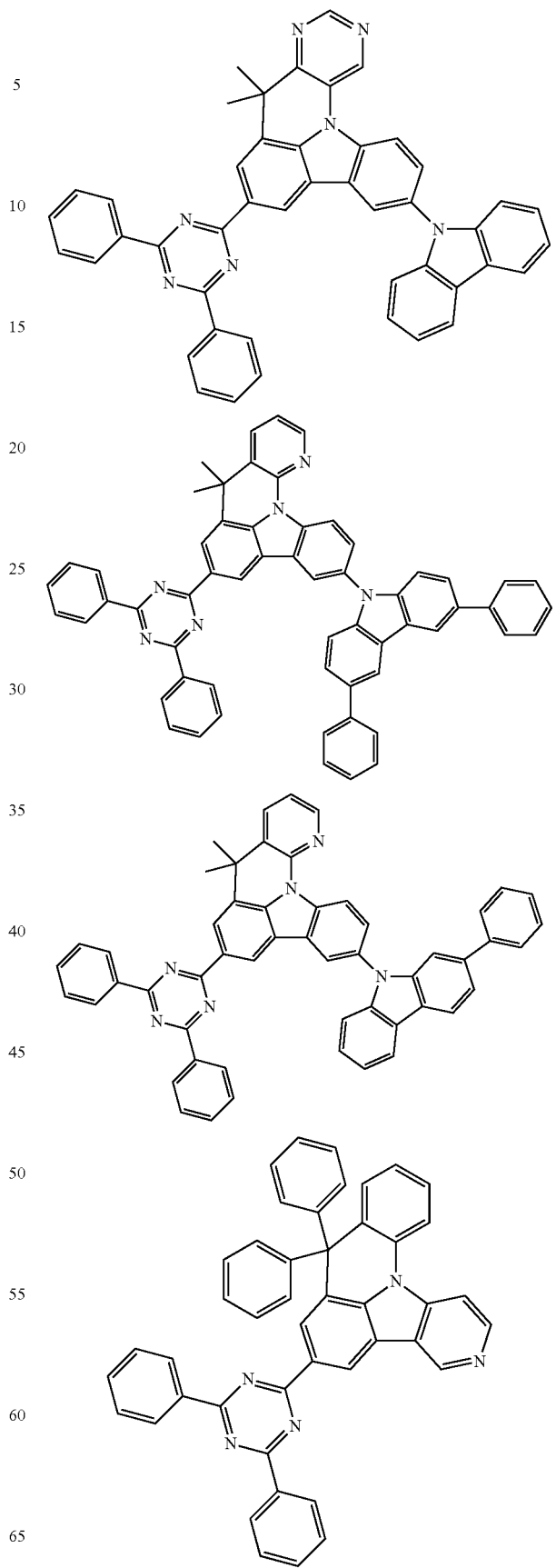

75
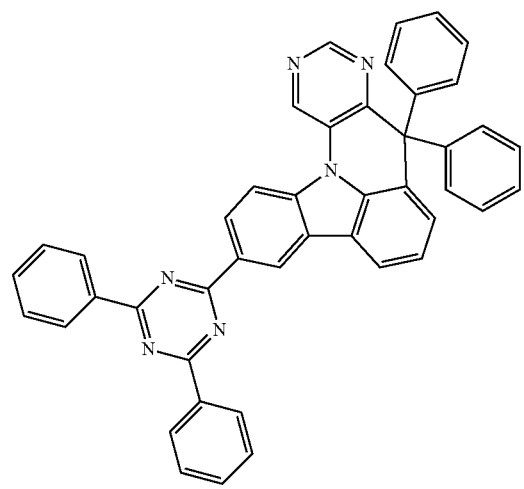
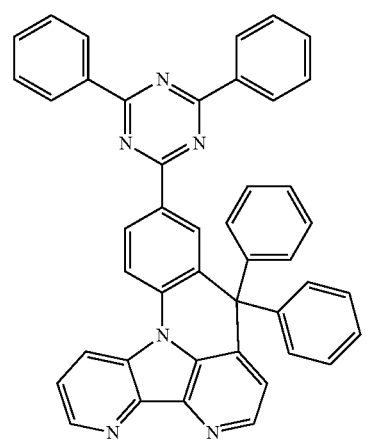
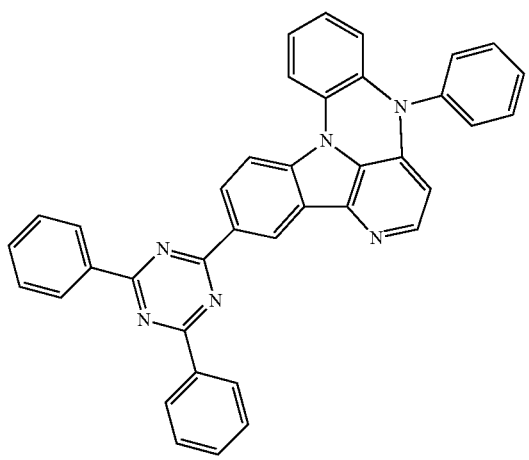
76
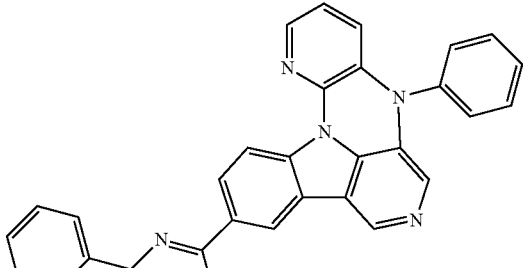
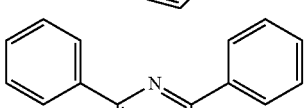
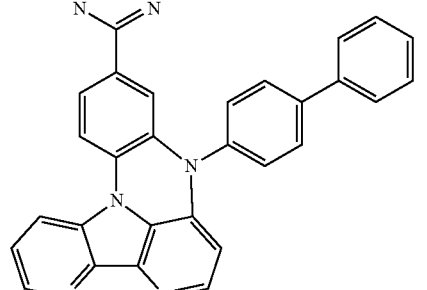
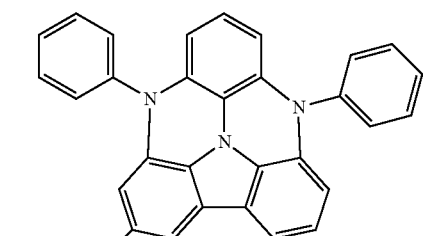
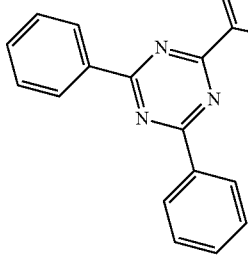
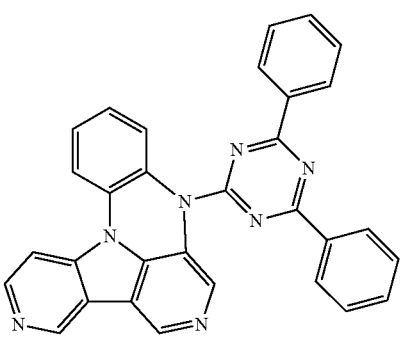

77
-continued
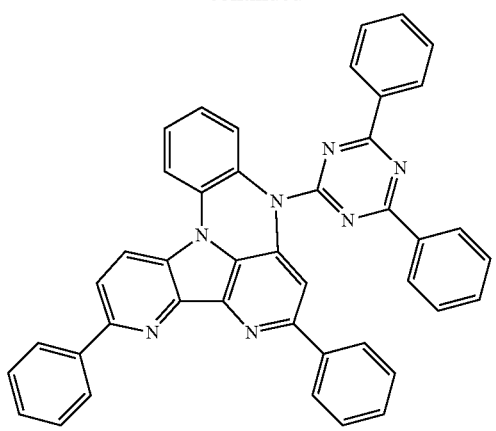
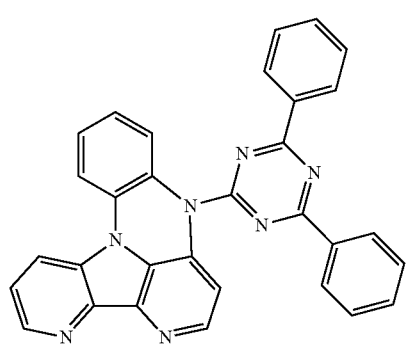
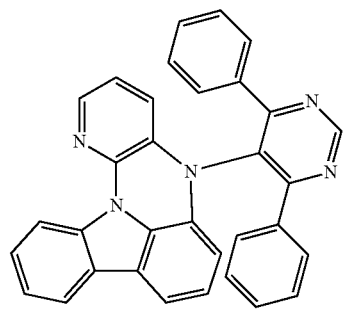
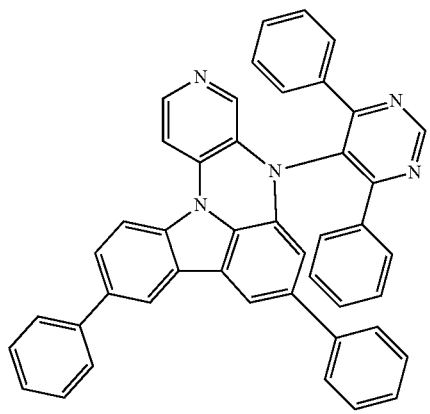
78
-continued
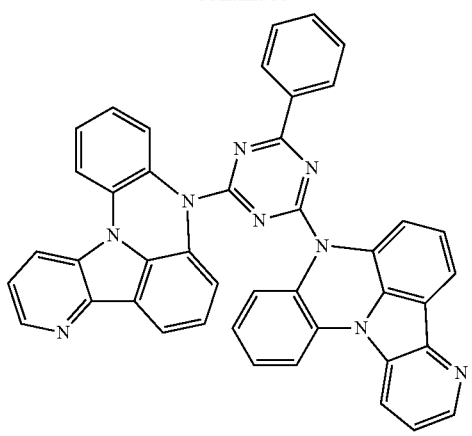
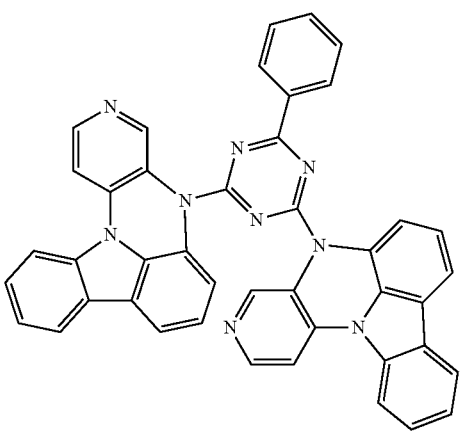
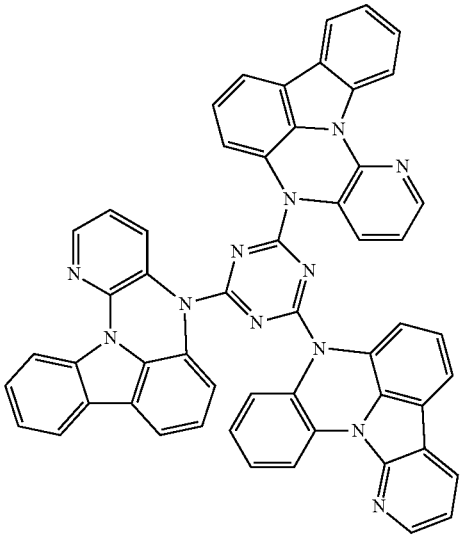

79
-continued
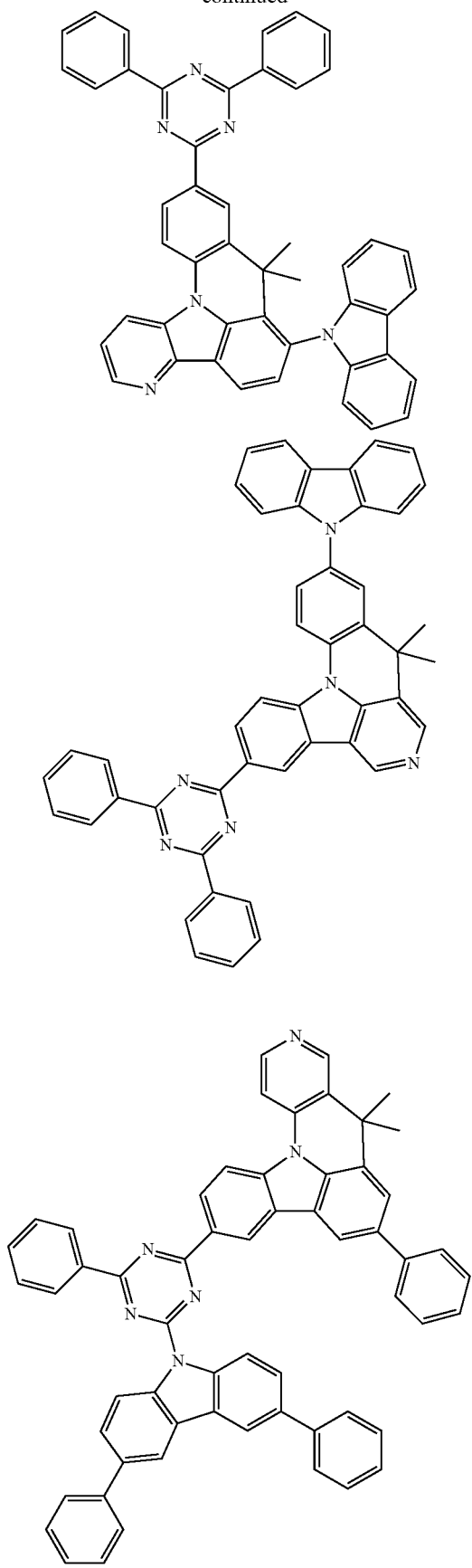
80
-continued
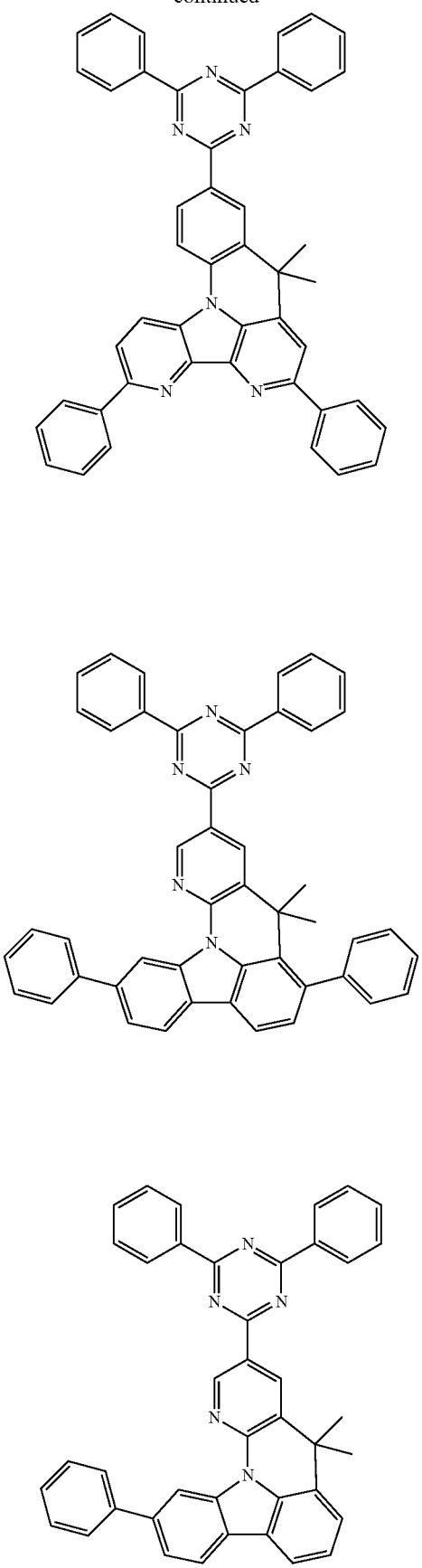

81
-continued
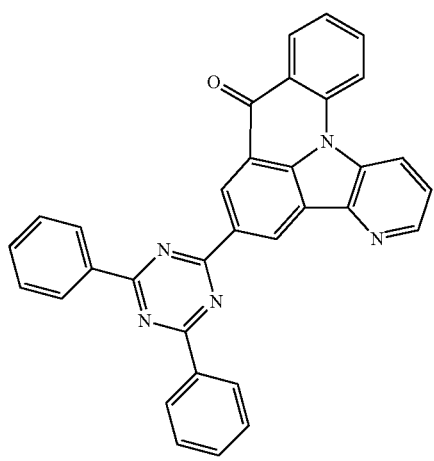
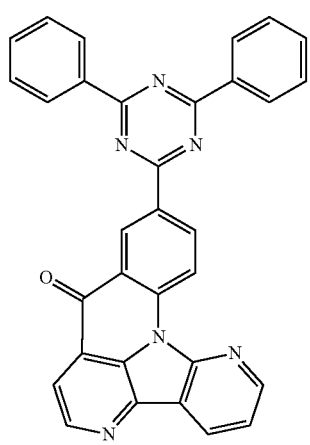
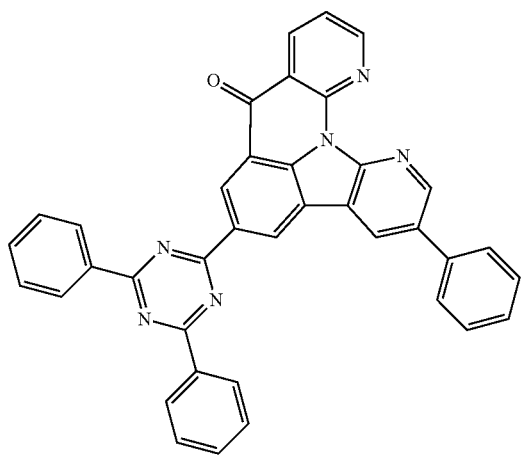
82
-continued
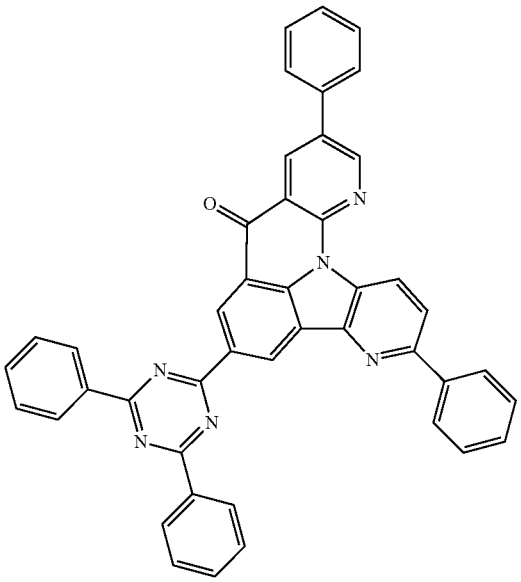
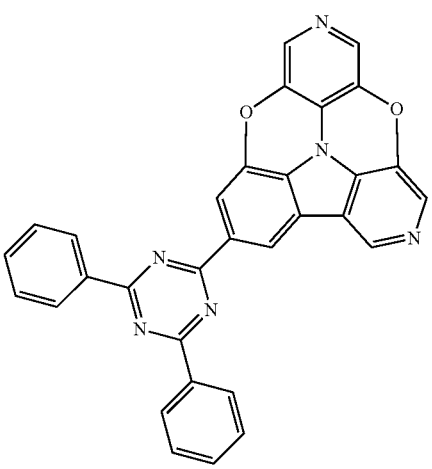
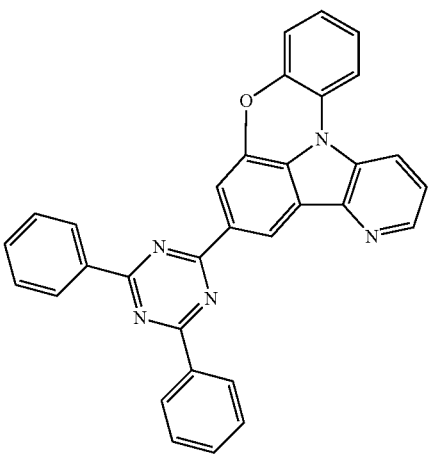

83
-continued
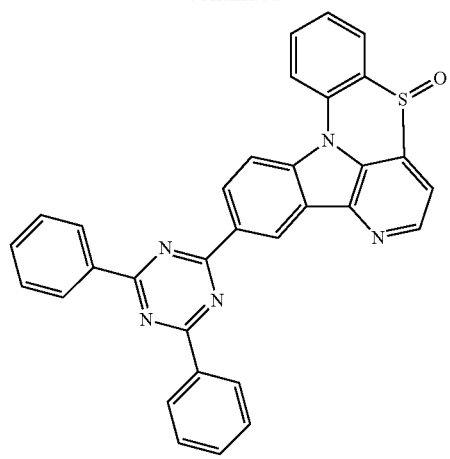
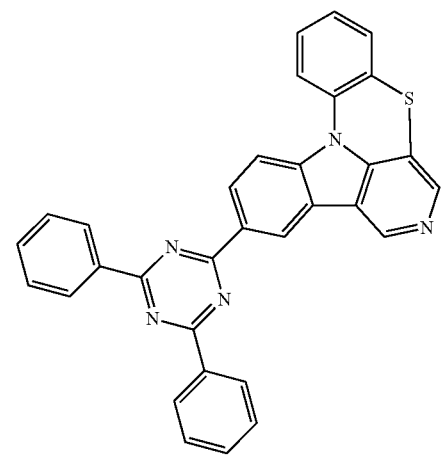
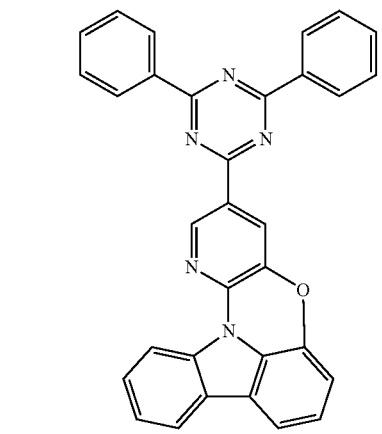
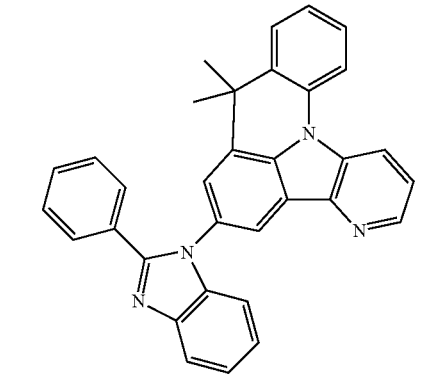
84
-continued
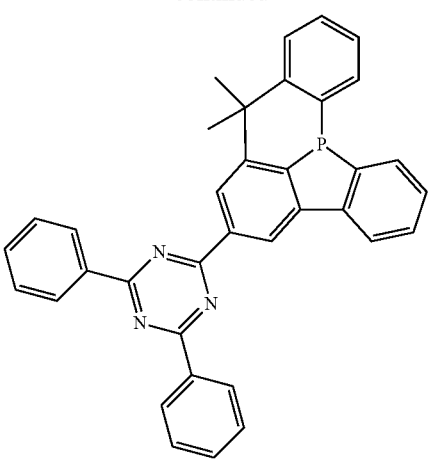
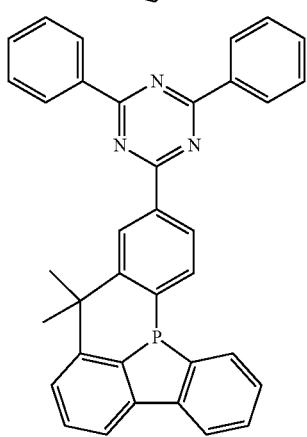
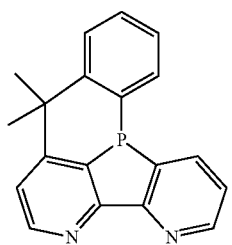
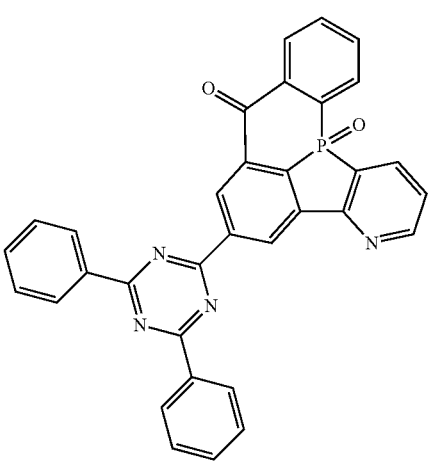

85
-continued
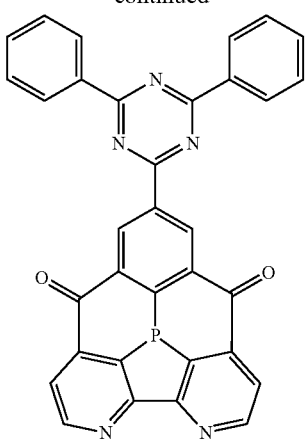
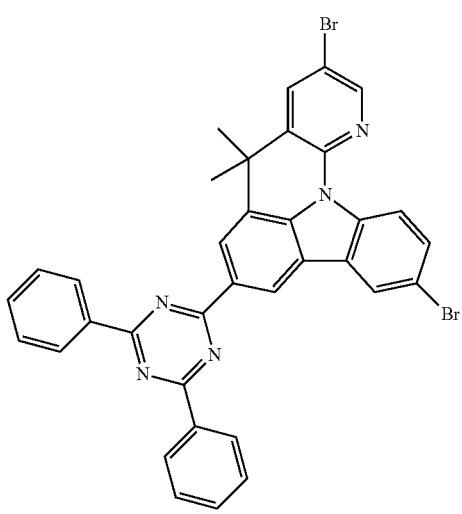
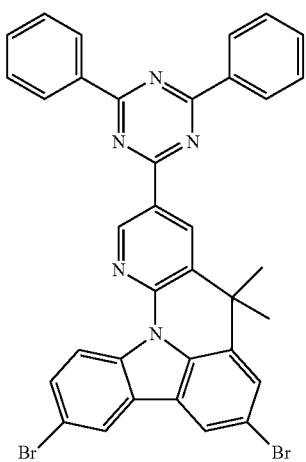
86
-continued
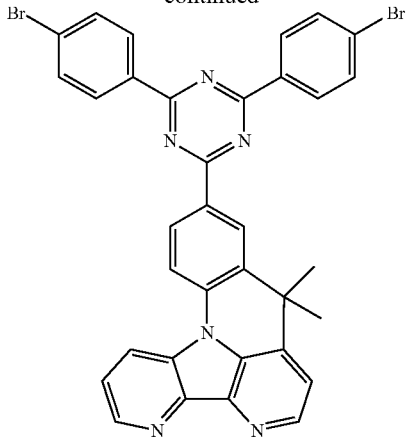
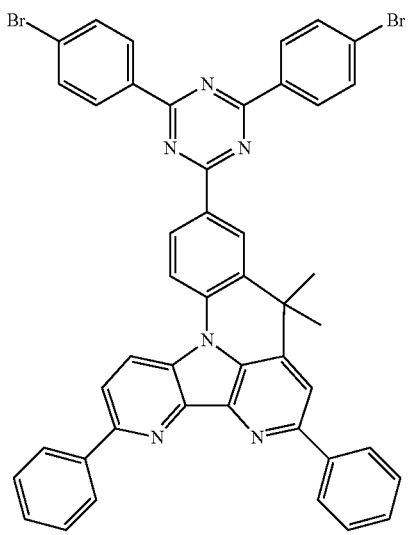
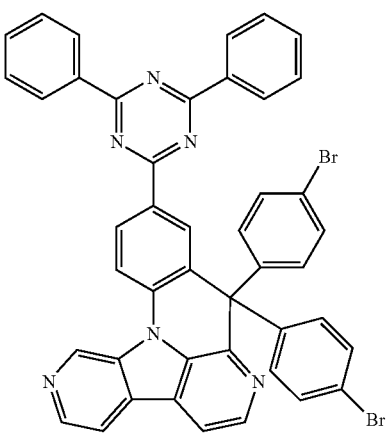

87
-continued
88
-continued
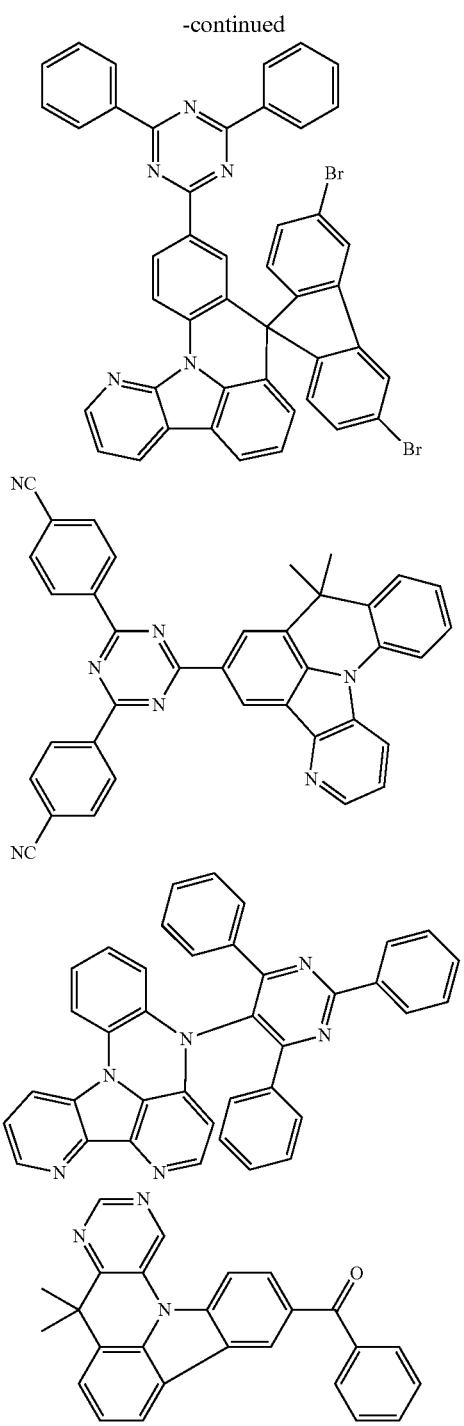
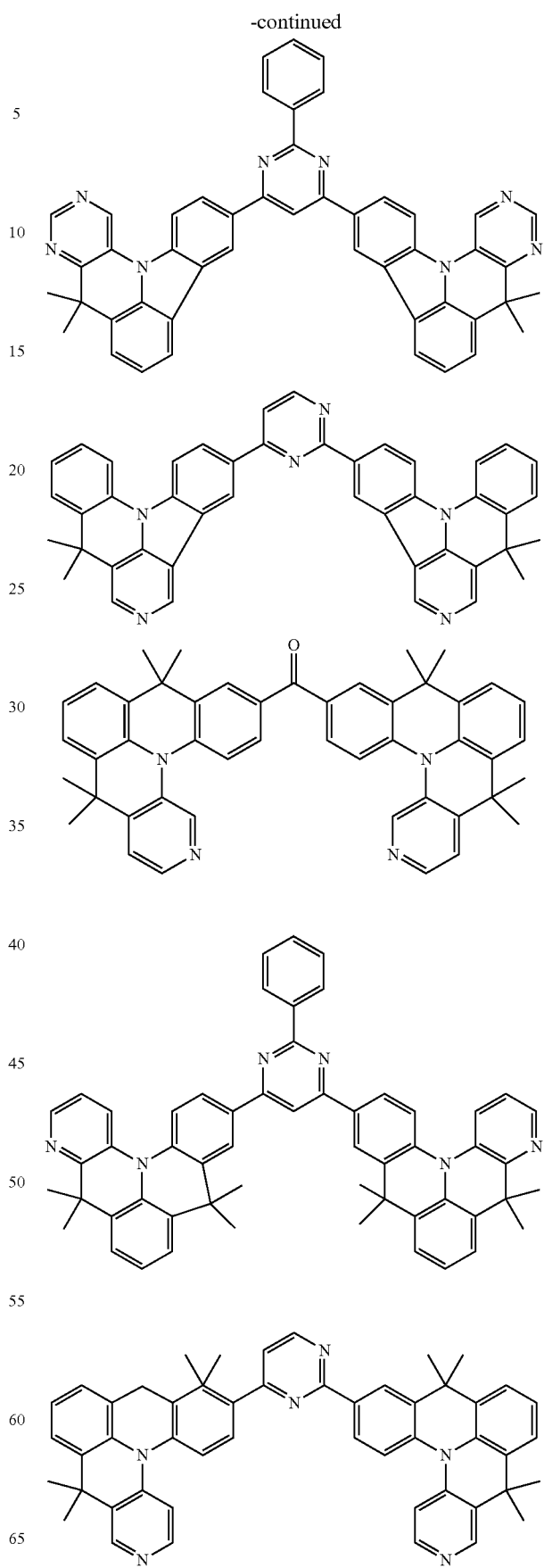

89
-continued
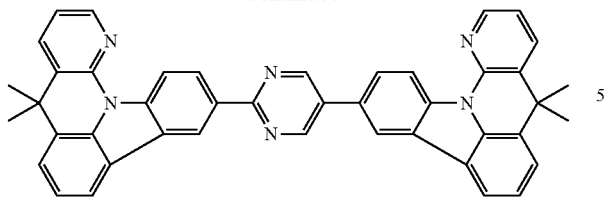
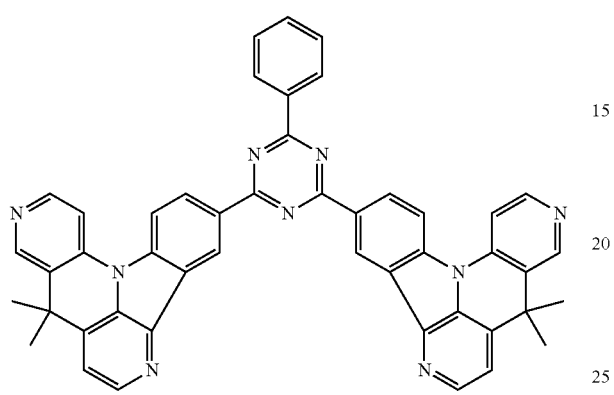
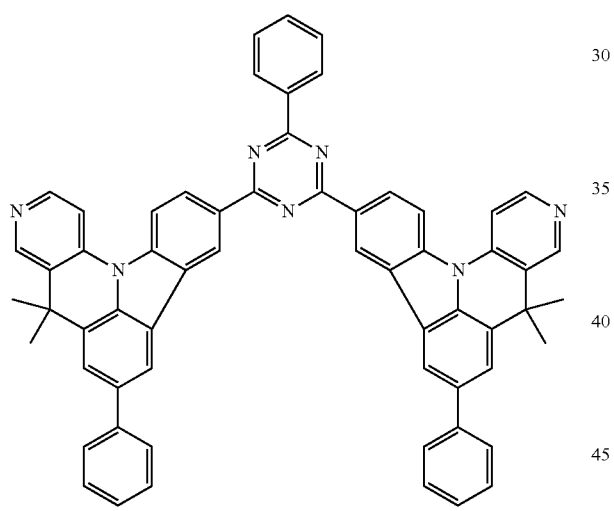
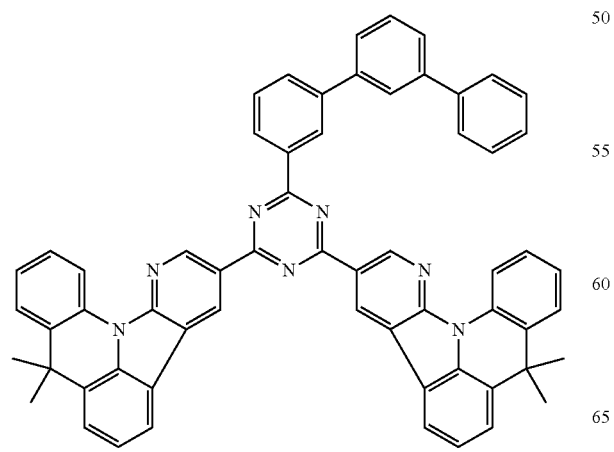
90
-continued
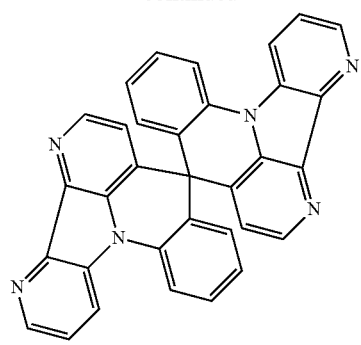
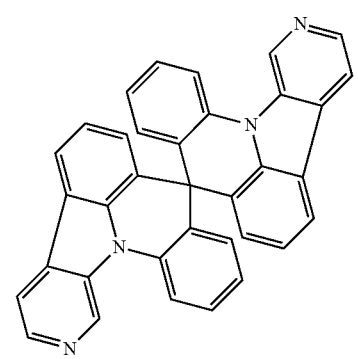
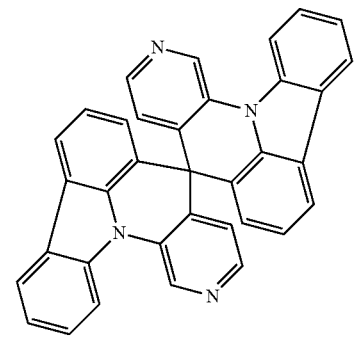
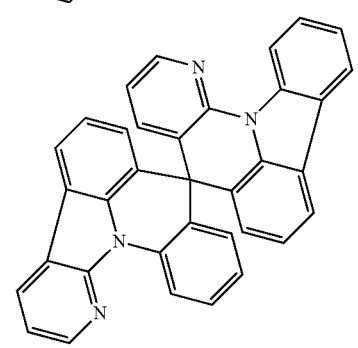
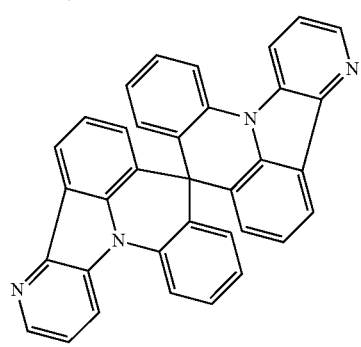

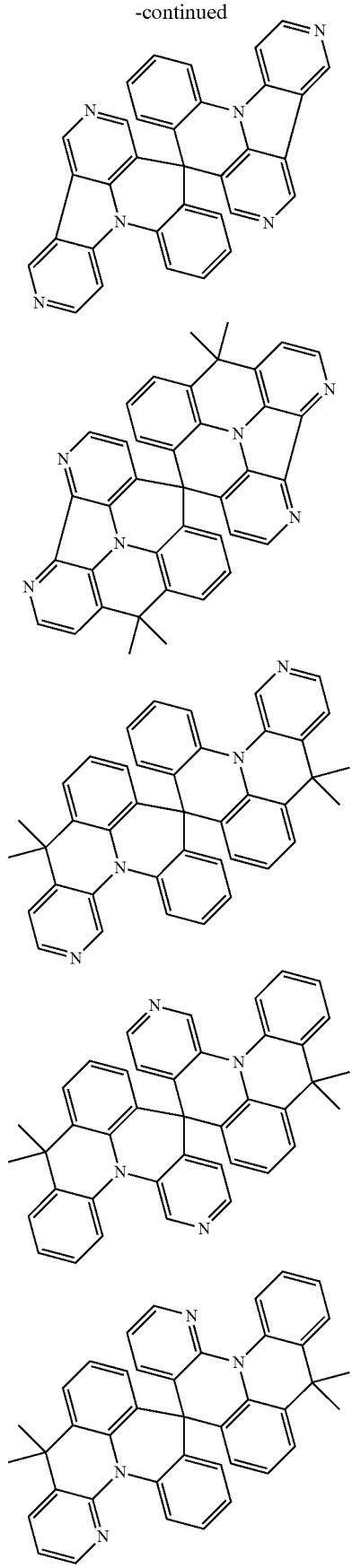
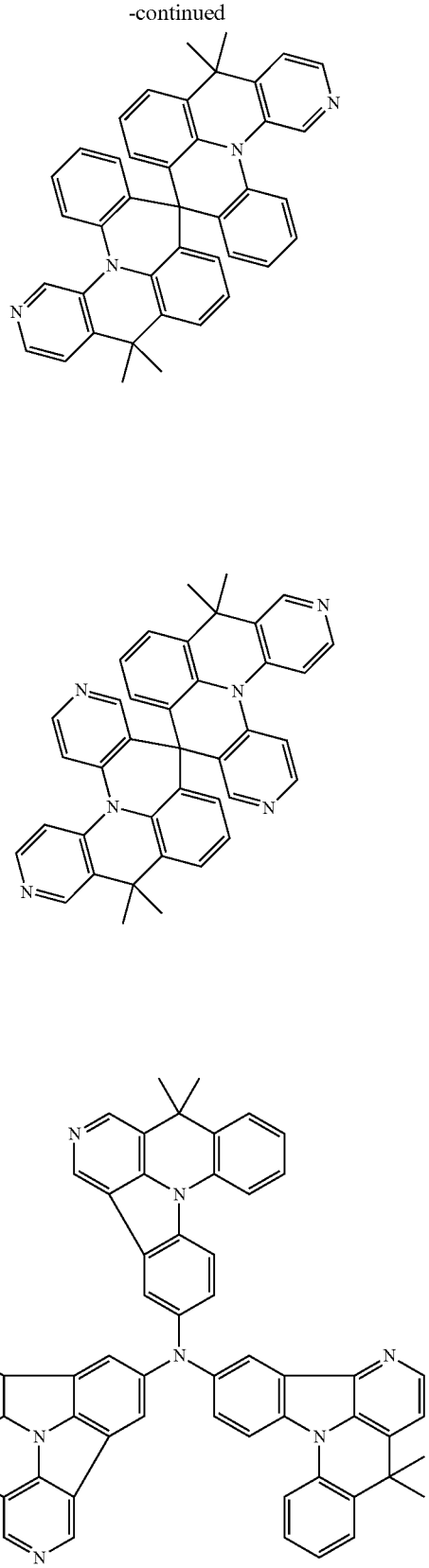

93
-continued
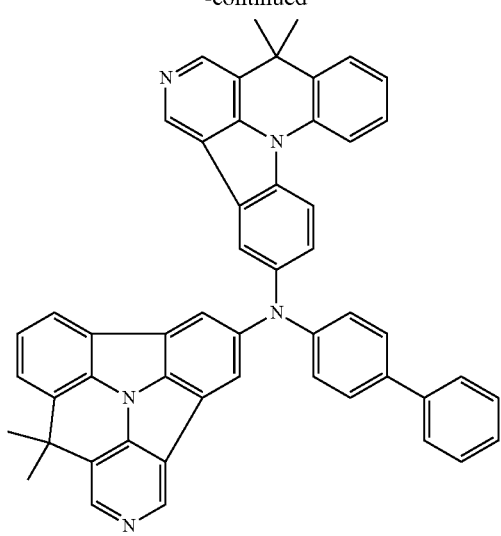
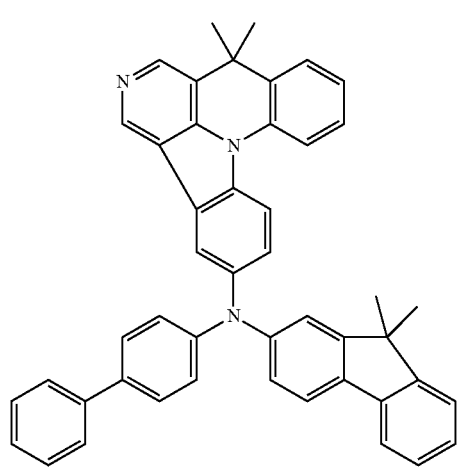
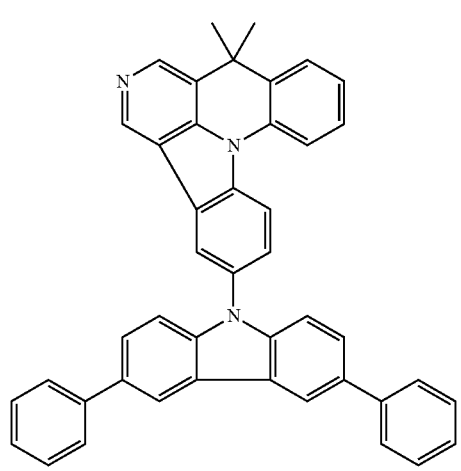
94
-continued
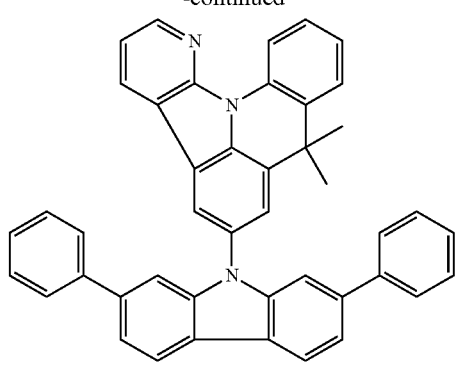
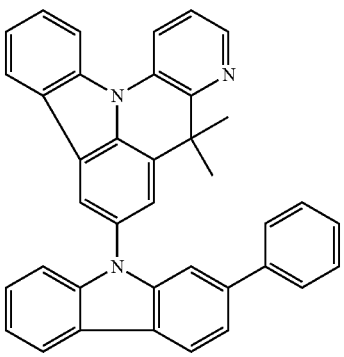
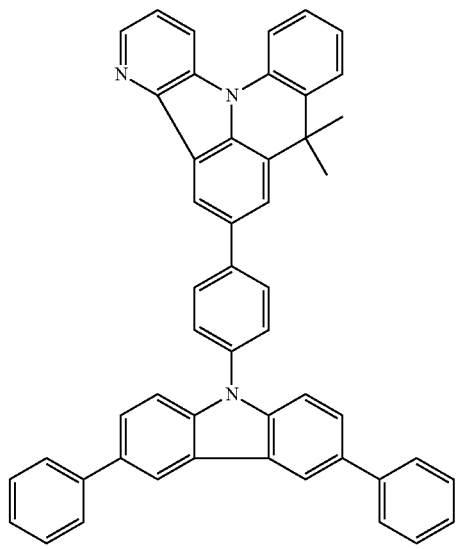

95
-continued
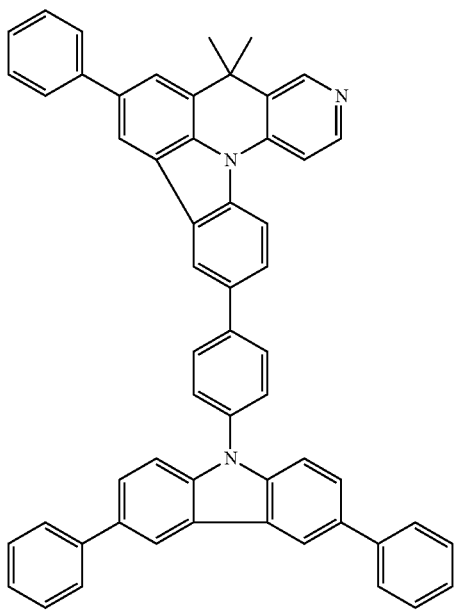
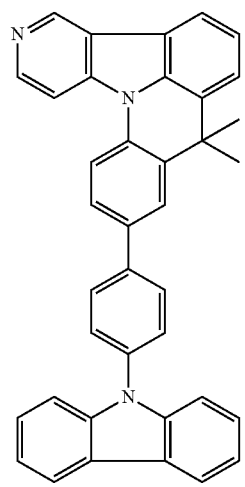
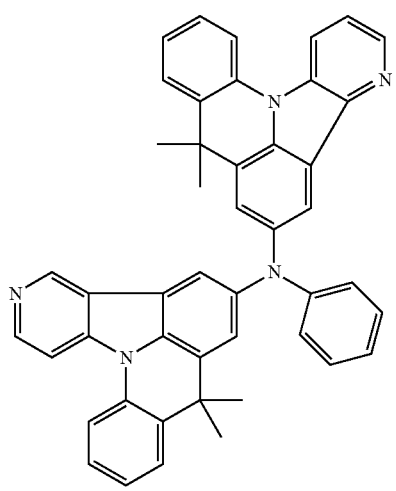
96
-continued
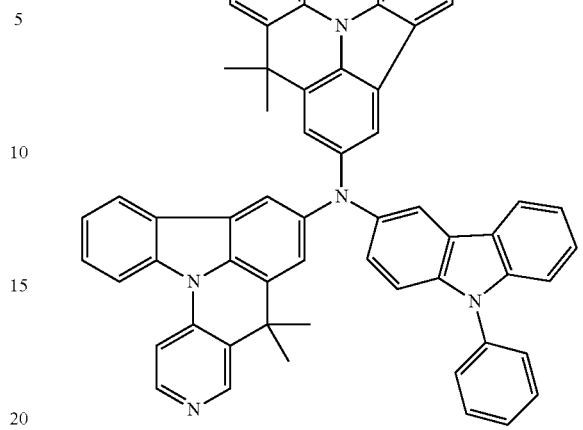
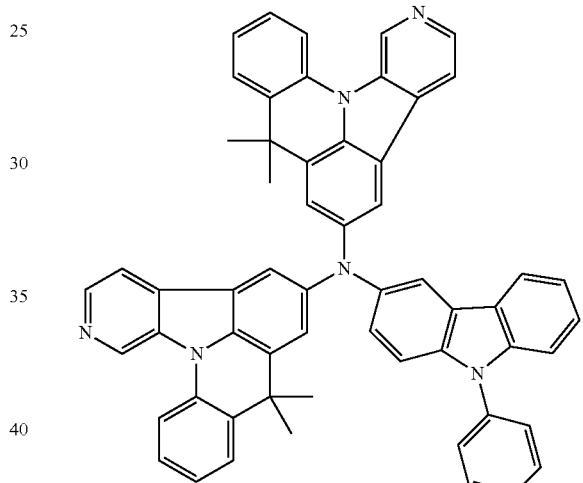
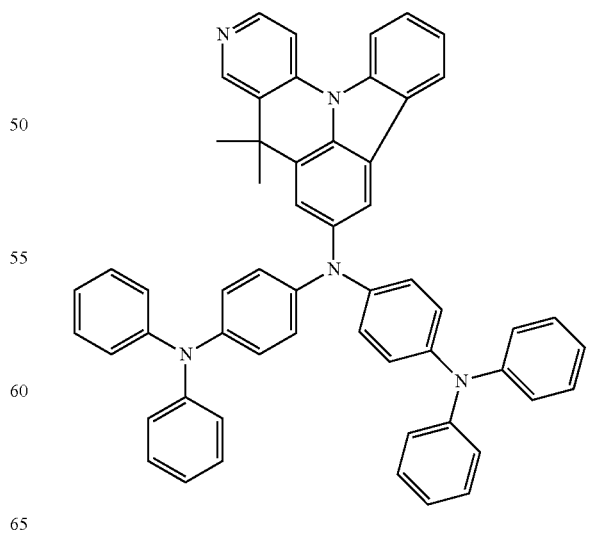

97
-continued
98
-continued
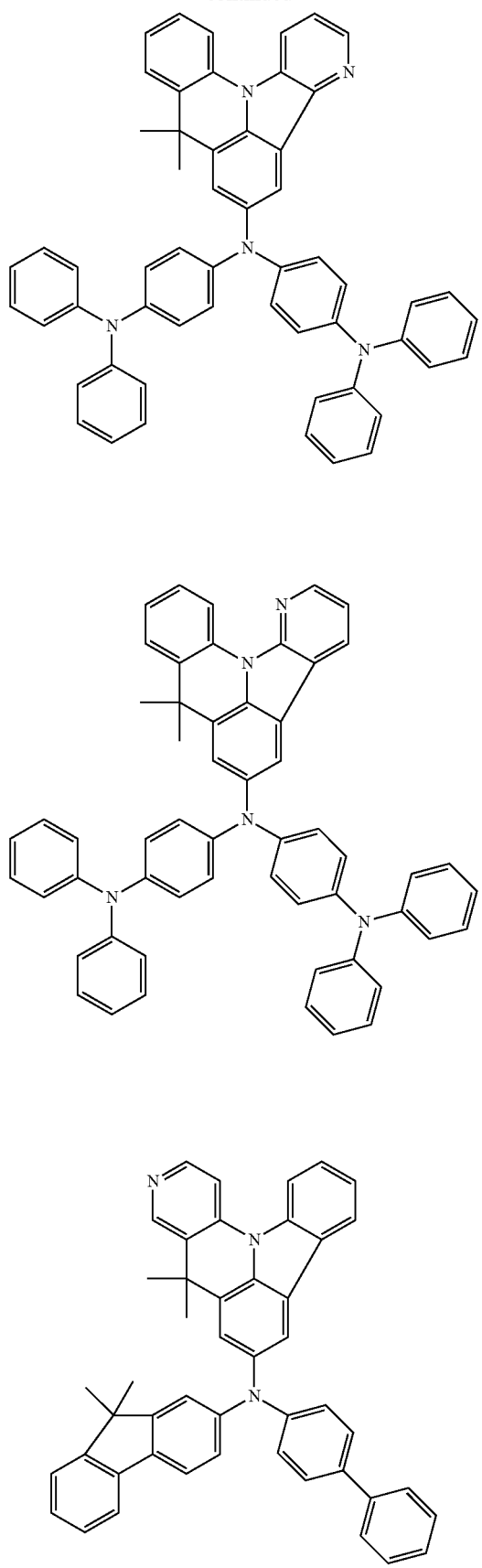
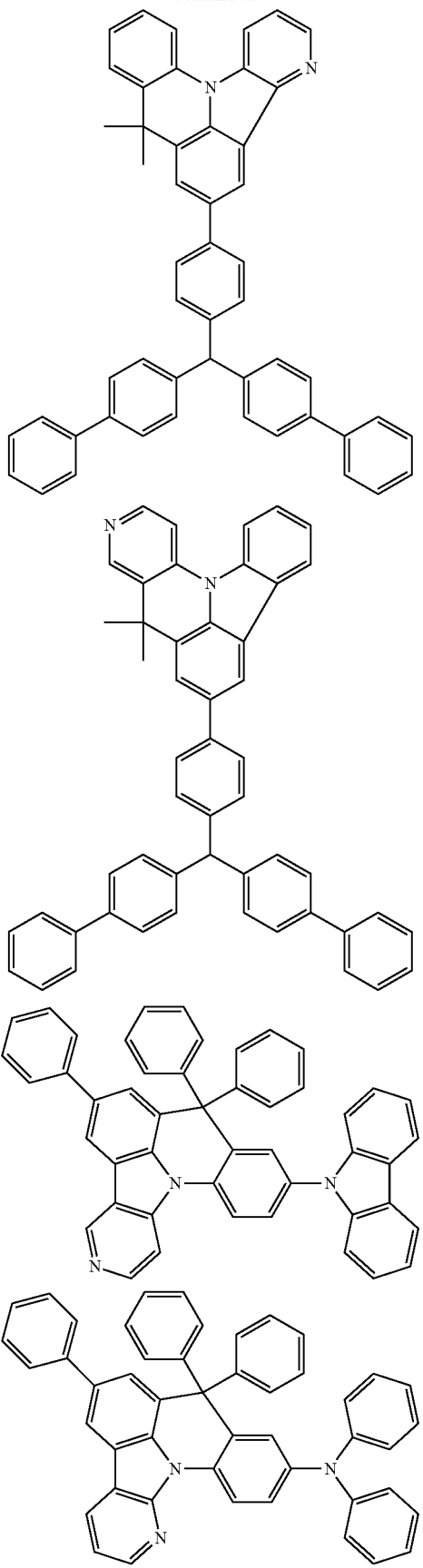

99
-continued
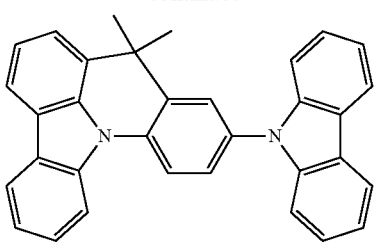
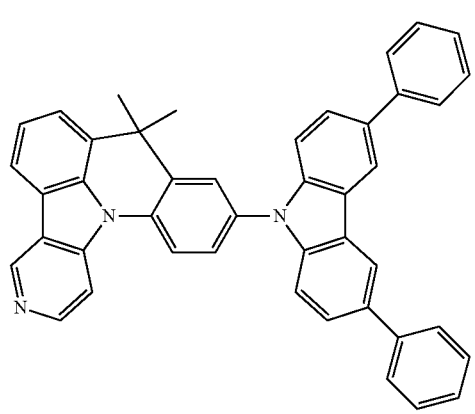
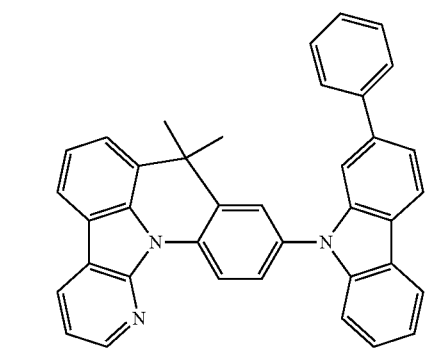
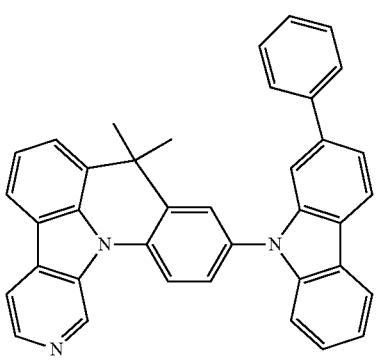
100
-continued
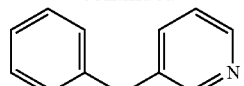
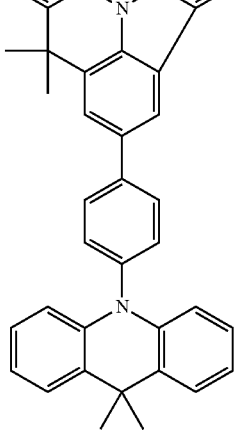
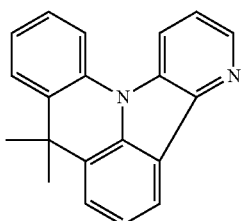
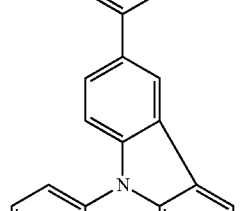
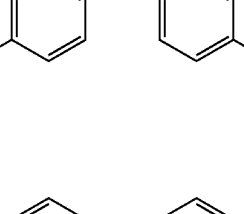
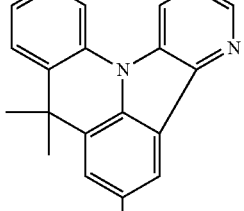
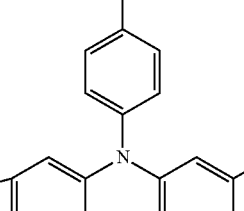
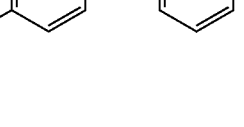

101
-continued
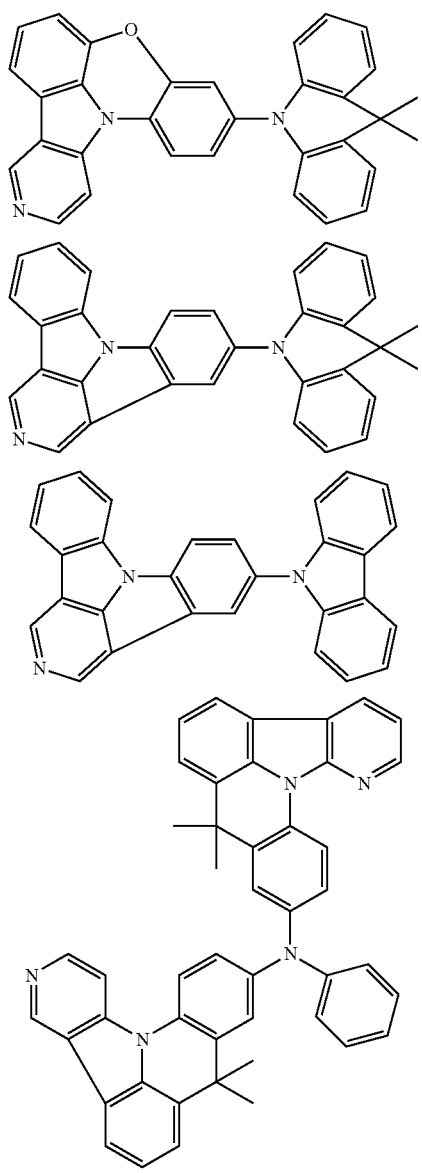
102
-continued
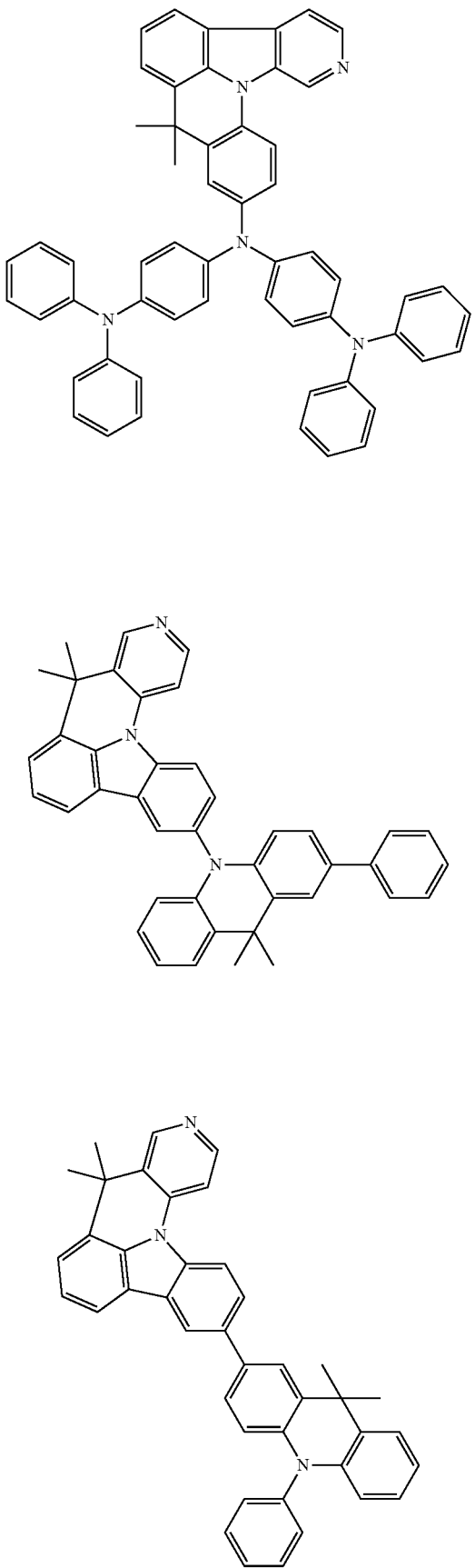

103
-continued
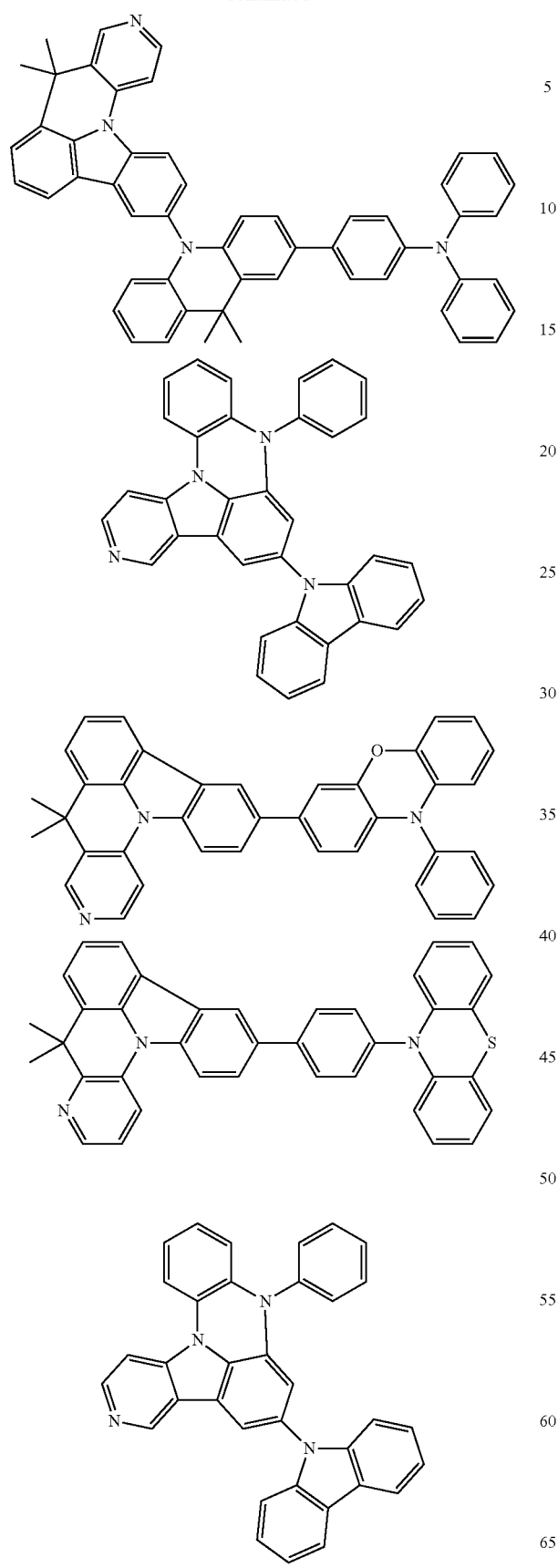
104
-continued
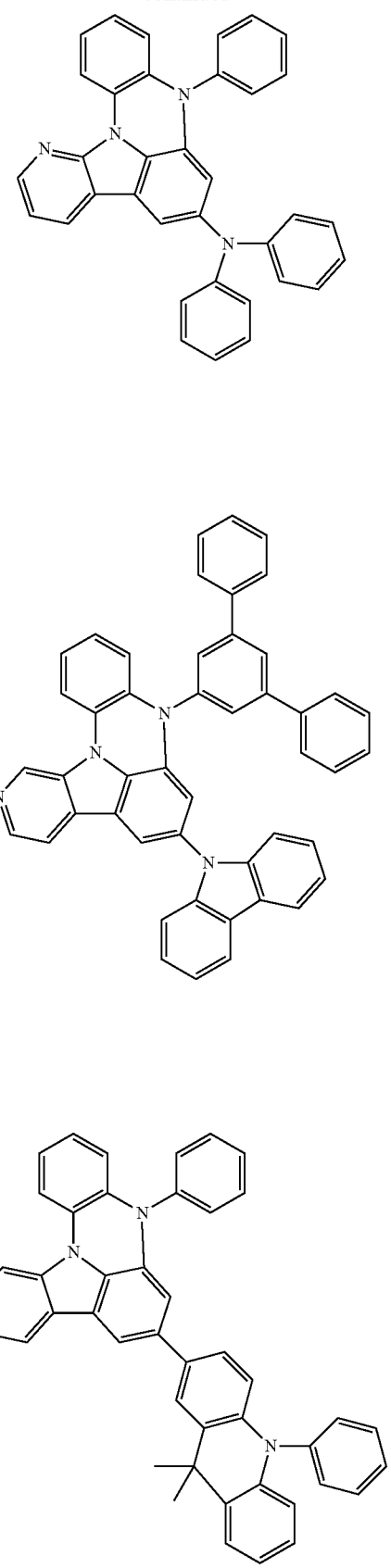

105
-continued
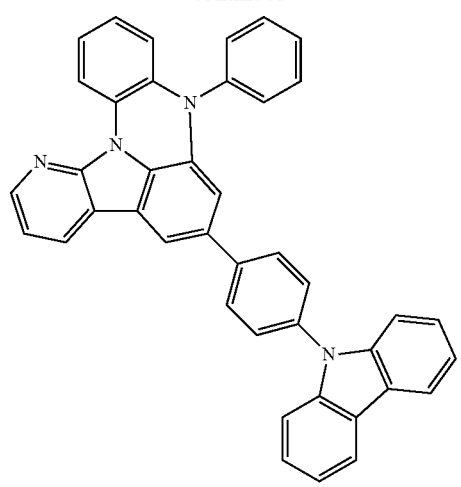
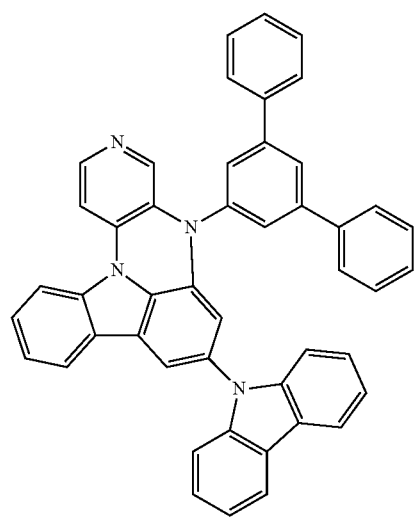
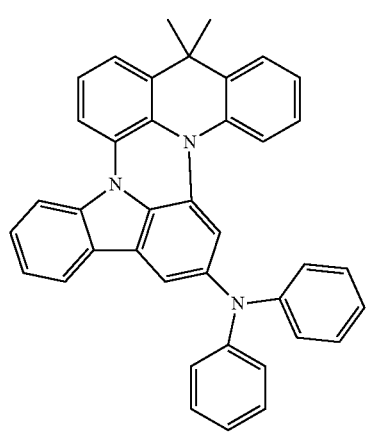
106
-continued
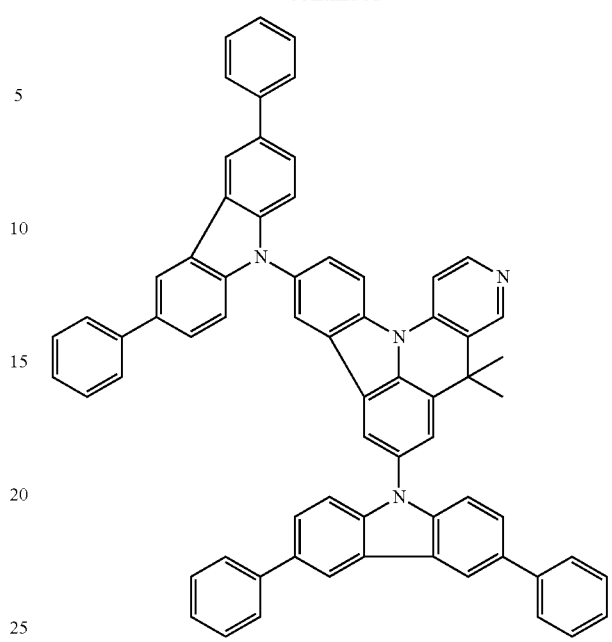

107
-continued
108
-continued
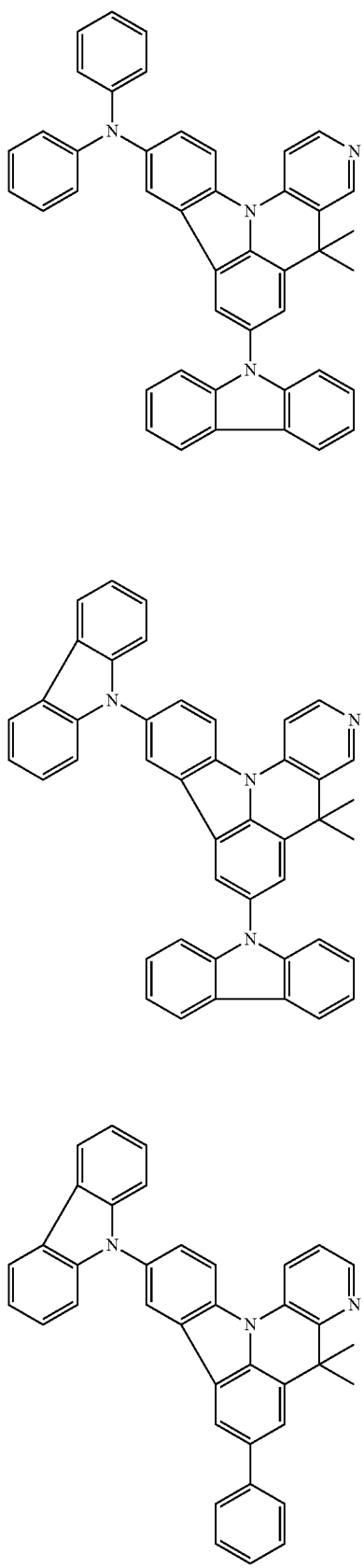
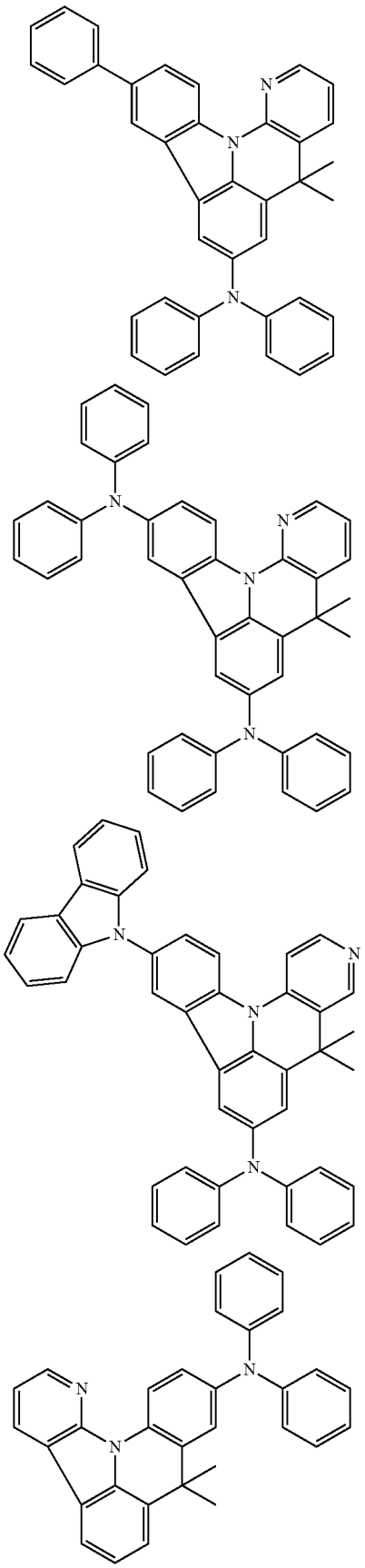

109
-continued
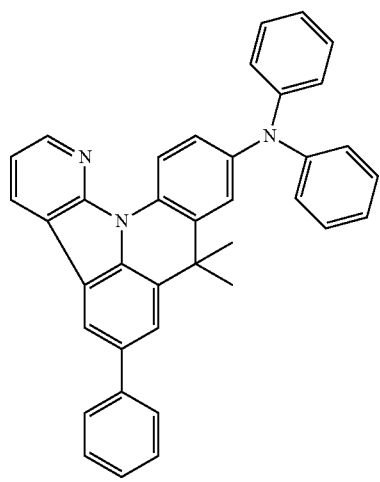
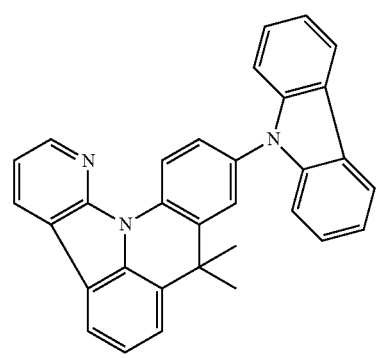
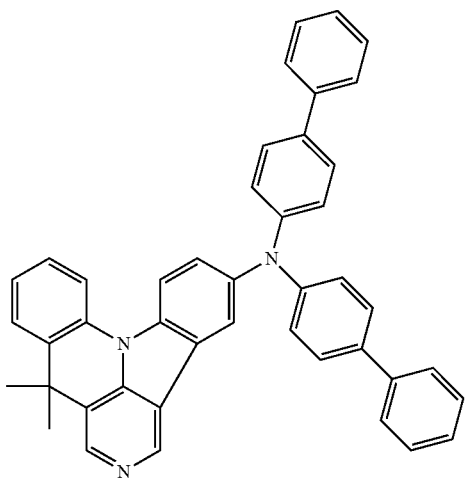
110
-continued
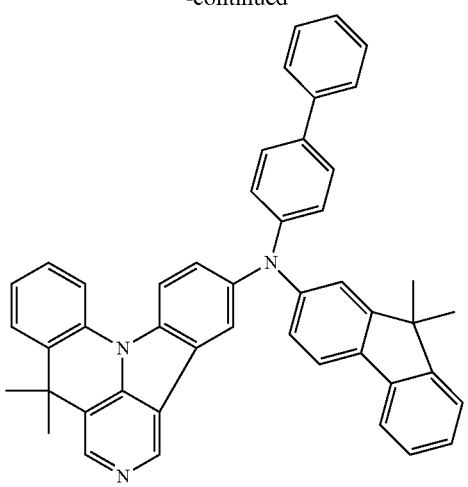
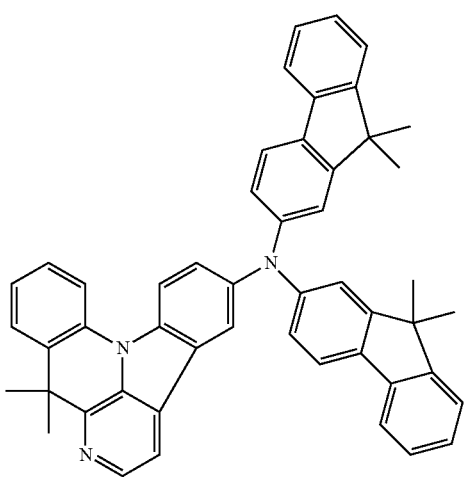
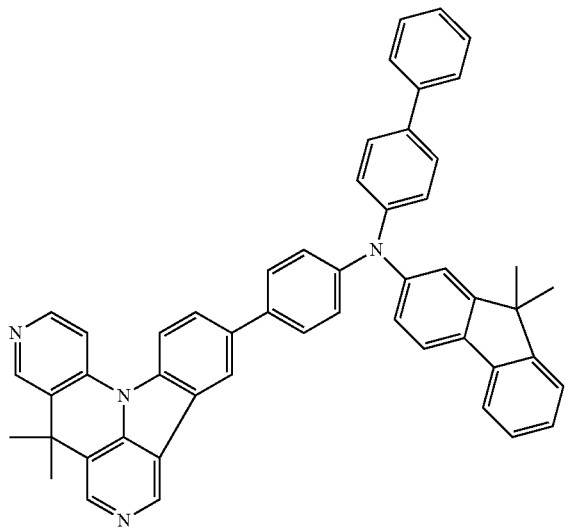

111
-continued
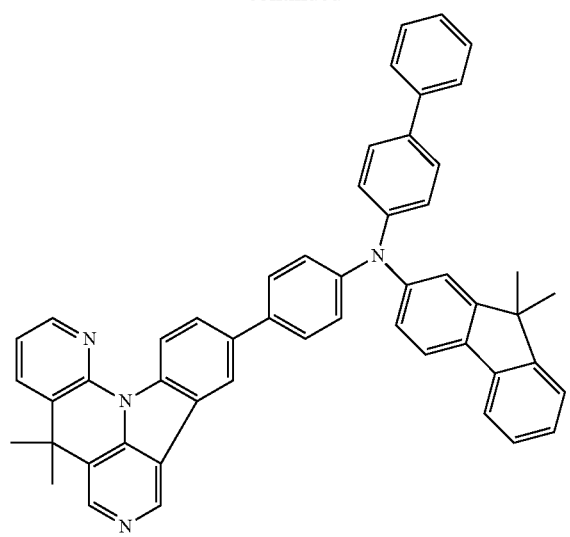
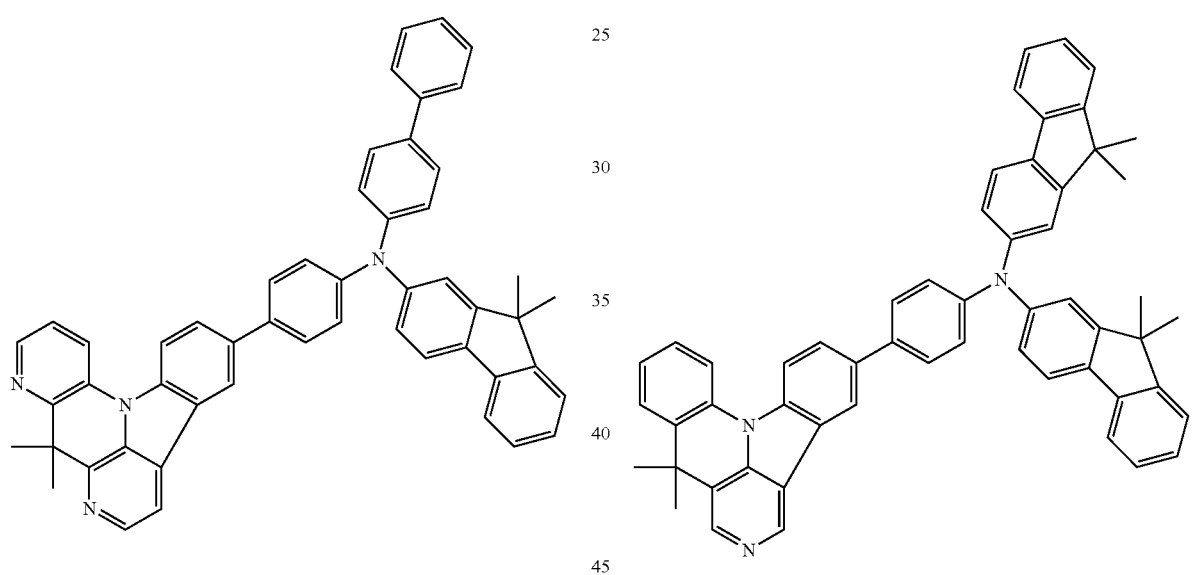
112
-continued
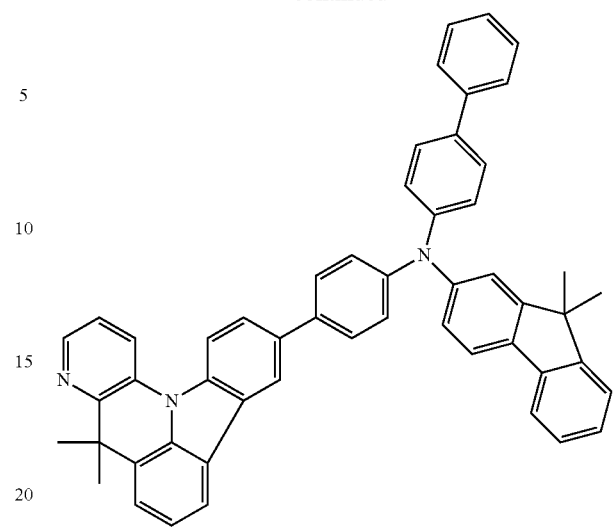
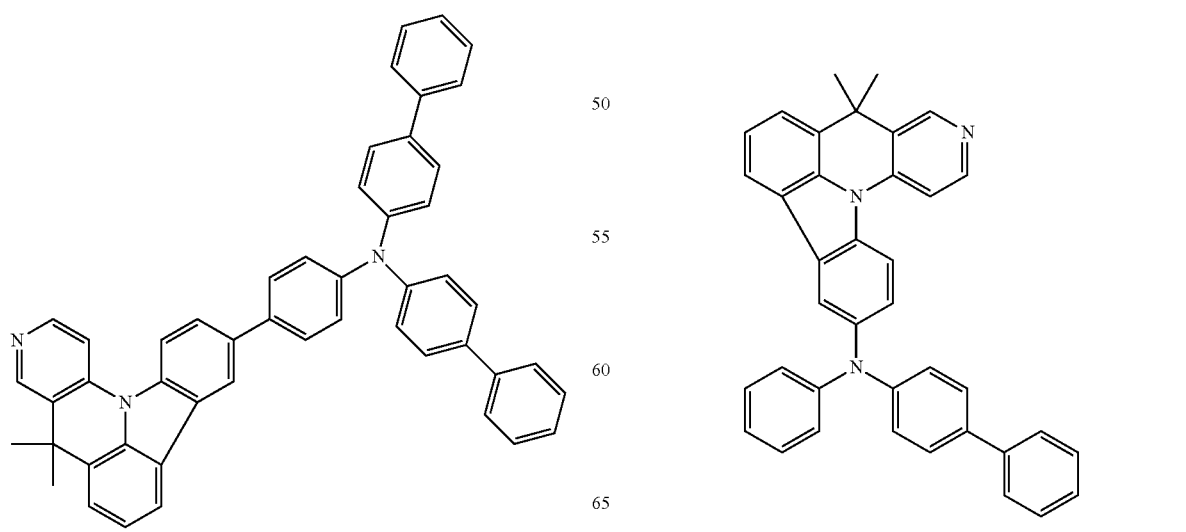

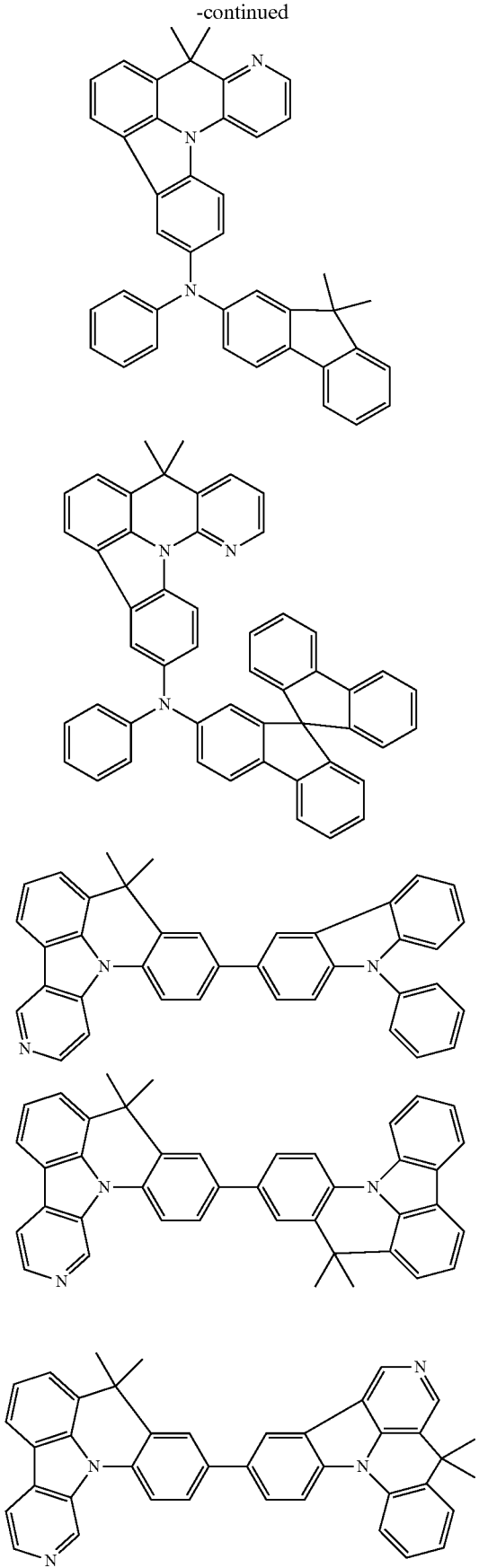

-continued

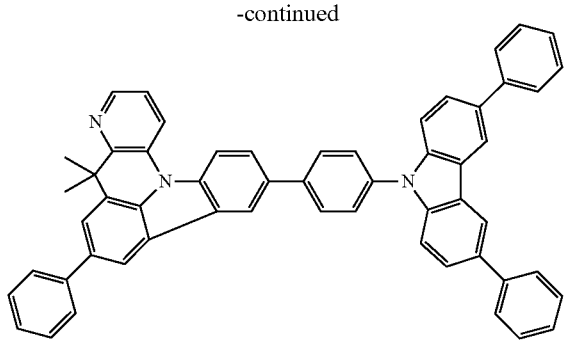

Two routes to compounds according to the invention are shown in Scheme 1 with reference to the substance class of the H-3,12b-diazabenzo-[a]aceanthryles. The compounds according to the invention obtained in this way can be functionalised further by conventional reaction sequences, such as bromination and subsequent C—C or C—N coupling reactions (Scheme 2). Compounds which are isomeric with respect to the pyridine N atom can be prepared entirely analogously.

Scheme 1:

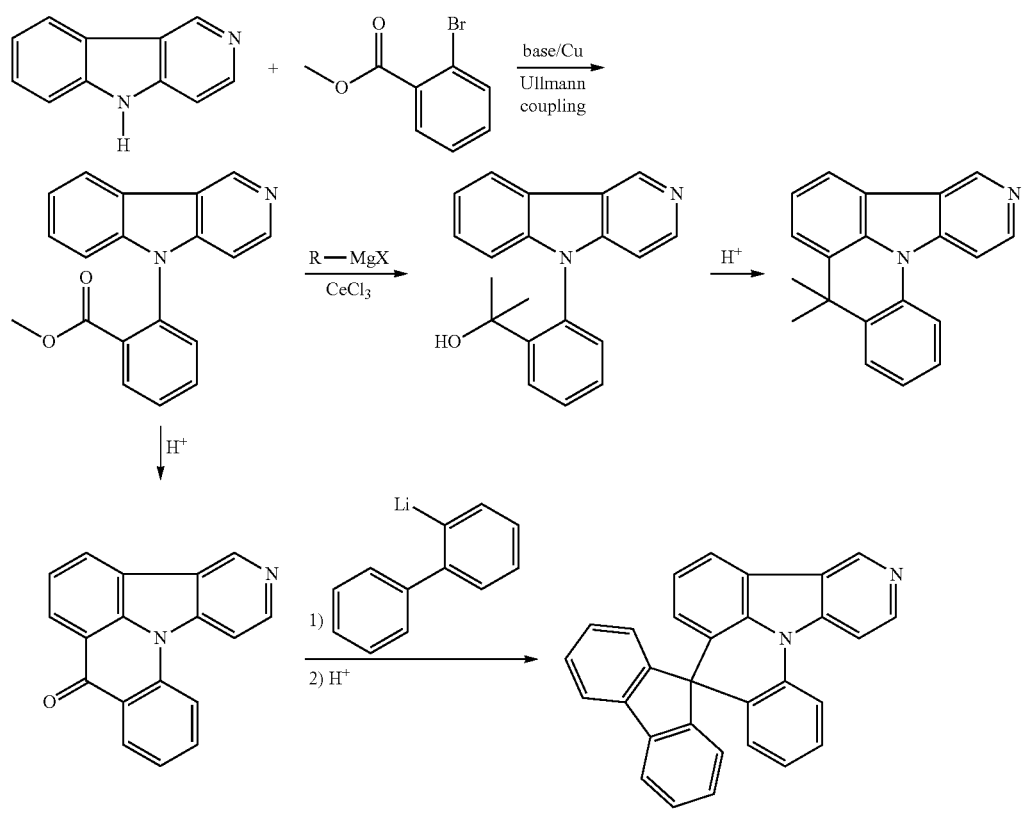

Scheme 2:

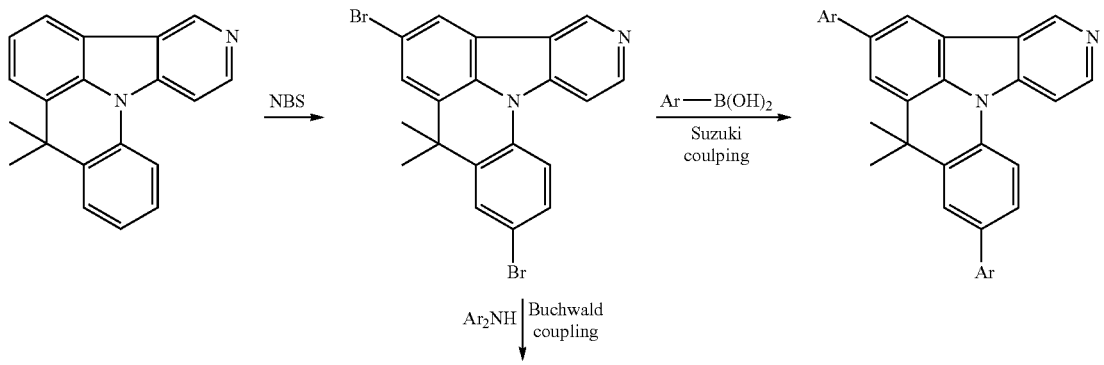

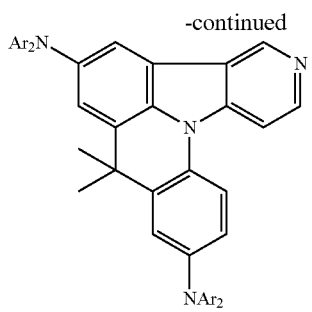

Compounds according to the invention containing two pyridine N atoms can be obtained in accordance with Scheme 3, where compounds which are isomeric with respect to the pyridine N atoms can also be prepared by this route and functionalised further as shown above.

Scheme 3:

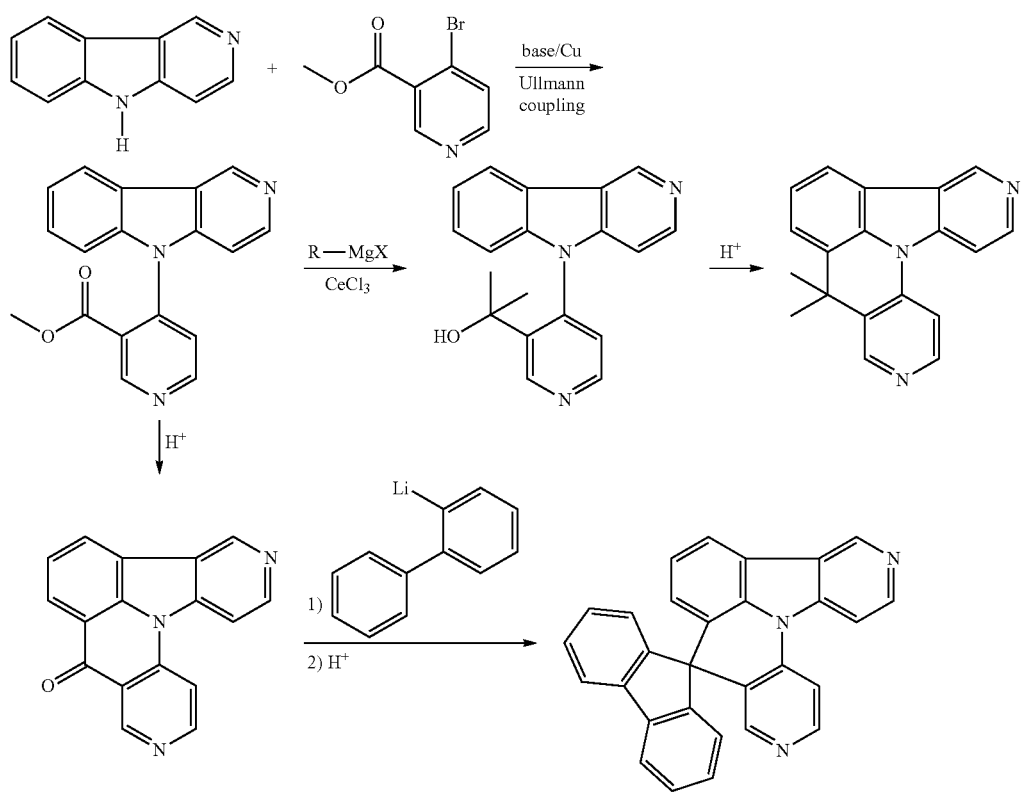

Compounds according to the invention containing three bridges Y are accessible in accordance with Scheme 4, where compounds which are isomeric with respect to the pyridine N atoms can also be prepared by this route and functionalised further as shown above.

Scheme 4:

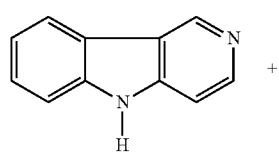

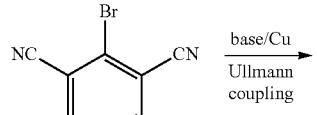

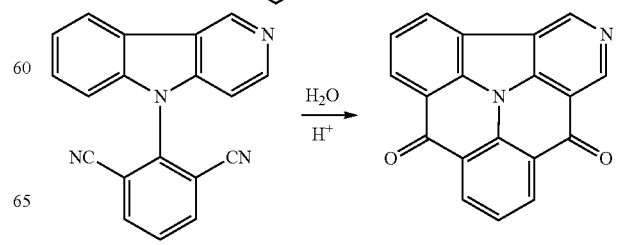

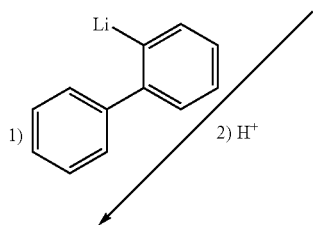
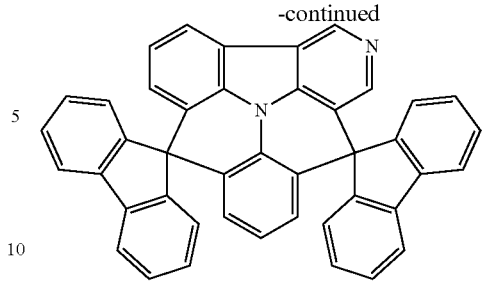
Compounds according to the invention can likewise be obtained starting from acridones and can be functionalised further as described above (bromination followed by C—C or C—N coupling) (Scheme 5). Compounds which are isomeric with respect to the pyridine N atom can also be prepared by this route.
Scheme 5:
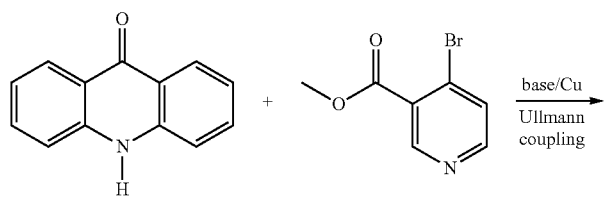
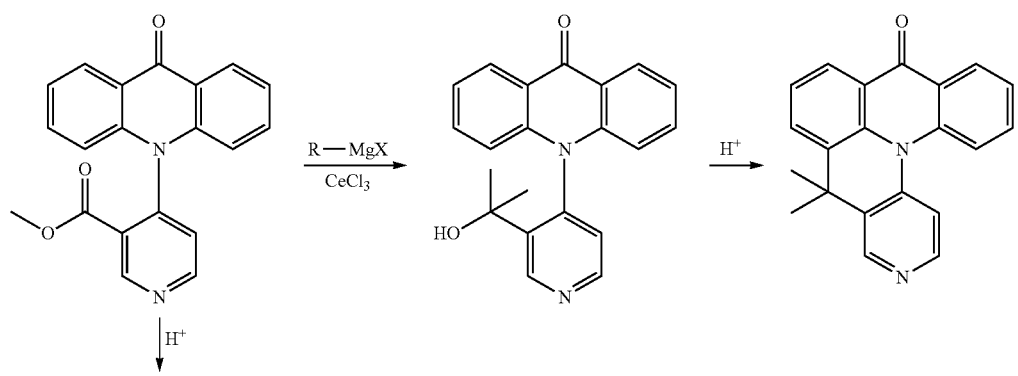
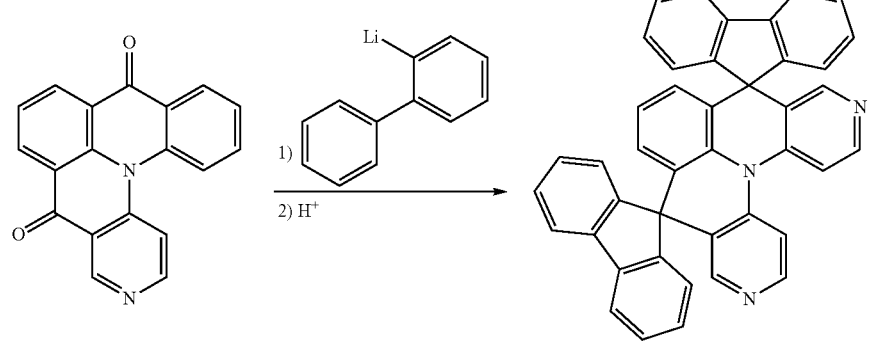

Compounds containing two sub-units according to the invention which are linked via a spiro C atom are accessible by the sequence shown in Scheme 6. The compounds obtained in this way can likewise be functionalised further by bromination followed by C—C or C—N coupling. Compounds which are isomeric with respect to the pyridine N atoms can also be prepared by this route.

The compounds according to the invention described above, in particular compounds which are substituted by reactive leaving groups, such as bromine, iodine, chlorine, boronic acid or boronic acid ester, or by reactive, polymerisable groups, such as olefins or oxetanes, can be used as monomers for the preparation of corresponding oligomers, dendrimers or polymers. The oligomerisation or polymerisa-

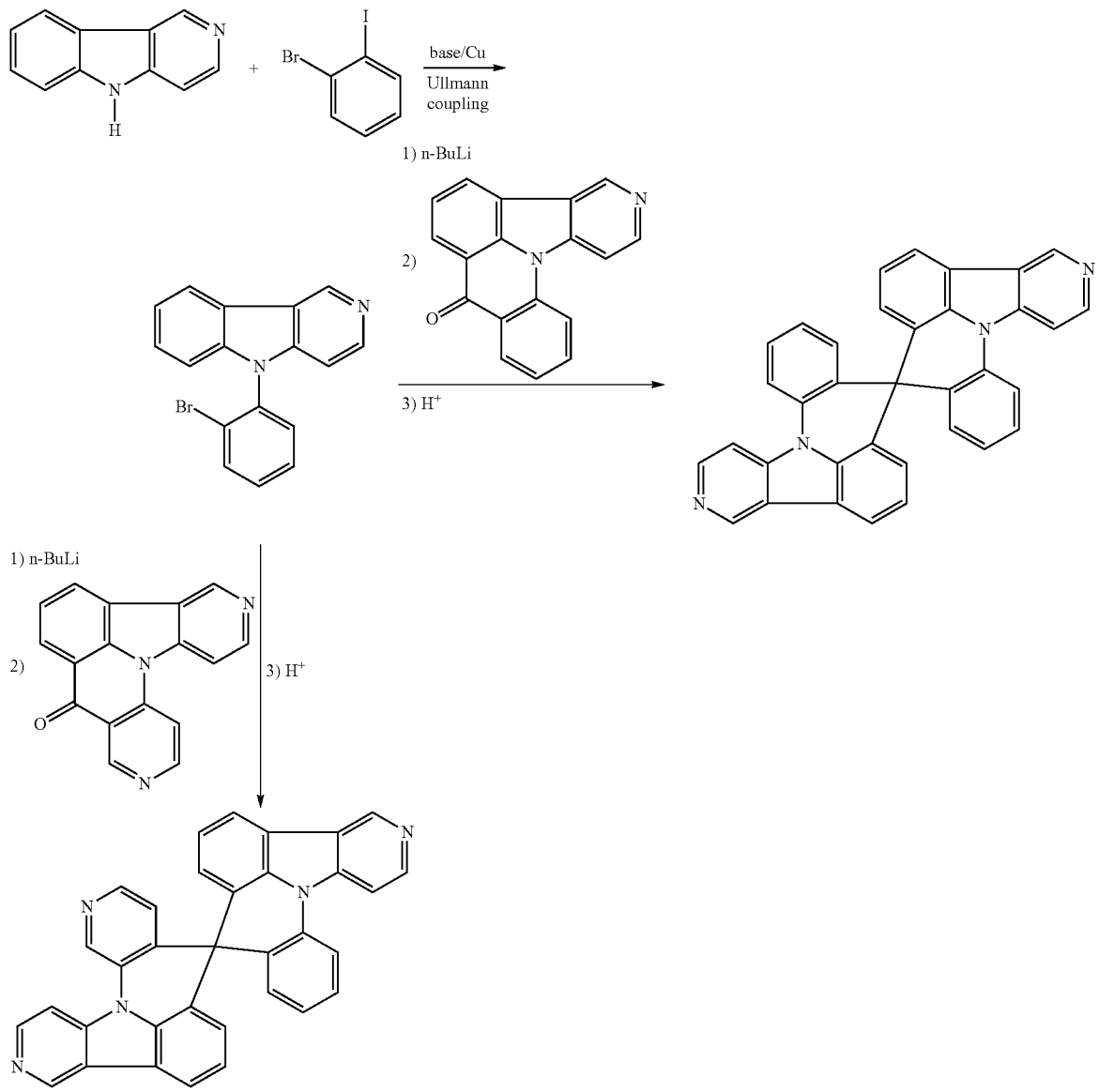

Scheme 6:

The present invention therefore furthermore relates to a process for the preparation of a compound of the formula (1), (2), (3) or (4), comprising the reaction steps of:
a) synthesis of the skeleton which is only bridged by one group Y;
b) introduction of the second and optionally third group Y, for example by an intramolecular ring-closure reaction;
c) optionally introduction of the radical(s) R.

The intramolecular ring-closure reaction is, in particular, an intramolecular Friedel-Crafts alkylation. The radicals R are preferably introduced by a metal-catalysed coupling reaction.

tion here is preferably carried out via the halogen functionality or the boronic acid functionality or via the polymerisable group. It is furthermore possible to crosslink the polymers via groups of this type. The compounds and oligomers, polymers and dendrimers according to the invention can be employed as crosslinked or uncrosslinked layer.

The invention therefore furthermore relates to oligomers, polymers or dendrimers comprising one or more of the compounds according to the invention mentioned above, in which, instead of one or more radicals R, $R^1$ and/or $R^2$, one or more bonds are present from the compound according to the invention to the polymer, oligomer or dendrimer. Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers in which the units of the formulae (1) to (31) and (11a) to (31e) are present to the extent of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers may also comprise further units, for example hole-transport units, in particular those based on triarylamines, and/or electron-transport units. In addition, the polymers may comprise phosphorescent emitters, either copolymerised or mixed in as a blend. It is precisely the combination of units of the formulae (1) to (31) and (11a) to (31e) with phosphorescent emitters that gives particularly good results.

Furthermore, the compounds of the formulae (1) to (31) and (11a) to (31e) may also be functionalised further and thus converted into extended structures. An example which may be mentioned here is the Suzuki reaction with arylboronic acids or the Hartwig-Buchwald reaction with primary or secondary amines. Thus, the compounds of the formulae (1) to (31) and (11a) to (31e) can also be bonded directly to phosphorescent metal complexes or also to other metal complexes.

The present invention furthermore relates to mixtures comprising at least one compound according to the invention or a corresponding oligomer, polymer or dendrimer and at least one further compound. The further compound can be, for example, a fluorescent or phosphorescent dopant if the compound according to the invention is used as matrix material. Suitable fluorescent and phosphorescent dopants are mentioned below in connection with the organic electroluminescent devices and are also preferred for the mixtures according to the invention. The further compound may also be a dopant if the compound according to the invention is a hole-transport or electron-transport compound. Suitable dopants are mentioned below in connection with the organic electroluminescent devices.

For processing from solution or from the liquid phase, for example by spin coating or by printing processes, solutions or formulations of the compounds according to the invention are necessary. It may be preferred to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, a suspension or a mini-emulsion, comprising at least one compound according to the invention and one or more solvents, in particular organic solvents. The way in which solutions of this type can be prepared is known to the person skilled in the art and is described, for example, in WO 02/072714, WO 03/019694 and the literature cited therein.

The compounds, oligomers, polymers and dendrimers according to the invention are suitable for use in an electronic device. An electronic device here is taken to mean a device which comprises at least one layer which comprises at least one organic compound. However, the component may also comprise inorganic materials or also layers which are built up completely from inorganic materials.

The present invention therefore furthermore relates to the use of the compounds, oligomers, polymers or dendrimers according to the invention mentioned above in an electronic device, in particular in an organic electroluminescent device.

The present invention still furthermore relates to an electronic device comprising at least one of the compounds, oligomers, polymers or dendrimers according to the invention mentioned above. The preferences mentioned above likewise apply to the electronic devices.

The electronic device is preferably selected from the group consisting of organic electroluminescence (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), but preferably organic electroluminescent devices (OLEDs, PLEDs), particularly preferably phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers which have, for example, an exciton-blocking function to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 05/011013). These may be fluorescent or phosphorescent emission layers or hybrid systems, in which fluorescent and phosphorescent emission layers are combined with one another.

The compound according to the invention in accordance with the embodiments mentioned above can be employed in different layers, depending on the precise structure. Preference is given to an organic electroluminescent device comprising a compound of the formulae (1) to (31) or formulae (11a) to (31e) as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution. The preferred embodiments mentioned above also apply here to the use of the materials in organic electronic devices.

In a preferred embodiment of the invention, the compound of the formulae (1) to (31) or formulae (11a) to (31e) is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formulae (1) to (31) or formulae (11a) to (31e) is employed as matrix material for an emitting compound in an emitting layer, it is preferably employed in combination with one or more phosphorescent materials (triplet emitters). Phosphoresce in the sense of this invention is taken to mean the luminescence from an excited state having relatively high spin multiplicity, i.e. a spin state>1, in particular from an excited triplet state. For the purposes of this application, all luminescent transition-metal complexes and all luminescent lanthanide complexes, in particular all iridium, platinum and copper complexes, are to be regarded as phosphorescent compounds.

The mixture of the compound of the formulae (1) to (31) and (11a) to (31e) and the emitting compound comprises between 99 and 1% by vol., preferably between 98 and 10% by vol., particularly preferably between 97 and 60% by vol., in particular between 95 and 80% by vol., of the compound of the formulae (1) to (31) and (11a) to (31e), based on the mixture as a whole comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the mixture as a whole comprising emitter and matrix material.

A further preferred embodiment of the present invention is the use of the compound of the formulae (1) to (31) or formulae (11a) to (31e) as matrix material for a phosphorescent emitter in combination with a further matrix material. Particularly suitable matrix materials which can be employed in combination with the compounds of the formulae (1) to (31) or formulae (11a) to (31e) are aromatic ketones, aromatic phosphine oxides or aromatic sulfoxides or sulfones, for example in accordance with WO 04/013080, WO 04/093207, WO 06/005627 or WO 2010/006680, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056,746, indenocarbazole derivatives, for example in accordance with the unpublished applications DE 102009023155.2 or DE 102009031021.5, azacarbazole derivatives, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, triazine derivatives, for example in accordance with WO 10/015,306, WO 07/063,754 or WO 08/056,746, zinc complexes, for example in accordance with EP 652273 or WO 09/062,578, diazasilole or tetraazasilole derivatives, for example in accordance with WO 10/054,729, diazaphosphole derivatives, for example in accordance with WO 10/054,730, or bridged carbazole derivatives, for example in accordance with US 2009/0136779 or the unpublished application DE 102009048791.3. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible range, on suitable excitation and in addition contain at least one atom having an atomic number greater than 20, preferably greater than 38 and less than 84, particularly preferably greater than 56 and less than 80, in particular a metal having this atomic number. The phosphoresce emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373, US 2005/0258742, WO 09/146,770, WO 10/015,307, WO 10/031,485, WO 10/054,731, WO 10/054,728 and WO 10/086,089. Also suitable are the complexes in accordance with the unpublished applications DE 102009011223.5 and DE 102009013041.1. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without an inventive step.

Examples of suitable phosphorescent compounds are shown in the following table.

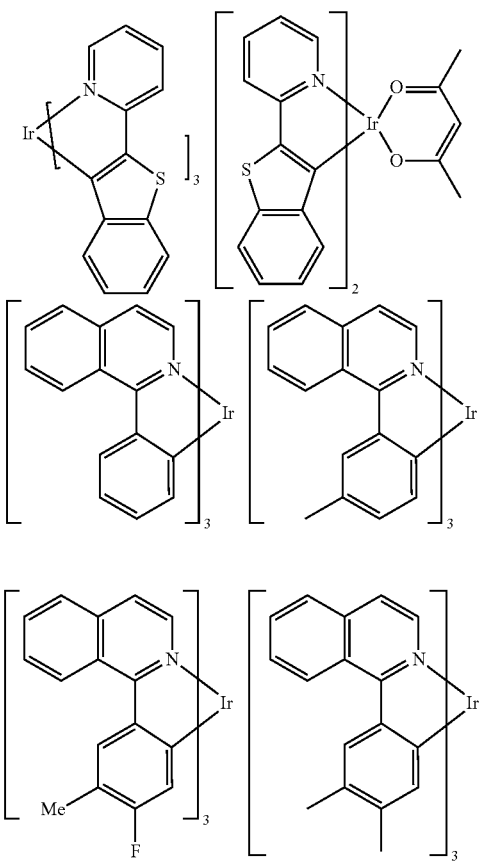

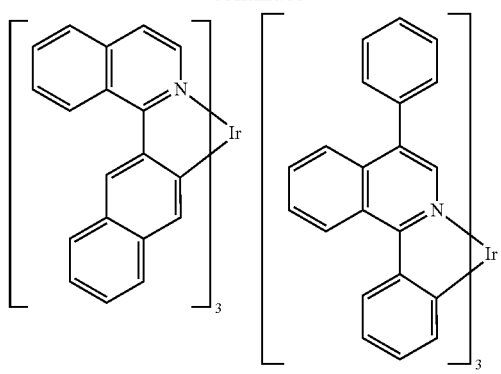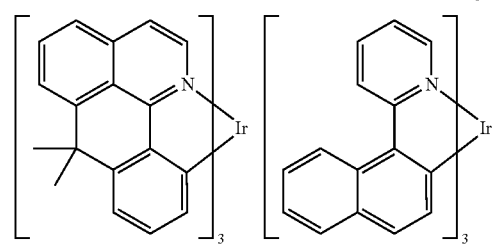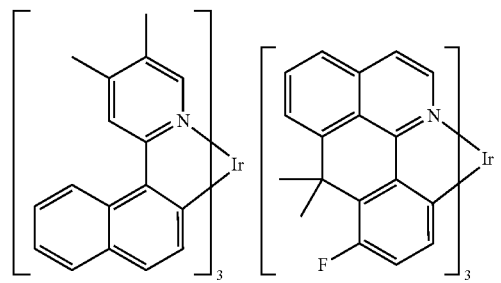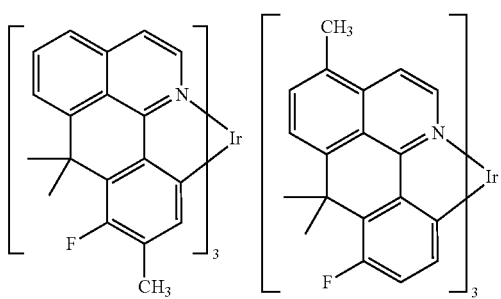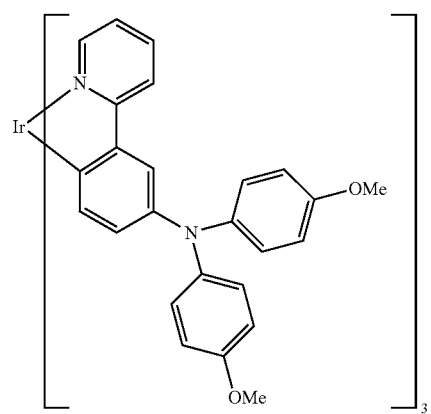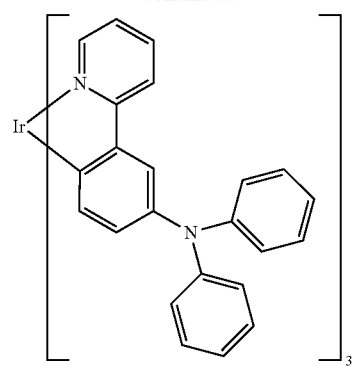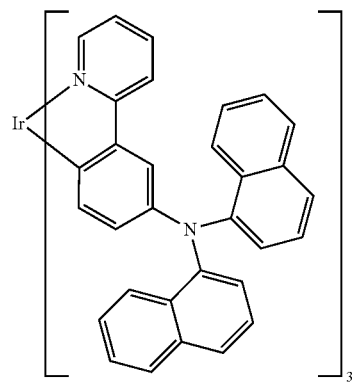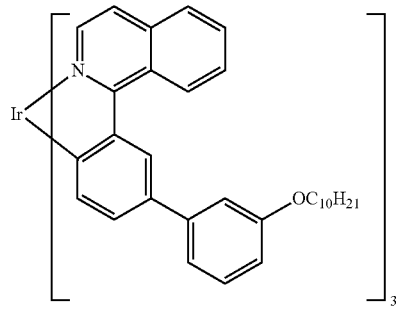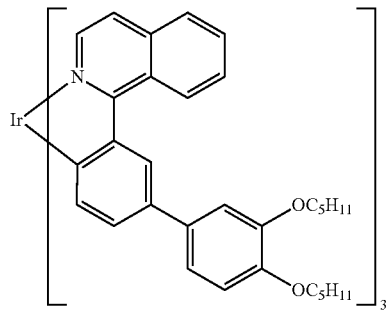

129
-continued
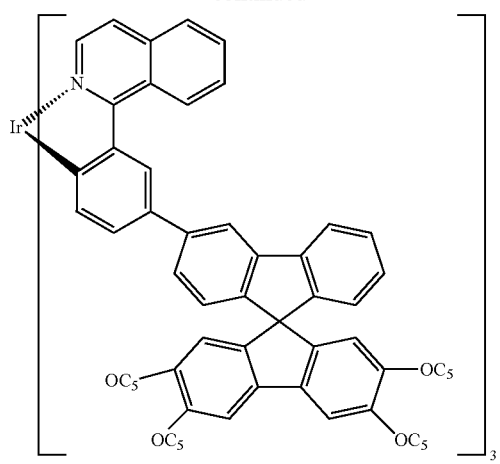
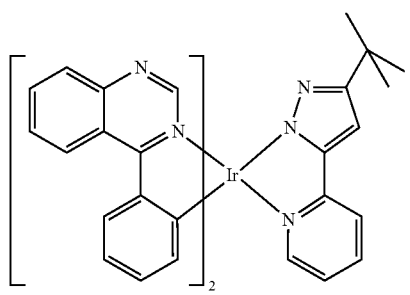
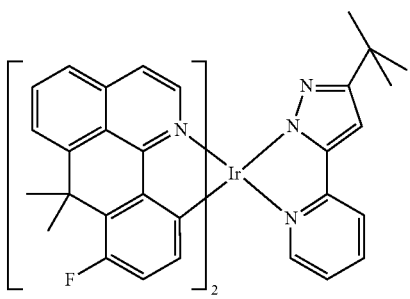
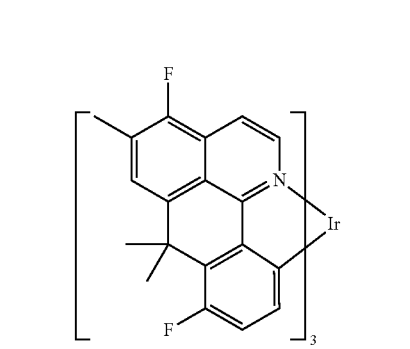
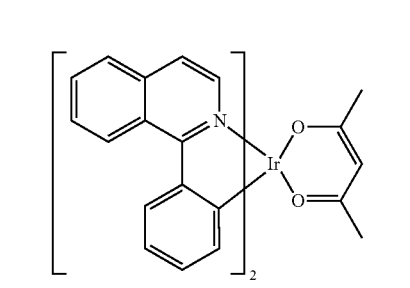
130
-continued
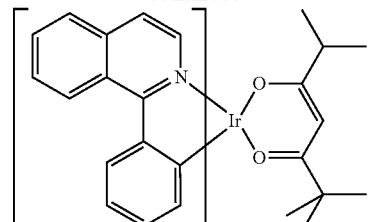
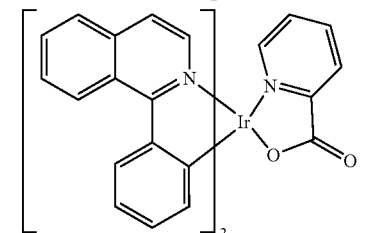
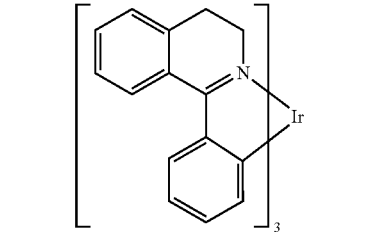
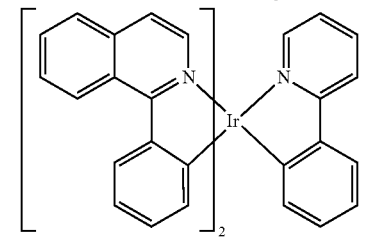
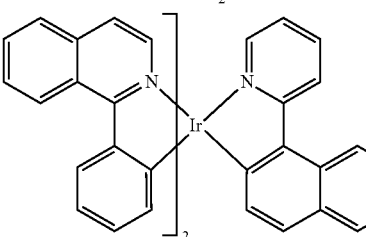
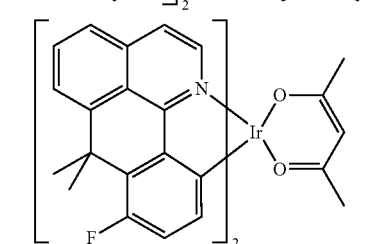
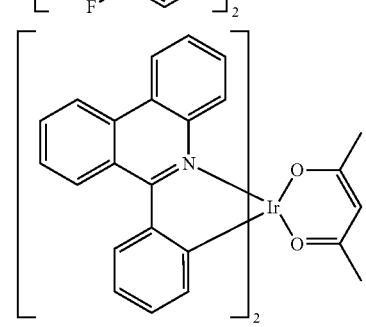

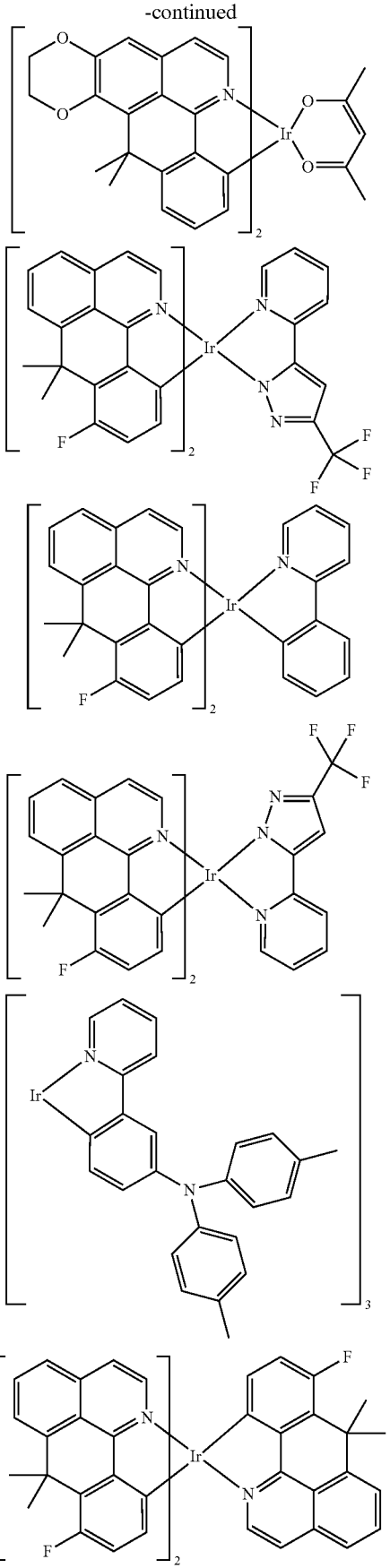
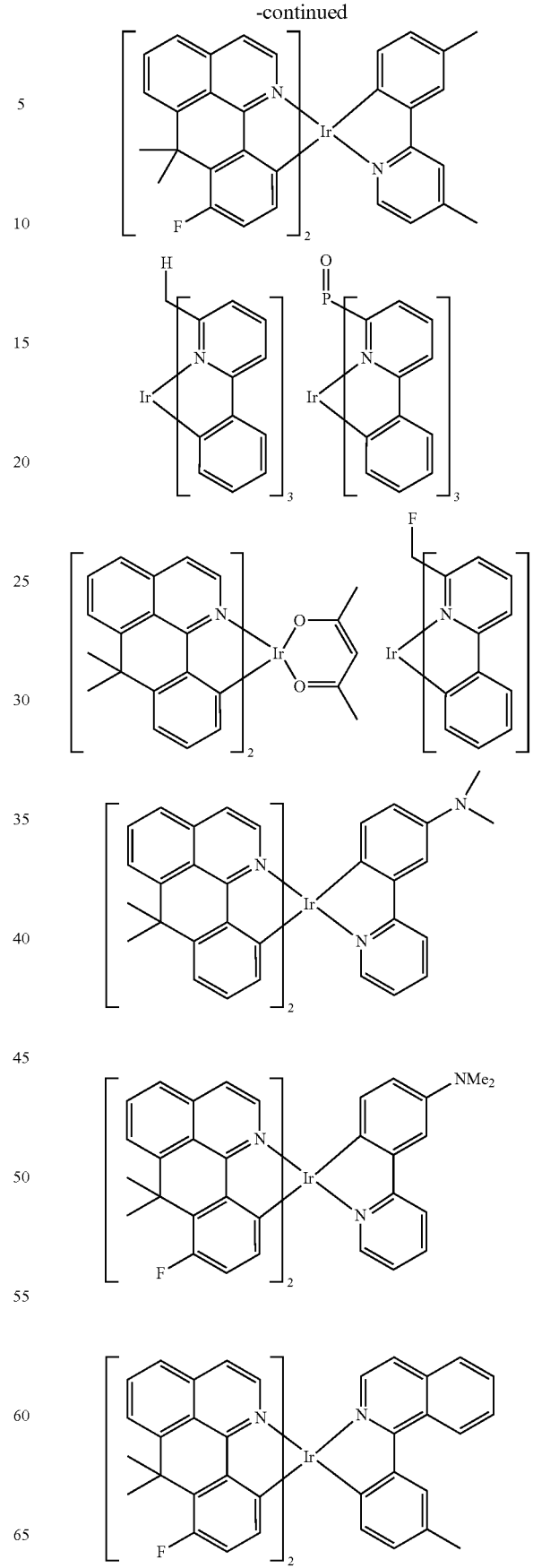

133
-continued
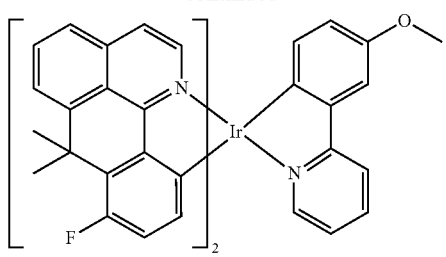
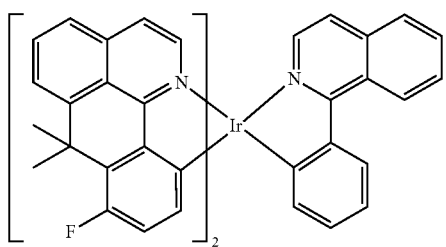
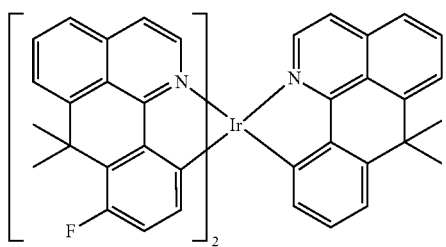
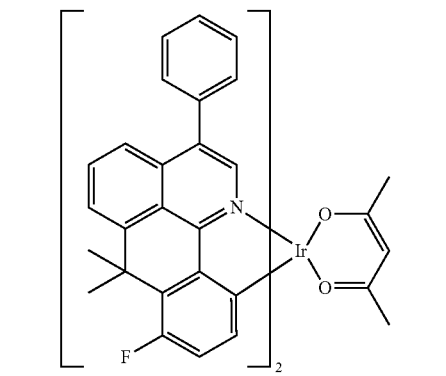
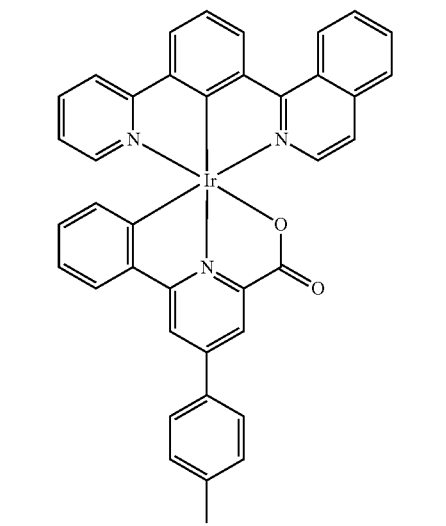
134
-continued
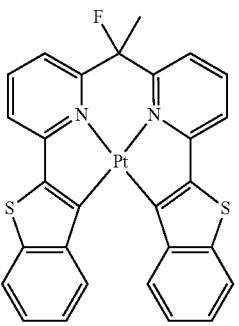
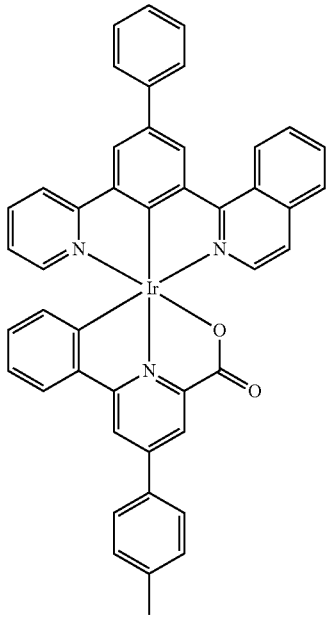
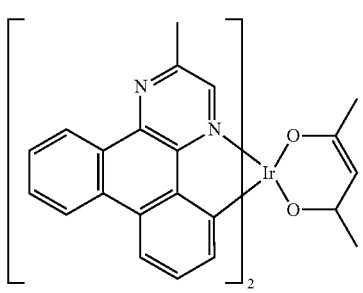
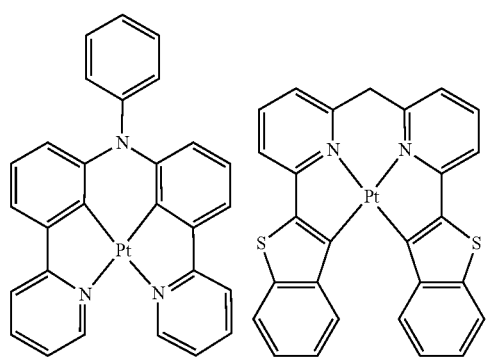

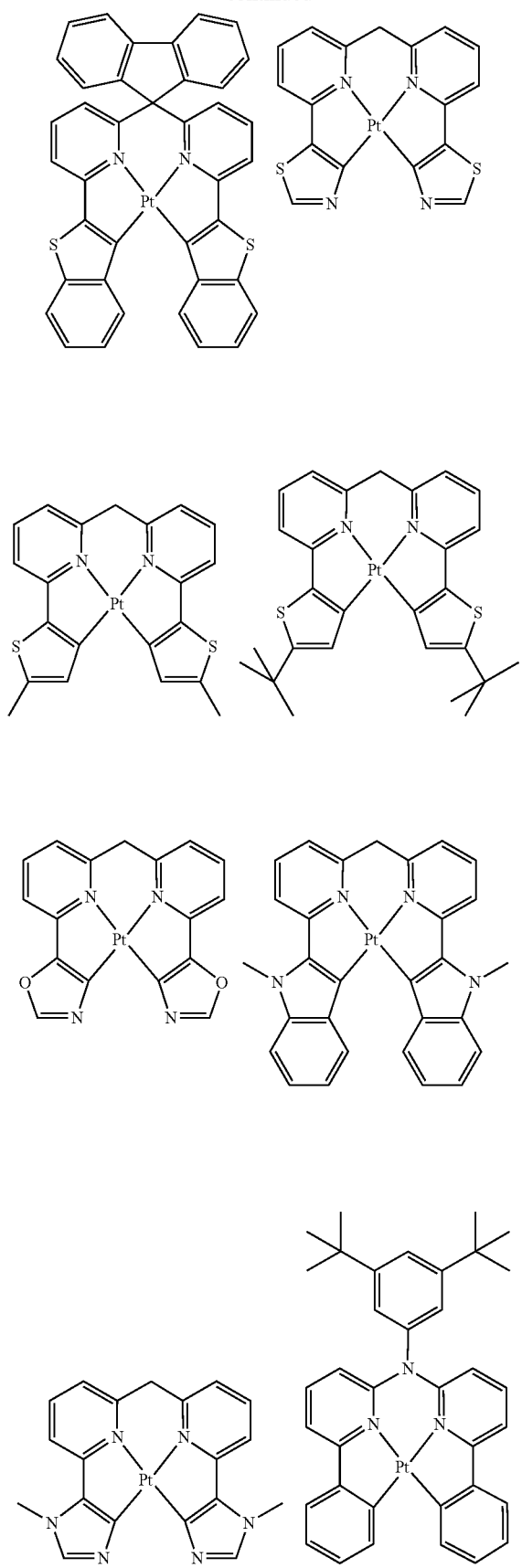
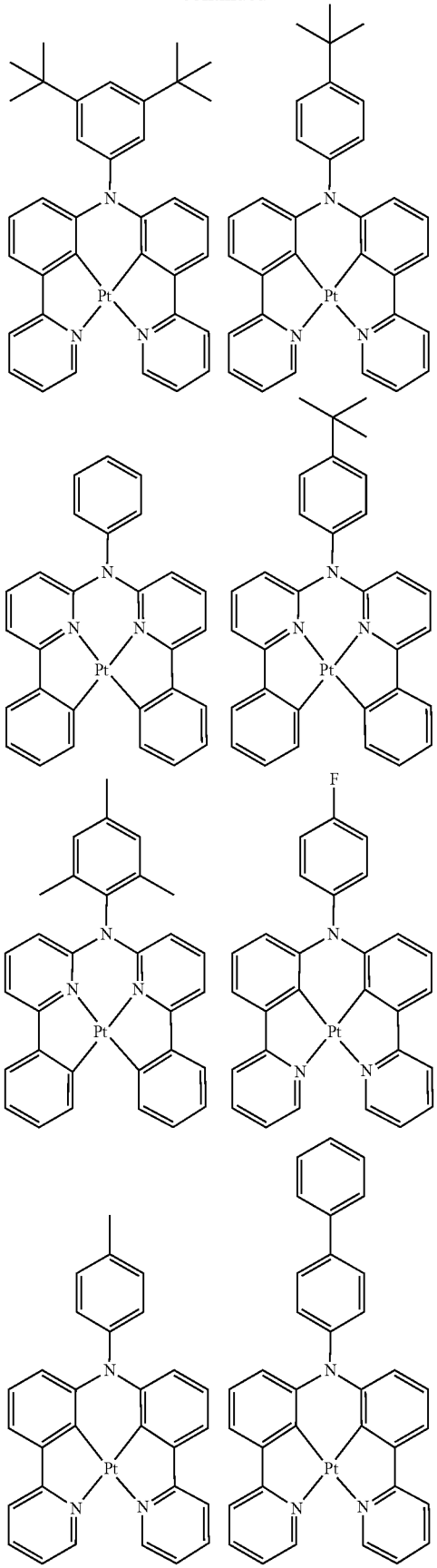

137
-continued
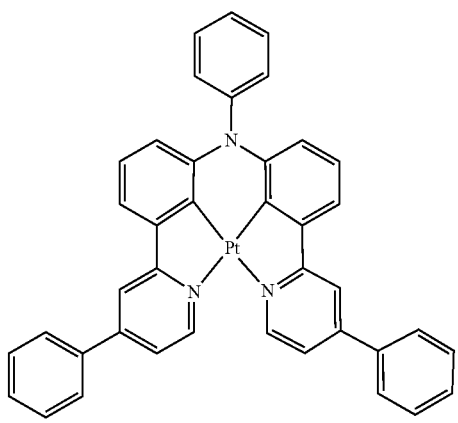
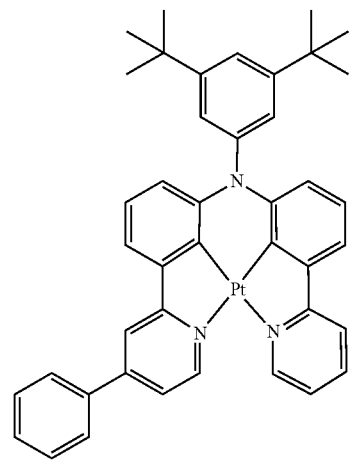
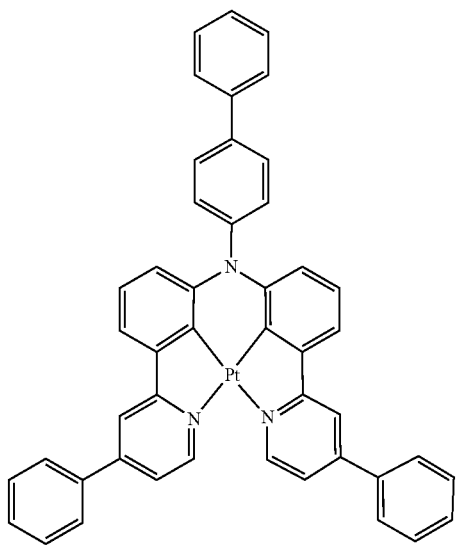
138
-continued
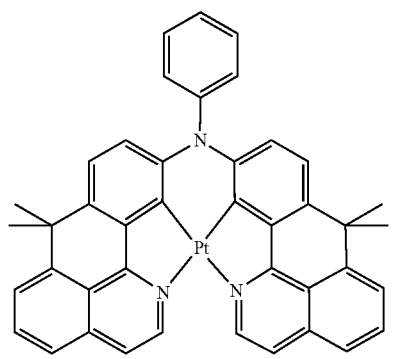
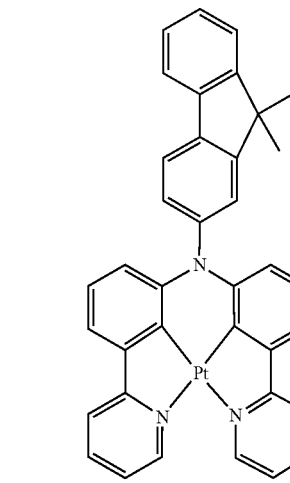
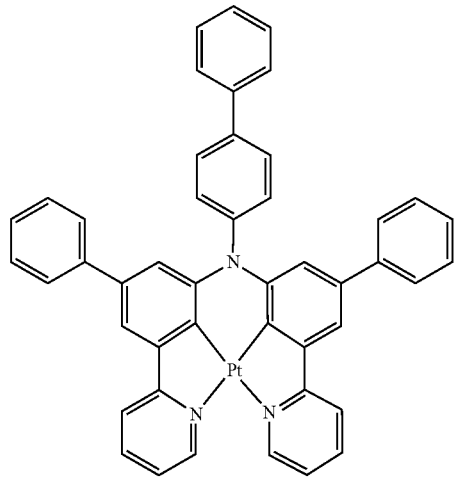
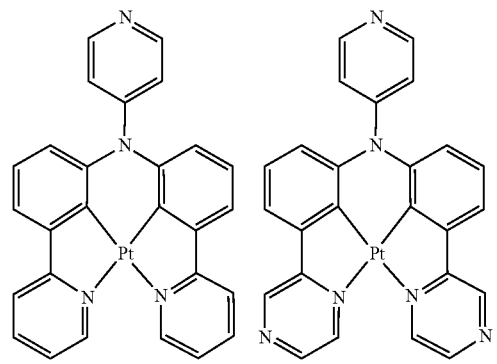

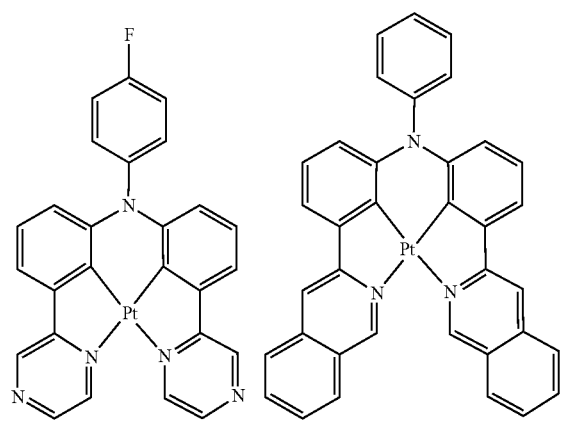
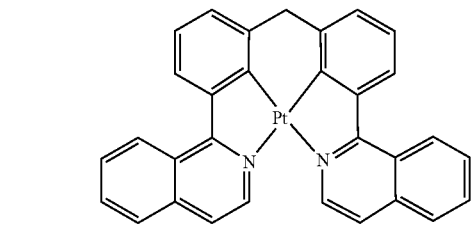
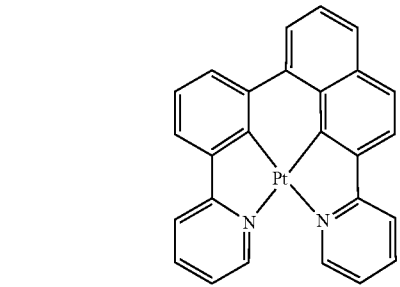
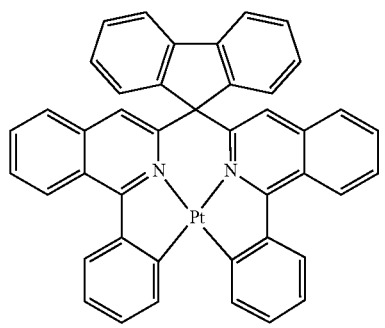
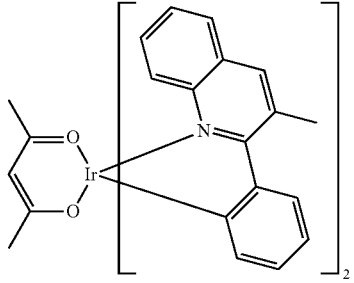
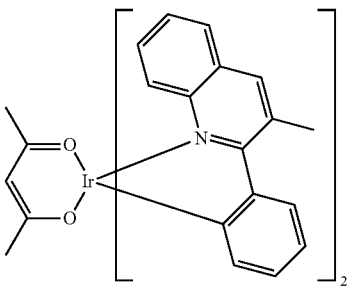
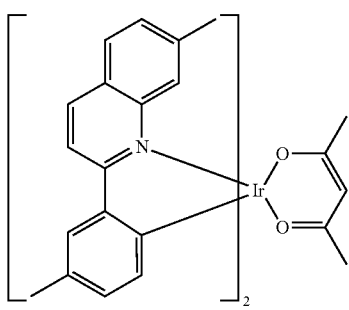
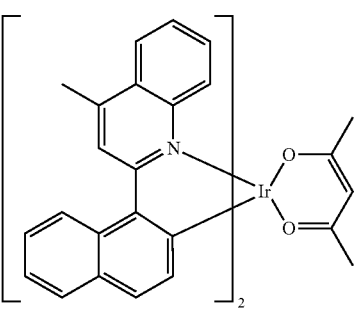
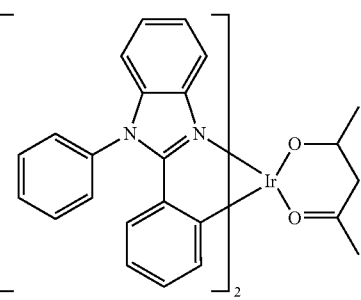

141
-continued
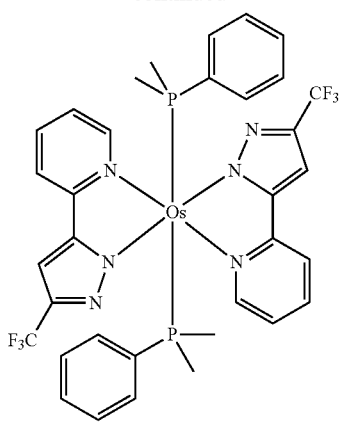
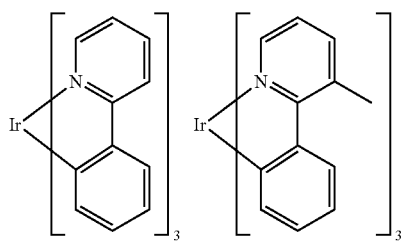
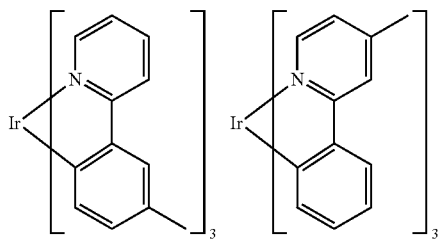
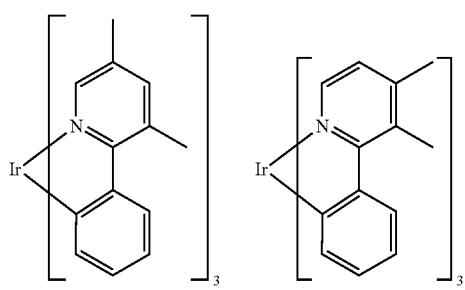
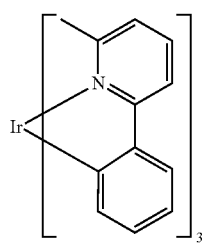
142
-continued
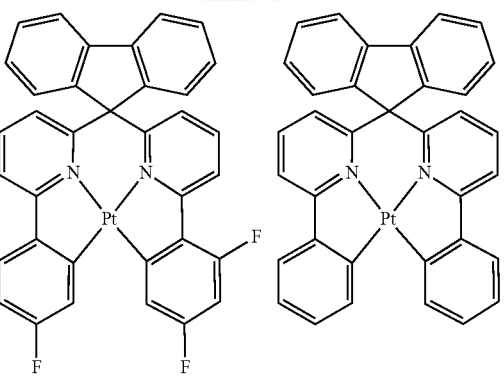
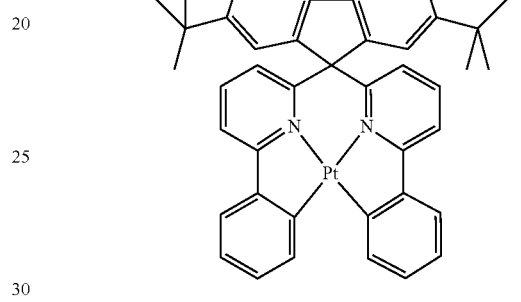
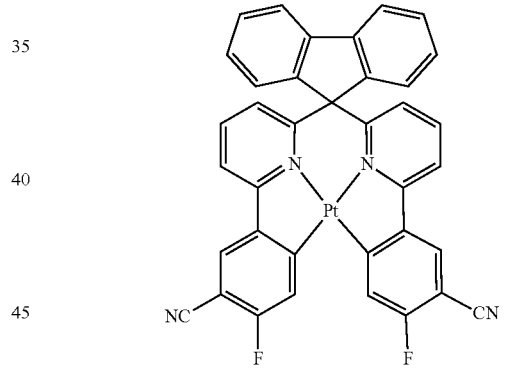
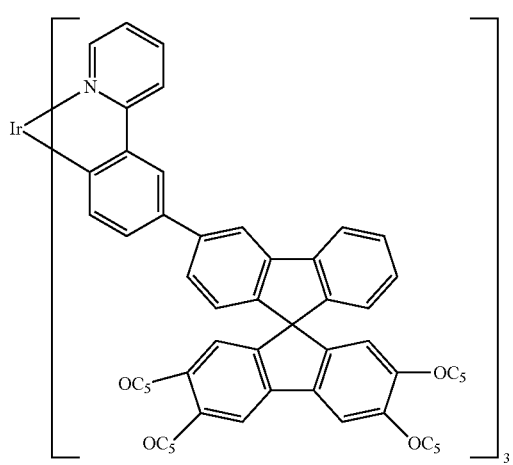

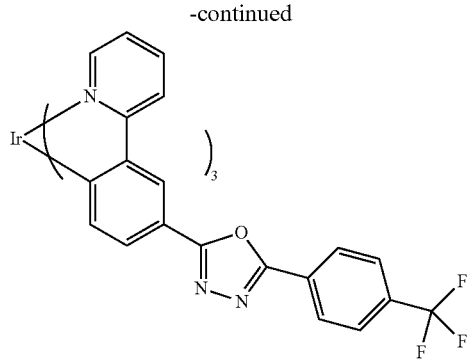
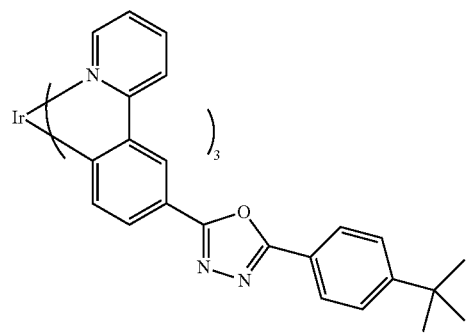
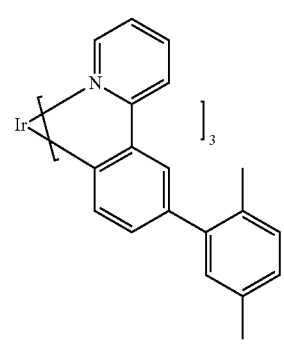
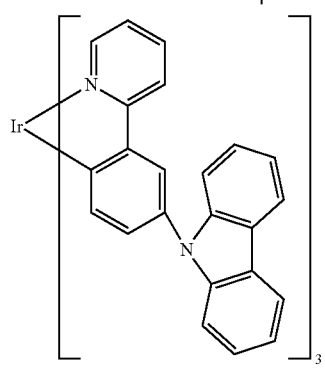
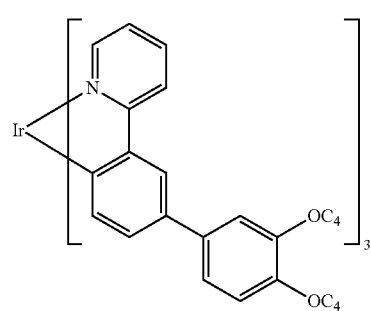
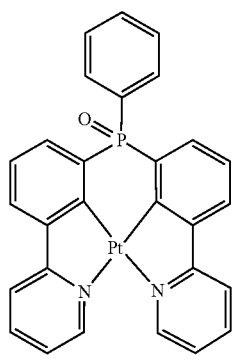
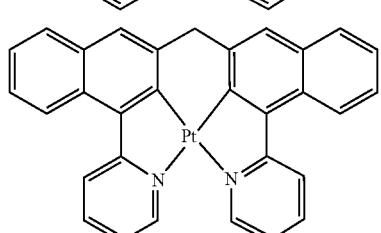
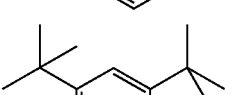
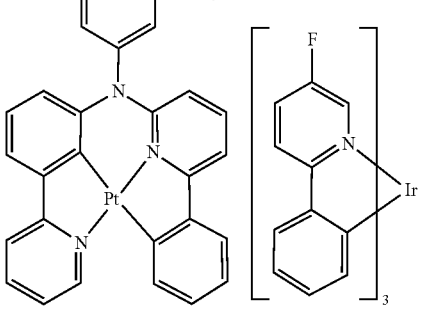
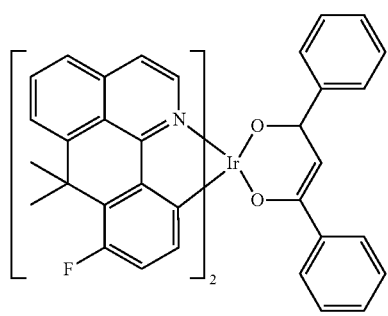
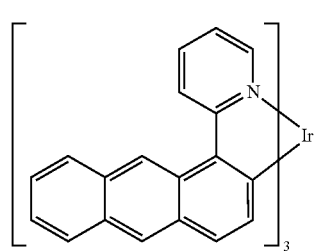

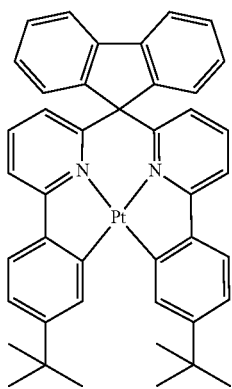
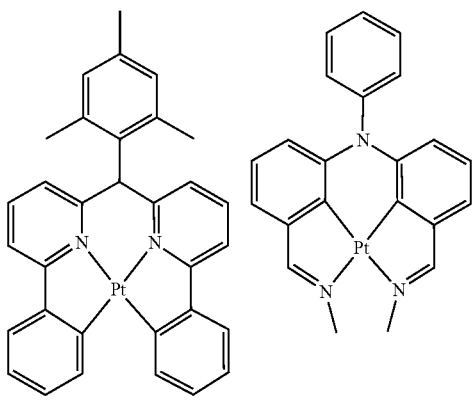
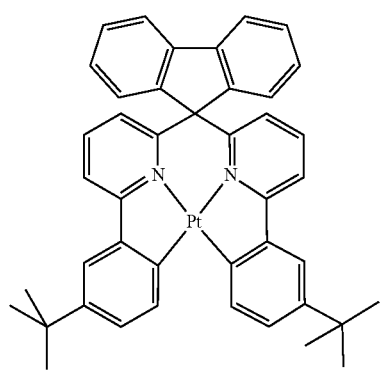
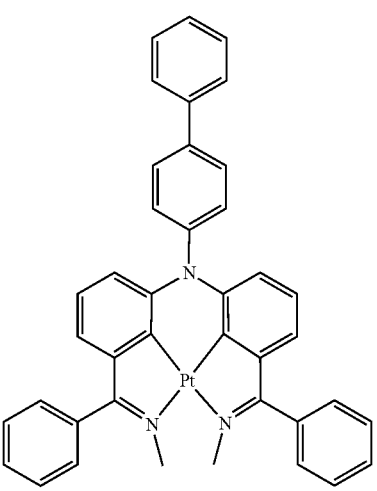
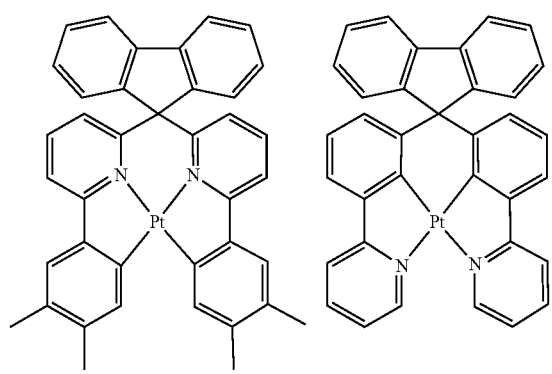
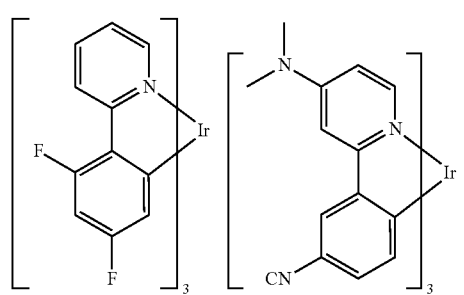
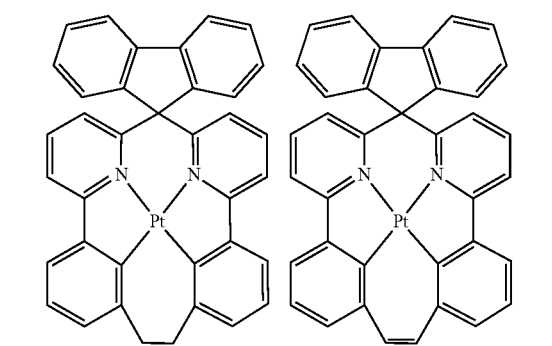
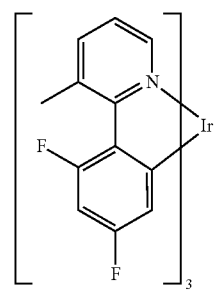

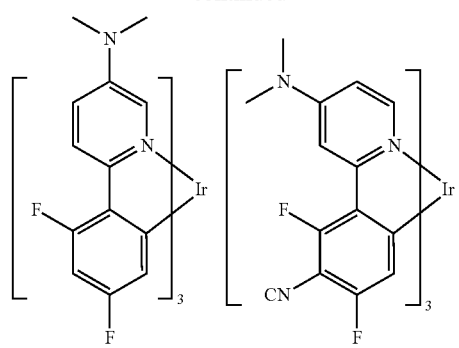
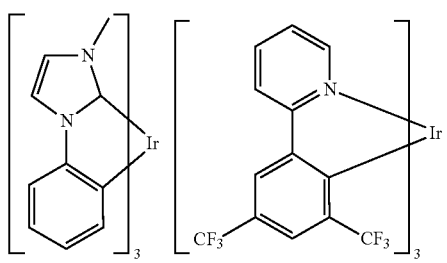
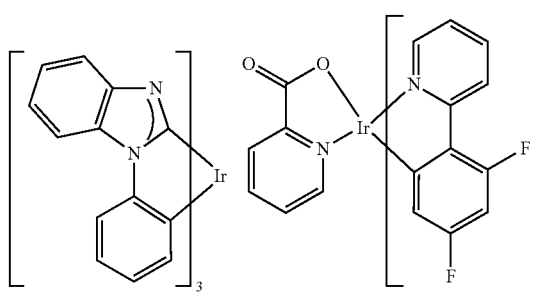
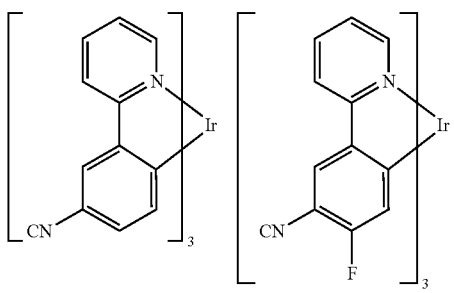
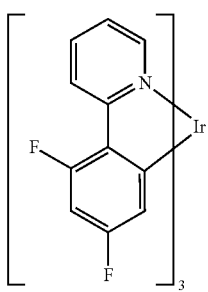
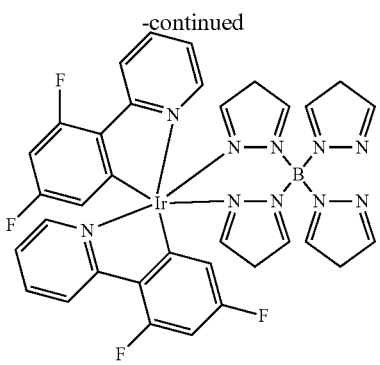
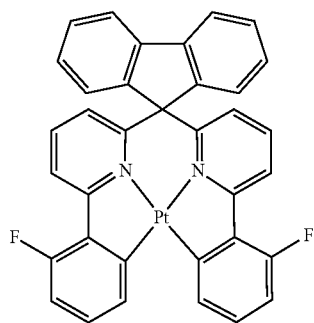
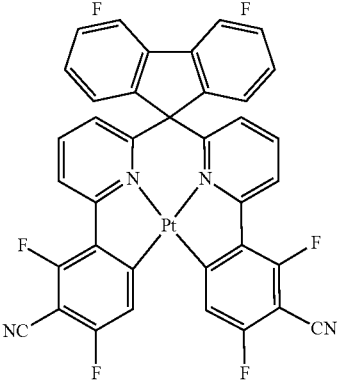
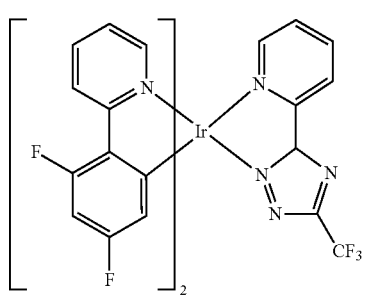
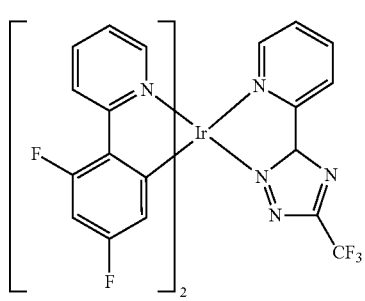

-continued

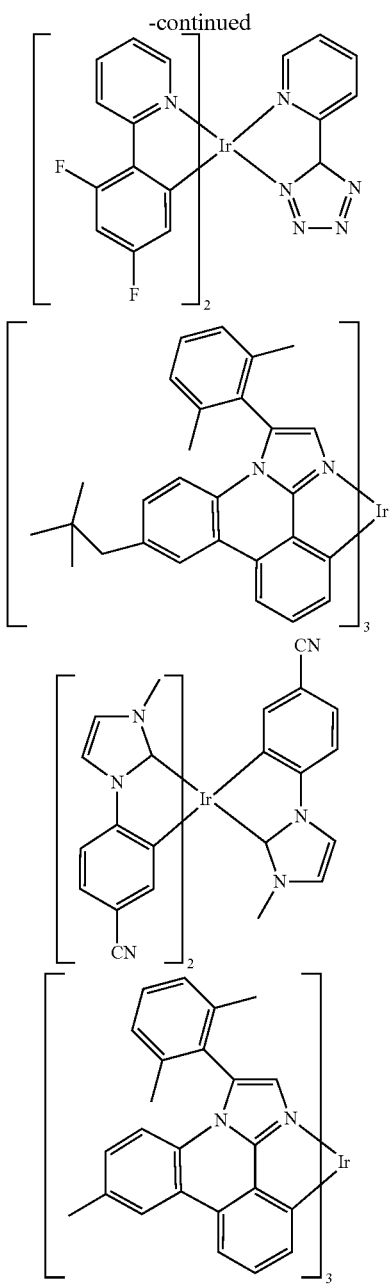

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 05/053051. It is furthermore possible to use a metal complex which is identical or similar to the metal complex in the emitting layer, as hole-transport or hole-injection material directly adjacent to the emitting layer, as described, for example, in WO 09/030,981.

In a further preferred embodiment of the invention, the compound of the formulae (1) to (31) and (11a) to (31e) is employed as electron-transport material in an electron-transport or electron-injection layer. At least one substituent R or $R^1$, in particular R, here is preferably selected here from structures of the above-mentioned formulae (32) to (53). The emitting layer here may be fluorescent or phosphorescent. If the compound is employed as electron-transport material, it may be preferred for it to be doped, for example with alkali-metal complexes, such as, for example, Liq (lithium hydroxyquinolinate).

In still a further preferred embodiment of the invention, the compound of the formulae (1) to (31) and (11a) to (31e) is employed in a hole-blocking layer. At least one substituent R or $R^1$, in particular R, here is preferably selected from structures of the above-mentioned formulae (32) to (53). A hole-blocking layer is taken to mean a layer which is directly adjacent to an emitting layer on the cathode side.

It is furthermore possible to use the compound of the formulae (1) to (31) and (11a) to (31e) both in a hole-blocking layer or electron-transport layer and also as matrix in an emitting layer. The materials here may be identical or different. At least one substituent R or $R^1$, in particular R, here is preferably selected from structures of the above-mentioned formulae (32) to (53).

In still a further embodiment of the invention, the compound of the formulae (1) to (31) and (11a) to (31e) is employed in a hole-transport layer or in a hole-injection layer or in an electron-blocking layer or exciton-blocking layer. At least one substituent R or $R^1$, in particular R, here is preferably selected from structures of the above-mentioned formulae (54) to (67).

It is furthermore possible for the compound of the formulae (1) to (31) and (11a) to (31e) to be used both in a hole-transport layer or in a hole-injection layer or in an electron-blocking layer or exciton-blocking layer and also as matrix in an emitting layer. The materials here may be identical or different.

In the further layers of the organic electroluminescent device according to the invention, all materials as are usually employed in accordance with the prior art can be used. The person skilled in the art will therefore be able, without inventive step, to employ all materials known for organic electroluminescent devices in combination with the compounds of the formulae (1) to (31) and formulae (11a) to (31e) according to the invention.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, where the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose. These processes are also particularly suitable for oligomers, dendrimers and polymers.

Also suitable are hybrid processes, in which, for example, one or more layers are applied from solution and one or more further layers are applied by vapour deposition. Thus, for example, it is possible to apply the emitting layer from solution and to apply the electron-transport layer by vapour deposition.

These processes are generally known to the person skilled in the art and can be applied by him, without inventive step, to organic electroluminescent devices comprising the compounds according to the invention.

The compounds according to the invention and the organic electroluminescent devices according to the invention are distinguished by the following surprising advantages over the prior art:

1. The compounds according to the invention or compounds of the formulae (1) to (31) and formulae (11a) to (31e), employed as matrix material for fluorescent or phosphorescent emitters, result in very high efficiencies and long lifetimes. This applies, in particular, if the compounds are employed as matrix material for a phosphorescent emitter.
2. The compounds according to the invention or compounds of the formulae (1) to (31) and (11a) to (31e) are suitable not only as matrix for red- and green-phosphorescent compounds, but also, in particular, for blue-phosphorescent compounds.
3. In contrast to many compounds in accordance with the prior art which undergo partial or complete pyrolytic decomposition on sublimation, the compounds according to the invention have high thermal stability.
4. The compounds according to the invention, employed in organic electroluminescent devices, result in high efficiencies and steep current/voltage curves with low use voltages.
5. Also on use as electron-transport material or as hole-transport material, the compounds according to the invention result in very good properties with respect to the efficiency, lifetime and operating voltage of organic electroluminescent devices.

These above-mentioned advantages are not accompanied by an impairment in the other electronic properties.

The invention is explained in greater detail by the following examples, without wishing it to be restricted thereby. The person skilled in the art will be able to use the descriptions to carry out the invention throughout the range disclosed and to prepare further compounds according to the invention without an inventive step and use them in electronic devices or use the process according to the invention.

EXAMPLES

The following syntheses are carried out, unless indicated otherwise, under a protective-gas atmosphere. The starting materials can be purchased from ALDRICH or ABCR or obtained in accordance with literature procedures. The numbers for the compounds in each case indicate the CAS numbers.

Example 1

6-Bromo-8,8-dimethyl-8H-3,12b-diazabenzo[a]aceanthrylene

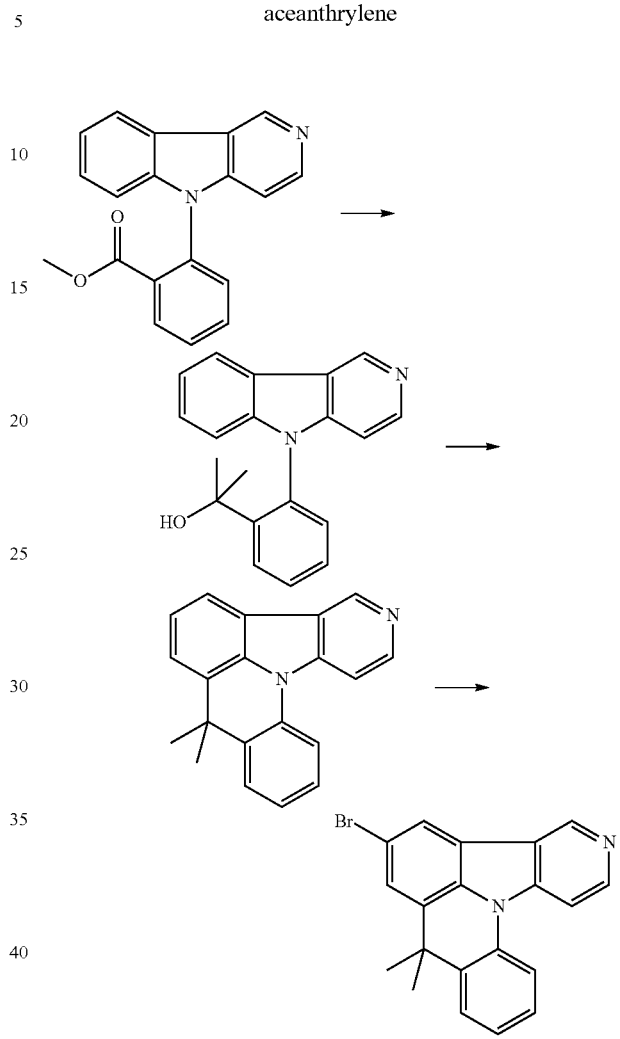

1a) Methyl 2-pyrido[4,3-b]indol-5-ylbenzoate

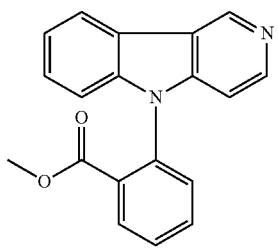 [SMILES: COC(=O)c1ccccc1-n1c2ccccc2c2cnccc21]

A mixture of 16.8 g (100 mmol) of 5H-pyrido[4,3-b]indole [244-69-9], 28.8 g (110 mmol) of methyl 2-iodobenzoate [610-97-9], 34.6 g (250 mmol) of potassium carbonate, 6.4 g (100 mmol) of copper powder and 100 g of glass beads (diameter 3 mm) in 300 ml of DMF is stirred at 130° C. for 24 h. After cooling, the mixture is filtered through a short Celite bed, the bed is rinsed with DMF, and the latter is removed in vacuo. The residue is dissolved in 500 ml of dichloromethane, and the solution is washed three times with 200 ml of 0.5 N sodium hydroxide solution each time and dried over magnesium sulfate. After removal of the dichloromethane in vacuo, the residue is recrystallised once from ethyl acetate and dried in vacuo (p=0.1 mbar, T=60° C.). Yield: 19.3 g (64 mmol), 64%; purity: 97% ($^1$H-NMR).

The following compounds are obtained analogously:

| Ex. | Starting material 1 | Starting material 2 | Product | Yield |
|---|---|---|---|---|
| 1a1 | 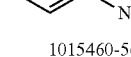 1015460-56-6 |  |  | 60% |
| 1a2 | 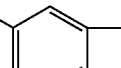 59444-69-8 |  |  | 58% |
| 1a3 |  26066-88-6 |  |  | 52% |
| 1a4 |  |  13959-01-8 |  | 78% |
| 1a5 | 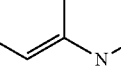 |  53636-56-9 |  | 39% |

| Ex. | Starting material 1 | Starting material 2 | Product | Yield |
|---|---|---|---|---|
| 1a6 | carbazole | methyl 4-bromonicotinate 1043419-29-9 | product | 66% |
| 1a7 | carbazole | methyl 2-bromonicotinate 52718-95-3 | product | 53% |
| 1a8 | 6-bromo-pyrido[2,3-b]indole 26066-88-6 | methyl 4-bromonicotinate 1043419-29-9 | product | 69% |

1b) 2-(2-Pyrido[4,3-b]indol-5-ylphenyl)propan-2-ol

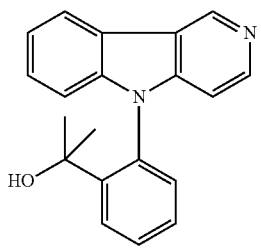 [SMILES: CC(C)(O)c1ccccc1-n1c2ccccc2c2cnccc21]

500 ml of THF are added to 14.8 g (60 mmol) of anhydrous cerium(III) chloride with ice-cooling. This mixture is stirred at room temperature for 5 h, and a solution of 15.1 g (50 mmol) of methyl 2-pyrido[4,3-b]indol-5-yl-benzoate in 100 ml of THF is then added dropwise. The reaction mixture is cooled to −5° C., and 150 ml (150 mmol) of methylmagnesium bromide, 1 N solution in THF, are added dropwise, and the mixture is stirred for a further 30 min. and then allowed to warm to room temperature with stirring. The reaction mixture is subsequently re-cooled to −5° C., and the excess Grignard reagent is quenched by dropwise addition of 100 ml of methanol. The THF/methanol mixture is removed in vacuo, the residue is taken up in 500 ml of dichloromethane, 200 ml of saturated sodium hydrogencarbonate solution are added, the mixture is stirred for a further 30 min., and the organic phase is separated off and washed once with 100 ml of saturated sodium chloride solution. After removal of the dichloromethane, the residue is dried in vacuo (p=0.1 mbar, T=30° C.). Yield: 10.9 g (36 mmol), 72%; purity: 97% ($^1$H-NMR).

The following compounds are obtained analogously:

| Ex. | Starting material | Product | Yield |
|---|---|---|---|
| 1b1 | bromo-pyrido[4,3-b]indole with methyl benzoate substituent | bromo-pyrido[4,3-b]indole with 2-hydroxypropyl substituent | 73% |

-continued

| Ex. | Starting material | Product | Yield |
|---|---|---|---|
| 1b2 | | | 70% |
| 1b3 | | | 65% |

1c)
8,8-Dimethyl-H-3,12b-diazabenzo[a]aceanthrylene

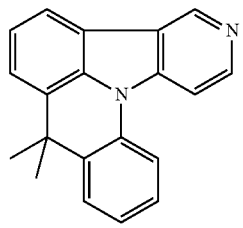 [SMILES: CC1(C)c2ccccc2-n2c3ccncc3c3cccc1c32]

A mixture of 15 ml of methanesulfonic acid and 15 g of polyphosphoric acid is homogenised by stirring (24 h at room temperature). This mixture is added dropwise over the course of 30 min. to a vigorously stirred solution, cooled to −20° C., of 9.1 g (30 mmol) of 2-(2-pyrido[4,3-b]indol-5-ylphenyl)-propan-2-ol in 300 ml of dichloromethane. The mixture is subsequently stirred at −20° C. for a further 1 h, the cooling bath is removed, and the reaction mixture is allowed to warm slowly to room temperature, stirred at room temperature for a further 1 h and then poured onto 500 g of ice. The mixture is adjusted to pH=9 by addition of 2 N sodium hydroxide solution, and the organic phase is separated off and dried over magnesium sulfate. After removal of the solvent in vacuo, the residue is recrystallised from toluene:ethanol. Yield: 6.8 g (24 mmol), 80%; purity: 99% ($^1$H-NMR).

The following compounds are obtained analogously:

| Ex. | Starting material | Product | Yield |
|---|---|---|---|
| 1c1 | | | 59% |
| 1c2 | | | 72% |

| Ex. | Starting material | Product | Yield |
|---|---|---|---|
| 1c3 | 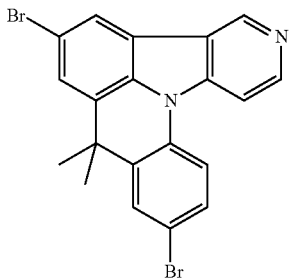 [SMILES: CC1(C)c2cc(Br)ccc2-n2c3ccncc3c3cc(Br)cc1c32] | | 78% |

Example 2

8,8-Dimethyl-6,10-bis[1,1';3',1''']terphenyl-5'-yl-8H-3,12b-diazabenzo[a]aceanthrylene 2a) 6,10-Dibromo-8,8-dimethyl-H-3,12b-diazabenzo[a]aceanthrylene

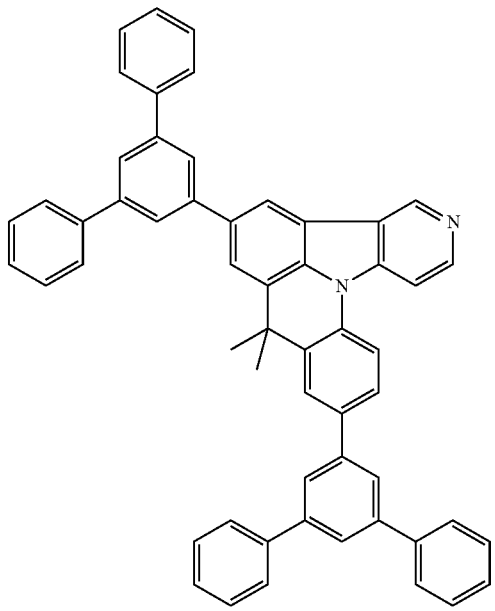 [SMILES: CC1(C)c2cc(-c3cc(-c4ccccc4)cc(-c4ccccc4)c3)ccc2-n2c3ccncc3c3cc(-c4cc(-c5ccccc5)cc(-c5ccccc5)c4)cc1c32]

A mixture of 28.4 g (100 mmol) of 8,8-dimethyl-H-3,12b-diazabenzo[a]-aceanthrylene and 36.5 g (205 mmol) of N-bromosuccinimide in 200 ml of DMF is stirred at 80° C. for 16 h. After cooling, 100 ml of ethanol are added, and the precipitated solid is filtered off with suction, washed three times with 50 ml of ethanol and dried in vacuo (p=0.1 mbar, T=60° C.). Yield: 16.3 g (77 mmol), 77%; purity: 98% ($^1$H-NMR).

2b) 8,8-Dimethyl-6,10-bis[1,1';3',1''']terphenyl-5'-yl-8H-3,12b-diaza-benzo[a]aceanthrylene A mixture of 13.3 g (30 mmol) of 6,10-dibromo-8,8-dimethyl-H-3,12b-diaza-benzo[a]aceanthrylene, 24.7 g (90 mmol) of [1,1:3',1''-terphenyl]-5'-yl-boronic acid [128388-54-5], 34.8 g (180 mmol) of tripotassium phosphate, 67 mg (0.3 mmol) of palladium(II) acetate, 548 mg (1.8 mmol) of tri-o-tolylphosphine, 100 ml of toluene, 30 ml of dioxane and 50 ml of water is heated under reflux for 24 h with vigorous stirring. After cooling, the reaction mixture is diluted with 400 ml of toluene, the aqueous phase is separated off, and the organic phase is washed once with 300 ml of water and dried over magnesium sulfate. After removal of the solvent in vacuo, the residue is recrystallised five times from DMF and subsequently sublimed in vacuo (p=$10^{-5}$ mbar, T=365° C.). Yield: 12.8 g (17 mmol), 57%; purity: 99.9% (HPLC).

Example 3

Spiro[fluorenyl-9,8'-H-3,12b-diazabenzo[a]aceanthrylene]

3a) 3,12b-Diazabenzo[a]aceanthrylen-8-one

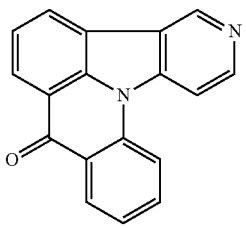 [SMILES: O=c1c2ccccc2n2c3ccncc3c3cccc1c32]

15.1 g (50 mmol) of methyl 2-pyrido[4,3-b]indol-5-ylbenzoate are suspended in a mixture of 200 ml of glacial acetic acid and 5 ml of concentrated sulfuric acid. The suspension is heated under reflux for 5 h, the acetic acid is then removed in vacuo, and the residue is taken up in 500 ml of dichloromethane and neutralised using 1 N sodium hydroxide solution. The organic phase is separated off, dried over magnesium sulfate and evaporated in vacuo. The residue is taken up in 30 ml of ethyl acetate, and 100 ml of ethanol are slowly added at elevated temperature. After cooling, the precipitated solid is filtered off with suction, washed three times with 50 ml of ethanol and dried in vacuo (p=0.1 mbar, T=60° C.). Yield: 10.5 g (39 mmol), 78%; purity: 97% ($^1$H-NMR).

3b) Spiro[fluorenyl-9,8'-H-3,12b-diazabenzo[a]aceanthrylene]

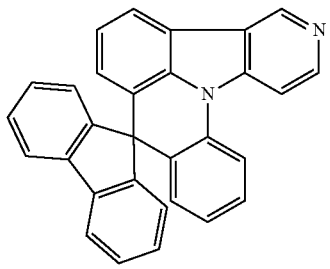 [SMILES: c1ccc2c(c1)-c1ccccc1C21c2ccccc2-n2c3ccncc3c3cccc1c32]

9.3 g (40 mmol) of 2-bromobiphenyl in a mixture of 50 ml of THF, 30 ml of toluene and 1 ml of 1,2-dichloroethane are reacted with 1.3 g (57 mmol) of magnesium to give the corresponding Grignard reagent. A solution of 9.5 g (30 mmol) of 3,12b-diazabenzo[a]aceanthrylen-8-one in 100 ml of THF is added dropwise to this Grignard solution at about 30° C., and the mixture is then stirred under reflux for a further 5 h. After cooling, the THF is removed in vacuo, the residue is taken up in 200 ml of glacial acetic acid, 5 ml of concentrated sulfuric acid are added, and the mixture is heated under reflux for 3 h. After cooling, the precipitated solid is filtered off with suction and suspended in 300 ml of dichloromethane, 100 ml of 1 N sodium hydroxide solution are added, the mixture is stirred until the solid has dissolved, and the organic phase is then separated off, washed with 100 ml of 1 N sodium hydroxide solution and dried over magnesium sulfate. After removal of the solvent in vacuo, the residue is recrystallised five times from DMF and subsequently sublimed (p=$10^{-5}$ mbar, T=300° C.). Yield: 5.3 g (13 mmol), 43%; purity: 99.9% (HPLC).

Example 4

8,8'-[Spiro-H-3,12b-diazabenzo[a]aceanthrylene]

4-a) 5-(2-Bromophenyl)-5H-pyrido[4,3-b]indole

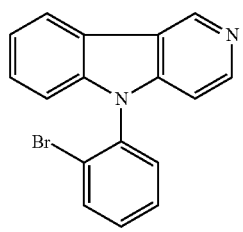 [SMILES: Brc1ccccc1-n1c2ccccc2c2cnccc21]

A mixture of 84.1 g (500 mmol) of 5H-pyrido[4,3-b]indole [244-69-9], 147.1 g (520 mmol) of 2-bromoiodobenzene [583-55-1], 103.7 g (750 mmol) of potassium carbonate, 31.8 g (500 mmol) of copper powder and 300 g of glass beads (diameter 3 mm) in 800 ml of DMF is stirred at 130° C. for 24 h. After cooling, the mixture is filtered through a short Celite bed, the bed is rinsed with DMF, and the latter is removed in vacuo. The residue is dissolved in 1500 ml of dichloromethane, and the solution is washed three times with 500 ml of concentrated ammonia solution each time and dried over magnesium sulfate. After removal of the dichloromethane in vacuo, the oily residue is distilled in a short-path evaporator (p=$5 \times 10^{-3}$ mbar, T=120° C.). Yield: 56.1 g (173 mmol), 35%; purity: 98% ($^1$H-NMR).

4b) 8,8'-[Spiro-H-3,12b-diazabenzo[a]aceanthrylene]

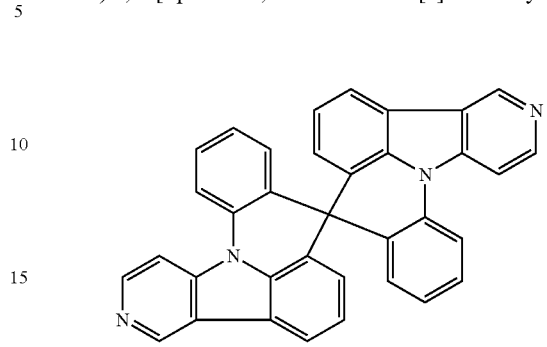

62.5 ml (100 mmol) of n-butyllithium, 1.6 M in hexane, are added dropwise to a solution, cooled to −78° C., of 32.3 g (100 mmol) of 5-(2-bromophenyl)-5H-pyrido[4,3-b]indole in 500 ml of THF, the mixture is stirred at −78° C. for a further 30 min., and a solution of 27.0 g (100 mmol) of 3,12b-diazabenzo-[a]aceanthrylen-8-one in 300 ml of THF is then added dropwise. After the reaction mixture has warmed to room temperature, it is quenched by addition of 20 ml of methanol, and the solvent is removed in vacuo. The residue is taken up in 500 ml of glacial acetic acid, 14 ml of concentrated sulfuric acid are added, and the mixture is heated under reflux for 3 h. After cooling, the precipitated solid is filtered off with suction and suspended in 1000 ml of dichloromethane, 500 ml of 1 N sodium hydroxide solution are added, the mixture is stirred until the solid has dissolved, and the organic phase is then separated off, washed with 100 ml of 1 N sodium hydroxide solution and dried over magnesium sulfate. After removal of the solvent in vacuo, the residue is recrystallised five times from DMF and subsequently sublimed in vacuo (p=$10^{-5}$ mbar, T=340° C.). Yield: 22.8 g (46 mmol), 46%; purity: 99.9% (HPLC).

Example 5

3-Bromo-8,8-dimethyl-8H-10,12b-diazabenzo[a]aceanthrylene

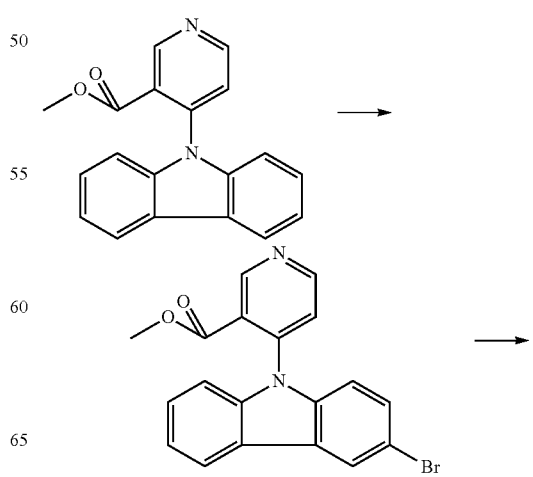

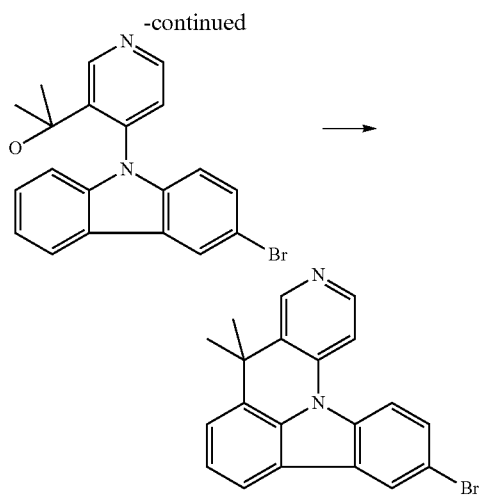

5a) Methyl 4-(3-bromocarbazol-9-yl)nicotinate 62.5 g (207 mmol) of methyl 4-carbazol-9-ylnicotinate in 2000 ml of DMF are cooled to −10° C., 37.3 g (207 mmol) of N-bromosuccinimide are added in portions, and the mixture is stirred at room temperature for 6 h. 500 ml of water are subsequently added to the mixture, which is then extracted with CH$_2$Cl$_2$. The organic phase is dried over MgSO$_4$, and the solvent is removed in vacuo. The product is washed by stirring with hot toluene and filtered off with suction. Yield: 71 g (186 mmol), 90% of theory, purity according to $^1$H-NMR about 98%.

The following compounds are obtained analogously:

| Ex. | Starting material | Product | Yield |
|---|---|---|---|
| 5a1 | | | 77% |
| 5a2 | | | 79% |
| 5a3 | | | 81% |
| 5a4 | | | 78% |
| 5a5 | | | 86% |

5b) 2-[4-(3-Bromocarbazol-9-yl)pyridin-3-yl]propan-2-ol 81.2 g (213 mmol) of methyl 4-(3-bromocarbazol-9-yl)nicotinate are dissolved in 1500 ml of dried THF and degassed. The mixture is cooled to −78° C., and 569 ml (854 mmol) of methyllithium are added over the course of 40 min. The mixture is allowed to warm to −40° C. over the course of 1 h, and the reaction is monitored by TLC. When the reaction is complete, the mixture is carefully quenched at −30° C. using MeOH. The reaction solution is evaporated to ⅓, 1 l of CH$_2$Cl$_2$ is added, the mixture is washed, and the organic phase is dried over MgSO$_4$ and evaporated. Yield: 70 g (183 mmol), 88% of theory, purity according to $^1$H-NMR about 94%.

The following compounds are obtained analogously:

| Ex. | Starting material | Product | Yield |
|---|---|---|---|
| 5b1 | | | 73% |

| Ex. | Starting material | Product | Yield |
|---|---|---|---|
| 5b2 | 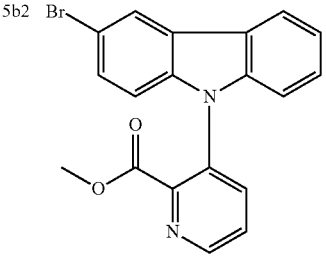 | 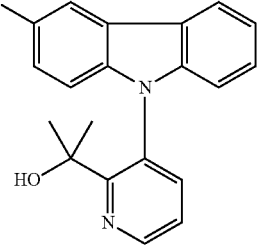 | 70% |
| 5b3 | 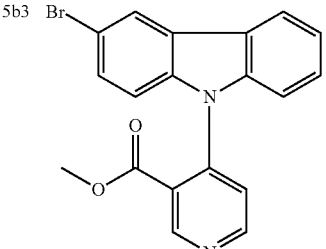 | 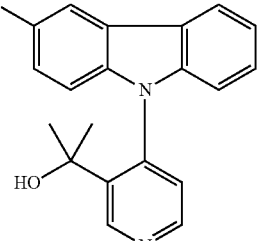 | 69% |
| 5b4 | 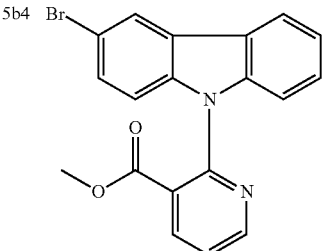 | 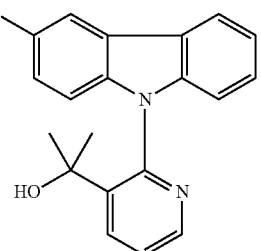 | 73% |
| 5b6 | 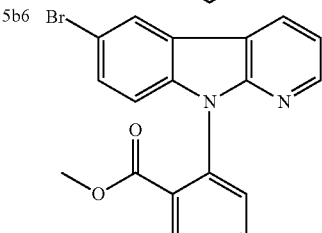 | 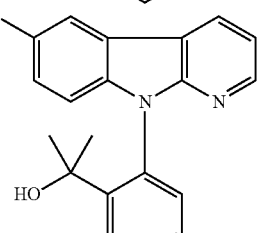 | 68% |

5c) 3-Bromo-8,8-dimethyl-8H-10,12b-diazabenzo[a]aceanthrylene 16.7 g (44 mmol) of 2-[2-(3-bromocarbazol-9-yl)phenyl]propan-2-ol are dissolved in 1200 ml of degassed toluene, a suspension of 40 g of polyphosphoric acid and 28 ml of methanesulfonic acid is added, and the mixture is heated at 60° C. for 1 h. The batch is cooled, and water is added. A solid precipitates out and is dissolved in $CH_2Cl_2$/THF (1:1). The solution is carefully rendered alkaline using 20% NaOH, and the phases are separated and dried over $MgSO_4$. The solid obtained is washed by stirring in heptane. Yield: 13.6 g (37 mmol), 85% of theory, purity according to $^1$H-NMR about 95%.

The following compounds are obtained analogously:

| Ex. | Starting material | Product | Yield |
|---|---|---|---|
| 5c1 | 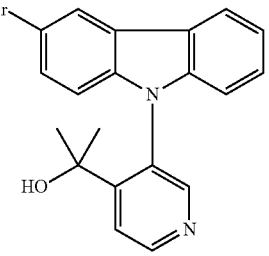 | 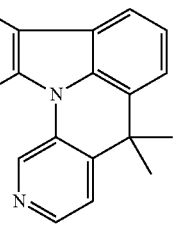 | 73% |

-continued
| Ex. | Starting material | Product | Yield |
|---|---|---|---|
| 5c2 | | | 70% |
| 5c3 | | | 69% |
| 5c4 | | | 73% |
| 5c5 | | | 68% |
Example 6
6a) 8,8-Dimethyl-8H-10,12b-diazabenzo[a]aceanthrylene-3-boronic acid
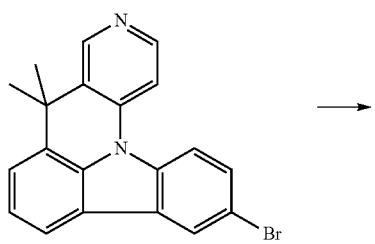
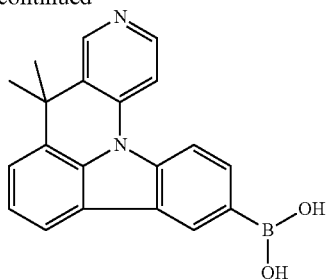
94 g (259 mmol) of 3-bromo-8,8-dimethyl-8H-10,12b-diazabenzo[a]aceanthrylene are dissolved in 1500 ml of dry THF, 135 ml (337 mmol) of a 2.5 M solution of n-butyllithium in cyclohexane are added dropwise at −70° C., after 1 h 37 ml of trimethyl borate (336 mmol) are added dropwise, the mixture is warmed to room temperature over the course of 1 h, the solvent is removed, and the residue, which is uniform according to ¹H-NMR, is employed in the subsequent reaction without further purification. Yield: 59 g (181 mmol), 70% of theory, purity according to ¹H-NMR about 96%.

The following compounds are obtained analogously:

| Ex. | Starting material | Product | Yield |
|---|---|---|---|
| 6b | | | 49% |
| 6c | | | 51% |
| 6d | | | 48% |
| 6e | | | 55% |
| 6f | | | 49% |

-continued

| Ex. | Starting material | Product | Yield |
|---|---|---|---|
| 6g | 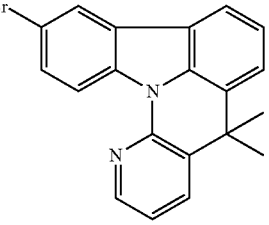 | 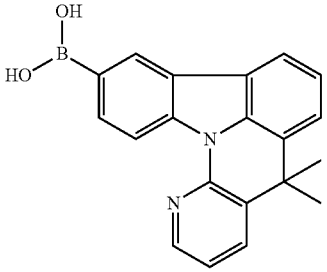 [SMILES: CC1(C)c2cccnc2-n2c3ccc(B(O)O)cc3c3cccc1c32] | 50% |

Example 7

7a) 8,8-Dimethyl-3-(9-phenyl-9H-carbazol-3-yl)-8H-10,12b-diaza-benzo[a]aceanthrylene

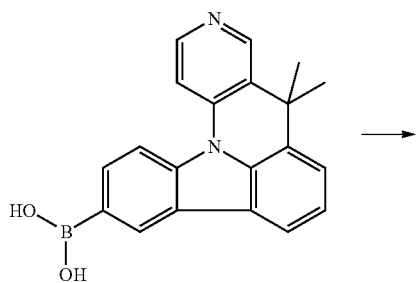

→

-continued

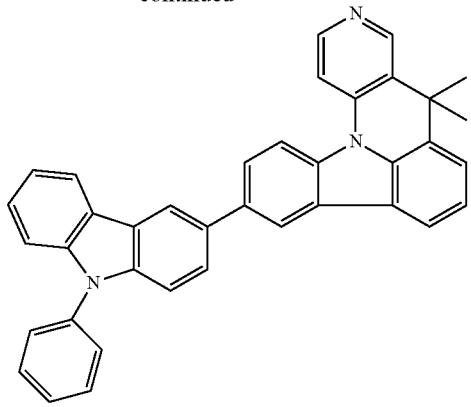

36 g (110 mmol) of 8,8-dimethyl-8H-10,12b-diazabenzo[a]aceanthrylene-3-boronic acid, 35 g (110 mmol) of 3-bromo-9-phenyl-9H-carbazole and 9.7 g (92 mmol) of sodium carbonate are suspended in 350 ml of toluene, 350 ml of dioxane and 500 ml of water. 913 mg (3.0 mmol) of tri-o-tolylphosphine and 112 mg (0.5 mmol) of palladium(II) acetate are added to this suspension, and the reaction mixture is heated under reflux for 16 h. After cooling, the organic phase is separated off, filtered through silica gel, washed three times with 200 ml of water each time and subsequently evaporated to dryness. The residue is recrystallised from toluene and from $CH_2Cl_2$/isopropanol and finally sublimed in a high vacuum. Yield: 50 g (99 mmol), 89% of theory, purity according to HPLC 99.9%.

The following compounds are obtained analogously:

| Ex. | Starting material | Product | Yield |
|---|---|---|---|
| 7b | 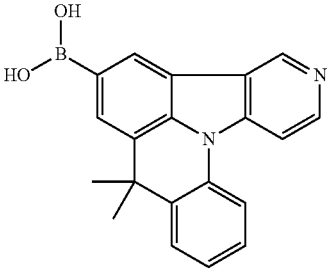 [SMILES: CC1(C)c2ccccc2-n2c3ccncc3c3cc(B(O)O)cc1c32] | 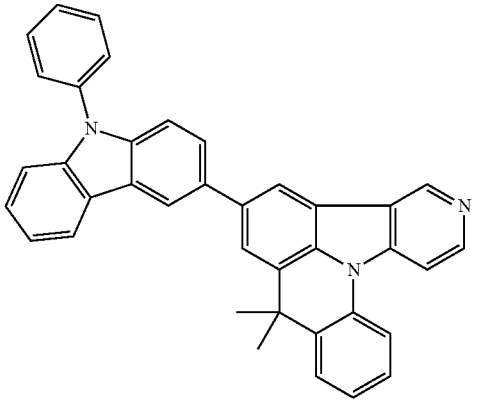 [SMILES: CC1(C)c2ccccc2-n2c3ccncc3c3cc(-c4ccc5c(c4)c4ccccc4n5-c4ccccc4)cc1c32] | 81% |

-continued

| Ex. | Starting material | Product | Yield |
|---|---|---|---|
| 7c | | | 51% |
| 7d | | | 48% |
| 7e | | | 55% |

| Ex. | Starting material | Product | Yield |
|---|---|---|---|
| 7f | | | 49% |
| 7g | | | 50% |

Example 8

8a) [4-(8,8-Dimethyl-8H-10,12b-diazabenzo[a]aceanthrylen-3-yl)-phenyl]diphenylamine

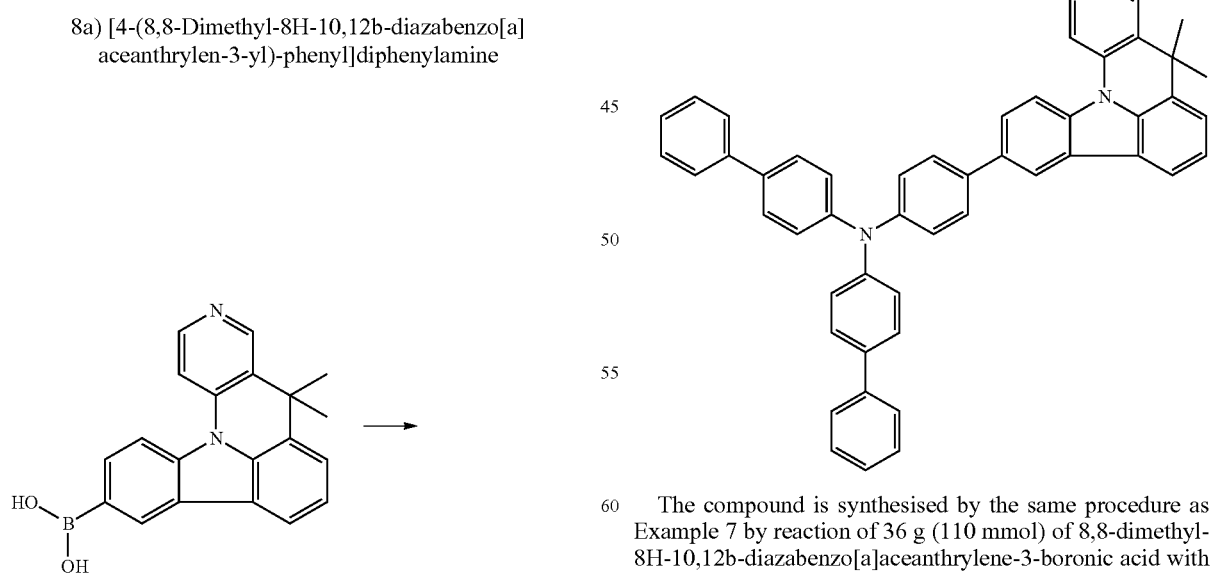

The compound is synthesised by the same procedure as Example 7 by reaction of 36 g (110 mmol) of 8,8-dimethyl-8H-10,12b-diazabenzo[a]aceanthrylene-3-boronic acid with 52 g (110 mmol) of bis-biphenyl-4-yl(4-bromophenyl)amine. The residue is recrystallised from toluene and from $CH_2Cl_2$/isopropanol and finally sublimed in a high vacuum. Yield: 65 g (95 mmol), 88% of theory, purity according to HPLC 99.9%.

The following compounds are obtained analogously:

| Ex. | Starting material | Product | Yield |
|---|---|---|---|
| 8b | | | 85% |
| 8c | | | 66% |
| 8d | | | 69% |

-continued

| Ex. | Starting material | Product | Yield |
|---|---|---|---|
| 8e | | | 65% |
| 8f | | | 59% |
| 8g | | | 55% |

Example 9

9a) 3-(4-Carbazol-9-ylphenyl)-8,8-dimethyl-8H-10,12b-diazabenzo[a]-aceanthrylene

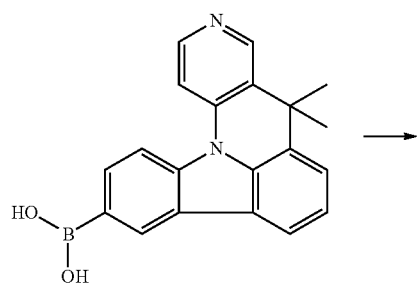
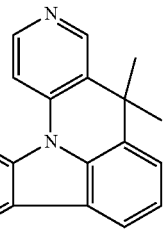
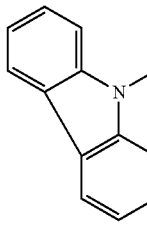

The compound is synthesised by the same procedure as Example 7 by reaction of 36 g (110 mmol) of 8,8-dimethyl-8H-10,12b-diazabenzo[a]aceanthrylene-3-boronic acid with 35.4 g (110 mmol) of 9-(4-bromophenyl)-9H-carbazole. The residue is recrystallised from toluene and from $CH_2Cl_2$/isopropanol and finally sublimed in a high vacuum. Yield: 47 g (99 mmol), 82% of theory, purity according to HPLC 99.9%.

The following compounds are obtained analogously:

| Ex. | Starting material | Product | Yield |
|---|---|---|---|
| 9b | 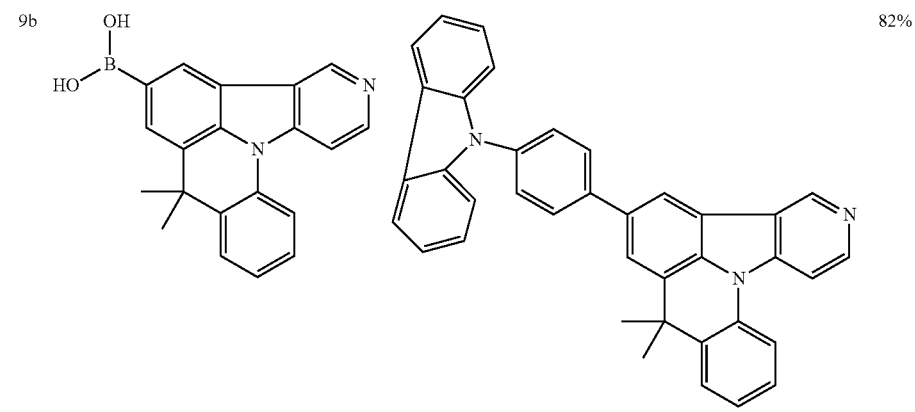 | | 82% |
| 9c | 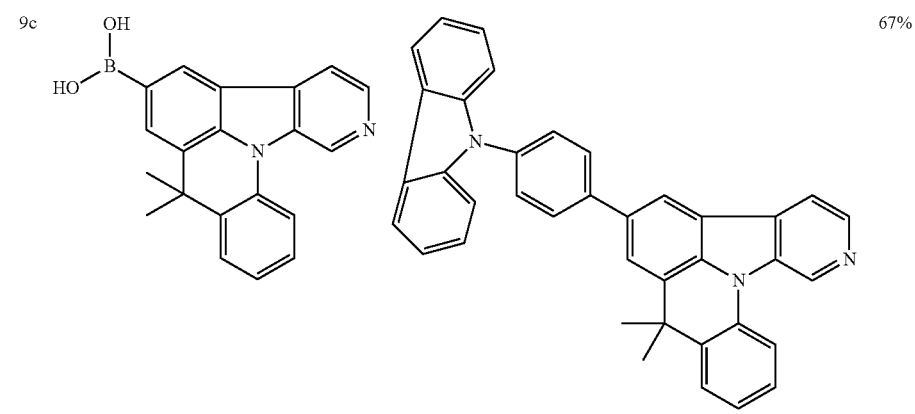 | | 67% |

| Ex. | Starting material | Product | Yield |
|---|---|---|---|
| 9d | [structure] | [structure] | 72% |
| 9e | [structure] | [structure] | 69% |
| 9f | [structure] | [structure] | 54% |

| Ex. | Starting material | Product | Yield |
|---|---|---|---|
| 9g | | | 59% |

Example 10

10a) 8,8,8',8'-Tetramethyl-8H,8'H-[3,3']bi[10,12b-diazabenzo[a]aceanthrylenyl]

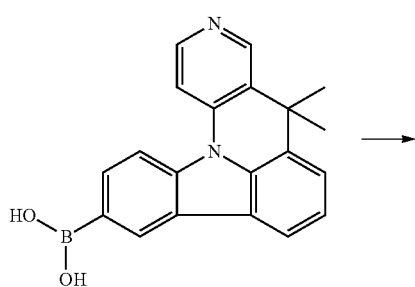

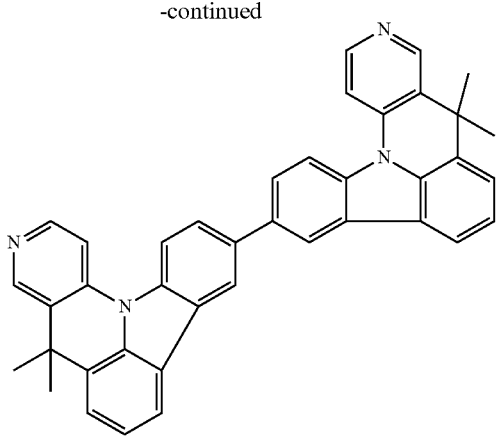

The compound is synthesised by the same procedure as Example 7 by reaction of 36 g (110 mmol) of 8,8-dimethyl-8H-10,12b-diazabenzo[a]aceanthrylene-3-boronic acid with (110 mmol) of 3-bromo-8,8-dimethyl-8H-10,12b-diazabenzo[a]aceanthrylene. The residue is recrystallised from toluene and from CH$_2$Cl$_2$/isopropanol and finally sublimed in a high vacuum. Yield: 50 g (88 mmol), 80% of theory, purity according to HPLC 99.9%.

The following compounds are obtained analogously:

| Ex. | Starting material 1 | Starting material 2 | Product | Yield |
|---|---|---|---|---|
| 10b | | | | 80% |

-continued

| Ex. | Starting material 1 | Starting material 2 | Product | Yield |
|---|---|---|---|---|
| 10c | | | | 65% |
| 10d | | | | 66% |
| 10e | | | | 79% |
| 10f | | | | 56% |

-continued
| Ex. | Starting material 1 | Starting material 2 | Product | Yield |
|---|---|---|---|---|
| 10g | 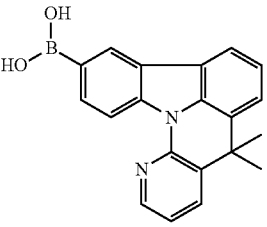 [SMILES: CC1(C)c2cccnc2-n2c3ccc(B(O)O)cc3c3cccc1c32] | 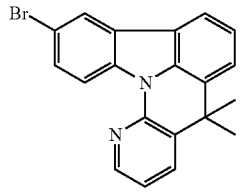 [SMILES: CC1(C)c2cccnc2-n2c3ccc(Br)cc3c3cccc1c32] | 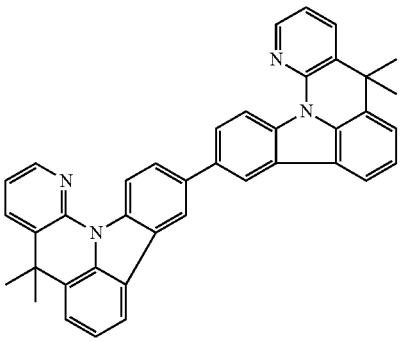 [SMILES: CC1(C)c2cccnc2-n2c3ccc(-c4ccc5c(c4)c4cccc6c4n5-c4ncccc4C6(C)C)cc3c3cccc1c32] | 54% |
| 10h | 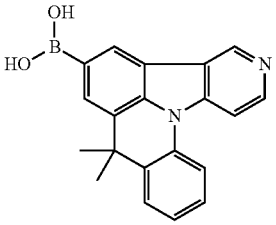 [SMILES: CC1(C)c2ccccc2-n2c3ccncc3c3cc(B(O)O)cc1c32] | 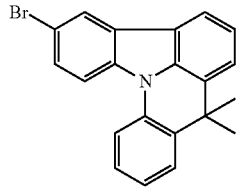 [SMILES: CC1(C)c2ccccc2-n2c3ccc(Br)cc3c3cccc1c32] | 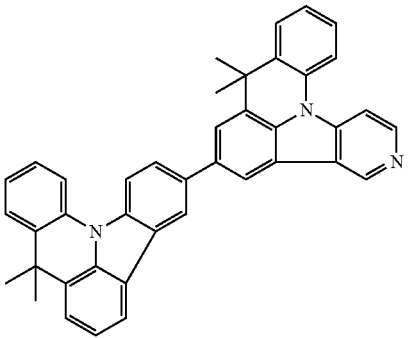 [SMILES: CC1(C)c2ccccc2-n2c3ccc(-c4cc5c6c(c4)c4cnccc4n6-c4ccccc4C5(C)C)cc3c3cccc1c32] | 68% |
| 10i | 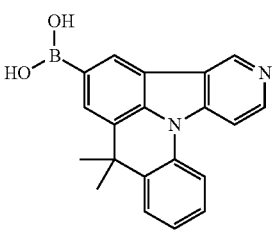 [SMILES: CC1(C)c2ccccc2-n2c3ccncc3c3cc(B(O)O)cc1c32] | 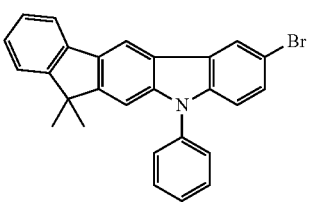 [SMILES: CC1(C)c2ccccc2-c2cc3c4cc(Br)ccc4n(-c4ccccc4)c3cc21] | 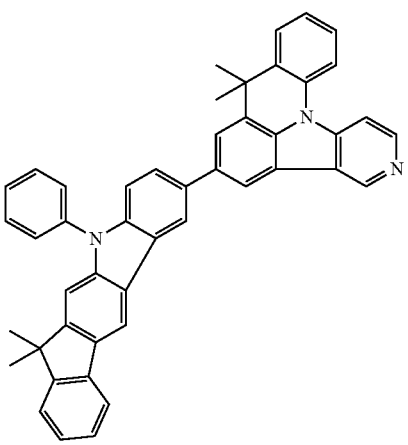 [SMILES: CC1(C)c2ccccc2-c2cc3c4cc(-c5cc6c7c(c5)c5cnccc5n7-c5ccccc5C6(C)C)ccc4n(-c4ccccc4)c3cc21] | 59% |

Example 11

11a) 8,8-Dimethyl-8H-10,12b-diazabenzo[a]acean-thrylen-3-yl)diphenyl-amine

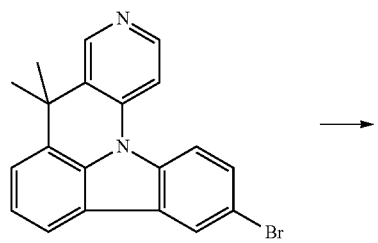

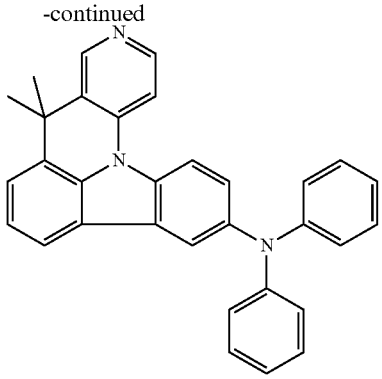

A degassed solution of 31.4 g (86.6 mmol) of 3-bromo-8,8-dimethyl-8H-10,12b-diazabenzo[a]aceanthrylene and 16 g (95.9 mmol) of diphenyl-amine in 1000 ml of dioxane is saturated with $N_2$ for 1 h. Then, firstly 0.9 ml (4.3 mmol) of $P(tBu)_3$, then 0.48 g (2.1 mmol) of palladium(II) acetate are added, and 12.6 g (131 mmol) of NaOtBu in the solid state are subsequently added. The reaction mixture is heated under reflux for 18 h. After cooling to room temperature, 1000 ml of water are carefully added. The organic phase is washed with 4×50 ml of water and dried over $MgSO_4$, and the solvent is removed in vacuo. The pure product is obtained by recrystallisation and final sublimation. Yield: 35 g (77 mmol), 90% of theory, purity according to HPLC 99.9%.

The following compounds are obtained analogously:

| Ex. | Starting material 1 | Starting material 2 | Product | Yield |
|---|---|---|---|---|
| 11b | | | | 83% |
| 11c | | | | 78% |

Example 12

12a) 6-(4,6-Diphenyl-1,3,5-triazin-2-yl)-8,8-dimethyl-8H-indolo-[3,2,1-de]-acridine

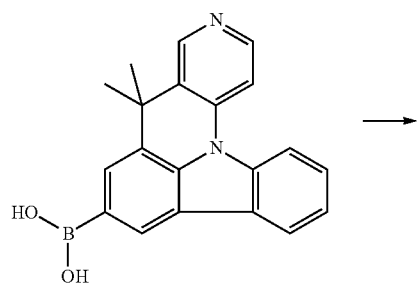

→

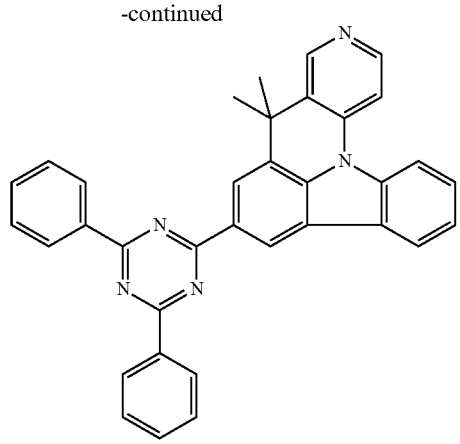

36 g (110.0 mmol) of 8,8-dimethyl-8H-10,12b-diazabenzo[a]aceanthrylene-3-boronic acid, 29.5 g (110.0 mmol) of 2-chloro-4,6-diphenyl-1,3,5-triazine and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum. The purity is 99.9%. The yield is 46 g (89 mmol), corresponding to 83% of theory.

The following compounds are obtained analogously:

| Ex. | Starting material 1 | Starting material 2 | Product | Yield |
|---|---|---|---|---|
| 12b | | | | 83% |
| 12c | | | | 78% |

-continued

| Ex. | Starting material 1 | Starting material 2 | Product | Yield |
|---|---|---|---|---|
| 12d | (structure) | (structure) | (structure) | 69% |
| 12e | (structure) | (structure) | (structure) | 72% |

Example 13

Production of OLEDs

OLEDs according to the invention and OLEDs in accordance with the prior art are produced by a general process in accordance with WO 04/058911, which is adapted to the circumstances described here (layer-thickness variation, materials used).

The results for various OLEDs are presented in Examples 14 to 25 below (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin-coating from water; purchased from H.C. Starck, Goslar, Germany) for improved processing. These coated glass plates form the substrates to which the OLEDs are applied. The OLEDs have basically the following layer structure: substrate/hole-injection layer (HIL, comprising HIM1, 20 nm)/hole-transport layer (HTL, comprising HTM1, 20 nm)/electron-blocking layer (EBL, comprising EBM1, 20 nm)/emission layer (EML, 40 nm)/electron-transport layer (ETL, comprising ETM1, 20 nm)/electron-injection layer (EIL, LiF, 1 nm) and finally a cathode. The cathode is formed by an aluminium layer with a thickness of 100 nm. The structure of the EML and the results obtained using these OLEDs are shown in Table 1 for green-emitting OLEDs and Table 2 for blue-emitting OLEDs. The materials used for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by coevaporation.

The as yet unoptimised OLEDs are characterised by standard methods. For this purpose, the electroluminescence spectra, the current efficiency (measured in cd/A) and the voltage are determined. The efficiencies and voltages indicated in the tables relate to the corresponding values at an operating luminance of 1000 cd/m$^2$.

TABLE 1

Results for green-emitting OLEDs

| Ex. | EML | Efficiency [cd/A] | Voltage [V] | CIE, x/y |
|---|---|---|---|---|
| 14 | M1: TEG1 (15%) | 46.0 | 4.5 | 0.33/0.62 |
| 15 | M2: TEG1 (15%) | 39.8 | 4.5 | 0.33/0.62 |
| 16 | M3: TEG1 (15%) | 49.0 | 4.3 | 0.33/0.61 |
| 17 | M1: TEG2 (15%) | 53.9 | 4.4 | 0.32/0.61 |
| 18 | M3: TEG2 (15%) | 46.3 | 4.3 | 0.32/0.61 |
| 19 | M3: TEG2 (15%) | 51.2 | 4.3 | 0.32/0.61 |

TABLE 2

Results for blue-emitting OLEDs

| Ex. | EML | Efficiency [cd/A] | Voltage [V] | CIE, x/y |
|---|---|---|---|---|
| 20 | M2: TEB1 (15%) | 21.3 | 7.2 | 0.16/0.26 |
| 21 | M3: TEB1 (15%) | 22.1 | 6.9 | 0.16/0.27 |

TABLE 2-continued
Results for blue-emitting OLEDs
| Ex. | EML | Efficiency [cd/A] | Voltage [V] | CIE, x/y |
|---|---|---|---|---|
| 22 | M2: TEB2 (15%) | 24.3 | 4.7 | 0.16/0.24 |
| 23 | M3: TEB2 (15%) | 26.1 | 4.7 | 0.15/0.25 |
| 24 | M2: TEB3 (10%) | 23.3 | 4.5 | 0.16/0.41 |
| 25 | M3: TEB3 (10%) | 28.5 | 4.7 | 0.16/0.41 |
TABLE 3
Structural formulae of the materials used (the numbers indicated in square brackets are the CAS numbers of the materials)
HIM1
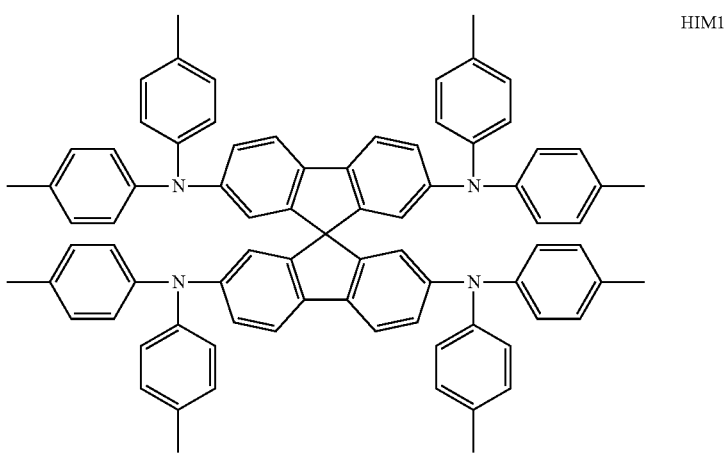
[515834-67-0]
HTM1
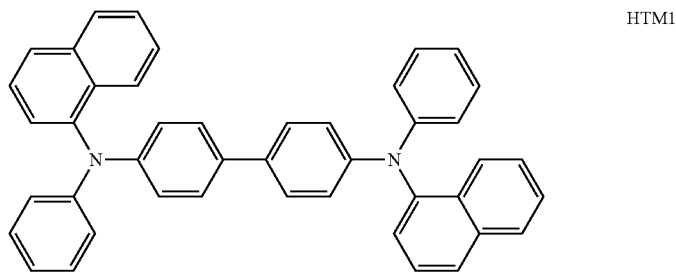
[123847-85-8]
(NPB)
EBM1
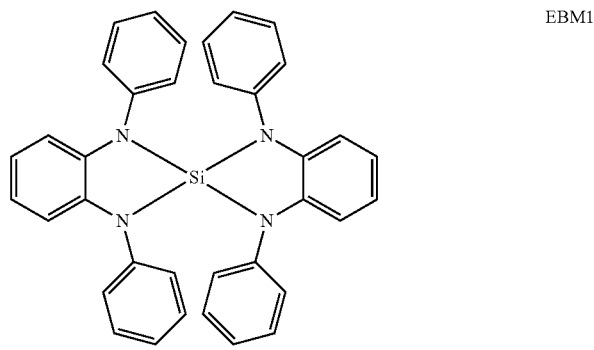
DE 102008056688.8

TABLE 3-continued
Structural formulae of the materials used (the numbers indicated in square brackets are the CAS numbers of the materials)
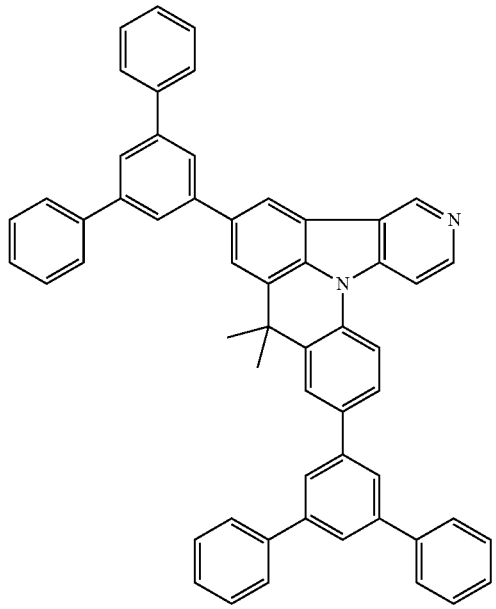 [SMILES: CC1(C)c2cc(-c3cc(-c4ccccc4)cc(-c4ccccc4)c3)ccc2-n2c3ccncc3c3cc(-c4cc(-c5ccccc5)cc(-c5ccccc5)c4)cc1c32]
M1
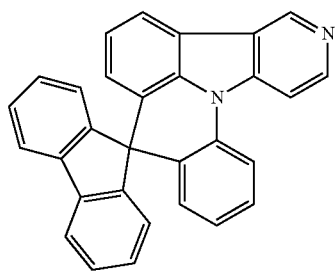 [SMILES: c1ccc2c(c1)-c1ccccc1C21c2ccccc2-n2c3ccncc3c3cccc1c32]
M2
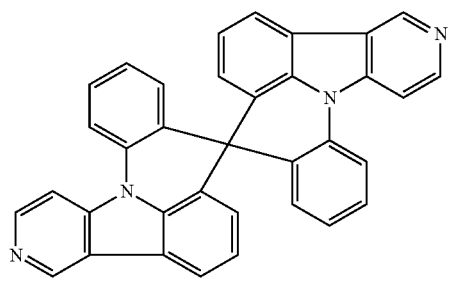 [SMILES: c1ccc2c(c1)-n1c3ccncc3c3cccc(c31)C21c2ccccc2-n2c3ccncc3c3cccc1c32]
M3
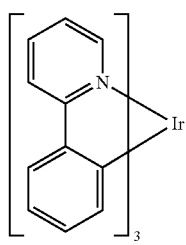
TEG1
[94928-86-6]

TABLE 3-continued
Structural formulae of the materials used (the numbers indicated in square brackets are the CAS numbers of the materials)
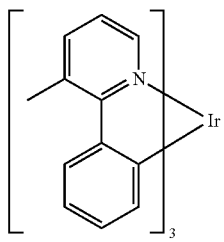
[359014-71-4]
TEG2
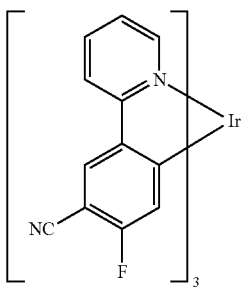
[613682-85-2]
TEB1
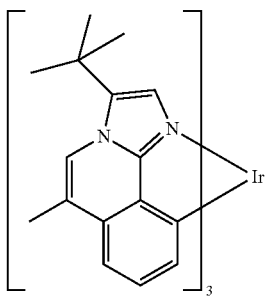
DE 102009007038.9
TEB2
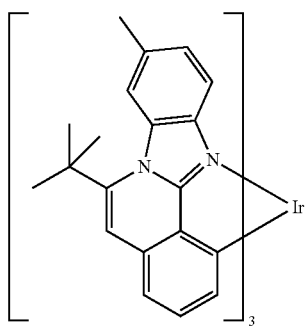
DE 102009007038.9
TEB3
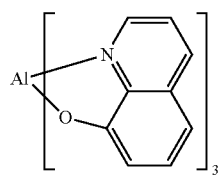
[2085-33-8]
(Alq$_3$)
ETM1

As can clearly be seen from the examples given above, the materials according to the invention are particularly suitable for use as matrix materials for phosphorescent emitters, where they result in high efficiencies and low operating voltages.

Example 26

Production of Further OLEDs

OLEDs according to the invention and OLEDs in accordance with the prior art are produced by a general process in accordance with WO 04/058911, which is adapted to the circumstances described here (layer-thickness variation, materials).

The data for various OLEDs are presented in Examples C1-I44 below (see Tables 4 and 5). Glass plates coated with structured ITO (indium tin oxide) in a thickness of 150 nm are coated with 20 nm of PEDOT (poly(3,4-ethyl-enedioxy-2,5-thiophene), applied by spin-coating from water; purchased from H.C. Starck, Goslar, Germany) for improved processing. These coated glass plates form the substrates to which the OLEDs are applied. The OLEDs basically have the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 4. The materials required for the production of the OLEDs are shown in Table 6.

All materials are applied by thermal vapour deposition in a vacuum chamber. The emission layer here always consists of at least one matrix material (host material) and an emitting dopant (emitter) which is admixed with the matrix material or materials in a certain proportion by volume by coevaporation. A specification such as ST1:CBP:TER1 (55%:35%:10%) here means that material ST1 is present in the layer in a proportion by volume of 55%, CBP is present in the layer in a proportion by volume of 35% and TER1 is present in the layer in a proportion by volume of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), and the lifetime are determined. The electroluminescence spectra are determined at a luminous density of 1000 cd/m$^2$, and the CIE 1931 x and y colour coordinates are calculated therefrom. The term U1000 in Table 5 denotes the voltage required for a luminous density of 1000 cd/m$^2$. CE1000 and PE1000 denote the current and power efficiencies achieved at 1000 cd/m$^2$. Finally, EQE1000 is the external quantum efficiency at an operating luminous density of 1000 cd/m$^2$. The lifetime LT is defined as the time after which the luminous density has dropped from the initial luminous density L0 to a certain proportion L1 on operation at constant current. A specification of L0=4000 cd/m$^2$ and L1=80% in Table 5 means that the lifetime indicated in column LT corresponds to the time after which the initial luminous density of the corresponding OLEDs has dropped from 4000 cd/m$^2$ to 3200 cd/m$^2$. The values for the lifetime can be converted into a specification for other initial luminous densities with the aid of conversion formulae known to the person skilled in the art. The lifetime for an initial luminous density of 1000 cd/m$^2$ is a usual specification here.

The data for the various OLEDs are summarised in Table 5. Examples C1-C9 are comparative examples in accordance with the prior art, Examples I1-I44 show data of OLEDs comprising materials according to the invention. The numbers used in Table 5 for the materials according to the invention correspond to the numbers of the synthesis examples described above.

Some of the examples are explained in greater detail below in order to illustrate the advantages of the compounds according to the invention. However, it should be pointed out that this only represents a selection of the data shown in Table 5. As can be seen from the table, improvements over the prior art are also achieved on use of the compounds according to the invention which are not described in greater detail, in some cases in all parameters, but in some cases only an improvement in the efficiency or voltage or lifetime is observed. However, even the improvement of one of the said parameters represents a significant advance, since different applications require optimisation with respect to different parameters.

Use of Compounds According to the Invention as Matrix Material in Phosphorescent OLEDs If the compounds according to the invention are employed as the only matrix material in the emission layer of phosphorescent OLEDs, significant improvements over the prior art are obtained. For example, excellent quantum efficiencies of up to 15.5% at a voltage of only 3.4 V and with a lifetime of 480 h are obtained with compound 12b according to the invention. Compared with material ST1 in accordance with the prior art, these values represent significant improvements by about 30% (power efficiency) and 45% (lifetime); the improvements are even clearer compared with Ket1 (Ex. I3, C3 and C4).

In many cases, the lifetime of phosphorescent OLEDs can be improved by co-evaporating not just one, but instead two matrix materials with an emitter (mixed matrix systems). Suitable for this purpose in accordance with the prior art are, for example, combinations of spirotriazines, ketones or also diazaphospholes with carbazoles or pure hydrocarbons. Data for corresponding OLEDs are shown in Ex. C7, C8 and C9. Data for OLEDs in which materials according to the invention are used are shown in Ex. I15-I33.

If CBP is replaced, for example, by material 10 h according to the invention, the power efficiency on combination with ST1 can be increased from 34 lm/W to 46 lm/W, i.e. by about 35%, and the lifetime is likewise improved by about 35% (Ex. I22, C7). The improvement in the power efficiency is mainly attributable here to the reduction in the operating voltage.

In combination with Ket1 or DAP1, similar increases in the performance data compared with CBP or FTPh are obtained (Ex. I32, I33, C8 and C9).

The materials according to the invention thus give rise to significant improvements over the prior art in all parameters, especially with respect to lifetime and power efficiency, on use as matrix materials in phosphorescent OLEDs.

In mixed matrix systems, the materials according to the invention give rise to very good performance data in combination with a very wide variety of classes of material (spirotriazines, ketones, diazaphospholes). Very good performance data can thus also be expected in combination with other classes of material.

Use of Compounds According to the Invention as Hole-Transport Materials

In accordance with the prior art, the hole-transport materials employed are, in particular, diarylamines, such as, for example, NPB or also BPA1. If these materials are replaced by materials according to the invention which are substituted by arylamine, significant improvements are obtained in fluorescent and phosphorescent OLEDs. Data for corresponding OLEDs are shown in Ex. I34-I43.

If, for example, compound 8 g according to the invention is employed as hole-transport material in a green-phosphorescent OLED, a 0.3 V lower voltage, a 10% improved quantum yield and thus an increase in the power efficiency from 38 to 44 lm/W are obtained compared with PBA1. The lifetime increases by about 55% to 480 h (Ex. I38, C2).

In blue-fluorescent OLEDs, the improvements are not quite as large, but are still very significant (Ex. I41-I43 and C1).

The use of compounds according to the invention on the hole-transport side of OLEDs thus produces significant improvements with respect to operating voltage, power efficiency and lifetime.

Use of Compounds According to the Invention as Electron-Transport Materials

If compound 12c according to the invention is employed with LiQ as electron-injection material, a more than 10% improved power efficiency is obtained compared with an ST1:LiQ (50%:50%) mixture, with the lifetime remaining approximately the same (Ex. C2, I44).

TABLE 4

Structure of the OLEDs

| Ix. | HIL thickness | HTL thickness | IL thickness | EBL thickness | EML thickness | HBL thickness | ETL thickness | EIL thickness |
|---|---|---|---|---|---|---|---|---|
| C1 | HATCN 5 nm | SpNPB 40 nm | — | NPB 20 nm | BA1:VP1 (98.5%:1.5%) 30 nm | — | ST2:LiQ (50%:50%) 20 nm | — |
| C2 | — | HIL1 70 nm | HATCN 5 nm | BPA1 20 nm | ST1:TEG2 (90%:10%) 30 nm | — | ST1:LiQ (50%:50%) 30 nm | — |
| C3 | — | HIL1 70 nm | HATCN 5 nm | BPA1 20 nm | ST1:TEG2 (90%:10%) 30 nm | ST1 10 nm | ST1:LiQ (50%:50%) 30 nm | — |
| C4 | — | HIL1 70 nm | HATCN 5 nm | BPA1 90 nm | Ket1:TEG2 (90%:10%) 30 nm | — | ST1:LiQ (50%:50%) 40 nm | — |
| C5 | — | HIL1 20 nm | — | NPB 20 nm | ST1:TER1 (85%:15%) 30 nm | — | $Alq_3$ 20 nm | LiF 1 nm |
| C6 | — | HIL1 20 nm | — | NPB 20 nm | ST1:TER2 (85%:15%) 30 nm | — | $Alq_3$ 20 nm | LiF 1 nm |
| C7 | — | HIL1 70 nm | HATCN 5 nm | BPA1 90 nm | ST1:CBP:TEG2 (30%:60%:10%) 30 nm | ST1 10 nm | ST1:LiQ (50%:50%) 30 nm | — |
| C8 | HATCN 20 nm | — | — | BPA1 20 nm | Ket1:FTPh:TEG2 (30%:60%:10%) 30 nm | Ket1 10 nm | ETM2 20 nm | LiF 1 nm |
| C9 | — | HIL1 70 nm | HATCN 5 nm | BPA1 90 nm | DAP1:CBP:TEG2 (30%:60%:10%) 30 nm | — | ST1:LiQ (50%:50%) 30 nm | — |
| I1 | — | HIL1 70 nm | HATCN 5 nm | BPA1 20 nm | 12a:TEG2 (90%:10%) 30 nm | — | ST1:LiQ (50%:50%) 30 nm | — |
| I2 | — | HIL1 70 nm | HATCN 5 nm | BPA1 20 nm | 12b:TEG2 (90%:10%) 30 nm | — | ST1:LiQ (50%:50%) 30 nm | — |
| I3 | — | HIL1 70 nm | HATCN 5 nm | BPA1 20 nm | 12b:TEG2 (90%:10%) 30 nm | ST1 10 nm | ST1:LiQ (50%:50%) 30 nm | — |
| I4 | — | HIL1 20 nm | — | NPB 20 nm | 12b:TER1 (85%:15%) 30 nm | — | $Alq_3$ 20 nm | LiF 1 nm |
| I5 | — | HIL1 20 nm | — | NPB 20 nm | 12b:TER2 (85%:15%) 30 nm | — | $Alq_3$ 20 nm | LiF 1 nm |
| I6 | — | HIL1 70 nm | HATCN 5 nm | BPA1 20 nm | 12c:TEG2 (90%:10%) 30 nm | — | ST1:LiQ (50%:50%) 30 nm | — |
| I7 | — | HIL1 70 nm | HATCN 5 nm | BPA1 20 nm | 12d:TEG2 (90%:10%) 30 nm | — | ST1:LiQ (50%:50%) 30 nm | — |
| I8 | — | HIL1 70 nm | HATCN 5 nm | BPA1 20 nm | 12e:TEG2 (90%:10%) 30 nm | — | ST1:LiQ (50%:50%) 30 nm | — |
| I9 | — | HIL1 70 nm | HATCN 5 nm | BPA1 20 nm | M3:TEG2 (90%:10%) 30 nm | IC1 10 nm | ST1:LiQ (50%:50%) 50 nm | — |

TABLE 4-continued

Structure of the OLEDs

| Ix. | HIL thickness | HTL thickness | IL thickness | EBL thickness | EML thickness | HBL thickness | ETL thickness | EIL thickness |
|---|---|---|---|---|---|---|---|---|
| I10 | — | HIL1 70 nm | HATCN 5 nm | BPA1 20 nm | 7c:TEG2 (90%:10%) 30 nm | IC1 10 nm | ST1:LiQ (50%:50%) 50 nm | — |
| I11 | — | HIL1 70 nm | HATCN 5 nm | BPA1 20 nm | 9c:TEG2 (90%:10%) 30 nm | IC1 10 nm | ST1:LiQ (50%:50%) 50 nm | — |
| I12 | — | HIL1 70 nm | HATCN 5 nm | BPA1 20 nm | 9d:TEG2 (90%:10%) 30 nm | IC1 10 nm | ST1:LiQ (50%:50%) 50 nm | — |
| I13 | — | HIL1 70 nm | HATCN 5 nm | BPA1 20 nm | 10d:TEG2 (90%:10%) 30 nm | IC1 10 nm | ST1:LiQ (50%:50%) 50 nm | — |
| I14 | — | HIL1 70 nm | HATCN 5 nm | BPA1 20 nm | 3a:TEG2 (90%:10%) 30 nm | — | ST1:LiQ (50%:50%) 30 nm | — |
| I15 | — | HIL1 70 nm | HATCN 5 nm | BPA1 90 nm | ST1:7a:TEG2 (30%:60%:10%) 30 nm | ST1 10 nm | ST1:LiQ (50%:50%) 30 nm | — |
| I16 | — | HIL1 70 nm | HATCN 5 nm | BPA1 90 nm | ST1:7b:TEG2 (30%:60%:10%) 30 nm | ST1 10 nm | ST1:LiQ (50%:50%) 30 nm | — |
| I17 | — | HIL1 70 nm | HATCN 5 nm | BPA1 90 nm | ST1:7d:TEG2 (30%:60%:10%) 30 nm | ST1 10 nm | ST1:LiQ (50%:50%) 30 nm | — |
| I18 | — | HIL1 70 nm | HATCN 5 nm | BPA1 90 nm | ST1:7e:TEG2 (30%:60%:10%) 30 nm | ST1 10 nm | ST1:LiQ (50%:50%) 30 nm | — |
| I19 | — | HIL1 70 nm | HATCN 5 nm | BPA1 90 nm | ST1:7f:TEG2 (30%:60%:10%) 30 nm | ST1 10 nm | ST1:LiQ (50%:50%) 30 nm | — |
| I20 | — | HIL1 70 nm | HATCN 5 nm | BPA1 90 nm | ST1:7g:TEG2 (30%:60%:10%) 30 nm | ST1 10 nm | ST1:LiQ (50%:50%) 30 nm | — |
| I21 | — | HIL1 70 nm | HATCN 5 nm | BPA1 90 nm | ST1:10i:TEG2 (30%:60%:10%) 30 nm | ST1 10 nm | ST1:LiQ (50%:50%) 30 nm | — |
| I22 | — | HIL1 70 nm | HATCN 5 nm | BPA1 90 nm | ST1:10h:TEG2 (30%:60%:10%) 30 nm | ST1 10 nm | ST1:LiQ (50%:50%) 30 nm | — |
| I23 | — | HIL1 70 nm | HATCN 5 nm | BPA1 90 nm | ST1:9b:TEG2 (30%:60%:10%) 30 nm | ST1 10 nm | ST1:LiQ (50%:50%) 30 nm | — |
| I24 | — | HIL1 70 nm | HATCN 5 nm | BPA1 90 nm | ST1:9e:TEG2 (30%:60%:10%) 30 nm | ST1 10 nm | ST1:LiQ (50%:50%) 30 nm | — |
| I25 | — | HIL1 70 nm | HATCN 5 nm | BPA1 90 nm | ST1:9f:TEG2 (30%:60%:10%) 30 nm | ST1 10 nm | ST1:LiQ (50%:50%) 30 nm | — |
| I26 | — | HIL1 70 nm | HATCN 5 nm | BPA1 90 nm | ST1:9g:TEG2 (30%:60%:10%) 30 nm | ST1 10 nm | ST1:LiQ (50%:50%) 30 nm | — |
| I27 | — | HIL1 70 nm | HATCN 5 nm | BPA1 90 nm | ST1:10b:TEG2 (30%:60%:10%) 30 nm | ST1 10 nm | ST1:LiQ (50%:50%) 30 nm | — |
| I28 | — | HIL1 70 nm | HATCN 5 nm | BPA1 90 nm | ST1:10d:TEG2 (30%:60%:10%) 30 nm | ST1 10 nm | ST1:LiQ (50%:50%) 30 nm | — |
| I29 | — | HIL1 70 nm | HATCN 5 nm | BPA1 90 nm | ST1:10e:TEG2 (30%:60%:10%) 30 nm | ST1 10 nm | ST1:LiQ (50%:50%) 30 nm | — |
| I30 | — | HIL1 70 nm | HATCN 5 nm | BPA1 90 nm | ST1:10f:TEG2 (30%:60%:10%) 30 nm | ST1 10 nm | ST1:LiQ (50%:50%) 30 nm | — |
| I31 | — | HIL1 70 nm | HATCN 5 nm | BPA1 90 nm | ST1:10g:TEG2 (30%:60%:10%) 30 nm | ST1 10 nm | ST1:LiQ (50%:50%) 30 nm | — |
| I32 | HATCN 20 nm | — | — | BPA1 20 nm | Ket1:10h:TEG2 (30%:60%:10%) 30 nm | Ket1 10 nm | ETM2 20 nm | LiF 1 nm |
| I33 | — | HIL1 70 nm | HATCN 5 nm | BPA1 90 nm | DAPI:CBP:TEG2 (30%:60%:10%) 30 nm | — 30 nm | ST1:LiQ (50%:50%) | — |
| I34 | — | HIL1 70 nm | HATCN 5 nm | 8a 20 nm | ST1:TEG2 (90%:10%) 30 nm | — | ST1:LiQ (50%:50%) 30 nm | — |

TABLE 4-continued

Structure of the OLEDs

| Ix. | HIL thickness | HTL thickness | IL thickness | EBL thickness | EML thickness | HBL thickness | ETL thickness | EIL thickness |
|---|---|---|---|---|---|---|---|---|
| I35 | — | HIL1 70 nm | HATCN 5 nm | 8d 20 nm | ST1:TEG2 (90%:10%) 30 nm | — | ST1:LiQ (50%:50%) 30 nm | — |
| I36 | — | HIL1 70 nm | HATCN 5 nm | 8e 20 nm | ST1:TEG2 (90%:10%) 30 nm | — | ST1:LiQ (50%:50%) 30 nm | — |
| I37 | — | HIL1 70 nm | HATCN 5 nm | 8f 20 nm | ST1:TEG2 (90%:10%) 30 nm | — | ST1:LiQ (50%:50%) 30 nm | — |
| I38 | — | HIL1 70 nm | HATCN 5 nm | 8g 20 nm | ST1:TEG2 (90%:10%) 30 nm | — | ST1:LiQ (50%:50%) 30 nm | — |
| I39 | — | HIL1 70 nm | HATCN 5 nm | 11a 20 nm | ST1:TEG2 (90%:10%) 30 nm | — | ST1:LiQ (50%:50%) 30 nm | — |
| I40 | — | HIL1 70 nm | HATCN 5 nm | 11c 20 nm | ST1:TEG2 (90%:10%) 30 nm | — | ST1:LiQ (50%:50%) 30 nm | — |
| I41 | HATCN 5 nm | SpNPB 40 nm | — | 8b 20 nm | BA1:VP1 (98.5%:1.5%) 30 nm | — | ST2:LiQ (50%:50%) 20 nm | — |
| I42 | HATCN 5 nm | SpNPB 40 nm | — | 8c 20 nm | BA1:VP1 (98.5%:1.5%) 30 nm | — | ST2:LiQ (50%:50%) 20 nm | — |
| I43 | HATCN 5 nm | SpNPB 40 nm | — | 11b 20 nm | BA1:VP1 (98.5%:1.5%) 30 nm | — | ST2:LiQ (50%:50%) 20 nm | — |
| I44 | — | HIL1 70 nm | HATCN 5 nm | BPA1 20 nm | ST1:TEG2 (90%:10%) 30 nm | — | 12c 30 nm | LiQ 3 nm |

TABLE 5

Data for the OLEDs

| Ex. | U1000 (V) | CE1000 (cd/A) | PE1000 (lm/W) | EQE 1000 | CIE x/y at 1000 cd/m² | L0 (cd/m²) | L1 % | LT (h) |
|---|---|---|---|---|---|---|---|---|
| C1 | 4.3 | 9.8 | 7.1 | 7.6% | 0.14/0.16 | 6000 | 50 | 210 |
| C2 | 4.1 | 50 | 38 | 13.9% | 0.37/0.61 | 4000 | 80 | 310 |
| C3 | 4.2 | 52 | 39 | 14.5% | 0.36/0.60 | 4000 | 80 | 330 |
| C4 | 3.9 | 41 | 33 | 11.0% | 0.36/0.61 | 4000 | 80 | 315 |
| C5 | 5.0 | 7.2 | 4.5 | 12.0% | 0.69/0.31 | 1000 | 50 | 14000 |
| C6 | 6.5 | 9.0 | 4.3 | 8.3% | 0.66/0.33 | 1000 | 50 | 18000 |
| C7 | 4.4 | 48 | 34 | 13.3% | 0.37/0.60 | 4000 | 80 | 450 |
| C8 | 4.3 | 45 | 33 | 12.6% | 0.36/0.61 | 4000 | 80 | 420 |
| C9 | 4.6 | 47 | 32 | 13.2% | 0.36/0.60 | 4000 | 80 | 490 |
| I1 | 3.3 | 53 | 50 | 14.7% | 0.36/0.60 | 4000 | 80 | 450 |
| I2 | 3.4 | 55 | 51 | 15.2% | 0.36/0.61 | 4000 | 80 | 460 |
| I3 | 3.4 | 56 | 51 | 15.5% | 0.36/0.61 | 4000 | 80 | 480 |
| I4 | 4.7 | 8.0 | 5.4 | 13.3% | 0.69/0.31 | 1000 | 50 | 22000 |
| I5 | 5.6 | 11 | 6.2 | 10.1% | 0.66/0.33 | 1000 | 50 | 23000 |
| I6 | 3.5 | 57 | 51 | 15.7% | 0.36/0.60 | 4000 | 80 | 430 |
| I7 | 3.7 | 47 | 39 | 12.9% | 0.36/0.60 | 4000 | 80 | 350 |
| I8 | 3.4 | 50 | 45 | 13.8% | 0.36/0.60 | 4000 | 80 | 460 |
| I9 | 3.8 | 54 | 45 | 14.9% | 0.36/0.61 | 4000 | 80 | 430 |
| I10 | 3.9 | 52 | 41 | 14.4% | 0.36/0.61 | 4000 | 80 | 480 |
| I11 | 4.0 | 48 | 38 | 13.2% | 0.36/0.61 | 4000 | 80 | 300 |
| I12 | 3.8 | 50 | 41 | 13.7% | 0.36/0.61 | 4000 | 80 | 370 |
| I13 | 3.8 | 53 | 44 | 14.7% | 0.36/0.61 | 4000 | 80 | 440 |
| I14 | 3.7 | 46 | 39 | 12.8% | 0.35/0.58 | 4000 | 80 | 360 |
| I15 | 4.1 | 50 | 38 | 13.9% | 0.36/0.61 | 4000 | 80 | 440 |
| I16 | 4.0 | 47 | 37 | 12.9% | 0.36/0.60 | 4000 | 80 | 510 |
| I17 | 3.9 | 52 | 42 | 14.5% | 0.36/0.61 | 4000 | 80 | 420 |
| I18 | 3.8 | 51 | 42 | 14.0% | 0.37/0.61 | 4000 | 80 | 480 |
| I19 | 4.2 | 49 | 37 | 13.5% | 0.36/0.60 | 4000 | 80 | 450 |
| I20 | 4.2 | 53 | 39 | 14.6% | 0.36/0.60 | 4000 | 80 | 530 |
| I21 | 3.8 | 50 | 41 | 13.8% | 0.36/0.61 | 4000 | 80 | 570 |
| I22 | 3.7 | 53 | 46 | 14.7% | 0.35/0.60 | 4000 | 80 | 610 |
| I23 | 4.3 | 48 | 35 | 13.2% | 0.36/0.61 | 4000 | 80 | 490 |
| I24 | 3.9 | 52 | 42 | 14.5% | 0.36/0.60 | 4000 | 80 | 500 |
| I25 | 3.7 | 51 | 43 | 14.1% | 0.36/0.60 | 4000 | 80 | 390 |

TABLE 5-continued
Data for the OLEDs
| Ex. | U1000 (V) | CE1000 (cd/A) | PE1000 (lm/W) | EQE 1000 | CIE x/y at 1000 cd/m$^2$ | L0 (cd/m$^2$) | L1 % | LT (h) |
|---|---|---|---|---|---|---|---|---|
| I26 | 3.9 | 47 | 37 | 13.0% | 0.36/0.60 | 4000 | 80 | 520 |
| I27 | 4.3 | 52 | 38 | 14.4% | 0.36/0.61 | 4000 | 80 | 470 |
| I28 | 3.8 | 54 | 44 | 14.9% | 0.36/0.61 | 4000 | 80 | 550 |
| I29 | 3.9 | 49 | 40 | 13.7% | 0.37/0.61 | 4000 | 80 | 510 |
| I30 | 4.1 | 48 | 37 | 13.3% | 0.35/0.60 | 4000 | 80 | 530 |
| I31 | 3.8 | 49 | 41 | 13.6% | 0.36/0.60 | 4000 | 80 | 570 |
| I32 | 4.1 | 47 | 36 | 12.9% | 0.36/0.61 | 4000 | 80 | 520 |
| I33 | 4.2 | 51 | 38 | 14.2% | 0.36/0.61 | 4000 | 80 | 560 |
| I34 | 4.2 | 51 | 39 | 14.2% | 0.37/0.61 | 4000 | 80 | 390 |
| I35 | 4.0 | 45 | 36 | 12.6% | 0.36/0.60 | 4000 | 80 | 330 |
| I36 | 4.0 | 53 | 42 | 14.8% | 0.37/0.61 | 4000 | 80 | 430 |
| I37 | 4.1 | 52 | 40 | 14.4% | 0.37/0.61 | 4000 | 80 | 450 |
| I38 | 3.9 | 55 | 44 | 15.2% | 0.37/0.61 | 4000 | 80 | 480 |
| I39 | 4.3 | 55 | 41 | 15.3% | 0.36/0.61 | 4000 | 80 | 280 |
| I40 | 3.9 | 52 | 52 | 14.3% | 0.37/0.61 | 4000 | 80 | 380 |
| I41 | 4.1 | 10.2 | 7.8 | 7.9% | 0.14/0.16 | 6000 | 50 | 280 |
| I42 | 4.0 | 8.1 | 6.3 | 6.3% | 0.14/0.16 | 6000 | 50 | 230 |
| I43 | 4.3 | 9.9 | 7.3 | 7.7% | 0.14/0.16 | 6000 | 50 | 240 |
| I44 | 3.9 | 52 | 42 | 14.3% | 0.36/0.60 | 4000 | 80 | 320 |
TABLE 6
Structural formulae of the materials for the OLEDs
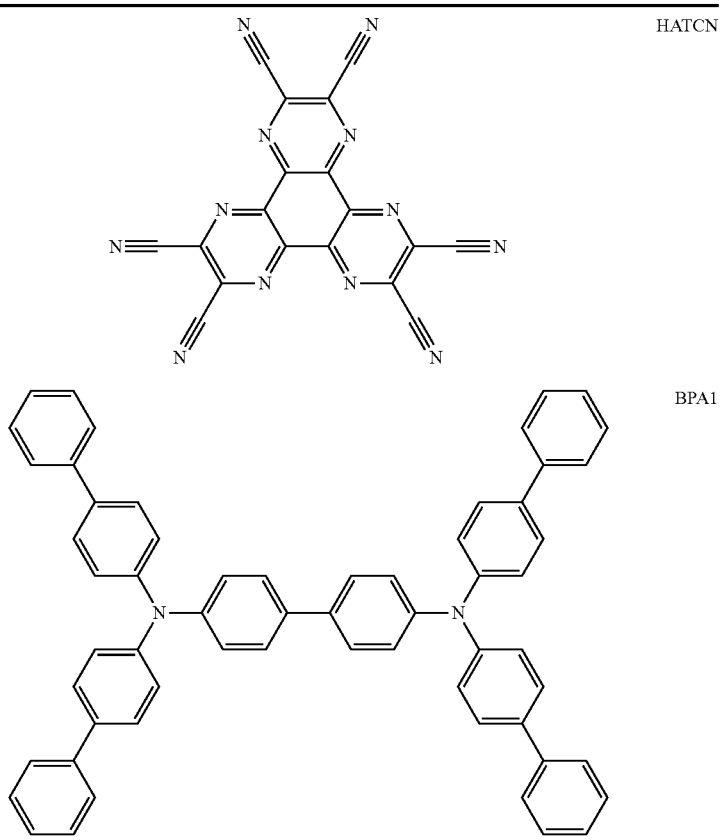
HATCN
BPA1
(prior art)

TABLE 6-continued
Structural formulae of the materials for the OLEDs
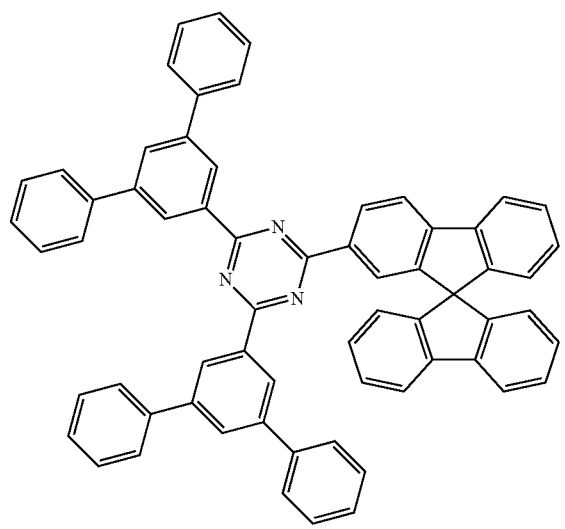 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
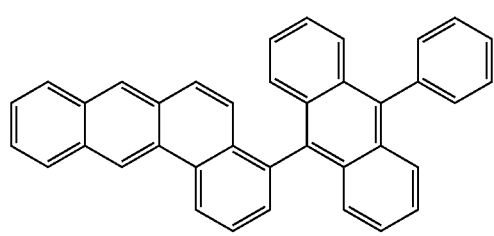 [SMILES: c1ccc(-c2c3ccccc3c(-c3cccc4c3ccc3cc5ccccc5cc34)c3ccccc23)cc1]
BA1
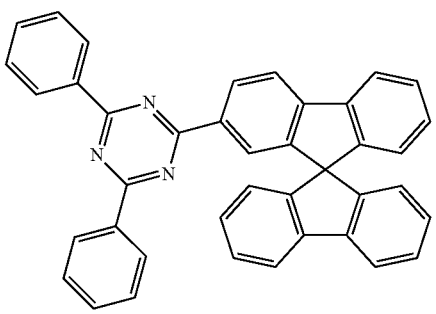 [SMILES: c1ccc(-c2nc(-c3ccccc3)nc(-c3ccc4c(c3)C3(c5ccccc5-c5ccccc53)c3ccccc3-4)n2)cc1]
ST1
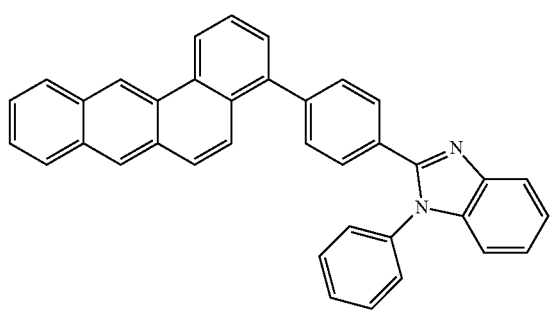 [SMILES: c1ccc(-n2c(-c3ccc(-c4cccc5c4ccc4cc6ccccc6cc45)cc3)nc3ccccc32)cc1]
ETM2
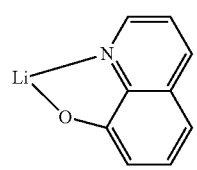
LiQ TABLE 6-continued
Structural formulae of the materials for the OLEDs
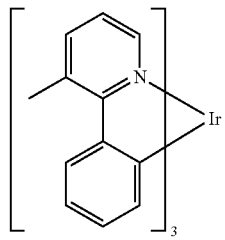
TEG2
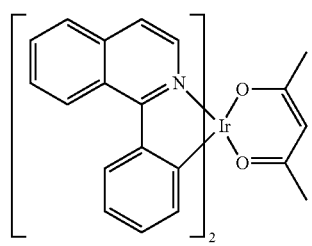
TER1
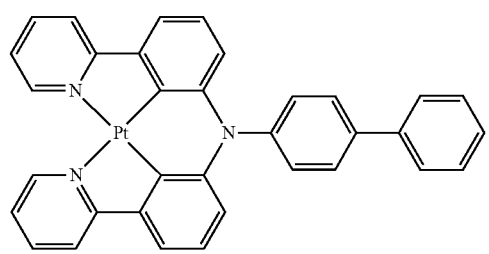
TER2
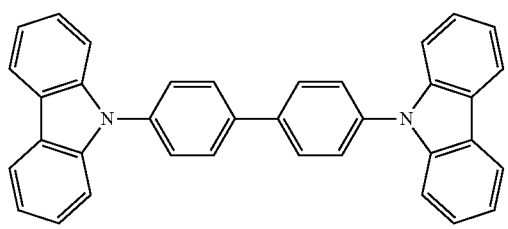
CBP
(prior art)
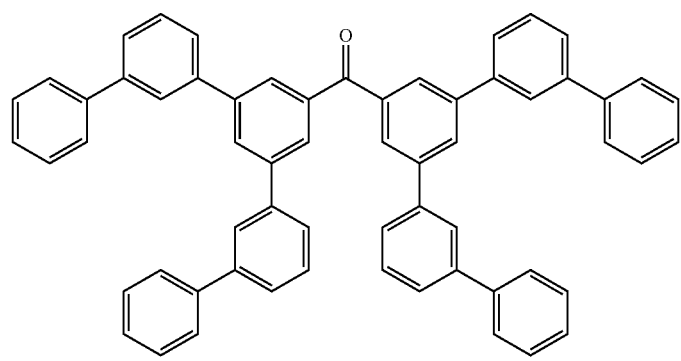
Ket1
(prior art)

TABLE 6-continued
Structural formulae of the materials for the OLEDs
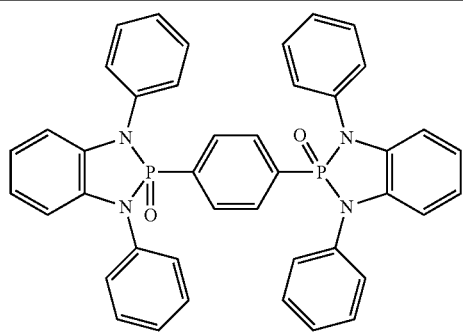
DAP1
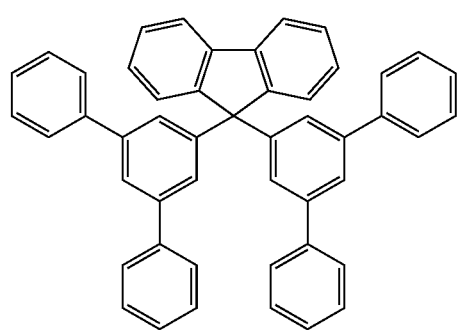
FTPh
(prior art)
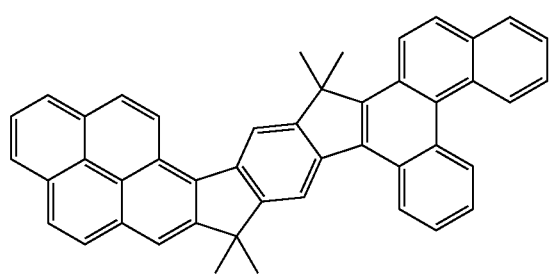 [SMILES: CC1(C)c2cc3c(cc2-c2c1cc1ccc4cccc5ccc2c1c45)C(C)(C)c1c-3c2ccccc2c2c1ccc1ccccc12]
VP1
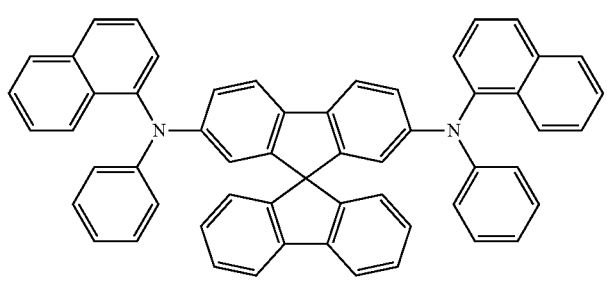 [SMILES: c1ccc(N(c2ccc3c(c2)C2(c4ccccc4-c4ccccc42)c2cc(N(c4ccccc4)c4cccc5ccccc45)ccc2-3)c2cccc3ccccc23)cc1]
SpNBP
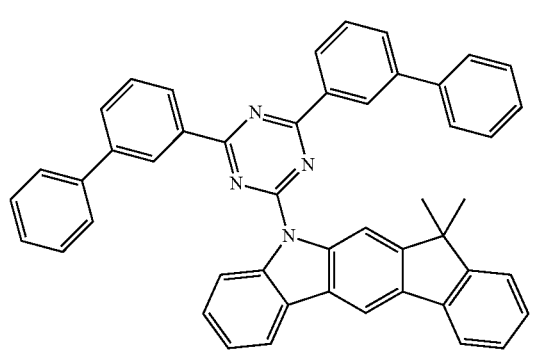 [SMILES: CC1(C)c2ccccc2-c2cc3c4ccccc4n(-c4nc(-c5cccc(-c6ccccc6)c5)nc(-c5cccc(-c6ccccc6)c5)n4)c3cc21]
IC1

The invention claimed is:
1. A compound of the formula (1), formula (2), formula (3) or formula (4):
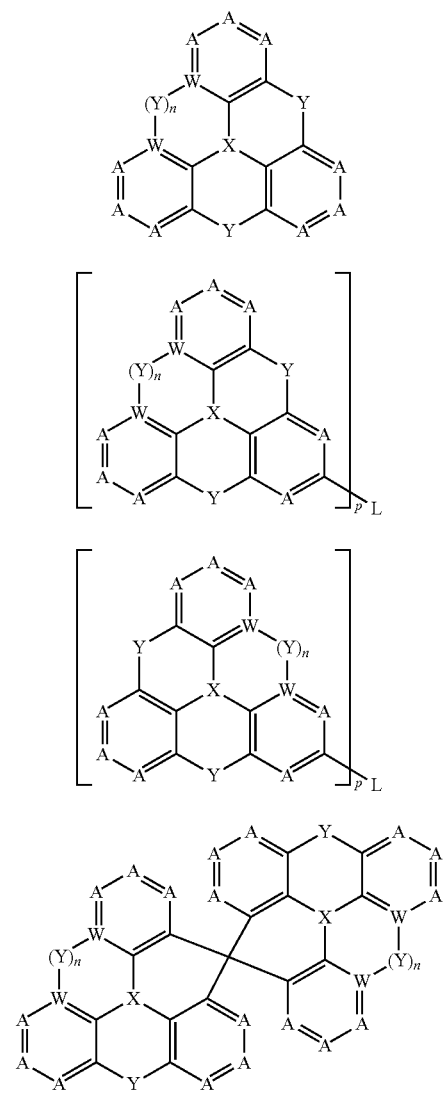
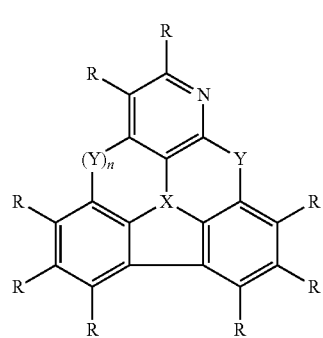
wherein the compound of the formula (1) is selected from compounds of the following formulae (11a) to (31b):
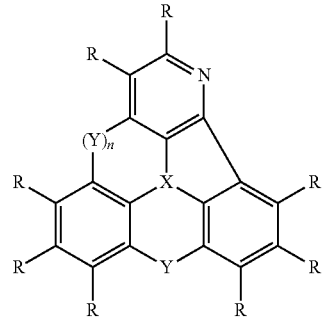
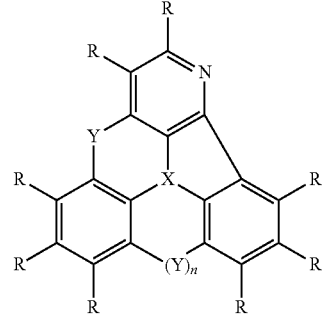
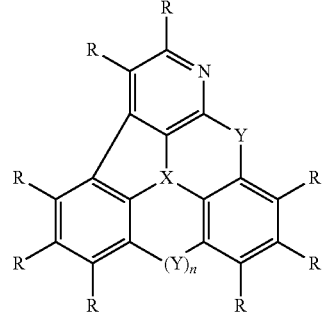
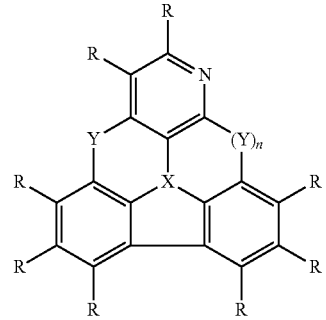
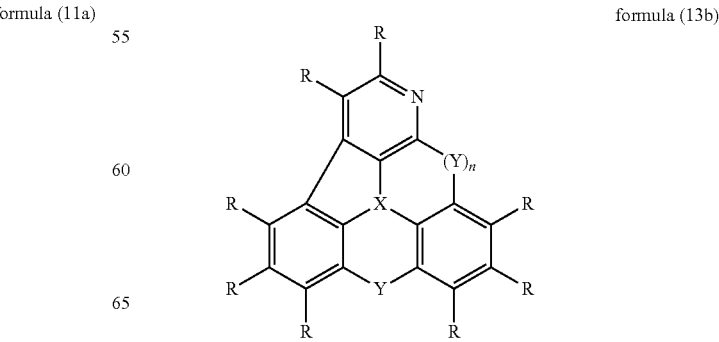

formula (14a)
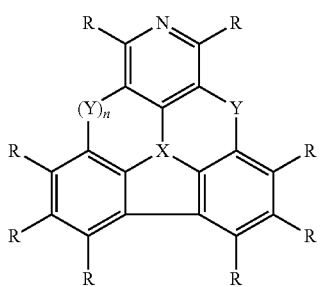
formula (14b)
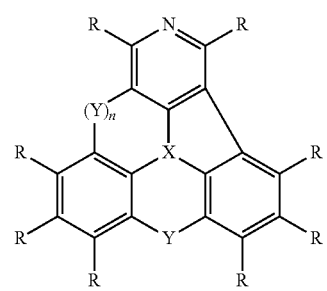
formula (15a)
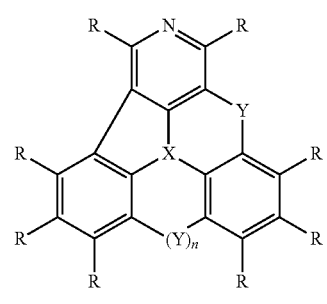
formula (16a)
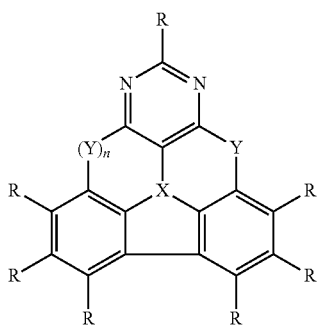
formula (16b)
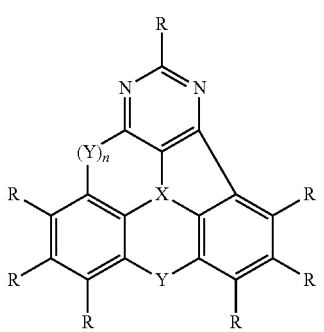
formula (17a)
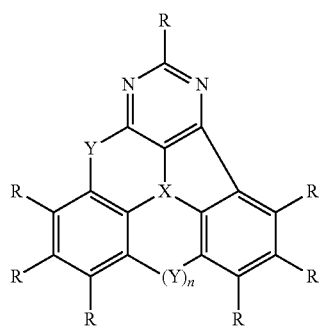
formula (18a)
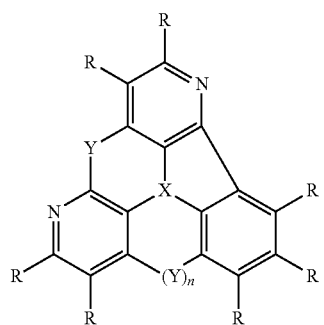
formula (18b)
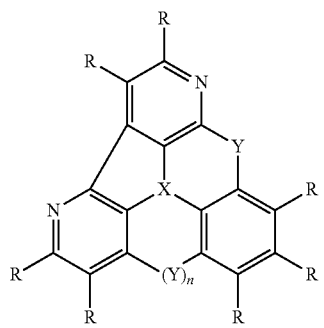
formula (19a)
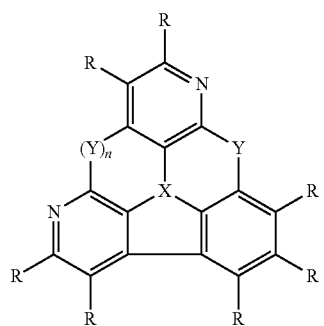
formula (19b)
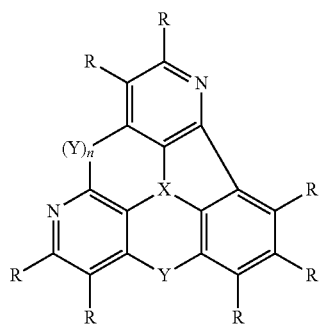

-continued
formula (20a)
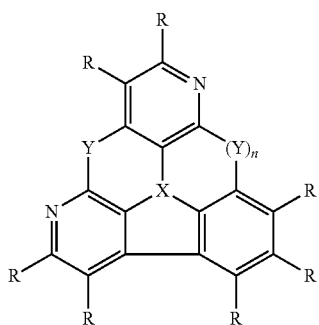
formula (20b)
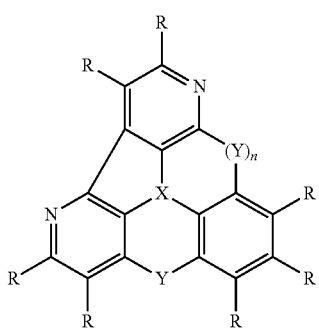
formula (21a)
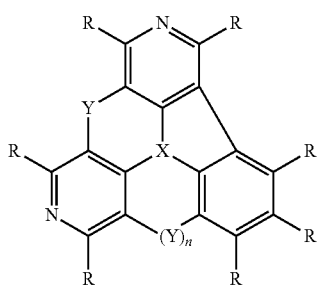
formula (21b)
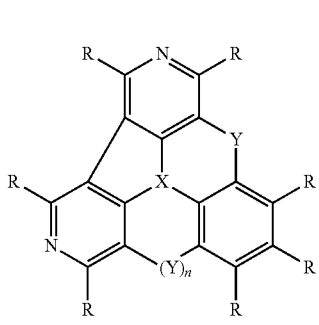
formula (22a)
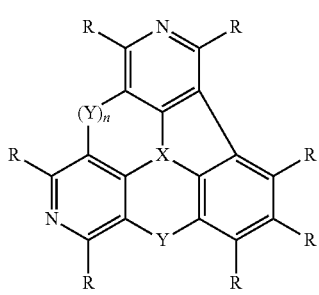
-continued
formula (23a)
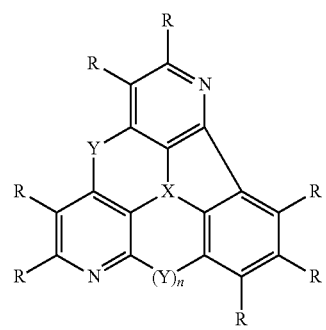
formula (23b)
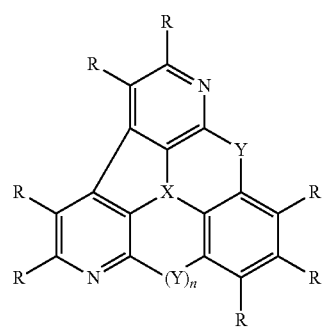
formula (24a)
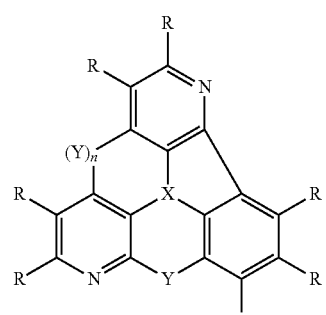
formula (25a)
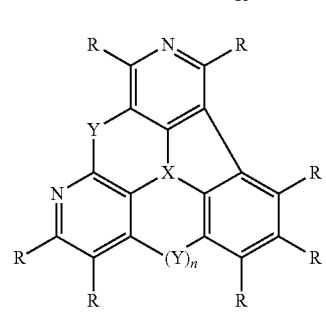
formula (25b)
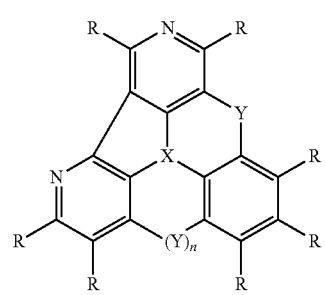

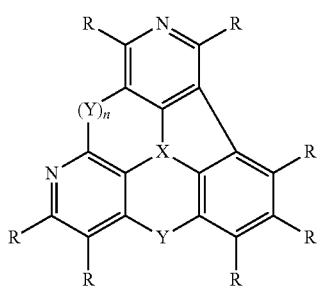
formula (26a)
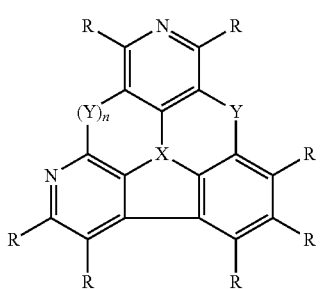
formula (26b)
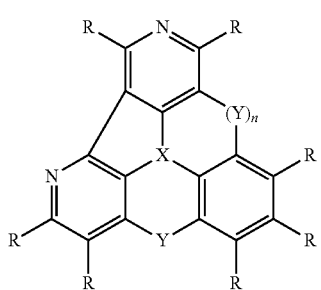
formula (27a)
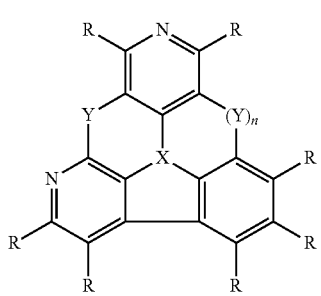
formula (27a)
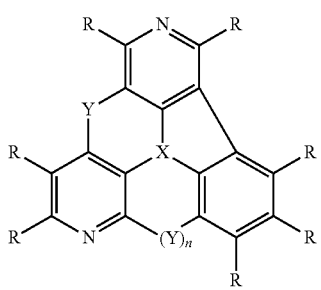
formula (28a)
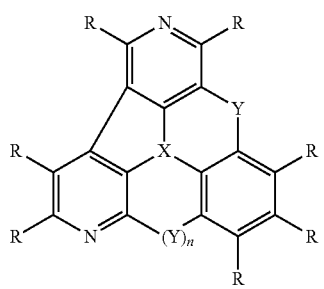
formula (28b)
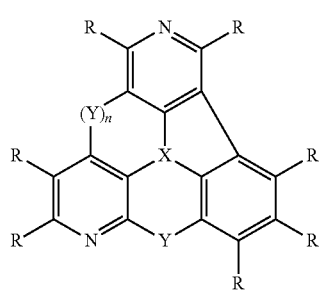
formula (29a)
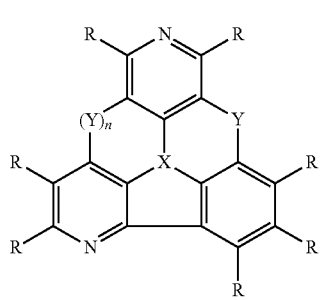
formula (29b)
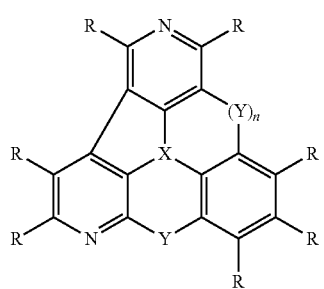
formula (30a)
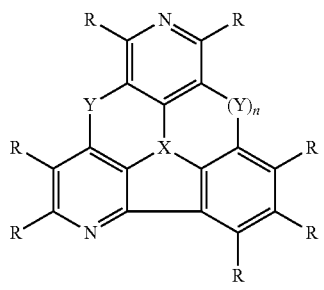
formula (30b)

formula (31a)

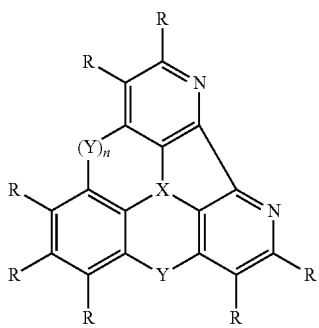

formula (31b)

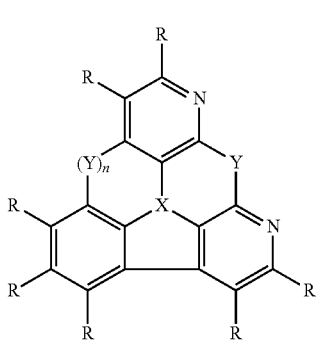

where the following applies to the symbols and indices used:

A is on each occurrence, identically or differently, CR or N;

W is C if a group Y is bonded to this group W and is CR or N if no group Y is bonded to this group W;

with the proviso that at least one symbol A and/or at least one symbol W stands for N;

X is on each occurrence, identically or differently, N, P or P=O;

Y is $C(R^1)_2$;

wherein one or two R groups are selected from structures of the following formulae (32) to (67):

formula (32)

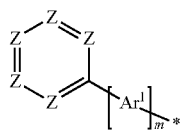

formula (33)

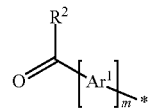

formula (34)

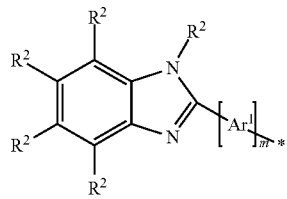

formula (35)

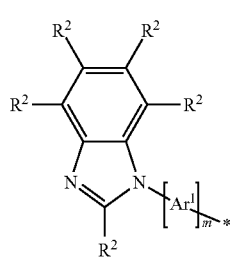

formula (36)

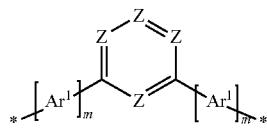

formula (37)

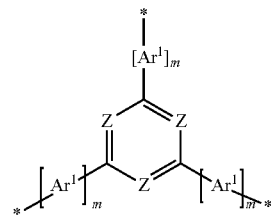

formula (38)

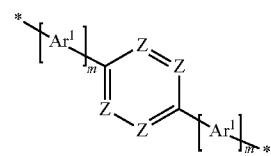

formula (39)

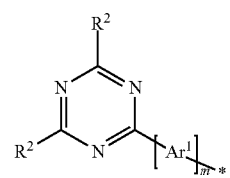

formula (40)

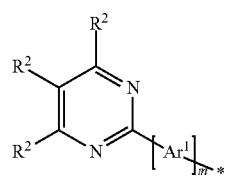

formula (41)

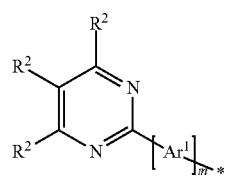

formula (42)

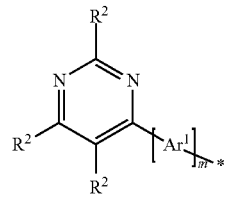

-continued
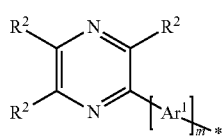
formula (43)
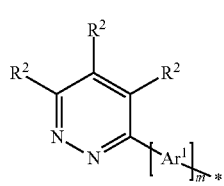
formula (44)
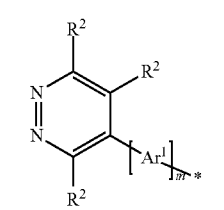
formula (45)
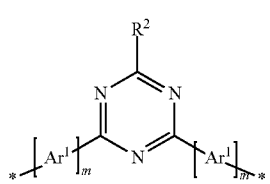
formula (46)
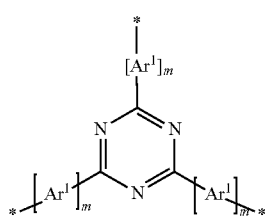
formula (47)
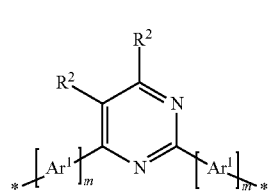
formula (48)
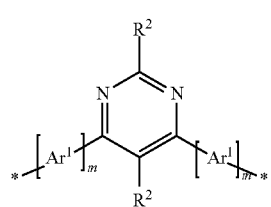
formula (49)
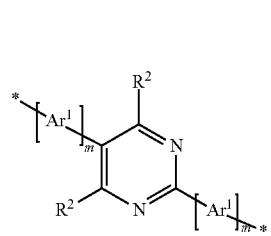
formula (50)
-continued
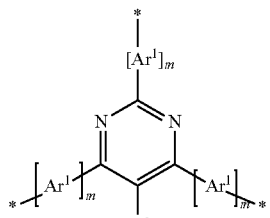
formula (51)
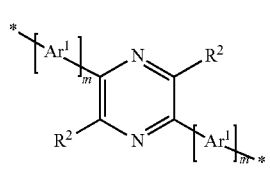
formula (52)
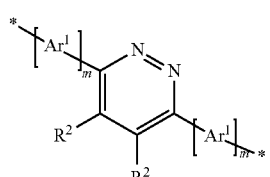
formula (53)
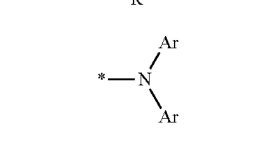
formula (54)
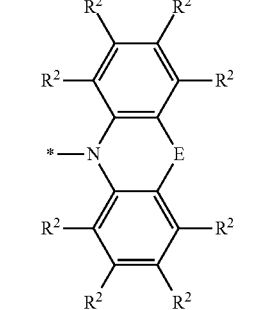
formula (55)
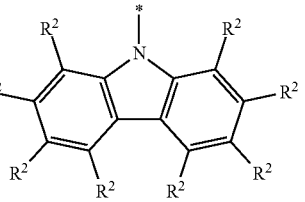
formula (56)
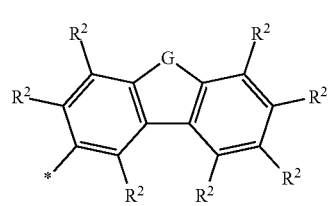
formula (57)
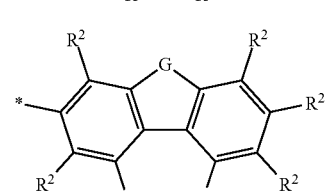
formula (58)

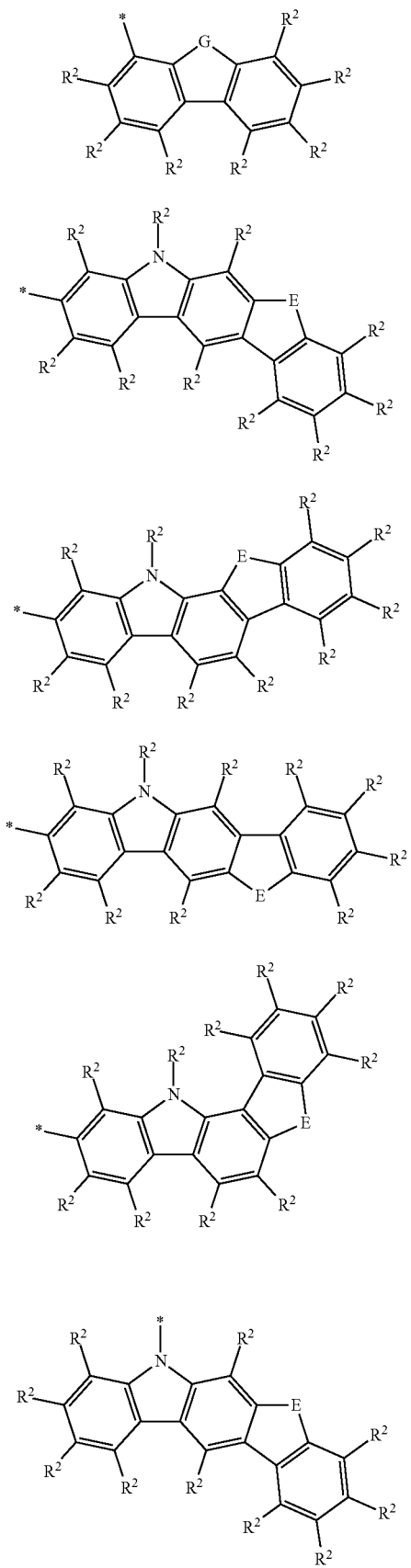

formula (59)

formula (60)

formula (61)

formula (62)

formula (63)

formula (64)

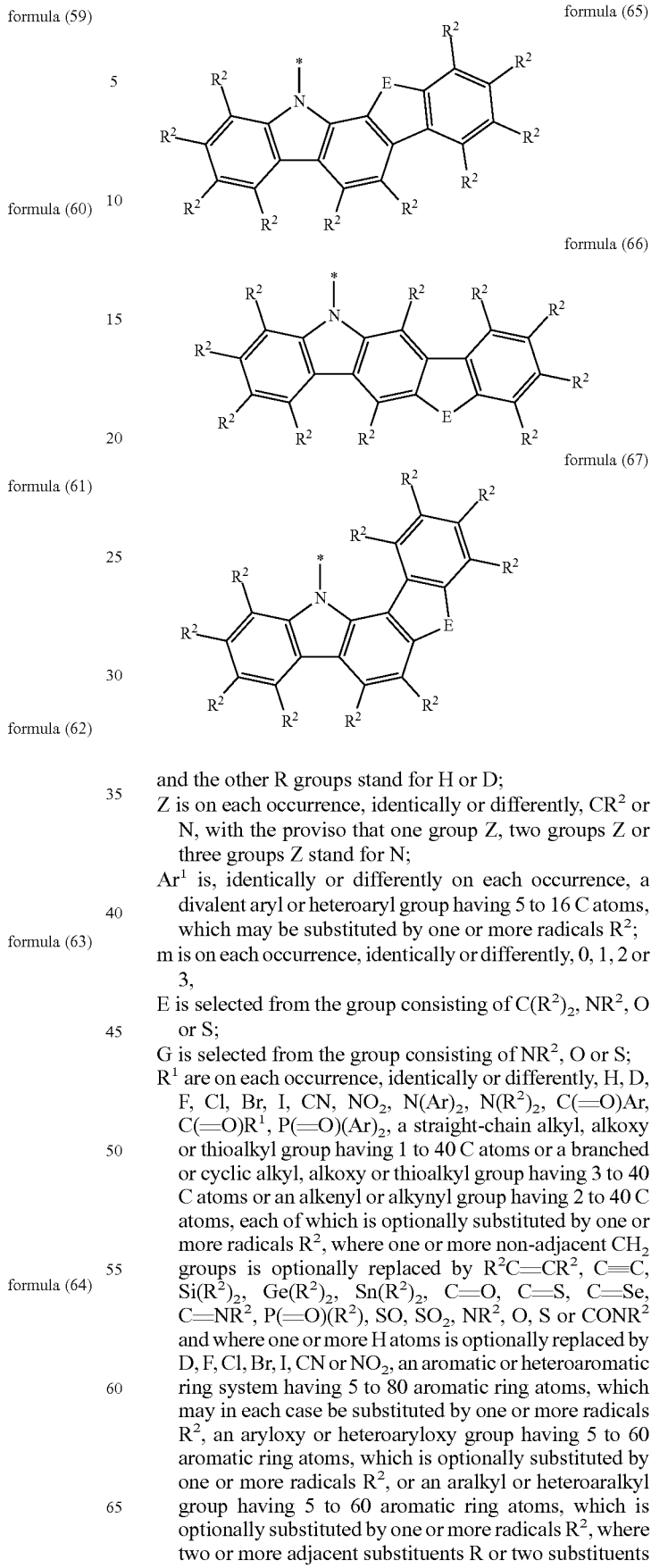

formula (65)

formula (66)

formula (67)

and the other R groups stand for H or D;

Z is on each occurrence, identically or differently, $CR^2$ or N, with the proviso that one group Z, two groups Z or three groups Z stand for N;

$Ar^1$ is, identically or differently on each occurrence, a divalent aryl or heteroaryl group having 5 to 16 C atoms, which may be substituted by one or more radicals $R^2$;

m is on each occurrence, identically or differently, 0, 1, 2 or 3,

E is selected from the group consisting of $C(R^2)_2$, $NR^2$, O or S;

G is selected from the group consisting of $NR^2$, O or S;

$R^1$ are on each occurrence, identically or differently, H, D, F, Cl, Br, I, CN, $NO_2$, $N(Ar)_2$, $N(R^2)_2$, C(=O)Ar, $C(=O)R^1$, $P(=O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, an aromatic or heteroaromatic ring system having 5 to 80 aromatic ring atoms, which may in each case be substituted by one or more radicals $R^2$, an aryloxy or heteroaryloxy group having 5 to 60 aromatic ring atoms, which is optionally substituted by one or more radicals $R^2$, or an aralkyl or heteroaralkyl group having 5 to 60 aromatic ring atoms, which is optionally substituted by one or more radicals $R^2$, where two or more adjacent substituents R or two substituents R$^1$ which are bonded in the same group Y may optionally form a mono- or polycyclic, aliphatic, aromatic or heteroaromatic ring system, which is optionally substituted by one or more radicals R$^2$, with one another;

R$^2$ is selected on each occurrence, identically or differently, from the group consisting of H, D, F, Cl, Br, I, CN, NO$_2$, N(Ar)$_2$, N(R$^3$)$_2$, C(=O)Ar, C(=O)R$^3$, P(=O)(Ar)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R$^3$, where one or more non-adjacent CH$_2$ groups is optionally replaced by R$^3$C=CR$^3$, C≡C, Si(R$^3$)$_2$, Ge(R$^3$)$_2$, Sn(R$^3$)$_2$, C=O, C=S, C=Se, C=NR$^3$, P(=O)(R$^3$), SO, SO$_2$, NR$^3$, O, S or CONR$^3$ and where one or more H atoms is optionally replaced by D, F, Cl, Br, I, CN or NO$_2$, an aromatic or heteroaromatic ring system having 5 to 60 aromatic ring atoms, which may in each case be substituted by one or more radicals R$^3$, an aryloxy or heteroaryloxy group having 5 to 60 aromatic ring atoms, which is optionally substituted by one or more radicals R$^3$, or an aralkyl or heteroaralkyl group having 5 to 60 aromatic ring atoms, where two or more adjacent substituents R$^2$ may optionally form a monocyclic or polycyclic, aliphatic, aromatic or heteroaromatic ring system, which is optionally substituted by one or more radicals R$^3$;

R$^3$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents R$^3$ may form a mono- or polycyclic, aliphatic, aromatic or heteroaromatic ring system with one another;

Ar is on each occurrence, identically or differently, an aromatic or heteroaromatic ring system having 5-30 aromatic ring atoms, which is optionally substituted by one or more non-aromatic radicals R$^3$; two radicals Ar here which are bonded to the same N atom or P atom may also be bridged to one another by a single bond or a bridge selected from N(R$^3$), C(R$^3$)$_2$, O or S;

L is a di-, tri-, tetra-, penta- or hexavalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms or an alkenylene or alkynylene group having 2 to 40 C atoms, each of which may be substituted by one or more radicals R$^2$, where one or more non-adjacent CH$_2$ groups is optionally replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, P(=O)R$^2$, S=O, SO$_2$, —O—, —S— or —CONR$^2$— and where one or more H atoms is optionally replaced by D, F, Cl, Br, I, CN or NO$_2$, or a di-, tri-, tetra-, penta- or hexavalent aromatic or heteroaromatic ring system having 5 to 80 aromatic ring atoms, which is optionally substituted by one or more radicals R$^2$, or P(R$^2$)$_{3-p}$, P(=O)(R$^2$)$_{3-p}$, C(R$^2$)$_{4-p}$, Si(R$^2$)$_{4-p}$, N(Ar)$_{3-p}$, or a combination of two, three, four or five of these systems; or L is a chemical bond;

n is on each occurrence, identically or differently, 0 or 1; and p is 2, 3, 4, 5 or 6, with the proviso that p is not greater than the maximum valence of L.

2. The compound according to claim 1, wherein the compounds of the formulae (2) and (3) are compounds of the above-mentioned formulae (11d) to (31e) in which in each case two or more of these units, which is optionally identical or different, are bridged to one another by a divalent or polyvalent group L, which is in each case bonded instead of a substituent R in the para-position to X;

or in that the compounds of the formula (4) are compounds of the above-mentioned formulae (11d) to (31e) in which in each case two of these units, which is optionally identical or different, are bridged to one another by a spiro carbon atom, which is present instead of the group Y.

3. The compound according to claim 1, wherein

R$^1$ are on each occurrence, identically or differently, H, D, F, Cl, Br, I, CN, NO$_2$, N(Ar)$_2$, N(R$^2$)$_2$, C(=O)Ar, C(=O)R$^1$, P(=O)(Ar)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R$^2$, where one or more non-adjacent CH$_2$ groups is optionally replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms is optionally replaced by D, F, Cl, Br, I, CN or NO$_2$, an aromatic or heteroaromatic ring system having 5 to 60, aromatic ring atoms, which may in each case be substituted by one or more radicals R$^2$, an aryloxy or heteroaryloxy group having 5 to 60 aromatic ring atoms, which is optionally substituted by one or more radicals R$^2$, or an aralkyl or heteroaralkyl group having 5 to 60 aromatic ring atoms, which is optionally substituted by one or more radicals R$^2$, where two or more adjacent substituents R or two substituents R$^1$ which are bonded in the same group Y may optionally form a mono- or polycyclic, aliphatic, aromatic or heteroaromatic ring system, which is optionally substituted by one or more radicals R$^2$, with one another;

L is a di-, tri-, tetra-, penta- or hexavalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms or an alkenylene or alkynylene group having 2 to 40 C atoms, each of which may be substituted by one or more radicals R$^2$, where one or more non-adjacent CH$_2$ groups is optionally replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, P(=O)R$^2$, S=O, SO$_2$, —O—, —S— or —CONR$^2$— and where one or more H atoms is optionally replaced by D, F, Cl, Br, I, CN or NO$_2$, or a di-, tri-, tetra-, penta- or hexavalent aromatic or heteroaromatic ring system having 5 to 40, aromatic ring atoms, which is optionally substituted by one or more radicals R$^2$, or P(R$^2$)$_{3-p}$, P(=O)(R$^2$)$_{3-p}$, C(R$^2$)$_{4-p}$, Si(R)$_{4-p}$, N(Ar)$_{3-p}$, or a combination of two, three, four or five of these systems; or L is a chemical bond and X is N.

4. The compound according to claim 1, wherein X stands on each occurrence, identically or differently, for N or P.

5. The compound according to claim 1, wherein at least one substituent R, R$^1$ and/or R$^2$ is selected from structures of the following formulae (32) to (35):

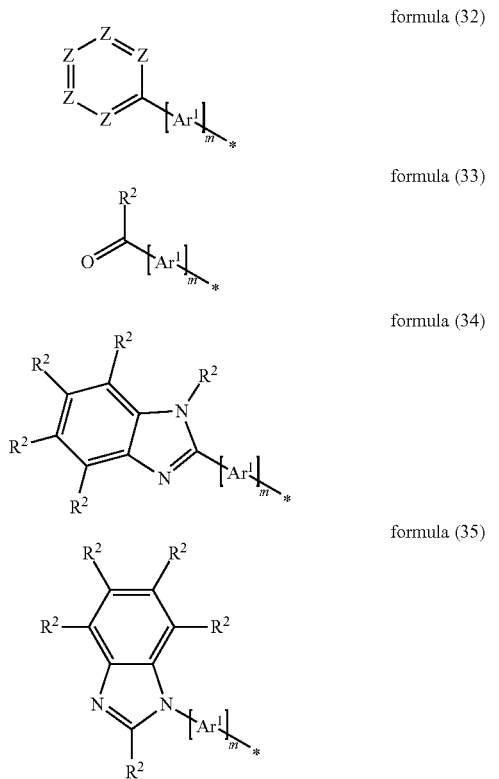

formula (32)

formula (33)

formula (34)

formula (35)

and/or in that at least one group L is selected from structures of the following formulae (36) to (38):

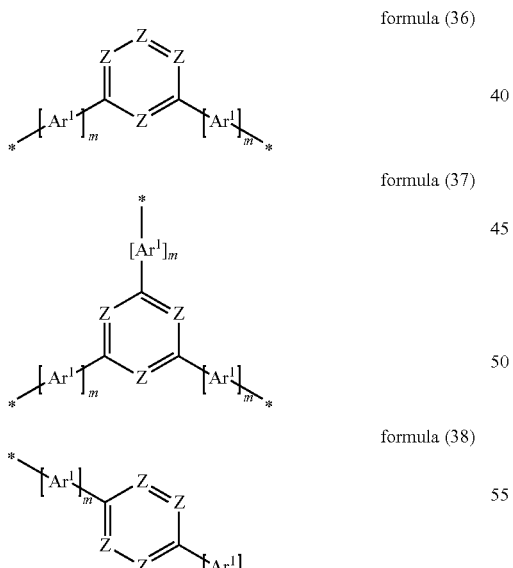

formula (36)

formula (37)

formula (38)

where $R^2$ has the meaning given in claim 1, * indicates the position of the bond from the group of the formulae (32) to (38).

6. The compound according to claim 1, wherein at least substituent R, is selected from structures of the following formulae (32) to (35):

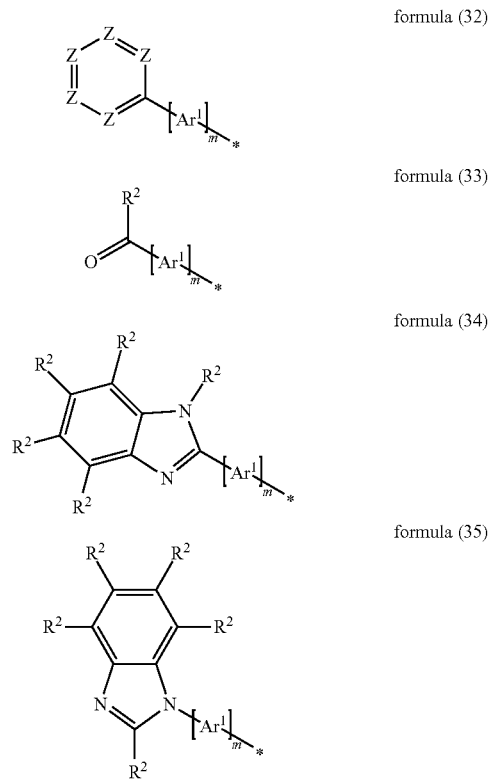

formula (32)

formula (33)

formula (34)

formula (35)

and/or in that at least one group L is selected from structures of the following formulae (36) to (38):

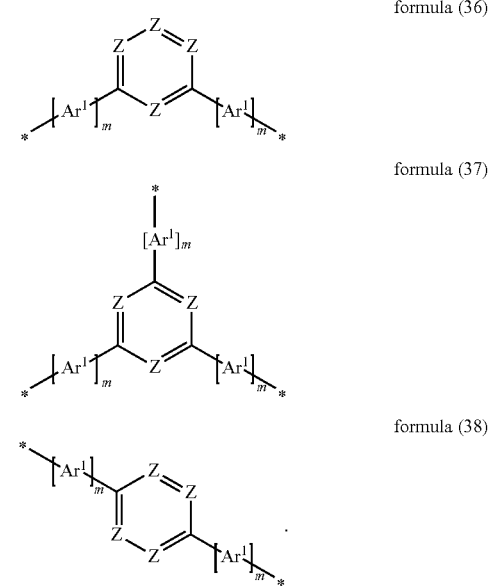

formula (36)

formula (37)

formula (38)

7. A process for the preparation of the compound according to claim 1, comprising the reaction steps of:
  a) synthesis of the skeleton which is only bridged by one group Y;
  b) introducing the second and optionally third group Y, by an intramolecular ring-closure reaction;
  c) introducing the radical(s) R.

8. An oligomer, polymer or dendrimer comprising one or more compounds according to claim 1, where one or more bonds to the polymer, oligomer or dendrimer are present instead of one or more radicals R, $R^1$ and/or $R^2$.

9. An electronic device which comprises the compound according to claim 1.

10. An electronic device which comprises an oligomer, polymer or dendrimer according to claim 6.

11. An organic electroluminescent device which comprises the compound according to claim 1.

12. An organic electroluminescent device which comprises an oligomer, polymer or dendrimer according to claim 6.

13. The electronic device as claimed in claim 9, wherein the device is an organic electroluminescent device (OLED, PLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC), an organic laser diode (O-laser) or an organic plasmon emitting device.

14. An organic electroluminescent device which comprises the compound according to claim 1 as matrix material for fluorescent or phosphorescent emitters, in particular for phosphorescent emitters, in an emitting layer and/or as hole-blocking material in a hole-blocking layer and/or as electron-transport material in an electron-transport layer and/or as electron- or exciton-blocking material in an electron-blocking or exciton-blocking layer and/or as hole-transport material in a hole-transport or hole-injection layer.

\* \* \* \* \*